US 12,037,383 B2

(12) United States Patent
Roodink et al.

(10) Patent No.: US 12,037,383 B2
(45) Date of Patent: Jul. 16, 2024

(54) ANTI-SPIKE GLYCOPROTEIN ANTIBODIES AND THE THERAPEUTIC USE THEREOF

(71) Applicant: Talem Therapeutics LLC, Fargo, ND (US)

(72) Inventors: Ilse Roodink, Loenen (NL); Yasmina Noubia Abdiche, Redwood City, CA (US); Jennifer L. Bath, Plymouth, MN (US)

(73) Assignee: Talem Therapeutics LLC, Fargo, ND (US)

( * ) Notice: Subject to any disclaimer, the term of this patent is extended or adjusted under 35 U.S.C. 154(b) by 0 days.

(21) Appl. No.: 18/173,772

(22) Filed: Feb. 23, 2023

(65) Prior Publication Data

US 2023/0250158 A1 Aug. 10, 2023

Related U.S. Application Data

(62) Division of application No. 17/586,539, filed on Jan. 27, 2022, now Pat. No. 11,623,949.

(60) Provisional application No. 63/142,787, filed on Jan. 28, 2021.

(51) Int. Cl.
*C07K 16/10* (2006.01)
*A61P 31/14* (2006.01)
*A61K 39/00* (2006.01)

(52) U.S. Cl.
CPC .............. *C07K 16/10* (2013.01); *A61P 31/14* (2018.01); *A61K 2039/505* (2013.01); *C07K 2317/21* (2013.01); *C07K 2317/31* (2013.01); *C07K 2317/565* (2013.01); *C07K 2317/732* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 6,180,370 B1 * | 1/2001 | Queen | ................. | C07K 16/2803 435/69.6 |
| 10,787,501 B1 * | 9/2020 | Babb | .................. | C07K 16/1003 |
| 2022/0251174 A1 | 8/2022 | Roodink et al. | | |

OTHER PUBLICATIONS

Kipriyanov, Sergey M., and Fabrice Le Gall. "Generation and production of engineered antibodies." Molecular biotechnology 26.1 (2004): 39-60. (Year: 2004).*
Janeway, Charles A. "Immunobiology: The Immune System in Health and Disease." 2001 (Year: 2001).*
Abdiche, Y. N. et al. Antibodies Targeting Closely Adjacent or Minimally Overlapping Epitopes Can Displace One Another. PloS One 12, e0169535 (2017).
Ahmad, J., Jiang, J., Boyd, L. F., Natarajan, K. & Margulies, D. H. Synthetic nanobody-SARS-CoV-2 receptor-binding domain structures identify distinct epitopes. bioRxiv 2021.01.27.428466 (2021).
Al-Lazikani, B. et al., Standard conformations for the canonical structures of immunoglobulins, *J. Mol. Biol.* 273:927-948 (1997).
Baum, A. et al. Antibody cocktail to SARS-CoV-2 spike protein prevents rapid mutational escape seen with individual antibodies. Science 369, 1014-1018 (2020).
Baum, A. et al. REGN-COV2 antibodies prevent and treat SARS-CoV-2 infection in rhesus macaques and hamsters. Science 370, 1110-1115 (2020).
Chen, J., Gao, K., Wang, R. & Wei, G.-W. Revealing the threat of emerging SARS-CoV-2 mutations to antibody therapies. bioRxiv 2021.04.12.439473 (2021).
Corman, V. M. et al. Detection of 2019 novel coronavirus (2019-nCoV) by real-time RT-PCR. Eurosurveillance 25, 2000045 (2020).
De Kruif, J., Bakker, A.B.H., Marissen, W.E., et al. A Human Monoclonal Antibody Cocktail as a Novel Component of Rabies Postexposure Prophylaxis. Annual Review of Medicine 58:1, 359-368 (2007).
Ge, J. et al. Antibody neutralization of SARS-CoV-2 through ACE2 receptor mimicry. Nat Commun 12, 250 (2021).
GenBank Accession No. MN908947.3 (2020). "Severe acute respiratory syndrome coronavirus 2 isolate Wuhan-Hu-1, complete genome," 11 total pages.
GenBank Accession No. NC_045512.2 (2020). "Severe acute respiratory syndrome coronavirus 2 isolate Wuhan-Hu-1, complete genome," 16 total pages.
GenBank Accession No. NM_021804.3 (2022). "*Homo sapiens* angiotensin converting enzyme 2 (ACE2), transcript variant 2, mRNA," 7 total pages.
GenBank Accession No. QHD43416.1 (2020). "Surface glycoprotein [severe acute respiratory syndrome coronavirus 2]" 3 total pages.
GenBank Accession No. YP_009724390.1 (2020). "Surface glycoprotein [severe acute respiratory syndrome coronavirus 2]" 3 total pages.
GenBank Accession No. YP_009825051.1 (2020). "Spike glycoprotein [SARS coronavirus Tor2]" 3 total pages.
Gottlieb, R.L. et al. (2021). "Effect of Bamlanivimab as Monotherapy or in Combination with Etesevimab on Viral Load in Patients with Mild to Moderate COVID-19: A randomized Clinical Trial," JAMA 325:632-644.

(Continued)

*Primary Examiner* — Michael Szperka
*Assistant Examiner* — Lia E Taylor
(74) *Attorney, Agent, or Firm* — Cooley LLP

(57) ABSTRACT

The present application relates to neutralizing antibodies or antigen-binding fragments thereof against betacoronaviruses such as severe acute respiratory syndrome coronavirus 2 (SARS-CoV-2), to nucleic acid(s) encoding such neutralizing antibodies or antigen-binding fragments thereof, and to mixture and compositions comprising such antibodies, antigen-binding fragments or nucleic acids. Such neutralizing antibodies or antigen-binding fragments thereof are able to block betacoronavirus entry into cells and/or to induce complement-dependent cytotoxicity (CDC), antibody-dependent cellular cytotoxicity (ADCC) and/or antibody-dependent cellular phagocytosis (ADCP) against betacoronavirus-infected cells. Methods and uses of the antibodies, antigen-binding fragments thereof, nucleic acid(s) or compositions, including therapeutic, diagnostic, and preventative methods and uses for betacoronavirus infections and related diseases such as COVID-19, are also described.

30 Claims, 28 Drawing Sheets

Specification includes a Sequence Listing.

(56) References Cited

OTHER PUBLICATIONS

Hansen, J. et al. Studies in humanized mice and convalescent humans yield a SARS-CoV-2 antibody cocktail. Science 369, 1010-1014 (2020).
Hu, B. et al. Characteristics of SARS-CoV-2 and COVID-19, Nat Rev Microbiol 19, 141-154 (2020).
International Search Report mailed on Jun. 30, 2022, for PCT Application No. PCT/US2022/014103, filed on Jan. 27, 2022, 9 pages.
Janeway, Charles A. "Immunobiology: The Immune System in Health and Disease." 2001.
Kazane et al. Self-assembled antibody multimers through peptide nucleic acid conjugation., *J. Am. Chem. Soc.* [Epub: Dec. 4, 2012].
Kipriyanov, S.M. et al. (2004). "Generation and production of engineered antibodies," Molecular biotechnology 26.1:39-60.
Klein, C. et al. Progress in overcoming the chain association issue in bispecific heterodimeric IgG antibodies, mAbs 4:6, 1-11 (2012).
Ku, Z. et al. Molecular determinants and mechanism for antibody cocktail preventing SARS-CoV-2 escape. Nat. Commun. 12, 469 (2021).
Lee, W.S., et al. Antibody-dependent enhancement and SARS-CoV-2 vaccines and therapies Nat Microbiol 5, 1185-1191 (2020).
Li, W. et al. Angiotensin-converting enzyme 2 is a functional receptor for the SARS coronavirus. Nature 426, 450-454 (2003).
Lin, S. (2022). "Characterization of SARS-CoV-2 Omicron spike RBD reveals significantly decreased stability, severe evasion of neutralizing-antibody recognition but unaffected engagement by decoy ACE2 modified for enhanced RBD binding," Signal Transduction and Targeted Therapy 7:56.
MacCallum R.M. et al., Antibody-antigen interactions: contact analysis and binding site topography, *J. Mol. Biol.* 262, 732-745 (1996).
Martin et al., Modeling antibody hypervariable loops: a combined algorithm, *Proc. Natl. Acad. Sci. USA* 86:9268-9272 (1989).
Meulen, J. et al. Human Monoclonal Antibody Combination against SARS Coronavirus: Synergy and Coverage of Escape Mutants. PLoS Med. 3, e237 (2006).
Ng et al. Preexisting and de novo humoral immunity to SARS-CoV-2 in humans, Science (370)6522: 1339-1343 (2020).
Non-Final Office Action mailed on Sep. 28, 2022, for U.S. Appl. No. 17/586,539, filed Jan. 27, 2022, 12 pages.
Notice of Allowance mailed on Jan. 19, 2023, for U.S. Appl. No. 17/586,539, filed Jan. 27, 2022, 10 pages.
Pinto, D. et al. (2020). "Cross-neutralization of SARS-CoV-2 by a human monoclonal SARS-CoV antibody," Nature 583:290-295.
Rosenke, K. et al. Defining the Syrian hamster as a highly susceptible preclinical model for SARS-CoV-2 infection. Emerg. Microbes Infect. 9, 2673-2684 (2020).
Sanz, L. et al. Engineered mRNA and the Rise of Next-Generation Antibodies, Antibodies (Basel), 10(4):37 (2021).
Schäfer, A. et al. Antibody potency, effector function, and combinations in protection and therapy for SARS-CoV-2 infection in vivo. J. Exp. Med. 218, e20201993 (2021).
Shi, R. et al. A human neutralizing antibody targets the receptor-binding site of SARS-CoV-2. Nature 584, 120-124 (2020).
Sia, S.F. et al. Pathogenesis and transmission of SARS-CoV-2 in golden hamsters. Nature 583, 834-838 (2020).
Simoes, E.A. et al. Suptavumab for the Prevention of Medically Attended Respiratory Syncytial Virus Infection in Preterm Infants, Clinical Infectious Diseases, ciaa951 (2020).
Snow, D.M. et al. A Monoclonal Antibody Combination against both Serotypes A and B Botulinum Toxin Prevents Inhalational Botulism in a Guinea Pig Model. Toxins 2021, 13, 31.
Starr, T.N. et al. Complete map of SARS-CoV-2 RBD mutations that escape the monoclonal antibody LY-CoV555 and its cocktail with LY-CoV016. BioRxiv Prepr. Serv. Biol. (2021).
Swindells, M.B. et al. abYsis: Integrated Antibody Sequence and Structure-Management, Analysis, and Prediction.*J Mol Biol* 429(3):356-364 (2017).
Tang, D. et al. The hallmarks of COVID-19 disease. PLoS Pathogens 16(5): e1008536 (2020).
Tao, K. et al. (2021). "The biological and clinical significance of emerging SARS-CoV-2 variants," Nature Reviews Genetics 22:757-773.
Tortorici, M.A. et al. (2020). "Ultrapotent human antibodies protect against SARS-CoV-2 challenge via multiple mechanisms," Science 370:950-957 (with Supplemental Materials).
VanBlargan, L.A. et al. (2021). "A potently neutralizing SARS-CoV-2 antibody inhibits variants of concern by utilizing unique binding residues in a highly conserved epitope," Immunity 54:2399-2416.
Van Hoecke, L. et al. How mRNA therapeutics are entering the monoclonal antibody field, *Journal of Translational Medicine*, vol. 17(1): 54 (2019).
Walser, M. et al. Highly potent anti-SARS-CoV-2 multi-DARPin therapeutic candidates. bioRxiv 2020.08.25.256339 (2020).
Walter, J. D. et al. Sybodies targeting the SARS-CoV-2 receptor-binding domain. bioRxiv 2020.04.16.045419 (2020).
Wang, C. et al. A human monoclonal antibody blocking SARS-CoV-2 infection. Nat. Com. 2251(2020).
Wec A.Z. et al. Broad neutralization of SARS-related viruses by human monoclonal antibodies. *Science.* 2020;369:731-736.
Wec, A.Z. et al. Development of a Human Antibody Cocktail that Deploys Multiple Functions to Confer Pan-Ebolavirus Protection. Cell Host & Microbe 25, 39-48.e5 (2019).
Weisblum, Y. et al. Escape from neutralizing antibodies by SARS-CoV-2 spike protein variants. eLife 9, e61312 (2020).
Whitelegg N et al. WAM: an improved algorithm for modelling antibodies on the WEB, *Protein Eng.* 13(12):819-824 (2000).
Wrapp, D. et al. Structural Basis for Potent Neutralization of Betacoronaviruses by Single-Domain Camelid Antibodies. Cell 181, 1004-1015.e15 (2020).
Written Opinion of the International Searching Authority mailed on Jun. 30, 2022, for PCT Application No. PCT/US2022/014103, filed on Jan. 27, 2022, 11 pages.
Wu, G.Y. et al. Receptor-mediated in vitro gene transformation by a soluble DNA carrier. *J. Biol. Chem.* 262:4429-4432 (1987).
Wu, Y. et al. A noncompeting pair of human neutralizing antibodies block COVID-19 virus binding to its receptor ACE2. Science 368, 1274-1278 (2020).
Yi, C. et al. Key residues of the receptor binding motif in the spike protein of SARS-CoV-2 that interact with ACE2 and neutralizing antibodies. Cell Mol Immunol 17, 621-630 (2020).
Yuan, M. et al. A highly conserved cryptic epitope in the receptor binding domains of SARS-CoV-2 and SARS-CoV. Science 368, 630-633 (2020).
Zhong, J. et al., The immunology of COVID-19: is immune modulation an option for treatment? Lancet Rheumatol (2)7, E428-E436 (2020).
Zhou, B. et al. (2022). "An elite broadly neutralizing antibody protects SARS-CoV-2 Omicron variant challenge," bioRxiv, 27 total pages.
Zhou, D. et al. Robust SARS-CoV-2 infection in nasal turbinates after treatment with systemic neutralizing antibodies. Cell Host Microbe 29, 551-563.e5 (2021).
Zost, S. J. et al. Potently neutralizing and protective human antibodies against SARS-CoV-2. Nature 584, 443-449 (2020).

\* cited by examiner

ANTI-SPIKE GLYCOPROTEIN ANTIBODIES AND THE THERAPEUTIC USE THEREOF

CROSS REFERENCE TO RELATED APPLICATIONS

This application is a division of U.S. patent application Ser. No. 17/586,539, filed Jan. 27, 2022, now U.S. Pat. No. 11,623,949, which claims the benefit of U.S. provisional application Ser. No. 63/142,787, filed on Jan. 28, 2021, which is incorporated herein by reference in its entirety.

SEQUENCE LISTING

The contents of the electronic sequence listing (TALM_001_01US_SeqList_ST26.xml; Size: 195,638 bytes; and Date of Creation: Feb. 23, 2023) are herein incorporated by reference in its entirety.

TECHNICAL FIELD

The present disclosure generally relates to the field of viral infections and diseases, and more specifically to infections and diseases caused by coronaviruses such as severe acute respiratory syndrome coronavirus 2 (SARS-CoV-2).

BACKGROUND ART

The coronavirus disease 2019 (COVID-19) pandemic has created an unprecedented challenge for the global medical and scientific communities. Public health efforts to slow the spread of the disease and the incredible work of medical personnel have helped combat the pandemic, but modeling data suggests that the severe acute respiratory syndrome coronavirus 2 (SARS-CoV-2) virus (GenBank Accession Nos. NC_045512.2, MN908947.3, YP_009724390.1, and preferably QHD43416.1) will continue to circulate in the human population and cause disease even after the pandemic has subsided [Tang D, Comish P, Kang R, PLoS Pathogens 16(5): e1008536 (2020)]. The global spread and inter-species transmission of the virus further increases its resistance to eradication efforts by providing multiple reservoirs from which new outbreaks or mutated strains may arise [Hu, B., Guo, H., Zhou, P. et al. Nat Rev Microbiol (2020)]. These factors make it highly likely that the SARS-CoV-2 virus will continue to impact human health long into the foreseeable future.

While some pre-existing immunity against SARS-CoV-2 does exist in the population, this diminishes with age [Ng et al., Science (370)6522: 1339-1343 (2020)] and leaves those at highest risk for severe disease and death are still in danger until an effective vaccine can provide widespread immunity. To compound the problem, the most severe presentation of the disease is, in part, caused by an overactive immune response and damaging inflammation in the lungs (an effect which may be exacerbated by certain types of vaccines) [Tang D, Comish P, Kang R, PLoS Pathogens 16(5): e1008536 (2020)][Lee, W. S., Wheatley, A. K., Kent, S. J. et al. Nat Microbiol 5, 1185-1191 (2020). The common immune-modifying therapies, such as corticosteroids or inhibition of specific cytokines like IL-6, can pose a significant risk to the patient if not paired with effective virus-specific therapies to control the virus [Zhong et al., Lancet Rheumatol (2)7, E428-E436 (2020)].

Multiple variants of SARS-CoV-2 are circulating globally and within the United States. Four new variants that have rapidly become dominant within their countries have aroused concerns: B.1.1.7 (also known as VOC-202012/01 or alpha), 501Y.V2 (B.1.351, Beta), P.1 (B.1.1.28.1, Gamma), Delta (B.1.617.2) and B.1.1.529 (Omicron). Studies on these variants have provided compelling evidence that they have the potential to escape naturally-induced immunity as well as the immunity induced by currently approved vaccines.

Most neutralizing antibodies described so far target the ACE2-binding interface of the receptor-binding domain (RBD) of the SARS-CoV-2 Spike protein, making them vulnerable to escape by evolving viral mutations within the RBD. Antibody monotherapy significantly increases this risk. Dual-Ab cocktails from Regeneron (casirivimab and imdevimab, targeting adjacent, non-overlapping epitopes) and Eli Lilly (bamlanivimab and etesevimab, targeting overlapping epitopes) leaves both Abs in each cocktail potentially susceptible to evasion by single point mutations. Indeed, recent evidence shows that these cocktails are ineffective at neutralizing Omicron (www.medrxiv.org/content/10.1101/2021.12.07.21267432v4; www.medrxiv.org/content/10.1101/2021.12.14.21267769v1.full-text#T1).

Thus, there is a need for the development of therapies that elicit neutralizing activity against SARS-CoV-2, including SARS-CoV-2 variants, and that minimize the risk of viral escape.

The present disclosure refers to a number of documents, the content of which is herein incorporated by reference in their entirety.

SUMMARY OF THE DISCLOSURE

Provided herein are antibodies and antigen-binding regions thereof that bind SARS-CoV-2 Spike (S) protein. The antibodies are useful, inter alia, for inhibiting or neutralizing the activity of SARS-CoV-2 S protein. In some embodiments, the antibodies are useful for blocking binding of the virus to its host cell receptor angiotensin-converting enzyme 2 (ACE2), for preventing entry of SARS-CoV-2 virus into host cells and/or for eliciting Fc-mediated clearance of the virus. In certain embodiments, the antibodies are useful in preventing, treating or ameliorating at least one symptom of SARS-CoV-2 infection in a subject. In some embodiments, the antibodies are administered prophylactically or therapeutically to a subject having or at risk of having SARS-CoV-2 infection. Also provided are isolated heavy and light chain immunoglobulins derived from human anti-SARS-CoV-2 S protein antibodies and nucleic acid molecules encoding such immunoglobulins.

The antibodies can be full-length (e.g., IgG1 or IgG4 antibody) or may comprise only an antigen-binding portion thereof (e.g., a Fab, F(ab)$_2$ or scFv fragment) and may be modified to affect functionality (e.g., to increase persistence in a host or to eliminate residual effector functions. In certain embodiments, the antibodies are multispecific (e.g., bispecific).

In one aspect, isolated recombinant monoclonal antibodies or antigen-binding fragments thereof that bind specifically to the SARS-CoV-2 Spike protein are provided. In some embodiments, the antibodies are fully human monoclonal antibodies. In some embodiments, the antibodies and antigen-binding fragments thereof bind to an epitope within the receptor binding domain (RBD) of the Spike protein of SARS-CoV-2. In other embodiments, the antibodies and antigen-binding fragments thereof bind to an epitope outside the RBD of the Spike protein.

In some embodiments the antibodies are useful for blocking the attachment of the SARS-CoV-2 virus and/or preventing entry of the viral genome into host cells. In some embodiments, the antibodies are useful in preventing, treating, or ameliorating one or more symptoms of SARS-CoV-2 infection in human hosts. In certain embodiments, compositions containing one or more antibodies or antigen-binding fragments described herein may be useful for the treatment of SARS-CoV-2 infection.

In certain embodiments, the antibodies or antigen-binding fragments are bispecific. In related embodiments, a bispecific antibody or antigen-binding fragment thereof comprises a first binding specificity to a first epitope in the receptor binding domain of SARS-CoV-2 Spike protein and a second binding specificity to a second epitope in the receptor binding domain of SARS-CoV-2 Spike protein wherein the first and second epitopes are distinct and non-overlapping. In other related embodiments, a bispecific antibody or antigen-binding fragment thereof comprises a first binding specificity to a first epitope in the receptor binding domain of SARS-CoV-2 Spike protein and a second binding specificity to a second epitope outside the receptor binding domain of SARS-CoV-2 Spike protein wherein the first and second epitopes are distinct and non-overlapping.

Exemplary anti-SARS-CoV-2 Spike protein antibodies are listed in Tables 1 and 2. Tables 1 and 2 set forth the amino acid sequence identifiers of the heavy chain variable regions (HCVRs), light chain variable regions (LCVRs), heavy chain complementarity determining regions (HCDR1, HCDR2, HCDR3) and light chain complementarity determining regions (LCDR1, LCDR2, LCDR3) of exemplary anti-SARS-CoV-2 Spike protein antibodies.

In various aspects, provided herein are antibodies or antigen-binding fragments thereof comprising an HCVR comprising an amino acid sequence selected from any one of the HCVR amino acid sequences listed in Table 2, or a sequence having at least 70%, at least 75%, at least 80%, at least 85%, at least 90%, at least 95%, at least 98% or at least 99% sequence identity thereto.

Also provided herein are antibodies or antigen-binding fragments thereof comprising an LCVR comprising an amino acid sequence selected from any one of the LCVR amino acid sequences listed in Table 2, or a sequence having at least 70%, at least 75%, at least 80%, at least 85%, at least 90%, at least 95%, at least 98% or at least 99% sequence identity thereto.

Also provided herein are antibodies or antigen-binding fragments thereof comprising a heavy chain CDR1 (HCDR1) comprising an amino acid sequence selected from any one of the HCDR1 amino acid sequences listed in Table 1, or a sequence having at least 70%, at least 75%, at least 80%, at least 85%, at least 90%, at least 95%, at least 98% or at least 99% sequence identity thereto.

Also provided herein are antibodies or antigen-binding fragments thereof comprising a heavy chain CDR2 (HCDR2) comprising an amino acid sequence selected from any one of the HCDR2 amino acid sequences listed in Table 1, or a sequence having at least 70%, at least 75%, at least 80%, at least 85%, at least 90%, at least 95%, at least 98% or at least 99% sequence identity thereto.

Also provided herein are antibodies or antigen-binding fragments thereof comprising a heavy chain CDR1 (HCDR3) comprising an amino acid sequence selected from any one of the HCDR3 amino acid sequences listed in Table 1, or a sequence having at least 70%, at least 75%, at least 80%, at least 85%, at least 90%, at least 95%, at least 98% or at least 99% sequence identity thereto.

Also provided herein are antibodies or antigen-binding fragments thereof comprising a light chain CDR1 (LCDR1) comprising an amino acid sequence selected from any one of the LCDR1 amino acid sequences listed in Table 1, or a sequence having at least 70%, at least 75%, at least 80%, at least 85%, at least 90%, at least 95%, at least 98% or at least 99% sequence identity thereto.

Also provided herein are antibodies or antigen-binding fragments thereof comprising a light chain CDR2 (LCDR2) comprising an amino acid sequence selected from any one of the LCDR2 amino acid sequences listed in Table 1, or a sequence having at least 70%, at least 75%, at least 80%, at least 85%, at least 90%, at least 95%, at least 98% or at least 99% sequence identity thereto.

Also provided herein are antibodies or antigen-binding fragments thereof comprising a light chain CDR3 (LCDR3) comprising an amino acid sequence selected from any one of the LCDR3 amino acid sequences listed in Table 1, or a sequence having at least 70%, at least 75%, at least 80%, at least 85%, at least 90%, at least 95%, at least 98% or at least 99% sequence identity thereto.

Also provided are antibodies, or antigen-binding fragments thereof, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. Also provided herein are antibodies, or antigen-binding fragments thereof, comprising a set of six CDRs HCDR1-HCDR2-HCDR3-LCDR1-LCDR2-LCDR3) contained within an HCVR/LCVR amino acid sequence pair as defined by any of the exemplary anti-SARS-CoV-2 antibodies listed in Table 2.

In other aspects, also provided is an antibody or antigen-binding fragment thereof comprising (a) a HCDR1 domain comprising one of the following amino acid sequences: SEQ ID Nos: 1, 6, 11, 20, 25, 36, 39, 45, 50, 54, 57, 64, 74, 89, 94, 99, 103, 108, 113, 117, 122, 125, or 128 (b) a HCDR2 domain comprising one of the following amino acid sequences: SEQ ID Nos: 2, 7, 12, 16, 21, 26, 30, 40, 46, 51, 55, 58, 65, 69, 75, 90, 95, 100, 104, 109, 114, 118, 123, 126, or 129 (c) a HCDR3 domain comprising one of the following amino acid sequences: SEQ ID Nos: 3, 8, 13, 17, 22, 27, 31, 34, 41, 47, 52, 53, 56, 59, 62, 66, 70, 73, 76, 79, 82, 84, 91, 96, 101, 105, 110, 115, 119, 124, 127 or 130 (d) a LCDR1 domain comprising one of the following amino acid sequences: SEQ ID Nos:4, 9, 14, 18, 23, 28, 32, 35, 37, 42, 48, 60, 67, 71, 77, 80, 83, 85, 87, 92, 97, 106, 111 or 120, (e) a LCDR2 domain comprising one of the following amino acid sequences: GND, DNN, YDN, EDN, DDN, SAS, EDK, NNN, SEQ ID NO:43, AND, YDD, NNI, YDY, ANS, RDS, TNN, RND, AAS, YDT, DVS, WAS, ENN, EVS, DDT, GNS or EVA, and (f) a LCDR3 domain comprising one of the following amino acid sequences: SEQ ID Nos:5, 10, 15, 19, 24, 29, 33, 38, 44, 49, 61, 63, 68, 72, 78, 81, 86, 88, 93, 98, 102, 107, 112, 116, or 121.

In other aspects, also provided is an antibody or antigen-binding fragment thereof comprising CDRS having one or more amino acid substitutions relative to the above-noted CDRs.

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, the international ImMunoGeneTics information System® (IMGT) definition, the Contact definition and the AbM definition. In general terms, the Kabat definition is based on sequence variability, the Chothia definition is based on the location of the structural loop regions, the AbM definition is a compromise between the Kabat and Chothia approaches, the Contact definition is based on an analysis of which residues contact antigen in crystal structures, and the IMGT definition is based CDR and Framework definitions as defined by IMGT. See, e.g., Kabat, "Sequences of Proteins of Immunological Interest," National Institutes of Health, Bethesda, Md. (1991); Al-Lazikani et al., *J. Mol. Biol.* 273:927-948 (1997); Martin et al., *Proc. Natl. Acad. Sci. USA* 86:9268-9272 (1989); Whitelegg N & Rees A R, Protein Eng. 13(2000):819-824; Whitelegg N & Rees A R, *Methods Mol Biol.* 248(2004)51-91; MacCallum R M, Martin A C R & Thornton J M, *J. Mol. Biol.* 262(1996)732-745. Public databases are also available for identifying CDR sequences within an antibody (e.g., abYsis; Swindells et al., *J Mol Biol.* 2017 Feb. 3; 429(3): 356-364).

In some aspects, the antibody or antigen-binding fragment thereof specifically binds to the RBD region of the SARS-CoV-2 Spike protein and preferably inhibits interaction of SARS-CoV-2 with its cognate ACE2 receptor (e.g., GenBank Accession No. NM_021804.3). In other aspects, the antibody or antigen-binding fragment thereof binds to the 51 subunit of the SARS-CoV-2 Spike protein in a region other than the RBD or binds to the S2 subunit. In some embodiments, the antibodies are human antibodies. In some embodiments, the antibodies cross-react with the Spike protein of another coronavirus (e.g., the SARS-CoV-1 Spike protein, GenBank Accession No. YP_009825051.1). In some embodiments, an antibody or antigen-binding fragment thereof comprising HCVR CDRs and/or LCVR CDRs of SEQ ID Nos: 163 and 164 cross-reacts with the SARS-CoV-1 Spike protein.

The present disclosure also provides for antibodies and antigen-binding fragments thereof that compete for specific binding to SARS-CoV-2 Spike protein with an antibody or antigen-binding fragment thereof comprising the CDRs of a HCVR and the CDRs of a LCVR, wherein the HCVR and LCVR each has an amino acid sequence selected from the HCVR and LCVR sequences listed in Table 2.

In some embodiments, provided herein are isolated antibodies and antigen-binding fragments thereof that block SARS-CoV-2 Spike protein binding to ACE2. In some embodiments, the antibody or antigen-binding fragment thereof that blocks SARS-CoV-2 Spike protein binding to ACE2 may bind to the same epitope on SARS-CoV-2 Spike protein as ACE2 or may bind to a different epitope on SARS-CoV-2 Spike protein as ACE2. In some embodiments, the present disclosure provides antibodies or antigen-binding fragments thereof that block the binding of SARS-CoV-2 Spike protein to human ACE2 and/or elicit Fc-mediated clearance of the virus.

In one embodiment, the disclosure provides an isolated antibody or antigen-binding fragment thereof that has one or more of the following characteristics: (a) is a fully human monoclonal antibody; (b) interacts with one or more amino acid residues in the receptor binding domain of SARS-CoV-2 Spike protein selected from amino acid residues 345 to 490 of SEQ ID NO: 197 (e.g., 23-H7) or selected from amino acids 417 to 505 of SEQ ID NO:197 (e.g., 22-E8); (c) binds to SARS-CoV-2 Spike protein with an apparent dissociation constant ($K_D$) of less than 300 nM, preferably less than 50 nM, as measured in a label-free (biolayer interferometry) assay; (d) blocks binding of SARS-CoV-2 Spike protein to ACE2 as measured in a label-free (biolayer interferometry) or HTRF assay; (e) neutralizes SARS-CoV-2 infectivity of human host cells by at least 80%, preferably by at least 90% and with an $IC_{50}$ less than 10 mg/mL, preferably less than 5 mg/mL or less than 1 mg/mL, as measured in a live virus or pseudovirus neutralization assay; (f) neutralizes SARS-CoV-2 infectivity wherein the infectious particle is a pseudotyped virus expressing the SARS-CoV-2 surface glycoprotein (GenBank: YP_009724390) or the live SARS-Cov-2 virus isolate BetaCoV/Munich/BavPat1/2020 containing the D614G mutation in the surface glycoprotein; (g) is a bispecific antibody comprising a first binding specificity to a first epitope in the receptor binding domain of SARS-CoV-2 Spike protein and a second binding specificity to (i) a second epitope in the receptor binding domain of SARS-CoV-2 Spike protein wherein the first and second epitopes are distinct and non-overlapping or (ii) a second epitope in the Spike protein of SARS-CoV-2 outside the RBD and (h) induce complement-dependent cytotoxicity (CDC), antibody-dependent cellular cytotoxicity (ADCC) and/or antibody-dependent cellular phagocytosis (ADCP) against infected cells.

In other embodiments, a combination or cocktail (e.g., a pharmaceutical combination or cocktail) is provided comprising at least two (e.g., at least two, at least three, at least four, at least five or more) antibodies or antigen-binding fragments thereof as described herein. In certain embodiments, the combination or cocktail comprises two or more antibodies or antigen-binding fragments thereof that exhibit an additive or synergistic effect (e.g., according to a neutralization assay). In some aspects, antibodies of the combination or cocktail are for administration to a subject infected with SARS-CoV-2 (or prophylactically to a subject at risk of being infected with SARS-CoV-2) as part of the same pharmaceutical formulation. In other aspects, antibodies of the combination or cocktail are for administration to the subject simultaneously or sequentially in two or more different pharmaceutical formulations.

In other embodiments, a pharmaceutical composition is provided comprising an antibody or antigen-binding fragment thereof that binds to SARS-CoV-2 Spike protein as herein described. In related embodiments, the pharmaceutical composition comprises a combination of two or more antibodies or antigen-binding fragments thereof, that in an embodiment exhibit an additive or synergistic effect.

In other related embodiments, use of a pharmaceutical composition as herein described is provided to reduce viral shedding of a subject infected with SARS-CoV-2 and/or to treat COVID-19 and/or treat/prevent acute respiratory distress syndrome (ARDS) in a subject infected with SARS-CoV-2. In other related embodiments, a pharmaceutical composition as herein described is provided for use in the manufacture of a medicament to reduce viral shedding of a subject infected with SARS-CoV-2 and/or to treat COVID-19 and/or treat/prevent ARDS in a subject infected with SARS-CoV-2.

Also provided are therapeutic methods for treating a disorder, symptom or syndrome associated with SARS-CoV-2 such as viral infection in a subject using an antibody or antigen-binding portion thereof as herein described, wherein the therapeutic methods comprise administering a therapeutically effective amount of a pharmaceutical composition comprising an antibody or antigen-binding fragment thereof as herein described to a subject in need thereof. The disorder treated is any disease or condition which is improved, ameliorated, inhibited or prevented by inhibition of SARS-CoV-2 activity. In certain embodiments, the disclosure provides methods to prevent, treat or ameliorate at least one symptom of SARS-CoV-2 infection, the method comprising administering a therapeutically effective amount of an anti-SARS-CoV-2 Spike protein antibody or antigen-binding fragment thereof as herein described to a subject in need thereof. In some embodiments, methods are provided to ameliorate or reduce the severity of at least one symptom or indication of SARS-CoV-2 infection in a subject by administering an antibody as herein described, wherein the at least one symptom or indication is inflammation in the lung, alveolar damage, fever, cough, shortness of breath, diarrhea, organ failure, pneumonia, septic shock or death. In certain embodiments, the disclosure provides methods to decrease viral load in a subject, the methods comprising administering to the subject an effective amount of an antibody or fragment thereof as herein described that binds SARS-CoV-2 Spike protein and blocks SARS-CoV-2 binding to host cell receptor ACE2. In some embodiments, the antibody or antigen-binding fragment thereof may be administered prophylactically or therapeutically to a subject having or at risk of having SARS-CoV-2 infection and/or of developing a more severe form of COVID-19. The subjects at risk include, but are not limited to, an immunocompromised or immunosuppressed subject, an elderly adult (more than 65 years of age), healthcare workers, adults or children in close contact with a person(s) with confirmed or suspected SARS-CoV-2 infection, and people with underlying medical conditions (or comorbidities) such as pulmonary infection, heart disease, obesity or diabetes. In certain embodiments, a combination of antibodies or antigen-binding fragments thereof as herein described is administered to the subject in need thereof. A second therapeutic agent may be co-administered to the subject in need thereof with one or more antibodies or antigen-binding fragments thereof as herein described such as an anti-inflammatory drug (e.g., corticosteroids), an anti-infective drug, a different antibody to SARS-CoV-2 Spike protein, an anti-viral drug, a dietary supplement such as anti-oxidants and any other drug or therapy known in the art. In certain embodiments, the second therapeutic agent may be an agent that helps to counteract or reduce any possible side effect(s) associated with an antibody or antigen-binding fragment thereof as described herein, if such side effect(s) should occur. The antibody or fragment thereof may be administered subcutaneously, intravenously, intradermally, intraperitoneally, orally, intranasally, intramuscularly, or intracranially. In one embodiment, the antibody may be administered as a single intravenous infusion for maximum concentration of the antibody in the serum of the subject. The antibody or antigen-binding fragment thereof may be administered at a dose of about 0.1 mg/kg of body weight to about 100 mg/kg of body weight of the subject. In certain embodiments, an antibody of the present disclosure may be administered at one or more doses comprising between 50 mg to 600 mg.

In other embodiments, nucleic acid molecules encoding anti-SARS-CoV-2 antibodies or portions thereof as herein described are provided. For example, nucleic acid molecules encoding any of the HCVR, LCVR, HCDR1, HCDR2, HCDR3, LCDR1, LCDR2, and LCDR3 amino acid sequences listed in Tables 1-2 are provided.

In various aspects and embodiments, the present disclosure also provides the following items:

1. An isolated antibody or antigen-binding fragment thereof that specifically binds to severe acute respiratory syndrome coronavirus 2 (SARS-CoV-2) Spike protein, wherein the antibody or antigen-binding fragment comprises one of the combinations of heavy chain complementarity determining regions (CDRs) (HCDR1, HCDR2 and HCDR3) and light chain CDRs (LCDR1, LCDR2 and LCDR3) depicted in Table 6:

TABLE 6

| Clone | HCDR1 | HCDR2 | HCDR3 | LCDR1 | LCDR2 | LCDR3 |
|---|---|---|---|---|---|---|
| 23-H7 | GYTFSTYY (SEQ ID NO: 36) | IDPSGGTT (SEQ ID NO: 16) | ARGGFADAVDY (SEQ ID NO: 17) | SGSIAGNY (SEQ ID NO: 37) | EDN | QSYDASHLHVI (SEQ ID NO: 38) |
| 2-A6 | GFSLNTRGMS (SEQ ID NO: 125) | IDWEDDK (SEQ ID NO: 126) | ARTYSVGVKYFGMDV (SEQ ID NO: 127) | SLRNYY (SEQ ID NO: 198) | GGN | NSRDSSGNHVV (SEQ ID NO: 199) |
| 22-D9 | GGTFNTYS (SEQ ID NO: 57) | IIPIFDKP (SEQ ID NO: 58) | ARGTGYYYGMDV (SEQ ID NO: 59) | RSNIGNYP (SEQ ID NO: 60) | YDD | ATWDDSLNVWV (SEQ ID NO: 61) |
| 22-E7 | GFTFNNYP (SEQ ID NO: 103) | ISYDGNHK (SEQ ID NO: 104) | ASDLSGAEDS (SEQ ID NO: 105) | SSDVGGYNY (SEQ ID NO: 106) | EVS | SSYTSSSTWV (SEQ ID NO: 107) |
| 21-F2 | GYIFTNYD (SEQ ID NO: 54) | VNPNSGKV (SEQ ID NO: 55) | ARGHTDF (SEQ ID NO: 56) | SSNIGNNA (SEQ ID NO: 14) | YDD | AAWDDSLNGVV (SEQ ID NO: 5 |
| 22-F7 | GFSFTNYG (SEQ ID NO: 89) | ISYDGSIK (SEQ ID NO: 90) | TRERGTGIDY (SEQ ID NO: 91) | KSDIGAYNY (SEQ ID NO: 92) | DVS | SSYTTSGTVV (SEQ ID NO: 93) |
| 26-G2 | GYSFTSYW (SEQ ID NO: 1) | IYPGDSDT (SEQ ID NO: 2 | ARLGDYSGMDV (SEQ ID NO: 3) | SSNIGSNP (SEQ ID NO: 4) | GND | AAWDDSLNGVV (SEQ ID NO: 5) |
| 27-A11 | GYTFTSYY (SEQ ID NO: 6) | IDPSGGST (SEQ ID NO: 7) | ARSRDGYIDDAFDI (SEQ ID NO: 8) | SSNIGNNY (SEQ ID NO: 9) | DNN | GTWDSSLSAGV (SEQ ID NO: 10) |
| 11-H1 | GYTFTGYY (SEQ ID NO: 11) | INPNSGGT (SEQ ID NO: 12) | ARDKLPFSVGATHGMDV (SEQ ID NO: 13) | SSNIGNNA (SEQ ID NO: 14) | YDN | ASWDDRLDSPV (SEQ ID NO: 15) |

TABLE 6-continued

| Clone | HCDR1 | HCDR2 | HCDR3 | LCDR1 | LCDR2 | LCDR3 |
|---|---|---|---|---|---|---|
| 21-A6 | GYTFTSYY (SEQ ID NO: 6) | IDPSGGTT (SEQ ID NO: 16) | ARGGFADAVDY (SEQ ID NO: 17) | SGSIASNY (SEQ ID NO: 18) | EDN | QSYDSGNVI (SEQ ID NO: 19) |
| 27-F5 | GYTFTSYA (SEQ ID NO: 20) | INAGNGNT (SEQ ID NO: 21) | AREGMITFGGVIVTNYGMDV (SEQ ID NO: 22) | NIGSES (SEQ ID NO: 23) | DDN | QAWDGSTVV (SEQ ID NO: 24) |
| 21-H1 | GFTFSSYG (SEQ ID NO: 25) | ISYDGSNK (SEQ ID NO: 26) | AKEGELRGAFDI (SEQ ID NO: 27) | QSLLHSIGYNF (SEQ ID NO: 28) | SAS | MQALQRTLYT (SEQ ID NO: 29) |
| 27-G3 | GYTFTSYY (SEQ ID NO: 6) | IDPTGGST (SEQ ID NO: 30) | ASAGVGNTFDY (SEQ ID NO: 31) | SGSIARNY (SEQ ID NO: 32) | EDK | QSYDSSNQWV (SEQ ID NO: 33) |
| 8-D4 | GYSFTSYW (SEQ ID NO: 1) | IYPGDSDT (SEQ ID NO: 2) | ARNPSLYSSPTDY (SEQ ID NO: 34) | SSNIGSNT (SEQ ID NO: 35) | NNN | AAWDDSLNGVV (SEQ ID NO: 5) |
| 24-B8 | GGTFSNYA (SEQ ID NO: 39) | IIPILDTT (SEQ ID NO: 40) | VREEGFDY (SEQ ID NO: 41) | SGINVGAYN (SEQ ID NO: 42) | YNSDSDN (SEQ ID NO: 43) | MIWRSSAWV (SEQ ID NO: 44) |
| 21-F1 | GFTFDTYG (SEQ ID NO: 45) | ISNDGSKK (SEQ ID NO: 46) | GRVTEPYMVTPLMLFRMAIDN (SEQ ID NO: 47) | NFGTKS (SEQ ID NO: 48) | AND | QVWDSSADLRGVV (SEQ ID NO: 49) |
| 16-C6 | GRTFSSYA (SEQ ID NO: 50) | ISRSGGST (SEQ ID NO: 51) | AASNEGGTWYGSSWYRPSSYEH (SEQ ID NO: 52) | — | — | — |
| 16-G6 | GRTFSSYA (SEQ ID NO: 50) | ISRSGGST (SEQ ID NO: 51) | AASNEGGTWYGSSWYRPSSYEY (SEQ ID NO: 53) | — | — | — |
| 13-A1 | GYSFTSYW (SEQ ID NO: 1) | IYPGDSDT (SEQ ID NO: 2) | ARYLSSEGMDV (SEQ ID NO: 62) | SSNIGSNP (SEQ ID NO: 4) | NNI | ASWDDSLNEGV (SEQ ID NO: 63) |
| 22-E8 | GGTFSSYA (SEQ ID NO: 64) | IIPIFGTT (SEQ ID NO: 65) | ARDHGYYYGMDV (SEQ ID NO: 66) | DSNIGQNG (SEQ ID NO: 67) | YDY | ASWDDSLSAWV (SEQ ID NO: 68) |
| 5-B6 | GGTFSSYA (SEQ ID NO: 64) | IIPMFNSA (SEQ ID NO: 69) | ARESSGYYYVSNWFDP (SEQ ID NO: 70) | SSNIGAGYD (SEQ ID NO: 71) | ANS | QSYDSSLSGVV (SEQ ID NO: 72) |
| 13-H3 | GYSFTSYW (SEQ ID NO: 1) | IYPGDSDT (SEQ ID NO: 2) | ARGSHYGDYDY (SEQ ID NO: 73) | SSNIGNNY (SEQ ID NO: 9) | DNN | GTWDSSLSAGV (SEQ ID NO: 10) |
| 27-B4 | GDSVSSNSAA (SEQ ID NO: 74) | TYYRSKW (SEQ ID NO: 75) | ARTIGWYDS (SEQ ID NO: 76) | ALPKQF (SEQ ID NO: 77) | RDS | QSADSSATYEV (SEQ ID NO: 78) |
| 8-H1 | GYSFTSYW (SEQ ID NO: 1) | IYPGDSDT (SEQ ID NO: 2) | ARROSGSGYDY (SEQ ID NO: 79) | SSNVGSNS (SEQ ID NO: 80) | TNN | AAWDDSLNGWV (SEQ ID NO: 81) |
| 8-H5 | GYSFTSYW (SEQ ID NO: 1) | IYPGDSDT (SEQ ID NO: 2) | ARWSEGNGFDY (SEQ ID NO: 82) | SSNIGSNS (SEQ ID NO: 83) | RND | AAWDDSLNGVV (SEQ ID NO: 5) |
| 8-A2 | GYTFTGYY (SEQ ID NO: 11) | INPNSGGT (SEQ ID NO: 12) | LAVAGTGGDAFDI (SEQ ID NO: 84) | QSISSW (SEQ ID NO: 85) | AAS | QQGHSFPLT (SEQ ID NO: 86) |
| 23-A11 | GFTFSSYG (SEQ ID NO: 25) | ISYDGSNK (SEQ ID NO: 26) | AKEGELRGAFDI (SEQ ID NO: 27) | NIESKY (SEQ ID NO: 87) | YDT | QVWDRTSGHFV (SEQ ID NO: 88) |
| 30-C5 | GFTFSNYG (SEQ ID NO: 94) | ISYDGSIE (SEQ ID NO: 95) | ARDEDGAFDI (SEQ ID NO: 96) | ESVSYSSSNKNY (SEQ ID NO: 97) | WAS | QQYSSPLT (SEQ ID NO: 98) |

TABLE 6-continued

| Clone | HCDR1 | HCDR2 | HCDR3 | LCDR1 | LCDR2 | LCDR3 |
|---|---|---|---|---|---|---|
| 22-B10 | GFTFSDYP (SEQ ID NO: 99) | ISYDGWTK (SEQ ID NO: 100) | VRGTDYGDS (SEQ ID NO: 101) | SSNIGNNY (SEQ ID NO: 9) | ENN | GTWDNSLSAWV (SEQ ID NO: 102) |
| 6-A4 | GFTLSDYP (SEQ ID NO: 108) | MSYDGSLK (SEQ ID NO: 109) | ARGNSDGDFDY (SEQ ID NO: 110) | DIGSRS (SEQ ID NO: 111) | DDT | QAWDSSTVV (SEQ ID NO: 112) |
| 6-E1 | GFSFNTFP (SEQ ID NO: 113) | ISYDGSFK (SEQ ID NO: 114) | ASPGDSDWADFEN (SEQ ID NO: 115) | SSNIGAGYD (SEQ ID NO: 71) | GNS | QSYDSSLSGYV (SEQ ID NO: 116) |
| 6-F2 | GFNFSLYG (SEQ ID NO: 117) | ISYDGSQK (SEQ ID NO: 118) | VKGEGSLDY (SEQ ID NO: 119) | TSDVGGYGY (SEQ ID NO: 120) | EVA | VSYTLSSLVV (SEQ ID NO: 121) |
| 15-E4 | GSIPSVNV (SEQ ID NO: 122) | VTSDGRT (SEQ ID NO: 123) | LITNQDHNTLGV (SEQ ID NO: 124) | N/A | N/A | N/A |
| 15-C8 | GNVTSITL (SEQ ID NO: 128) | IINDDDRT (SEQ ID NO: 129) | SAKAGGNFY (SEQ ID NO: 130) | N/A | N/A | N/A |
| 15-F7 | GSIPSVNV (SEQ ID NO: 122) | VTSDGRT (SEQ ID NO: 123) | LITNSDHNTLG (SEQ ID NO: 203) | N/A | N/A | N/A |
| 15-H3 | GSIPSVNV (SEQ ID NO: 122) | VTSDGRT (SEQ ID NO: 123) | LITNSDHNTLGV (SEQ ID NO: 124) | N/A | N/A | N/A. |

2. The antibody or antigen-binding fragment according to item 1, comprising a heavy chain variable region (VH) depicted in Table 7:

TABLE 7

| Clone | | Heavy Chain variable (VH) and Light Chain variable (LH) sequences |
|---|---|---|
| 23-H7 | VH | QVQLVQSGAEVKLPGASMKVSCKASGYTFSTYYMHWVRQAPGQGPEWMGVIDPSGGTTSYAQKFHDRIAMTR DTSTSTAYLELSSLRSEDMAVYYCARGGFADAVDYWGQGTLVTVSS (SEQ ID NO: 147) |
| | VL | NFMLTQPHSVSGSPGKTVTISCTRNSGSIAGNYVQWYQQRPGSAPTTVIYEDNQRPSGVPDRFSGSIDSSSN SASLTISGLKTEDEADYYCQSYDASHLHVIFGGGTKVTVL (SEQ ID NO: 148) |
| 2-A6 | VH | QVTLRESGPALVKPTQTLTLTCTFSGFSLNTRGMSVSWIRQPPGKALEWLALIDWEDDKFYRTSLMTRLTIS KDIFKNQVVLTMTNVDPVDTGTYYCARTYSVGVKYFGMDVWGQGTTVTVSS (SEQ ID NO: 191) |
| | VL | SSELTQDPAVSVALGQTVRITCQGDSLRNYYASWYRQEPGQAPILLIYGGNYRPSGIPDRFSGSSSGNTASL TITGAQAEDEADYYCNSRDSSGNHVVFGGGTKLTVL (SEQ ID NO: 192) |
| 22-D9 | VH | QVQLVQSGAEVKKPGSSVNVSCKTSGGTFNTYSINWVRQAPGQGLEWMGEIIPIFDKPNYAQKFQGRVTITA DESTSTAYMELTSLRSDDTAVYYCARGTGYYYGMDVWGQGTTVTVSS (SEQ ID NO: 157) |
| | VL | QSVLTQPPSVSGAPRQTVTISCFGSRSNIGNYPVNWYHQVPGKAPKVVVYYDDLLPSGISDRFSGYKSGTSA SLTISGLRSEDEADYYCATWDDSLNVWVFGGGTKLTVL (SEQ ID NO: 158) |
| 22-D9 optimized | VH | QVQLVQSGAEVKKPGSSVKVSCKTSGGTFNTYSINWVRQAPGQGLEWMGEIIPIFDKPNYAQKFQGRVTITA DESTSTAYMELTSLRSDDTAVYYCARGTGYYYGMDVWGQGTTVTVSS (SEQ ID NO: 215) |
| | VL | QSVLTQPPSVSGAPRQTVTISCFGSRSNIGNYPVNWYHQVPGKAPKVVVYYDDLLPSGISDRFSGYKSGTSA SLTISGLRSEDEADYYCATWDDSLNVWVFGGGTKLTVL (SEQ ID NO: 158) |
| 22-E7 | VH | QVQLVESGGGVVQPGTSLRLSCAASGFTFNNYPMFWVRQAPGKGLEWLALISYDGNHKVYADSVKGRFTISR DNAKNTLYLQMHSLRAEDTALYYCASDLSGAEDSWGQGTLVTVSS (SEQ ID NO: 183) |
| | VL | QSALTQPASVSGSPGQSITISCTGTSSDVGGYNYVSWYQQHPGKAPKLLIYEVSNRPSGVSNRFSGSKSGNT ASLTISGLQAEDEADYYCSSYTSSSTWVFGGGTKLTVL (SEQ ID NO: 184) |
| 21-F2 | VH | SDSESTAYMELTNLTSDDTAVYYCARGHTDFWGQGTLVTVSS (SEQ ID NO: 155) |
| | VL | QSVLTQPPSVSEAPRQRVTISCSGSSSNIGNNAVNWYQQLPGRAPKLLIYYDDLLPSGVSDRFSGSKSGTSA SLAISGLQSEDEADYYCAAWDDSLNGVVFGGGTQLTVL (SEQ ID NO: 156) |

TABLE 7-continued

| Clone | | Heavy Chain variable (VH) and Light Chain variable (LH) sequences |
|---|---|---|
| 21-F2 optimized | VH | QVQLVQSGAEVKKPGASVTVSCKTSGYIFTNYDINWVRQAPGQGLEWVGWVNPNSGKVGYAQKFQGRVIMTR SDSESTAYMELTQLTSDDTAVYYCARGHTDFWGQGTLVTVSS (SEQ ID NO: 214) |
| | VL | QSVLTQPPSVSEAPRQRVTISCSGSSSNIGNNAVNWYQQLPGRAPKLLIYYDDLLPSGVSDRFSGSKSGTSA SLAISGLQSEDEADYYCAAWDDSLNGVVFGGGTQLTVL (SEQ ID NO: 156) |
| 22-F7 | VH | QVQLVESGGGVVQPGRSLRLSCAASGFSFTNYGMHWVRQAPGKGLEWVAVISYDGSIKYYEDSLKGRFTVSR DNSKKTLYLQMNSLRAEDTAVYYCTRERGTIDYWGLGTLVTVSS (SEQ ID NO: 177) |
| | VL | QSALTQPASVSGYPGQSITLSCTGTKSDIGAYNYVSWYQQHPGKAPKLMVYDVSNRPSGLSNRFSGSKSDNT ASLTISGLQAEDEAHYYCSSYTTSGTVVFGGGTKVTVL (SEQ ID NO: 178) |
| 26-G2 | VH | EVQLVQSGAEVKKPGKSLKISCKGSGYSFTSYWIGWVRQMPGKGLEWMGIIYPGDSDTRYSPSFQGQVTISA DKSISTAYLOWSSLKASDTAMYYCARLGDYSGMDVWGQGTMVTVSS (SEQ ID NO: 131) |
| | VL | QSVLTQPPSASGTPGQRVTISCSGSSSNIGSNPVNWYQHLPGTAPKLLISGNDQRPSGVPDRFSGSKSGTSA SLAISGLQSEDEGDYYCAAWDDSLNGVVFGGGTQLTVL (SEQ ID NO: 132) |
| 27-A11 | VH | QVQLVQSGAEVKKPGASVKVSCKASGYTFTSYYMHWVRQAPGQGLEWMGIIDPSGGSTSYAQKFQGRVTLTR DTSTSTVYMELSSLRSEDTAVYYCARSRDGYIDDAFDIWGQGTLVTVSS (SEQ ID NO: 133) |
| | VL | QSVLTQPPSVSAAPGQKVTISCSGSSSNIGNNYVSWYQQLPGTAPKLLIYDNNKRPSGIPDRFSGSKSGTSA TLGITGLQTGDEADYYCGTWDSSLSAGVFGGGTKLTVL (SEQ ID NO: 134) |
| 11-H1 | VH | QVQLVQSGAEVKKPGASVKVSCKASGYTFTGYYMHWVRQAPGQGLEWMGRINPNSGGTNYAQKFQGRVTMTR DTSISTAYMELSRLRSDDTAVYYCARDKLPFSVGATHGMDVWGQGTLVTVSS (SEQ ID NO: 135) |
| | VL | QSVLTQPPSVSEAPRQRVTISCSGSSSNIGNNAVNWYQQLPGQAPRLLIYYDNLLPSGVSDRFSASTSGTSA SLAISDLRSEDEADYYCASWDDRLDSPVFGGGTKLTVL (SEQ ID NO: 136) |
| 21-A6 | VH | QVQLVQSGAEVKKPGASVKVSCKASVKVSCKASGYTFTSYYMHWVRQAPGQGPEWMGVIDPSGGTTSYAQKF HDRIAMTRDTSTSTAYLELSSLRSEDTAVYYCARGGFADAVDYWGQGTLVTVSS (SEQ ID NO: 137) |
| | VL | NFMLTQPHSVSESPGKTVTISCTRSSGSIASNYVQWYQQRPGSSPTTVIYEDNQRPSGVPDRFSGSIDSSSN SASLTISGLKTEDEADYYCQSYDSGNVIFGGGTKVTVL (SEQ ID NO: 138) |
| 27-F5 | VH | EVQLVQSGAEVKKPGASVKVSCKASGYTFTSYAMHWVRQAPGQRLEWMGWINAGNGNTKYSQKFQGRVTITR DTSASTAYMELSSLRSEDTAVYYCAREGMITFGGVIVTNYGMDVWGQGTMVTVSS (SEQ ID NO: 139) |
| | VL | SYVLTQPPSVSVAPGQTARITCGGNNIGSESVHWYQQKPGQAPLLVVYDDNNRPSGIPERFSGSNSGNTATL TINRVEAGDEADYSCQAWDGSTVVFGGGTKLTVL (SEQ ID NO: 140) |
| 21-H1 | VH | QVQLVESGGGVVQPGRSLRLSCAASGFTFSSYGMHWVRQAPGKGLEWVAVISYDGSNKYYADSVKGRFTISR DNSKNTLYLQMNSLRAEDTAVYYCAKEGELRGAFDIWGQGTTVTVSS (SEQ ID NO: 141) |
| | VL | DIVMTQSPLSLPVTPGEPASISCTSSQSLLHSIGYNFVDWYLQKPGQSPQLLIYSASNRASGVPDRFSGSGS GTDFTLKISRVEAEDVGVYYCMQALQRTLYTFGQGTKVESK (SEQ ID NO: 142) |
| 27-G3 | VH | DTSTSTVYMELSSLRSEDTAVYYCASAGVGNTFDYWGQGTLVTVSS (SEQ ID NO: 143) |
| | VL | NFMLTQPHSVSASPGKTVTISCTRSSGSIARNYVQWYQQRPGRSPNILIFEDKQRPSGVPDRFSGSIDSSSN SASLTISGLKTEDEADYYCQSYDSSNQWVFGGGTKLTVL (SEQ ID NO: 144) |
| 8-D4 | VH | EVQLVQSGAEVKKPGESLKISCKGSGYSFTSYWIGWVRQMPGKGLEWMGITYPGDSDTRYSPSFQGQVTISA DKSISTAYLOWSSLKASDTAMYYCARNPSLYSSPTDYWGQGTLVTVSS (SEQ ID NO: 145) |
| | VL | QSVLTQPPSASGTPGQRVTISCSGSSSNIGSNTVNWYQQLPGTAPKLLIYNNNQRPSGVPDRFSGSKSGTSA SLAITGLQSEDEADYYCAAWDDSLNGVVFGGGTKVTVL (SEQ ID NO: 146) |
| 24-B8 | VH | QVQLVQSGAEVKKPGSSVKVSCKASGGTFSNYAISWVRQAPGQGLEWMGGIIPILDTTNYAQKFQGRVTITA DESTSTAYMELNSLRSEDTAVYYCVREEGFDYWGQGTLVTVSS (SEQ ID NO: 149) |
| | VL | QSVLTQPSSLSASPGASASLTCTLRSGINVGAYNIYWYQQKPGSPPQFVLRYNSDSDNQQGSGVPSRFSGSK DASANAGILLISGLQSEDEAEYYCMIWRSSAWVFGGGTKLTVL (SEQ ID NO: 150) |
| 21-F1 | VH | QVQLVESGGGVVQPGRSLRLSCGASGFTFDTYGMHWVRQAPGRGPEWVAVISNDGSKKYYADSVKGRFTISR DNSKNTVYLQMNSLRAEDTGVYYCGRVTEPYMVTPLMLFRMAIDNWGQGTLVTVSS (SEQ ID NO: 151) |
| | VL | SYVLTQPPSMSVAPGETARITCGGGNFGTKSVHWYQQRSGRAPVLVVYANDDRPSGIPERFSGSKSGDTATL TISRVEAGDEADYFCQVWDSSADLRGVVFGGGTQLTVL (SEQ ID NO: 152) |
| 16-C6 | VH | QVQLQESGGGLVQAGGSLRLSCAASGRTFSSYAMGWFRQVLGKERELVAAISRSGGSTYYADSVKGRFTVSR DNVKNTVYLQMNSLKPEDTAGYYCAASNEGGTWYGSSWYRPSSYEHWGQGTQVTVSS (SEQ ID NO: 153) |

TABLE 7-continued

| Clone | | Heavy Chain variable (VH) and Light Chain variable (LH) sequences |
|---|---|---|
| 16-G6 | VH | QVQLQQSGGGLVQAGGSLRLSCAASGRTFSSYAMGWFRQVLGKERELVAAISRSGGSTYYADSVKGRFTISR<br>DNVKNTVYLQMNSLKPEDTAGYYCAASNEGGTWYGSSWYRPSSYEYWGQGTQVTVSS<br>(SEQ ID NO: 154) |
| 13-A1 | VH | EVOLVQSGAEVKKPGESLKISCKGSGYSFTSYWIGWVRQMPGKGLEWMGIIYPGDSDTRYSPSFQGQVTISA<br>DKSISTAYLOWSSLKASDTAMYYCARYLSSEGMDVWGKGTTVTVSS (SEQ ID NO: 159) |
|  | VL | QSVLTQPPSASGTPGQRVTISCSGRSSNIGSNPVNWYQQLPGTAPKLLIYNNIQRPSGVPDRFSGSKSGTSA<br>SLAISGLQSEDEAVYYCASWDDSLNEGVFGGGTQLIVL (SEQ ID NO: 160) |
| 22-E8 | VH | QVQLVQSGAEVKKPGSSVKVSCKASGGTFSSYAISWVRQAPGQGLEWMGGIIPIFGTTNYAQKFQGRVTITA<br>DESTSTAYMELSSLRSEDTAVYYCARDHGYYYGMDVWGQGTTVTVSS (SEQ ID NO: 161) |
|  | VL | QSVLTQPSSVSAAPRQRVTLSCSGGDSNIGQNGVNWYLHVPGKAPRLVVYYDYLVSAGMSARFSGSRSGTSA<br>SLAISGLQSEDEGVYYCASWDDSLSAWVFGGGTKLTVL (SEQ ID NO: 162) |
| 5-B6 | VH | QVQLVQSGAEVKKPGSSVKVSCKASGGTFSSYAISWVRQAPGQGLEWVGGIIPMFNSASYAQKFQGKVTITA<br>DKATNTAYMELSSLRSEDTAVYYCARESSGYYYVSNWFDPWGQGTLVTVSS (SEQ ID NO: 163) |
|  | VL | QSVLTQPSSVSGAPGQRVTISCTGSSSNIGAGYDVHWYQQIPGTAPRLLIYANSGRASGVPDRFSGSKSGTS<br>ASLAITGLQAEDEADYYCQSYDSSLSGVVFGGGTKLTVL (SEQ ID NO: 164) |
| 13-H3 | VH | EVOLVQSGAEVKKPGESLKISCKGSGYSFTSYWIGWVRQMPGKGLEWMGIIYPGDSDTRYSPSFQGQVTISA<br>DKSISTAYLOWSSLKASDTAMYYCARGSHYGDYDYWGQGTLVTVSS (SEQ ID NO: 165) |
|  | VL | QSVLTQPPSVSAAPGQKVTISCSGSSSNIGNNYVSWYQQLPGTAPKLLIYDNNKRPSGIPDRFSGSKSGTSA<br>TLGITGLQTGDEADYYCGTWDSSLSAGVFGGGTKLTVL (SEQ ID NO: 166) |
| 27-B4 | VH | QVQLQQSGPGLVKPSQTLSLTCAISGDSVSSNSAAWNWIRQSPSRGLEWLGRTYYRSKWYNDYAVSVKNRIT<br>INPDTSKNQFSLQLNSVTPEDTAVYYCARTIGWYDSWGQGTLVTVSS (SEQ ID NO: 167) |
|  | VL | SYELMQPPSVSVSPGQTARITCSGDALPKQFANWYQQKPGQAPVLLVYRDSERPSGIPERFSGSTSGTTVTL<br>TISGVQAEDEADYYCQSADSSATYEVFGGGTKVTVL (SEQ ID NO: 168) |
| 8-H1 | VH | EVOLVQSGAEVKKPGESLKISCKGSGYSFTSYWIGWVRQMPGKGLEWMGTIYPGDSDTRYSPSFQGQVTISA<br>DKSISTAYLOWSSLKASDTAIYYCARROSGSGYDYWGQGTLVTVSS (SEQ ID NO: 169) |
|  | VL | QSVLTQPPSASGTPGQRVTISCSGSSSNVGSNSVSWYQQFPGTAPKLLIYTNNQRPSGVPDRFSGSKSGASA<br>SLAISGPQSEDEADYYCAAWDDSLNGWVFGGGTKLTVL (SEQ ID NO: 170) |
| 8-H5 | VH | EVOLVQSGAEVKKPGESLKISCKGSGYSFTSYWIGWVRQMPGKGLEWMGITYPGDSDTRYSPSFQGQVTISA<br>DKSISTAYLOWSSLKASDTAMYYCARWSEGNGFDYWGQGTMVTVSS (SEQ ID NO: 171) |
|  | VL | QSVLTQPPSTSGTPGQWVTISCSGSSSNIGSNSVSWYQQLPGMAPKLLIYRNDQRPSGVPDRFSASKSGTSA<br>SLAISGLQSEDEADYYCAAWDDSLNGVVFGGGTKLTVL (SEQ ID NO: 172) |
| 8-A2 | VH | QVQLVQSGAEVKKPGASVKVSCKASGYTFTGYYLHWVRQAPGQGLEWMGRINPNSGGTNYAQKFQGRVTMTR<br>DTSISTAYMELSRLTSDDTAVYYCLAVAGTGGDAFDIWGQGTTVTVSS (SEQ ID NO: 173) |
|  | VL | DIQMTQSPSTLSASVGDRVTITCRASQSISSWLAWYQQKPGKAPKLLIYAASSLESGVPSRFSGSGSGTDFT<br>LTISSLQPEDFATYYCQQGHSFPLTFGGGTKVDIK (SEQ ID NO: 174) |
| 23-A11 | VH | QVQLVESGGGVVQPGRSLRLSCAASGFTFSSYGMHWVRQAPGKGLEWVAVISYDGSNKYYADSVKGRFTISR<br>DNSKNTLYLQMNSLRAEDTAVYYCAKEGELRGAFDIWGQGTMVTVSS (SEQ ID NO: 175) |
|  | VL | SYVLTQPPSVSAPGKTARITCGGDNIESKYVHWYQQKPGQAPVLVIYYDTDRPSGIPERFSGANSGNSATL<br>TISRVEAGDEADYYCQVWDRTSGHFVFGPGTKVTVL (SEQ ID NO: 176) |
| 30-C5 | VH | QVQLVESGGGVVQPGRSLRLSCAASGFTFSNYGMHWVRQAPGKGLEWVAVISYDGSIEYYADSVKGRFTISR<br>DNSSNTLYLQMNSLRAEDTAVYYCARDEDGAFDIWGQGTTVTVSS (SEQ ID NO: 179) |
|  | VL | DIVMTQSPESLAVSLGERATINCKSSESVSYSSSNKNYLSWYQQIPGQPPKLLIYWASTRESGVPDRFSGSG<br>SGTDFTLTISSLQAEDVAVYYCQQYYSSPLTFGGGTKVEIK (SEQ ID NO: 180) |
| 22-B10 | VH | QVQLVESGGDVVQPGTSLRLSCAASGFTFSDYPLHWVRQAPGKGLEWLAVISYDGWTKYYADSVKGRFTISR<br>DNSKNTLSLQMDSLRPEDTAVYYCVRGTDYGDSWGQGTLVTVSS (SEQ ID NO: 181) |
|  | VL | QSVVTQPPSVSAAPGQKVTISCSGSSSNIGNNYVSWYQQFPGTAPKFLIYENNKRPSGIPDRFSGSKSGTSA<br>TLGITGLQTGDEADYYCGTWDNSLSAWVFGGGTKVTVL (SEQ ID NO: 182) |
| 6-A4 | VH | QVQLVESGGGVVQPARSLRLSCAASGFTLSDYPMHWVRQAPGKGLEWVALMSYDGSLKFYADSVKGRSTISR<br>DISENTMYLQMNSLRAEDTAVYYCARGNSDGDFDYWGRGTLVTVSS (SEQ ID NO: 185) |
|  | VL | SYVLTQPPSVSVAPGQTATITCGGRDIGSRSVHWYQQTPGQAPVLVVYDDTARPSEIRARFSGFNSGNTATL<br>TISRVEAGDEATYYCQAWDSSTVVFGGGTKLTVL (SEQ ID NO: 186) |

TABLE 7-continued

| Clone | | Heavy Chain variable (VH) and Light Chain variable (LH) sequences |
|---|---|---|
| 6-E1 | VH | QVQLVESGGGVVQPGTSLRLSCAASGFSFNTFPMHWVRQTPGKGLEWVASISYDGSFKFYADSVKGRFTISR<br>DNSKNTLILQLNSLRAEDTAVYYCASPGDSDWADFENWGQGTTVTVSS (SEQ ID NO: 187) |
| | VL | QSVLTQPPSVSGAPGQRVTISCTGSSSNIGAGYDVHWYQQLPGTAPKLLIYGNSNRPSGVPDRFSGSKSGTS<br>ASLAITGLQAEDEADYYCQSYDSSLSGYVFGTGTKVTVL (SEQ ID NO: 188) |
| 6-F2 | VH | QVQLVESGGGVVQPGRSLRLSCEASGFNFSLYGMHWVRQAPGKGLEWMAVISYDGSQKYYADSVKGRFTISR<br>DNSKNTMYLQMNSLRAEDTAVYYCVKGEGSLDYWGQGTLVTVSS (SEQ ID NO: 189) |
| | VL | QSALTQPASASGSPGQSVTISCTGTTSDVGGYGYVSWYQHHPGKAPQLLIYEVAKRPSGVPDRFSGSKSGNT<br>ASLTISGLQAEDEADYYCVSYTLSSLVVFGGGTKLTVL (SEQ ID NO: 190) |
| 15-E4 | VH | QVQLQESGGGLVQSGGSLKLSCAASGSIPSVNVMGWYRQAPGKQRELVAAVTSDGRTNYADSVKGRFTVSRD<br>NAKNTVALQMDSLKPEDTAVYYCLITNQDHNTLGVGKGTLVTVSS (SEQ ID NO: 196) |
| 15-C8 | VH | QVQLQESGGGLVQSGGSRRLSCAVSGNVTSITLMGWYRHAPGKQREAVGIINDDDRTRYEDSMKGRFTISRD<br>PAKNMLYLQMTNLKPEDTAVYYCSAKAGGNFYMGQGTQVTVSS (SEQ ID NO: 193) |
| 15-F7 | VH | QVQLQESGGGLVQSGGSLKLSCAASGSIPSVNVMGWYRQAPGKQRELVAAVTSDGRTNYADSVKGRFTVSRD<br>NAKNTVALQMDSLKPEDTAVYYCLITNSDHNTLGVGKGTLVTVSS (SEQ ID NO: 194) |
| 15-H3 | VH | QVQLQQSGGGLVQSGGSLKLSCAASGSIPSVNVMGWYRQAPGKQRELVAAVTSDGRTSYADSVKGRFTVSRD<br>NAKNTVALQMDSLKPEDTAVYYCLITNSDHNTLGVGKGTLVTVSS (SEQ ID NO: 195). |

3. The antibody or antigen-binding fragment according to item 1 or 2, comprising a light chain variable region (VL) depicted in Table 7.

4. The antibody or antigen-binding fragment thereof according to any one of items 1 to 3, comprising one of the following VH/VL pairs: a VH comprising the amino acid sequence of SEQ ID No:131 and a VL comprising the amino acid sequence of SEQ ID No: 132; a VH comprising the amino acid sequence of SEQ ID No:133 and a VL comprising the amino acid sequence of SEQ ID No: 134; a VH comprising the amino acid sequence of SEQ ID No:135 and a VL comprising the amino acid sequence of SEQ ID No: 136; a VH comprising the amino acid sequence of SEQ ID No:137 and a VL comprising the amino acid sequence of SEQ ID No: 138; a VH comprising the amino acid sequence of SEQ ID No:139 and a VL comprising the amino acid sequence of SEQ ID No: 140; a VH comprising the amino acid sequence of SEQ ID No:141 and a VL comprising the amino acid sequence of SEQ ID No: 142; a VH comprising the amino acid sequence of SEQ ID No:143 and a VL comprising the amino acid sequence of SEQ ID No: 144; a VH comprising the amino acid sequence of SEQ ID No:145 and a VL comprising the amino acid sequence of SEQ ID No: 146; a VH comprising the amino acid sequence of SEQ ID No:147 and a VL comprising the amino acid sequence of SEQ ID No: 148; a VH comprising the amino acid sequence of SEQ ID No:149 and a VL comprising the amino acid sequence of SEQ ID No: 150; a VH comprising the amino acid sequence of SEQ ID No:151 and a VL comprising the amino acid sequence of SEQ ID No: 152; a VH comprising the amino acid sequence of SEQ ID No:153 and a VL comprising the amino acid sequence of SEQ ID No: 154; a VH comprising the amino acid sequence of SEQ ID No:155 or 214 and a VL comprising the amino acid sequence of SEQ ID No: 156; a VH comprising the amino acid sequence of SEQ ID No:157 or 215 and a VL comprising the amino acid sequence of SEQ ID No: 158; a VH comprising the amino acid sequence of SEQ ID No:159 and a VL comprising the amino acid sequence of SEQ ID No: 160; a VH comprising the amino acid sequence of SEQ ID No:161 and a VL comprising the amino acid sequence of SEQ ID No: 162; a VH comprising the amino acid sequence of SEQ ID No:163 and a VL comprising the amino acid sequence of SEQ ID No: 164; a VH comprising the amino acid sequence of SEQ ID No:165 and a VL comprising the amino acid sequence of SEQ ID No: 166; a VH comprising the amino acid sequence of SEQ ID No:167 and a VL comprising the amino acid sequence of SEQ ID No: 168; a VH comprising the amino acid sequence of SEQ ID No:169 and a VL comprising the amino acid sequence of SEQ ID No: 170; a VH comprising the amino acid sequence of SEQ ID No:171 and a VL comprising the amino acid sequence of SEQ ID No: 172; a VH comprising the amino acid sequence of SEQ ID No:173 and a VL comprising the amino acid sequence of SEQ ID No: 174; a VH comprising the amino acid sequence of SEQ ID No:175 and a VL comprising the amino acid sequence of SEQ ID No: 176; a VH comprising the amino acid sequence of SEQ ID No:177 and a VL comprising the amino acid sequence of SEQ ID No: 178; a VH comprising the amino acid sequence of SEQ ID No:179 and a VL comprising the amino acid sequence of SEQ ID No: 180; a VH comprising the amino acid sequence of SEQ ID No:181 and a VL comprising the amino acid sequence of SEQ ID No: 182; a VH comprising the amino acid sequence of SEQ ID No:183 and a VL comprising the amino acid sequence of SEQ ID No: 184; a VH comprising the amino acid sequence of SEQ ID No:185 and a VL comprising the amino acid sequence of SEQ ID No: 186; a VH comprising the amino acid sequence of SEQ ID No:187 and a VL comprising the amino acid sequence of SEQ ID No: 188; a VH comprising the amino acid sequence of SEQ ID No:189 and a VL comprising the amino acid sequence of SEQ ID No: 190; or a VH comprising the amino acid sequence of SEQ ID No:191 and a VL comprising the amino acid sequence of SEQ ID No: 192.

5. The antibody or antigen-binding fragment thereof according to item 4, comprising one of the following VH/VL pairs: a VH comprising the amino acid sequence of SEQ ID No:147 and a VL comprising the amino acid sequence of SEQ ID No: 148; a VH comprising the amino acid sequence of SEQ ID No:191 and a VL comprising the amino acid sequence of SEQ ID No: 192; a VH comprising the amino acid sequence of SEQ ID No:157 or 215 and a VL comprising the amino acid sequence of SEQ ID No: 158; a VH comprising the amino acid sequence of SEQ ID No:183 and a VL comprising the amino acid sequence of SEQ ID No: 184; a VH comprising the amino acid sequence of SEQ ID No:155 or 214 and a VL comprising the amino acid sequence of SEQ ID No: 156; or a VH comprising the amino acid sequence of SEQ ID No:177 and a VL comprising the amino acid sequence of SEQ ID No: 178.

6. The antibody or antigen-binding fragment thereof according to item 5, comprising a VH comprising the amino acid sequence of SEQ ID No:147 and a VL comprising the amino acid sequence of SEQ ID No: 148.

7. The antibody or antigen-binding fragment thereof according to item 5, comprising a VH comprising the amino acid sequence of SEQ ID No:191 and a VL comprising the amino acid sequence of SEQ ID No: 192.

8. The antibody or antigen-binding fragment thereof according to item 5, comprising a VH comprising the amino acid sequence of SEQ ID No:157 or 215 and a VL comprising the amino acid sequence of SEQ ID No: 158.

9. The antibody or antigen-binding fragment thereof according to item 5, comprising a VH comprising the amino acid sequence of SEQ ID No:183 and a VL comprising the amino acid sequence of SEQ ID No: 184.

10. The antibody or antigen-binding fragment thereof according to item 5, comprising a VH comprising the amino acid sequence of SEQ ID No:155 or 214 and a VL comprising the amino acid sequence of SEQ ID No: 156.

11. The antibody or antigen-binding fragment thereof according to item 5, comprising a VH comprising the amino acid sequence of SEQ ID No:177 and a VL comprising the amino acid sequence of SEQ ID No: 178.

12. The antibody or antigen-binding fragment thereof according to any one of items 1 to 11, wherein the antibody or antigen-binding fragment thereof blocks the binding of SARS-CoV-2 to angiotensin converting enzyme 2 (ACE2) on a host cell and/or mediates Fc-mediated clearance of SARS-CoV-2.

13. The antibody or antigen-binding fragment thereof according to any one of items 1 to 12, wherein the antibody or antigen-binding fragment thereof induces complement-dependent cytotoxicity (CDC), antibody-dependent cellular cytotoxicity (ADCC) and/or antibody-dependent cellular phagocytosis (ADCP) against SARS-CoV-2-infected cells.

14. The antibody or antigen-binding fragment thereof according to item 12 or 13, wherein the cell is a human cell.

15. The antibody or antigen-binding fragment thereof according to any one of items 1 to 14, which is a polyclonal, monoclonal, chimeric, humanized or fully human antibody.

16. The antibody or antigen-binding fragment thereof according to item 15, which is a fully human antibody.

17. The antibody or antigen-binding fragment thereof according to any one of items 1 to 16, which is an Fab, F(ab)$_2$ or scFv fragment.

18. The antibody or antigen-binding fragment thereof according to any one of items 1 to 17, which is a bispecific antibody.

19. An antibody combination comprising at least two of the antibodies or antigen-binding fragments thereof according to any one of items 1 to 18.

20. The antibody combination of item 19, which comprises:
   (i) an antibody or antigen fragment thereof comprising the following combination of CDRs:

| HCDR1 | HCDR2 | HCDR3 | LCDR1 | LCDR2 | LCDR3 |
|---|---|---|---|---|---|
| GYTFSTYY (SEQ ID NO: 36) | IDPSGGTT (SEQ ID NO: 16) | ARGGFADAVDY (SEQ ID NO: 17) | SGSIAGNY (SEQ ID NO: 37) | EDN | QSYDASHLHVI (SEQ ID NO: 38) |

(ii) at least one additional antibody or antigen fragment thereof comprising one of the following combinations of CDRs:

| | HCDR1 | HCDR2 | HCDR3 | LCDR1 | LCDR2 | LCDR3 |
|---|---|---|---|---|---|---|
| (a) | GFSLNTRGMS (SEQ ID NO: 125) | IDWEDDK (SEQ ID NO: 126) | ARTYSVGVKYFGMDV (SEQ ID NO: 127) | SLRNYY (SEQ ID NO: 198) | GGN | NSRDSSGNHVV (SEQ ID NO: 199) |
| (b) | GYTFTGYY (SEQ ID NO: 11) | INPNSGGT (SEQ ID NO: 12) | LAVAGTGGDAFDI (SEQ ID NO: 84) | QSISSW (SEQ ID NO: 85) | AAS | QQGHSFPLT (SEQ ID NO: 86) |
| (c) | GFTFSSYG (SEQ ID NO: 25) | ISYDGSNK (SEQ ID NO: 26) | AKEGELRGAFDI (SEQ ID NO: 27) | NIESKY (SEQ ID NO: 87) | YDT | QVWDRTSGHFV (SEQ ID NO: 88) |
| (d) | GFTFSNYG (SEQ ID NO: 94) | ISYDGSIE (SEQ ID NO: 95) | ARDEDGAFDI (SEQ ID ID NO: 96) | ESVSYSSSNKWASNY (SEQ ID NO: 97) | | QQYYSSPLT (SEQ ID NO: 98) |
| (e) | GGTFNTYS (SEQ ID NO: 57) | IIPIFDKP (SEQ ID NO: 58) | ARGTGYYYGMDV (SEQ ID NO: 59) | RSNIGNYP (SEQ ID NO: 60) | YDD | ATWDDSLNVWV (SEQ ID NO: 61) |
| (f) | GYIFTNYD (SEQ ID NO: 54) | VNPNSGKV (SEQ ID NO: 55) | ARGHTDF (SEQ ID NO: 56) | SSNIGNNA (SEQ ID NO: 14) | YDD | AAWDDSLNGVV (SEQ ID NO: 5) |

| HCDR1 | HCDR2 | HCDR3 | LCDR1 | LCDR2 | LCDR3 |
|---|---|---|---|---|---|
| (g) GFTFNNYP (SEQ ID NO: 103) | ISYDGNHK (SEQ ID NO: 104) | ASDLSGAEDS (SEQ ID NO: 105) | SSDVGGYNY (SEQ ID NO: 106) | EVS | SSYTSSSTWV (SEQ ID NO: 107). |

21. The antibody combination of item 20, which comprises at least two of the additional antibodies or antigen fragment thereof defined in item (ii).
22. The antibody combination of item 20, which comprises at least three of the additional antibodies or antigen fragment thereof defined in item (ii).
23. The antibody combination of item 20, which comprises at least four of the additional antibodies or antigen fragment thereof defined in item (ii).
24. The antibody combination of item 19, which comprises:
 (i) an antibody or antigen fragment thereof comprising the following combination of CDRs:

| HCDR1 | HCDR2 | HCDR3 | LCDR1 | LCDR2 | LCDR3 |
|---|---|---|---|---|---|
| GGTFNTYS (SEQ ID NO: 57) | IIPIFDKP (SEQ ID NO: 58) | ARGTGYYYGMDV (SEQ ID NO: 59) | RSNIGNYP (SEQ ID NO: 60) | YDD | ATWDDSLNVWV (SEQ ID NO: 61) |

(ii) at least one additional antibody or antigen fragment thereof comprising one of the following combinations of CDRs:

| | HCDR1 | HCDR2 | HCDR3 | LCDR1 | LCDR2 | LCDR3 |
|---|---|---|---|---|---|---|
| (a) | GFSLNTRGMS (SEQ ID NO: 125) | IDWEDDK (SEQ ID NO: 126) | ARTYSVGVKYFGMDV (SEQ ID NO: 127) | SLRNYY (SEQ ID NO: 198) | GGN | NSRDSSGNHVV (SEQ ID NO: 199) |
| (b) | GYTFTGYY (SEQ ID NO: 11) | INPNSGGT (SEQ ID NO: 12) | LAVAGTGGDAFDI (SEQ ID NO: 84) | QSISSW (SEQ ID NO: 85) | AAS | QQGHSFPLT (SEQ ID NO: 86) |
| (c) | GFTFSSYG (SEQ ID NO: 25) | ISYDGSNK (SEQ ID NO: 26) | AKEGELRGAFDI (SEQ ID NO: 27) | NIESKY (SEQ ID NO: 87) | YDT | QVWDRTSGHFV (SEQ ID NO: 88) |
| (d) | GFTFSNYG (SEQ ID NO: 94) | ISYDGSIE (SEQ ID NO: 95) | ARDEDGAFDI (SEQ ID NO: 96) | ESVSYSSSNKNY (SEQ ID NO: 97) | WAS | QQYYSSPLT (SEQ ID NO: 98) |
| (e) | GFTFNNYP (SEQ ID NO: 103) | ISYDGNHK (SEQ ID NO: 104) | ASDLSGAEDS (SEQ ID NO: 105) | SSDVGGYNY (SEQ ID NO: 106) | EVS | SSYTSSSTWV (SEQ ID NO: 107). |

25. The antibody combination of item 24, which comprises at least two of the additional antibodies or antigen fragment thereof defined in item (ii).
26. The antibody combination of item 19, which comprises:
 (i) an antibody or antigen fragment thereof comprising the following combination of CDRs:

| HCDR1 | HCDR2 | HCDR3 | LCDR1 | LCDR2 | LCDR3 |
|---|---|---|---|---|---|
| GYIFTNYD (SEQ ID NO: 54) | VNPNSGKV (SEQ ID NO: 55) | ARGHTDF (SEQ ID NO: 56) | SSNIGNNA (SEQ ID NO: 14) | YDD | AAWDDSLNGVV (SEQ ID NO: 5) |

(ii) at least one additional antibody or antigen fragment thereof comprising one of the following combinations of CDRs:

| | HCDR1 | HCDR2 | HCDR3 | LCDR1 | LCDR2 | LCDR3 |
|---|---|---|---|---|---|---|
| (a) | GFSLNTRGMS (SEQ ID NO: 125) | IDWEDDK (SEQ ID NO: 126) | ARTYSVGVKYFGMDV (SEQ ID NO: 127) | SLRNYY (SEQ ID NO: 198) | GGN | NSRDSSGNHVV (SEQ ID NO: 199) |

-continued

|     | HCDR1 | HCDR2 | HCDR3 | LCDR1 | LCDR2 | LCDR3 |
|-----|-------|-------|-------|-------|-------|-------|
| (b) | GYTFTGYY (SEQ ID NO: 11) | INPNSGGT (SEQ ID NO: 12) | LAVAGTGGDAFDI (SEQ ID NO: 84) | QSISSW (SEQ ID NO: 85) | AAS | QQGHSFPLT (SEQ ID NO: 86) |
| (c) | GFTFSSYG (SEQ ID NO: 25) | ISYDGSNK (SEQ ID NO: 26) | AKEGELRGAFDI (SEQ ID NO: 27) | NIESKY (SEQ ID NO: 87) | YDT | QVWDRTSGHFV (SEQ ID NO: 88) |
| (d) | GFTFSNYG (SEQ ID NO: 94) | ISYDGSIE (SEQ ID NO: 95) | ARDEDGAFDI (SEQ ID NO: 96) | ESVSYSSSNKNY (SEQ ID NO: 97) | WAS | QQYYSSPLT (SEQ ID NO: 98) |
| (e) | GFTFNNYP (SEQ ID NO: 103) | ISYDGNHK (SEQ ID NO: 104) | ASDLSGAEDS (SEQ ID NO: 105) | SSDVGGYNY (SEQ ID NO: 106) | EVS | SSYTSSSTWV (SEQ ID NO: 107) |

27. The antibody combination of item 19, which comprises:
(i) a first antibody or antigen fragment thereof comprising the following combination of CDRs:

| HCDR1 | HCDR2 | HCDR3 | LCDR1 | LCDR2 | LCDR3 |
|-------|-------|-------|-------|-------|-------|
| GYTFSTYY (SEQ ID NO: 36) | IDPSGGTT (SEQ ID NO: 16) | ARGGFADAVDY (SEQ ID NO: 17) | SGSIAGNY (SEQ ID NO: 37) | EDN | QSYDASHLHVI (SEQ ID NO: 38) |

(ii) a second antibody or antigen fragment thereof comprising the following combinations of CDRs:

| HCDR1 | HCDR2 | HCDR3 | LCDR1 | LCDR2 | LCDR3 |
|-------|-------|-------|-------|-------|-------|
| GFSLNTRGMS (SEQ ID NO: 125) | IDWEDDK (SEQ ID NO: 126) | ARTYSVGVKYFGMDV (SEQ ID NO: 127) | SLRNYY (SEQ ID NO: 198) | GGN | NSRDSSGNHVV (SEQ ID NO: 199) |

(iii) a third antibody or antigen fragment thereof comprising one of the following combinations of CDRs:

|     | HCDR1 | HCDR2 | HCDR3 | LCDR1 | LCDR2 | LCDR3 |
|-----|-------|-------|-------|-------|-------|-------|
| (a) | GYIFTNYD (SEQ ID NO: 54) | VNPNSGKV (SEQ ID NO: 55) | ARGHTDF (SEQ ID NO: 56) | SSNIGNNA (SEQ ID NO: 14) | YDD | AAWDDSLNGVV (SEQ ID NO: 5) |
| (b) | GGTFNTYS (SEQ ID NO: 57) | IIPIFDKP (SEQ ID NO: 58) | ARGTGYYYGMDV (SEQ ID NO: 59) | RSNIGNYP (SEQ ID NO: 60) | YDD | ATWDDSLNVWV (SEQ ID NO: 61) | and
(iv) a fourth antibody or antigen fragment thereof comprising one of the following combinations of CDRs:

|     | HCDR1 | HCDR2 | HCDR3 | LCDR1 | LCDR2 | LCDR3 |
|-----|-------|-------|-------|-------|-------|-------|
| (c) | GFTFNNYP (SEQ ID NO: 103) | ISYDGNHK (SEQ ID NO: 104) | ASDLSGAEDS (SEQ ID NO: 105) | SSDVGGYNY (SEQ ID NO: 106) | EVS | SSYTSSSTWV (SEQ ID NO: 107) |
| (d) | GFSFTNYG (SEQ ID NO: 89) | ISYDGSIK (SEQ ID NO: 90) | TRERGTGIDY (SEQ ID NO: 91) | KSDIGAYNY (SEQ ID NO: 92) | DVS | SSYTTSGTVV (SEQ ID NO: 93) |

28. The antibody combination of item 27, wherein:
  (i) the first antibody or antigen fragment thereof comprises a VH comprising the sequence of SEQ ID NO:147 and a VL comprising the sequence of SEQ ID NO:148;
  (ii) the second antibody or antigen fragment thereof comprises a VH comprising the sequence of SEQ ID NO:191 and a VL comprising the sequence of SEQ ID NO:192;
  (iii) the third antibody or antigen fragment thereof comprises a VH comprising the sequence of SEQ ID NO:155 or 214 and a VL comprising the sequence of SEQ ID NO:156, or a VH comprising the sequence of SEQ ID NO:157 or 215 and a VL comprising the sequence of SEQ ID NO:158; and
  (iv) the fourth antibody or antigen fragment thereof comprises a VH comprising the sequence of SEQ ID NO:183 and a VL comprising the sequence of SEQ ID NO:184, or a VH comprising the sequence of SEQ ID NO:177 and a VL comprising the sequence of SEQ ID NO:178.

29. The antibody combination of item 19, which comprises:
  (i) a first antibody or antigen fragment thereof comprising the following combination of CDRs:

| HCDR1 | HCDR2 | HCDR3 | LCDR1 | LCDR2 | LCDR3 |
|---|---|---|---|---|---|
| GYTFSTYY (SEQ ID NO: 36) | IDPSGGTT (SEQ ID NO: 16) | ARGGFADAVDY (SEQ ID NO: 17) | SGSIAGNY (SEQ ID NO: 37) | EDN | QSYDASHLHVI (SEQ ID NO: 38) |

(ii) a second antibody or antigen fragment thereof comprising the following combinations of CDRs:

| HCDR1 | HCDR2 | HCDR3 | LCDR1 | LCDR2 | LCDR3 |
|---|---|---|---|---|---|
| GFSLNTRGMS (SEQ ID NO: 125) | IDWEDDK (SEQ ID NO: 126) | ARTYSVGVKYFGMDV (SEQ ID NO: 127) | SLRNYY (SEQ ID NO: 198) | GGN | NSRDSSGNHVV (SEQ ID NO: 199) |

(iii) a third antibody or antigen fragment thereof comprising the following combinations of CDRs:

| HCDR1 | HCDR2 | HCDR3 | LCDR1 | LCDR2 | LCDR3 |
|---|---|---|---|---|---|
| GYIFTNYD (SEQ ID NO: 54) | VNPNSGKV (SEQ ID NO: 55) | ARGHTDF (SEQ ID NO: 56) | SSNIGNNA (SEQ ID NO: 14) | YDD | AAWDDSLNGVV (SEQ ID NO: 5) | and
  (iv) a fourth antibody or antigen fragment thereof comprising the following combinations of CDRs:

| HCDR1 | HCDR2 | HCDR3 | LCDR1 | LCDR2 | LCDR3 |
|---|---|---|---|---|---|
| GGTFNTYS (SEQ ID NO: 57) | IIPIFDKP (SEQ ID NO: 58) | ARGTGYYYGMDV (SEQ ID NO: 59) | RSNIGNYP (SEQ ID NO: 60) | YDD | ATWDDSLNVWV (SEQ ID NO: 61) | and
  (v) a fifth antibody or antigen fragment thereof comprising comprising one of the following combinations of CDRs:

|  | HCDR1 | HCDR2 | HCDR3 | LCDR1 | LCDR2 | LCDR3 |
|---|---|---|---|---|---|---|
| (c) | GFTFNNYP (SEQ ID NO: 103) | ISYDGNHK (SEQ ID NO: 104) | ASDLSGAEDS (SEQ ID NO: 105) | SSDVGGYNY (SEQ ID NO: 106) | EVS | SSYTSSSTWV (SEQ ID NO: 107) |
| (d) | GFSFTNYG (SEQ ID NO: 89) | ISYDGSIK (SEQ ID NO: 90) | TRERGTGIDY (SEQ ID NO: 91) | KSDIGAYNY (SEQ ID NO: 92) | DVS | SSYTTSGTVV (SEQ ID NO: 93) |

30. The antibody combination of any one of items 27 to 29, wherein the first antibody, second antibody, third antibody, fourth antibody and, if present, fifth antibody, or antigen-binding fragments thereof, are fully human antibodies.

31. A nucleic acid comprising a sequence encoding the light and heavy chains of the antibody or antigen binding fragment thereof of any one of items 1 to 18; or a first nucleic acid comprising a sequence encoding the light chain of the antibody or antigen binding fragment thereof of any one of items 1 to 18 and a second nucleic acid comprising a sequence encoding the heavy chain of the antibody or antigen binding fragment thereof of any one of items 1 to 18.

32. Nucleic acids comprising sequences encoding the light and heavy chains of the antibodies or antigen-binding fragments thereof of the antibody combination of any one of items 19 to 30.

33. The nucleic acid or nucleic acids of item 31 or 32, which is/are in the form of mRNA.

34. The nucleic acid or nucleic acids of any one of items 31 to 33, which is/are encapsulated into lipid vesicles.

35. A pharmaceutical composition comprising (a) at least one antibody or antigen-binding fragment thereof according to any one of items 1 to 18, (b) the antibody combination of any one of items 19 to 30, or (c) the nucleic acid or nucleic acids of any one of items 31 to 34, and a pharmaceutically acceptable carrier.

36. The pharmaceutical composition of item 35, wherein the pharmaceutical composition is in the form of an injectable solution.

37. A method for blocking the entry of a betacoronavirus in an ACE2-expressing cell and/or for inducing complement-dependent cytotoxicity (CDC), antibody-dependent cellular cytotoxicity (ADCC) and/or antibody-dependent cellular phagocytosis (ADCP) against betacoronavirus-infected cells, the method comprising contacting the cell and/or the virus with an effective amount of the antibody or antigen fragment thereof according to any one of items 1 to 18, the antibody combination of any one of items 19 to 30, the nucleic acid or nucleic acids of any one of items 31 to 34, or the pharmaceutical composition according to item 35 or 36.

38. A method for preventing or treating a betacoronavirus infection or a related disease in a subject in need thereof, the method comprising administering to the subject an effective amount of the antibody or antigen fragment thereof according to any one of items 1 to 18, the antibody combination of any one of items 19 to 30, the nucleic acid or nucleic acids of any one of items 31 to 34, or the pharmaceutical composition according to item 35 or 36.

39. A method for reducing the risk of developing a betacoronavirus-related disease or the severity of a betacoronavirus-related disease in a subject, the method comprising administering to the subject an effective amount of the antibody or antigen fragment thereof according to any one of items 1 to 18, the antibody combination of any one of items 19 to 30, the nucleic acid or nucleic acids of any one of items 31 to 34, or the pharmaceutical composition according to item 35 or 36.

40. The method of any one of items 37 to 39, wherein the betacoronavirus is a sarbecovirus.

41. The method of item 40, wherein the sarbecovirus is SARS-CoV-2.

42. The method of item 41, wherein the SARS-CoV-2 is a variant of the Wuhan original SARS-CoV-2 strain.

43. The method of any one of items 37 to 42, wherein the antibody, antigen-binding fragment thereof, antibody combination, nucleic acid or nucleic acids, or pharmaceutical composition, is administered with (i) at least one additional anti-SARS-CoV-2 antibody or antigen-binding fragment thereof, or nucleic acid(s) encoding said at least one additional anti-SARS-CoV-2 antibody or antigen-binding fragment thereof; and/or (ii) at least one antiviral or anti-inflammatory drug.

44. The method of any one of items 37 to 43, wherein the subject is an immunosuppressed or immunocompromised subject.

45. Use of the antibody or antigen binding fragment thereof of any one of items 1 to 18, the antibody combination of any one of items 19 to 30, the nucleic acid or nucleic acids of any one of items 31 to 34, or the pharmaceutical composition according to item 35 or 36, for preventing or treating a betacoronavirus infection or a related disease in a subject.

46. Use of the antibody or antigen binding fragment thereof of any one of items 1 to 18, the antibody combination of any one of items 19 to 30, the nucleic acid or nucleic acids of any one of items 31 to 34, or the pharmaceutical composition according to item 35 or 36, for the manufacture of a medicament for preventing or treating a betacoronavirus infection or a related disease in a subject.

47. Use of the antibody or antigen binding fragment thereof of any one of items 1 to 18, the antibody combination of any one of items 19 to 30, the nucleic acid or nucleic acids of any one of items 31 to 34, or the pharmaceutical composition according to item 35 or 36, for reducing the risk of developing a betacoronavirus-related disease or the severity of a betacoronavirus-related disease in a subject.

48. Use of the antibody or antigen binding fragment thereof of any one of items 1 to 18, the antibody combination of any one of items 19 to 30, the nucleic acid or nucleic acids of any one of items 31 to 34, or the pharmaceutical composition according to item 35 or 36, for the manufacture of a medicament for reducing the risk of developing a betacoronavirus-related disease or the severity of a betacoronavirus-related disease in a subject.

49. Use of the antibody or antigen binding fragment thereof of any one of 1 to 18, the antibody combination of any one of items 19 to 30, the nucleic acid or nucleic acids of any one of items 31 to 34, or the pharmaceutical composition according to item 35 or 36, for blocking the entry of a betacoronavirus in an ACE2-expressing cell and/or for inducing complement-dependent cytotoxicity (CDC), antibody-dependent cellular cytotoxicity (ADCC) and/or antibody-dependent cellular phagocytosis (ADCP) against betacoronavirus-infected cells.

50. Use of the antibody or antigen binding fragment thereof of any one of items 1 to 18, the antibody combination of any one of items 19 to 30, the nucleic acid or nucleic acids of any one of items 31 to 34, or the pharmaceutical composition according to item 35 or 36, for the manufacture of a medicament for blocking the entry of a betacoronavirus in an ACE2-expressing cell and/or for inducing complement-dependent cytotoxicity (CDC), antibody-dependent cellular cytotoxicity (ADCC) and/or antibody-dependent cellular phagocytosis (ADCP) against betacoronavirus-infected cells.

51. The use of any one of items 45 to 50, wherein the betacoronavirus is a sarbecovirus.

52. The use of item 51, wherein the sarbecovirus is SARS-CoV-2.

53. The use of item 52, wherein the SARS-CoV-2 is a variant of the Wuhan original SARS-CoV-2 strain.

54. The use of any one of items 45 to 53, wherein the antibody, antigen-binding fragment thereof, antibody combination, nucleic acid or nucleic acids, or pharmaceutical composition is for administration with (i) at least one additional anti-SARS-CoV-2 antibody or antigen-binding fragment thereof, or nucleic acid(s) encoding said at least one additional anti-SARS-CoV-2 antibody or antigen-binding fragment thereof; and/or (ii) at least one antiviral or anti-inflammatory drug.

55. The use of any one of items 45 to 54, wherein the subject is an immunosuppressed or immunocompromised subject.

56. The antibody or antigen-binding fragment thereof of any one of 1 to 18, the antibody combination of any one of items 19 to 30, the nucleic acid or nucleic acids of any one of items 31 to 34, or the pharmaceutical composition according to item 35 or 36, for use in preventing or treating a betacoronavirus infection or a related disease in a subject.

57. The antibody or antigen-binding fragment thereof of any one of 1 to 18, the antibody combination of any one of items 19 to 30, the nucleic acid or nucleic acids of any one of items 31 to 34, or the pharmaceutical composition according to item 35 or 36, for use in reducing the risk of developing a betacoronavirus-related disease or the severity of a betacoronavirus-related disease in a subject.

58. The antibody or antigen-binding fragment thereof of any one of 1 to 18, the antibody combination of any one of items 19 to 30, the nucleic acid or nucleic acids of any one of items 31 to 34, or the pharmaceutical composition according to item 35 or 36, for use in blocking the entry of a betacoronavirus in an ACE2-expressing cell and/or for inducing complement-dependent cytotoxicity (CDC), antibody-dependent cellular cytotoxicity (ADCC) and/or antibody-dependent cellular phagocytosis (ADCP) against betacoronavirus-infected cells.

59. The antibody, antigen-binding fragment thereof, antibody combination, nucleic acid or nucleic acids, or pharmaceutical composition for use according to any one of items 56 to 58, wherein the betacoronavirus is a sarbecovirus.

60. The antibody, antigen-binding fragment thereof, antibody combination, nucleic acid or nucleic acids, or pharmaceutical composition for use according to item 59, wherein the sarbecovirus is SARS-CoV-2.

61. The antibody, antigen-binding fragment thereof, antibody combination, nucleic acid or nucleic acids, or pharmaceutical composition for use according to item 60, wherein the SARS-CoV-2 is a variant of the Wuhan original SARS-CoV-2 strain.

62. The antibody, antigen-binding fragment thereof, antibody combination, nucleic acid or nucleic acids, or pharmaceutical composition for use according to any one of items 56 to 61, wherein the antibody, antigen-binding fragment thereof, mixture or cocktail, or pharmaceutical composition is for administration with (i) at least one additional anti-SARS-CoV-2 antibody or antigen-binding fragment thereof, or nucleic acid(s) encoding said at least one additional anti-SARS-CoV-2 antibody or antigen-binding fragment thereof; and/or (ii) at least one antiviral or anti-inflammatory drug.

63. The antibody, antigen-binding fragment thereof, antibody combination, nucleic acid or nucleic acids, or pharmaceutical composition for use according to any one of items 56 to 62, wherein the subject is an immunosuppressed or immunocompromised subject.

Other objects, advantages and features of the present disclosure will become more apparent upon reading of the following non-restrictive description of specific embodiments thereof, given by way of example only with reference to the accompanying drawings.

BRIEF DESCRIPTION OF DRAWINGS

A fuller understanding of the foregoing may be had by reference to the accompanying drawings, wherein:

FIG. 1A: High-level schematic of the workflow.

FIG. 1B: Heat map for a pairwise analysis of 19 library-derived anti-SARS-CoV-2 S1-specific antibodies (Abs) merged with a panel of ten structural benchmarks (9 literature Abs and ACE2). Ab pairs that are blocked (b), partially blocked (pb), or not blocked (nb), are shown. Cells with a designation of "b, pb, or nb" were measured empirically, whereas those without a designation are "inferred". The black boxed cells along the diagonal indicate the "self-blocked" pairs. In the bin-definition, bin-members block one another and show similar blocking behaviors when tested against other Abs in the panel. RBD-specific clones were assigned to five bins (1-5). RBD binders that did not block ACE2 were assigned bin "1", which was split into sub-bins (bin 1a, 1b, and 1c) based on their nuanced blockade towards the structural benchmarks. A cluster of S1 non-RBD binders blocked bin 1 (but not the sub-bins) and did not block any of the literature Abs, so were assigned to bin "C", representing the C-terminal nub of the S1 fragment, between the RBD and the furin cleavage site, distinct from the N-terminal domain (NTD); hence, bin C's specificity is assigned as S1-nonRBD-nonNTD. One RBD-binder Ab (23-H7) blocked bin 1, REGN10987 (Imdevimab) and uniquely perturbed/partially blocked ACE2, and was assigned to bin 2. Within the ACE2 fully blocking clones, two discrete sets of Abs (bin 4 and bin 5) were identified. Bin 4 co-located with REGN10933 (Casirivimab) and CB6 (etesevimab), while bin 5 co-located with the "cryptic" epitope of CR3022, VHH-72 and SB68. Bin 3 blocked both bin 2 (23-H7) and bin 4.

FIG. 1C: Images of the Spike trimer and zoomed in view of the RBD in grey (PDB ID: 7BNM residues 330-520) showing the epitope contacts for benchmark Abs CR3022 (PDB ID: 6YMO) REGN10987 (PDB ID: 6XDG), REGN10933 (PDB ID: 6XDG), CB6 (PDB ID: 7C01), and REGN10933/CB6 shared residues. Depiction of the benchmark "bald spot" present on the RBD, an area of the Spike where none of the available literature controls bound. The C terminus of 51-nonRBD is shaded darker grey (residues 320-329; 521-593). Predicted epitope regions for Abs assigned to bin C, bin 1 and sub-bins 1a, 1b, and 1c (dotted ovals) are also indicated. RBD and benchmark antibody structures were imported from PDB to Maestro. Proteins were aligned via Protein Structure Alignment.

FIG. 1D: Wheel showing the composition of TATX-03 blends comprised from six lead Abs distributed across four distinct bins.

FIGS. 1E-G: Nuanced binning profiles for the sub-bins including a Venn diagram demonstrating cross-blockade between bins (FIG. 1E). Sensorgram overlay plots showing the sandwich binding of 27-G3 (FIG. 1F) (bin 1 b) or 21-H1 (FIG. 1G) (bin 1c) as analyte to recombinant S1-His (D614G) that is first tethered via sensors coated with benchmark Abs. In this example, 27-G3 (bin 1b) blocks REGN10987 and CB6 but not REGN10933, whereas 21-H1 (bin 1c) blocks REGN10933 but not CB6 of REGN10987.

FIG. 1H: Image of the RBD in grey (PDB ID: 7BNN residues 330-520) showing the epitope contacts for benchmark Abs REGN10987 (PDB ID: 6XDG), REGN10933 (PDB ID: 6XDG), CB6 (PDB ID: 7C01), and REGN10933/CB6 shared residues. Despite REGN10933 and CB6 sharing substantial overlapping epitope contacts, the library described herein contained clones that discriminated between them, as here shown by bin 1 b and bin 1c.

FIG. 1I shows "Waterfall" classical binning assays. Titration sensorgrams of analytes 23-H7 or 22-D9 over S1-His (D614G) that is tethered via ACE2-coated sensors showing that 23-H7 binding is kinetically perturbed (partially blocked) suggesting that 23-H7 and ACE2 target closely adjacent or minimally overlapping epitopes, whereas 22-D9 is fully blocked, suggesting that its epitope may overlap substantially with that of ACE2. Dose-dependent unhindered sandwiching signals of S1-His(D614G) tethered via anti-His mAb-coated sensors (right panel) serve as controls to indicate the results expected for analyte binding at a distinctly different and non-overlapping site relative to that of the immobilized binding partner on the sensor.

FIG. 2A: Tandem cocktail experimental scheme and sensorgrams showing that tethering Spike trimer protein via sensors coated with 23-H7 (bin 2) allows for the stepwise association of Abs from three other non-overlapping bins represented by 22-F7 (bin C), 2-A6 (bin S2), and 21-F2 (bin 4). FIG. 2B: Premix experimental scheme. Spike was premixed in solution phase with saturating concentrations of up to four Abs from non-overlapping epitope bins, used individually or as 2-, 3-, or 4-Ab cocktails and these premixed samples were presented to Ab-coated sensors (probes), which were blocked in a bin-specific manner. The Abs used for the premix assays were 23-H7 (bin 2), 21-F2 (bin S2) or 22-D9 (bin 4), 22-F7 or 22-E7 (bin C) and 2-A6 (bin S2). FIGS. 2B-D: Sensorgrams from FIG. 2A with each binding step aligned to Y=0 demonstrating similar magnitude of signal for association of 23-H7 (bin 2) (FIG. 2C), 2-A6 (bin S2) (FIG. 2D) or 21-F2 (bin 4) (FIG. 2E) regardless of whether the Spike has been saturated with other Abs. FIGS. 2F-H: Sensorgrams from premix assay showing the results from sensors coated with bin C (FIG. 2F), ACE2-hFc (FIG. 2G), or anti-His-mAb (FIG. 2H) to probe for "free" Spike binding sites in premixes of Spike with various Abs, individually, or as cocktails. Only premixes containing ACE2-blocker Abs (bin 2 or bin 4) blocked binding to ACE2-coated sensors, whereas none of the cocktails blocked anti-His-coated sensors, confirming universal access of the Spike's His tag irrespective of Ab decoration. These controls confirmed a bin-specific blockade of the Spike upon saturation with Abs from up to four non-overlapping bins, simultaneously.

FIGS. 3A-D: Examples of Octet-based affinity estimates determined in complementary assay orientations, Fab as analyte (FIGS. 3A-B), monovalent target as analyte (FIG. 3C) and solution affinity (FIG. 3D). The overlay plots show the sensorgrams (measured data, at different analyte concentration) and their global fits. The kinetic (left) and steady-state (right) analysis fitting routines gave comparable affinity determinations.

FIGS. 4A-C: In vitro cell-based neutralization data for representative multi-Ab cocktails comprising Abs from bins 2, 4 and C. FIG. 4A: Pseudovirus (Wuhan-1 isolate Spike sequence) neutralization by individual clones in bins 2, 4 and C respectively, with $IC_{50}$ values reported in μg/mL. 2-A6 (bin S2) was non-neutralizing in this assay. FIG. 4B: Pseudovirus neutralization of two 4-Ab cocktails with $IC_{50}$ values reported in μg/mL. FIG. 4C: $IC_{50}$ values of single Abs and cocktail combinations in authentic virus (D614G strain) neutralization assays. Dotted line represents non-neutralizing limit of detection. Individually, only 21-F2 (bin 4) showed any neutralization. All cocktails produced synergistic effects, boosting potencies over an order of magnitude compared with their individual components. All cocktails were mixed in a 1:1:1:1 (4-Ab) or 1:1:1:1:1 (5-Ab) concentration ratio. The 4-membered cocktails contained 23-H7+22-D9 (or 21-F2)+22-E7 (or 22-F7)+2-A6, while the 5-membered cocktail contained 23-H7+22-D9+21-F2+22-F7+2-A6. Thus, all cocktails contained both 23-H7 (bin 2) and 2-A6 (bin S2). The remaining bin 4 and bin C members were included as follows: cocktail #1 (4-Ab: TATX-03a) 22-D9+22-E7; cocktail #2 (4-Ab: TATX-03b) 21-F2+22-F7; cocktail #3 (4-Ab) 22-D9+22-F7; cocktail #4 (4-Ab) 21-F2+22-E7; and cocktail #5 (5-Ab: TATX-03c) 22-D9+21-F2+22-F7. Note that cocktail #1 (TATX-03a) and cocktail #3 were each comprised of non-neutralizing Abs (lacked 21-F2). Benchmark Abs used in these assays gave $IC_{50}$ values of 0.45 μg/mL (REGN10987), 0.67 μg/mL (REGN10933) and 0.58 μg/mL (REGN10987+REGN10933) in pseudovirus assays and 10.5 μg/mL (REGN10987), 0.7 μg/mL (REGN10933) 0.3 μg/mL (RGN10987+REGN10933) and 0.2 μg/mL when the last combination was repeated.

FIGS. 5A-I show the effect of antibodies in a Hamster challenge model for SARS-CoV-2 infection. FIG. 5A: Study design. Primary measures of in vivo efficacy of cocktails and individual Abs in blends TATX-03a (FIGS. 5B-C) and TATX-03b (FIGS. 5D-E). TATX-03a (23-H7, 22-D9, 22-E7, 2-A6) was administered pre-challenge (prophylactic, PPx) or post-challenge (therapeutic, Tx) as indicated at 40 mg/kg of body weight (bw) total Ab concentration (10 mg/kg bw/Ab in the 4-Ab blend), while the individual Abs of TATX-03a were on administered pre-challenge at 40 mg/kg bw. TATX-03b (23-H7, 21-F2, 22-F7, 2-A6) was administered at 20 mg/kg bw total Ab concentration (5 mg/kg bw/Ab in the 4-Ab blend) as Tx only. Individual antibodies were administered post-challenge at 20 mg/kg bw (23-H7, 21-F2 and 22-F7) and 5 mg/kg bw (23-H7 and 21-F2). In addition, one group was post-challenge treated with a 2-Ab combination of 23-H7 and 21-F2 at 5 mg/kg bw total Ab concentration (2.5 mg/kg bw/Ab). Replication-competent viral titers (Log10 Median Tissue Culture Infective Dose (TCID50) in throat swab (day 3 post-infection; lowest level of detection, LLOD=0.8) (FIGS. 5B, D) and lung (day 4 post-infection, endpoint; LLOD=1.3) (FIGS. 5C, E). Statistics are described in Example 1. $^*p<0.05$, $^{}p<0.01$, $^{*}p<0.001$.

FIGS. 5F-I: Additional data from the in vivo efficacy studies evaluating TATX-03. FIG. 5F: Study 1 throat swab real-time PCR analysis at day 1 confirming presence of viral RNA in all animals. FIG. 5G: Study 1 body weight change at day 4 (endpoint) expressed as a percentage of day 0 body weight. FIGS. 5H and I: Replication-competent viral titer in nasal turbinate homogenate at endpoint for study 1 and 2, respectively. Horizontal lines represent the lowest limit of detection (LLOD) for assay.

FIGS. 6A-D show the results of histopathology analysis of challenge infection model. FIG. 6A-B: Representative images from hematoxylin and eosin-stained slides of endpoint lung tissue shown at multiple magnifications for bronchitis scores of 0 (FIG. 6A) and 3 (FIG. 6B). Arrows point at areas of significant inflammatory cell infiltration. FIGS. 6C-D: Average bronchitis (FIG. 6C) and tracheitis (FIG. 6D) severity as scored by an independent pathological assessment. Scores were determined by the extent of inflammatory cell infiltration into the tissue section.

FIG. 7A: Heat map summarizing the complementary vulnerabilities of indicated clones of the TATX-03 cocktail against cell-associated Spike protein trimers expressing Alpha (B.1.1.7), Beta (B.1.351), Gamma (P.1), Epsilon (B.1.429), Iota (B.1.526) and Omicron (B.1.1.529) mutants. Corresponding dose-response graphs are shown in FIGS. 7B-C. FIG. 7D: ELISA results to plate-adsorbed recombinant Spike proteins.

FIG. 7E: ELISA using plate adsorbed SARS-CoV-2 Spike Trimer carrying B.1.1.529 Omicron lineage mutations. Antibodies were added in 3.2-fold titration. All antibodies were reactive to WT spike trimer. 21-F2 (optimized) refers to a variant of 21-F2 comprising a mutation at a glycosylation site in the VH chain (SEQ ID NO:214) and 22-D9 (optimized) refers to a variant of 22-D9 comprising a mutation at a glycosylation site in the VH chain (SEQ ID NO:215). FIG. 7F: heat map summary of ELISA-based reactivity profiles. FIG. 7G: In vitro virus neutralization screenings of TATX-03a-c using VSV-particles pseudo-typed with Spike proteins representing the original Wuhan-1 isolate and SARS-CoV-2 variants of concern Alpha, Beta, Delta and Omicron. FIG. 7H: In vitro virus neutralization screenings of antibodies 23-H7, 22-D9, 21-F2, 22-F7 and 2-A6 (upper panel) or of the TATX-03c cocktail (lower panel) using VSV-particles pseudo-typed with Spike proteins representing the original Wuhan-1 isolate and SARS-CoV-2 variant of concern Omicron.

FIG. 8A: SARS-CoV2-S CHO-K1 cells (reflecting wild-type, Wuhan-1) were incubated with a dose response of mAbs 21-F2 (optimized), 2-A6, 22-D9 (optimized), 22-F7, and 23-H7 (150 µg/mL to 10 µg/mL, four-fold dilution) in triplicate in presence of ADCP effector cells at a ratio of 3:2 effector cells to target cells. The mixtures were incubated for 4 h at 37° C., whereafter Bio-Glo substrate was added for 5 min. FIG. 8B: SARS-CoV2-S CHO-K1 cells were incubated with a dose response of positive and negative control benchmark mAbs (150 pg/mL to 10 µg/mL, four-fold dilution) in triplicate in presence of ADCP effector cells at a ratio of 3:2 effector cells to target cells. The mixtures were incubated for 6 hrs at 37° C., whereafter Bio-Glo substrate was added for 5 min. FIG. 8C: Control and candidate mAbs in dose response (150 pg/mL to 10 µg/mL, 4-fold dilution) were incubated in singlet with ADCP effector cells in the absence of SARS-CoV2-S CHO-K1 cells for 6 hrs at 37° C., whereafter Bio-Glo substrate was added for 5 min. Luminescence was read on an Envision spectrophotometer. Average luminescence+/−standard deviation is depicted against concentration of respective effector.

FIG. 9A: SARS-CoV2-S CHO-K1 cells (reflecting wild-type, Wuhan-1) were incubated with a dose response of mAbs 21-F2 (optimized), 2-A6, 22-D9 (optimized), 22-F7, and 23-H7 (230 pg/mL to 15 µg/mL, four-fold dilution) in triplicate in presence of ADCC effector cells at a ratio of 4:1 effector cells to target cells. The mixtures were incubated for 6 h at 37° C., whereafter Bio-Glo substrate was added for 10 min. FIG. 9B: SARS-CoV2-S CHO-K1 cells were incubated with a dose response of positive and negative control benchmark mAbs (230 pg/mL to 15 µg/mL, four-fold dilution) in triplicate in presence of ADCC effector cells at a ratio of 4:1 effector cells to target cells. The mixtures were incubated for 6 hrs at 37° C., whereafter Bio-Glo substrate was added for 10 min. FIG. 9C: Control and candidate mAbs in dose response (230 pg/mL to 15 µg/mL, four-fold dilution) were incubated in singlet with ADCC effector cells in the absence of SARS-CoV2-S CHO-K1 cells for 6 hrs at 37° C., whereafter Bio-Glo substrate was added for 10 min. Luminescence was read on an Envision spectrophotometer. Average luminescence+/−standard deviation is depicted against concentration of respective effector.

DETAILED DISCLOSURE

Figure 1A:
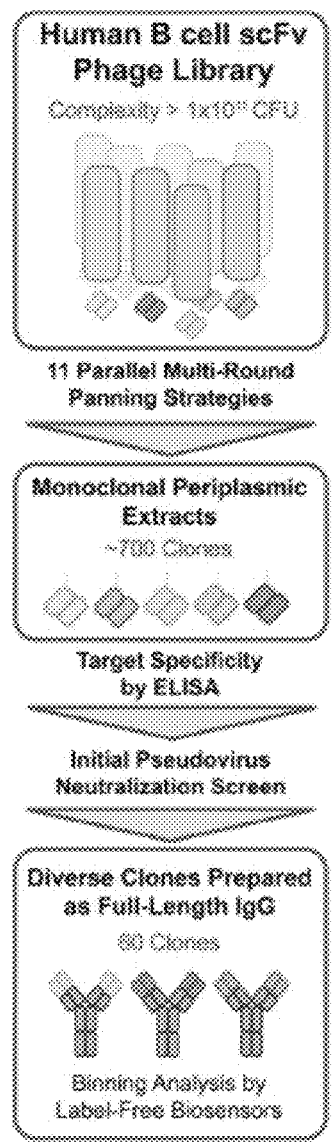
FIGS. 1A-I show the library-to-leads triage process used in the present study.

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

The use of any and all examples, or exemplary language (e.g., "such as") provided herein, is intended merely to better illustrate the invention and does not pose a limitation on the scope of the invention unless otherwise claimed.

No language in the specification should be construed as indicating any non-claimed element as essential to the practice of the invention.

Herein, the term "about" has its ordinary meaning. The term "about" is used to indicate that a value includes an inherent variation of error for the device or the method being employed to determine the value, or encompass values close to the recited values, for example within 10% or 5% of the recited values (or range of values).

As used herein the term "individual," "patient," or "subject" refers to individuals diagnosed with, suspected of being afflicted with, or at-risk of developing at least one disease for which the described compositions and method are useful for treating. In certain embodiments the individual is a mammal. In certain embodiments, the mammal is a mouse, rat, rabbit, dog, cat, horse, cow, sheep, pig, goat, llama, alpaca, or yak. In certain embodiments, the individual is a human.

As described herein severe SARS-CoV-2 infection refers to individuals infected with SARS-CoV-2 that develop difficulty breathing or persistent chest pressure or pain. Severe SARS-CoV-2 infection may require hospitalization, supplemental oxygen, and or mechanical ventilation. Many individuals are at high risk for severe SARS-CoV-2 including the elderly, diabetic, or those with pre-existing cardiovascular disease.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

An "isolated antibody", as used herein, is intended to refer to an antibody that is substantially free of other antibodies (Abs) having different antigenic specificities (e.g., an isolated antibody that specifically binds SARS-CoV-2 Spike protein, or a fragment thereof, is substantially free of Abs that specifically bind antigens other than SARS-CoV-2 Spike protein.

A "blocking antibody" or a "neutralizing antibody", as used herein (or an "antibody that neutralizes SARS-CoV-2 Spike protein activity" or "antagonist antibody"), is intended to refer to an antibody (or an antigen-binding fragment thereof) whose binding to SARS-CoV-2 Spike protein results in inhibition of at least one biological activity of SARS-CoV-2. For example, an antibody of the disclosure may prevent or block SARS-CoV-2 binding to ACE2. In another example, an antibody of the disclosure may induce complement-dependent cytotoxicity (CDC), antibody-dependent cellular cytotoxicity (ADCC) and/or antibody-dependent cellular phagocytosis (ADCP) against infected cells.

The term "label-free (biolayer interferometry)", as used herein, refers to an optical phenomenon that allows for the analysis of real-time biomolecular interactions by detection of alterations in protein concentrations within a biosensor matrix, for example using the Octet™ system (Sartorious, Gottingen, Germany).

The term "$K_D$", as used herein, is intended to refer to the equilibrium dissociation constant of a particular antibody-antigen interaction.

The term "epitope" refers to an antigenic determinant that interacts with a specific antigen-binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "SARS-CoV-2 Spike Protein", also called "Spike protein" is a trimeric glycoprotein found on the surface of the SARS-CoV-2 virus which mediates the attachment of the viral particle to the host cell via its canonical receptor Angiotensin Converting Enzyme 2 (ACE2) and entry into host cells by conformational change. The Spike protein is comprised of two unique subunits: S1 (containing a structural N-Terminal Domain [NTD] and the receptor binding domain [RBD]) and S2. The Spike protein of SARS-CoV-2 shares significant sequence similarity to the Spike protein from other related coronaviruses. It is produced as a single polypeptide chain, but is cleaved by the enzyme Furin during its production in host cells at the junction between the S1 and S2 subunits.

The amino acid sequence of the full-length Spike protein from SARS-CoV-2 is exemplified by the amino acid sequence provided in NCBI Reference Sequence number YP_009724390.1 (Wuhan original strain).

In some embodiments, the SARS-CoV-2 Spike protein has the following amino acid sequence (the S1 subunit, corresponding to amino acids 1-680, is underlined) or an amino acid sequence at least 85%, 90%, 95%, 96%, 97%, 98%, or at least 99% identical thereto:

```
                                                           (SEQ ID NO: 197)
  1   MFVFLVLLPL VSSQCVNLTT RTQLPPAYTN SFTRGVYYPD KVFRSSVLHS TQDLFLPFFS

61   NVTWFHAIHV SGTNGTKRFD NPVLPFNDGV YFASTEKSNI IRGWIFGTTL DSKTQSLLIV

121   NNATNVVIKV CEFQFCNDPF LGVYYHKNNK SWMESEFRVY SSANNCTFEY VSQPFLMDLE

181   GKQGNFKNLR EFVFKNIDGY FKIYSKHTPI NLVRDLPQGF SALEPLVDLP IGINITRFQT

241   LLALHRSYLT PGDSSSGWTA GAAAYYVGYL QPRTFLLKYN ENGTITDAVD CALDPLSETK

301   CTLKSFTVEK GIYQTSNFRV QPTESIVRFP NITNLCPFGE VFNATRFASV YAWNRKRISN

361   CVADYSVLYN SASFSTFKCY GVSPTKLNDL CFTNVYADSF VIRGDEVRQI APGQTGKIAD

421   YNYKLPDDFT GCVIAWNSNN LDSKVGGNYN YLYRLFRKSN LKPFERDIST EIYQAGSTPC

481   NGVEGFNCYF PLQSYGFQPT NGVGYQPYRV VVLSFELLHA PATVCGPKKS TNLVKNKCVN

541   FNFNGLTGTG VLTESNKKFL PFQQFGRDIA DTTDAVRDPQ TLEILDITPC SFGGVSVITP

601   GTNTSNQVAV LYQDVNCTEV PVAIHADQLT PTWRVYSTGS NVFQTRAGCL IGAEHVNNSY

661   ECDIPIGAGI CASYQTQTNS PRRARSVASQ SIIAYTMSLG AENSVAYSNN SIAIPTNFTI

721   SVTTEILPVS MTKTSVDCTM YICGDSTECS NLLLQYGSFC TQLNRALTGI AVEQDKNTQE

781   VFAQVKQIYK TPPIKDFGGF NFSQILPDPS KPSKRSFIED LLFNKVTLAD AGFIKQYGDC

841   LGDIAARDLI CAQKFNGLTV LPPLLTDEMI AQYTSALLAG TITSGWTFGA GAALQIPFAM

901   QMAYRFNGIG VTQNVLYENQ KLIANQFNSA IGKIQDSLSS TASALGKLQD VVNQNAQALN
```

-continued
```
 961  TLVKQLSSNF GAISSVLNDI LSRLDKVEAE VQIDRLITGR LQSLQTYVTQ QLIRAAEIRA

1021  SANLAATKMS ECVLGQSKRV DFCGKGYHLM SFPQSAPHGV VFLHVTYVPA QEKNFTTAPA

1081  ICHDGKAHFP REGVFVSNGT HWFVTQRNFY EPQIITTDNT FVSGNCDVVI GIVNNTVYDP

1141  LQPELDSFKE ELDKYFKNHT SPDVDLGDIS GINASVVNIQ KEIDRLNEVA KNLNESLIDL

1201  QELGKYEQYI KWPWYIWLGF IAGLIAIVMV TIMLCCMTSC CSCLKGCCSC GSCCKFDEDD

1261  SEPVLKGVKL HYT.
```

Residues 1-12 correspond to the signal peptide, residues 13-685 correspond to the Spike protein subunit 51 and residues 686-1273 correspond to the Spike protein subunit S2. The receptor-binding domain (RBD) is defined by residues 319-541 (receptor-binding motif=residues 437-508). Residues 816-837 define the fusion peptide 1, residues 835-855 define the fusion peptide 2, residues 920-970 define the heptad repeat 1 and residues 1163-1202 define the heptad repeat 2.

In related embodiments, the full-length Spike protein comprises one or more mutations relative to SEQ ID NO:197. In some embodiments, the Spike protein comprises one or more of an L5F, L18F, D80Y, S98F, A222V, N354D, F342L, V367F, A435S, W436R, N439K, Y453F, K458R, G476S, V483A, E484X, N501Y, A570D, D614G, A626S P681H, T716I, S982A, D1118H, V1122L, and G1124V substitution. The Spike protein may also comprise a deletion (e.g., an HV 69-70 deletion and/or a Y144 deletion).

SARS-CoV2 variants comprise mutations in the Spike protein including L5F, S13L, L18F, T19R, T20N, P26S, A67V, del69-70, G75V, T76I, D80Y, D80A, T95I, S98F, R102I, D138Y, G142D, del142-144, del144, W152C, E154K, EFR156-158G, F157L, R190S, ins214EPE, D215G, A222V, del246-252, D253G, W258L, N354D, F342L, V367F, K417N, K417T, A435S, W436R, N439K, N440K, G446V, L452R, Y453F, K458R, G476S, S477N, S477G, T478K, V483A, E484K, E484Q, F490S, N501Y, N501S, N501T, A570D, Q613H, D614G, A626S, A653V, H655Y, Q677H, Q677P, P681H, P681R, A701V, T716I, D796H, D796Y, T859N, F888L, D950N, S982A, T1027I, Q1071H, E1092K, H1101Y, D1118H, V1176F, G1219V, and V1122L. The Delta variant comprises the following Spike protein mutations: T19R, (V70F*), T95I, G142D, E156-, F157-, R158G, (A222V*), (W258L*), (K417N*), L452R, T478K, D614G, P681R, D950N.

The SARS-CoV-2 Omicron variant comprises the following Spike protein mutations: A67V, del69-70, T95I, G142D, del143-145, del211, L212I, ins214EPE, G339D, R346K, S371L, S373P, S375F, K417N, N440K, G446S, S477N, T478K, E484A, Q493R/K, G496S, Q498R, N501Y, Y505H, T547K, D614G, H655Y, N679K, P681H, A701V, N764K, D796Y, N856K, Q954H, N969K, L981F.

In an embodiment, the antibodies or antigen-binding fragments thereof described herein bind to the native Spike protein (SEQ ID NO:197). In an embodiment, the antibodies or antigen-binding fragments thereof described herein bind to a Spike protein variant comprising one or more of the mutations disclosed above. In an embodiment, the antibodies or antigen-binding fragments thereof described herein bind to a Spike protein variant comprising the mutations of the SARS-CoV-2 Omicron variant.

The term Spike protein also encompasses full-length or partial Spike proteins coupled to, for example, purification and identification tags, signal sequences, or other modifications of the native amino acid sequence necessary to perform analytical techniques described herein.

The term "SARS-CoV-2 infection", as used herein, also characterized as "COVID-19", refers to severe acute respiratory illness caused by the SARS-CoV-2 virus. The term also includes respiratory tract infection and symptoms including but not limited to fever, fatigue, cough (e.g., dry cough), loss of appetite, body aches, anosmia, gastrointestinal symptoms (e.g., diarrhea, abdominal pain, nausea and/or vomiting), dyspnea, and shortness of breath. The term also encompasses diseases and syndromes caused by the SARS-CoV-2 virus including but not limited to pneumonia, acute respiratory distress syndrome (ARDS), multi-system inflammatory syndrome in children (MIS-C) and sepsis. The term also includes asymptomatic infection in which virus replication is detectable by a PCR-based assay but the patient displays a subset of symptoms or no symptoms of active infection.

In some embodiments, novel antibodies are provided that bind to the receptor-binding domain (RBD) of SARS-CoV-2 Spike protein 51 and effectively block binding of angiotensin I converting enzyme 2 (ACE2) to the RBD. In other embodiments, novel antibodies are provided that bind to the SARS-CoV-2 S1 subunit in a region other than the RBD or bind to the SARS-CoV-2 S2 subunit.

In some aspects, an antibody provided herein effectively neutralizes SARS-CoV-2. In some aspects, a novel antibody provided herein neutralizes SARS-CoV-2 with an $IC_{50}$ value of less than about 10 μg/mL. In some aspects, neutralizing activity is assessed using a VSV pseudotyped virus neutralization assay such as that described in Wang et al., A human monoclonal antibody blocking SARS-CoV-2 infection. *Nat Commun* 11, 2251 (2020). In some aspects, neutralizing activity is assessed using a live virus neutralization assay such as that described in Wec A Z, et al. Broad neutralization of SARS-related viruses by human monoclonal antibodies. *Science.* 2020; 369:731-736.

In some aspects, an antibody or combination of antibodies provided herein effectively reduce viral load in a Syrian hamster model of SARS-CoV-2 infection such as that described in Imai et al. (*PNAS* 117(28) 16587-16595 (2020)). Syrian hamsters as a small animal model for SARS-CoV-2 infection and countermeasure development. In some aspects, reduction in viral load is determined by reduction in the amount of replication-competent virus isolated from swabs or tissue samples, or by the detection of viral RNA in the same.

In some aspects, an antibody or antigen fragment thereof comprises a heavy chain variable region (HCVR) comprising a heavy chain CDR1, CDR2 and CDR3 (HCDR1, HCDR2, HCDR3) having a sequence selected from among those in Table 1 and a light chain variable region (LCVR) comprising a light chain CDR1, CDR2 and CDR3 (LCDR1, LCDR2, LCDR3) having a sequence selected from those in Table 1:

TABLE 1

HCDR and LCDR sequences of exemplary anti-SARS-CoV-2 S antibodies (according to the I TABLE 1-continued HCDR and LCDR sequences of exemplary anti-SARS-CoV-2 S antibodies (according to the IMGT definition)

| Clone | HCDR1 | HCDR2 | HCDR3 | LCDR1 | LCDR2 | LCDR3 |
|---|---|---|---|---|---|---|
| 27-B4 | GDSVSSNSAA (SEQ ID NO: 74) | TYYRSKW (SEQ ID NO: 75) | ARTIGWYDS (SEQ ID NO: 76) | ALPKQF (SEQ ID NO: 77) | RDS | QSADSSATYEV (SEQ ID NO: 78) |
| 8-H1 | GYSFTSYW (SEQ ID NO: 1) | IYPGDSDT (SEQ ID NO: 2) | ARRQSGSGYDY (SEQ ID NO: 79) | SSNVGSNS (SEQ ID NO: 80) | TNN | AAWDDSLNGWV (SEQ ID NO: 81) |
| 8-H5 | GYSFTSYW (SEQ ID NO: 1) | IYPGDSDT (SEQ ID NO: 2) | ARWSEGNGFDY (SEQ ID NO: 82) | SSNIGSNS (SEQ ID NO: 83) | RND | AAWDDSLNGVV (SEQ ID NO: 5) |
| 8-A2 | GYTFTGYY (SEQ ID NO: 11) | INPNSGGT (SEQ ID NO: 12) | LAVAGTGGDAFDI (SEQ ID NO: 84) | QSISSW (SEQ ID NO: 85) | AAS | QQGHSFPLT (SEQ ID NO: 86) |
| 23-A11 | GFTFSSYG (SEQ ID NO: 25) | ISYDGSNK (SEQ ID NO: 26) | AKEGELRGAFDI (SEQ ID NO: 27) | NIESKY (SEQ ID NO: 87) | YDT | QVWDRTSGHFV (SEQ ID NO: 88) |
| 22-F7 | GFSFTNYG (SEQ ID NO: 89) | ISYDGSIK (SEQ ID NO: 90) | TRERGTGIDY (SEQ ID NO: 91) | KSDIGAYNY (SEQ ID NO: 92) | DVS | SSYTTSGTVV (SEQ ID NO: 93) |
| 30-C5 | GFTFSNYG (SEQ ID NO: 94) | ISYDGSIE (SEQ ID NO: 95) | ARDEDGAFDI (SEQ ID NO: 96) | ESVSYSSSNKNY (SEQ ID NO: 97) | WAS | QQYYSSPLT (SEQ ID NO: 98) |
| 22-B10 | GFTFSDYP (SEQ ID NO: 99) | ISYDGWTK (SEQ ID NO: 100) | VRGTDYGDS (SEQ ID NO: 101) | SSNIGNNY (SEQ ID NO: 9) | ENN | GTWDNSLSAWV (SEQ ID NO: 102) |
| 22-E7 | GFTFNNYP (SEQ ID NO: 103) | ISYDGNHK (SEQ ID NO: 104) | ASDLSGAEDS (SEQ ID NO: 105) | SSDVGGYNY (SEQ ID NO: 106) | EVS | SSYTSSSTWV (SEQ ID NO: 107) |
| 6-A4 | GFTLSDYP (SEQ ID NO: 108) | MSYDGSLK (SEQ ID NO: 109) | ARGNSDGDFDY (SEQ ID NO: 110) | DIGSRS (SEQ ID NO: 111) | DDT | QAWDSSTVV (SEQ ID NO: 112) |
| 6-E1 | GFSFNTFP (SEQ ID NO: 113) | ISYDGSFK (SEQ ID NO: 114) | ASPGDSDWADFEN (SEQ ID NO: 115) | SSNIGAGYD (SEQ ID NO: 71) | GNS | QSYDSSLSGYV (SEQ ID NO: 116) |
| 6-F2 | GFNFSLYG (SEQ ID NO: 117) | ISYDGSQK (SEQ ID NO: 118) | VKGEGSLDY (SEQ ID NO: 119) | TSDVGGYGY (SEQ ID NO: 120) | EVA | VSYTLSSLVV (SEQ ID NO: 121) |
| 15-E4 | GSIPSVNV (SEQ ID NO: 122) | VTSDGRT (SEQ ID NO: 123) | LITNQDHNTLGV (SEQ ID NO: 124) | N/A | N/A | N/A |
| 2-A6 | GFSLNTRGMS (SEQ ID NO: 125) | IDWEDDK (SEQ ID NO: 126) | ARTYSVGVKYFGMDV (SEQ ID NO: 127) | SLRNYY (SEQ ID NO: 198) | GGN | NSRDSSGNHVV (SEQ ID NO: 199) |
| 15-C8 | GNVTSITL (SEQ ID NO: 128) | IINDDDRT (SEQ ID NO: 129) | SAKAGGNFY (SEQ ID NO: 130) | N/A | N/A | N/A |
| 15-F7 | GSIPSVNV (SEQ ID NO: 122) | VTSDGRT (SEQ ID NO: 123) | LITNSDHNTLG (SEQ ID NO: 203) | N/A | N/A | N/A |
| 15-H3 | GSIPSVNV (SEQ ID NO: 122) | VTSDGRT (SEQ ID NO: 123) | LITNSDHNTLGV (SEQ ID NO: 124) | N/A | N/A | N/A |

N/A = not applicable (VHHs that do not comprise a light chain)

In other aspects, an antibody or antigen fragment thereof comprises a heavy chain variable region having a sequence selected from among those in Table 2 and a light chain variable region having a sequence selected from those in Table 2:

TABLE 2

HCVR/LCVR sequences of exemplary anti-SARS-COV-2 S antibodies

| Clone | | Heavy Chain variable (VH) and Light Chain variable (LH) sequences |
|---|---|---|
| 26-G2 | VH | EVQLVQSGAEVKKPGKSLKISCKGSGYSFTSYWIGWVRQMPGKGLEWMGITYPGDSDTRYSPSFQGQVTISA DKSISTAYLQWSSLKASDTAMYYCARLGDYSGMDVWGQGTMVTVSS (SEQ ID NO: 131) |
| | VL | QSVLTQPPSASGTPGQRVTISCSGSSSNIGSNPVNWYQHLPGTAPKLLISGNDQRPSGVPDRFSGSKSGTSA SLAISGLQSEDEGDYYCAAWDDSLNGVVFGGGTQLTVL (SEQ ID NO: 132) |
| 27-A11 | VH | QVQLVQSGAEVKKPGASVKVSCKASGYTFTSYYMHWVRQAPGQGLEWMGIIDPSGGSTSYAQKFQGRVTLTR DTSTSTVYMELSSLRSEDTAVYYCARSRDGYIDDAFDIWGQGTLVTVSS (SEQ ID NO: 133) |
| | VL | QSVLTQPPSVSAAPGQKVTISCSGSSSNIGNNYVSWYQQLPGTAPKLLIYDNNKRPSGIPDRFSGSKSGTSA TLGITGLQTGDEADYYCGTWDSSLSAGVFGGGTKLTVL (SEQ ID NO: 134) |
| 11-H1 | VH | QVQLVQSGAEVKKPGASVKVSCKASGYTFTGYYMHWVRQAPGQGLEWMGRINPNSGGTNYAQKFQGRVTMTR DTSISTAYMELSRLRSDDTAVYYCARDKLPFSVGATHGMDVWGQGTLVTVSS (SEQ ID NO: 135) |
| | VL | QSVLTQPPSVSEAPRQRVTISCSGSSSNIGNNAVNWYQQLPGQAPRLLIYYDNLLPSGVSDRFSASTSGTSA SLAISDLRSEDEADYYCASWDDRLDSPVFGGGTKLTVL (SEQ ID NO: 136) |
| 21-A6 | VH | QVQLVQSGAEVKKPGASVKVSCKASVKVSCKASGYTFTSYYMHWVRQAPGQGPEWMGVIDPSGGTTSYAQKF HDRIAMTRDTSTSTAYLELSSLRSEDTAVYYCARGGFADAVDYWGQGTLVTVSS (SEQ ID NO: 137) |
| | VL | NFMLTQPHSVSESPGKTVTISCTRSSGSIASNYVQWYQQRPGSSPTTVIYEDNQRPSGVPDRFSGSIDSSSN SASLTISGLKTEDEADYYCQSYDSGNVIFGGGTKVTVL (SEQ ID NO: 138) |
| 27-F5 | VH | EVQLVQSGAEVKKPGASVKVSCKASGYTFTSYAMHWVRQAPGQRLEWMGWINAGNGNTKYSQKFQGRVTITR DTSASTAYMELSSLRSEDTAVYYCAREGMITFGGVIVTNYGMDVWGQGTMVTVSS (SEQ ID NO: 139) |
| | VL | SYVLTQPPSVSVAPGQTARITCGGNNIGSESVHWYQQKPGQAPLLVVYDDNNRPSGIPERFSGSNSGNTATL TINRVEAGDEADYSCQAWDGSTVVFGGGTKLTVL (SEQ ID NO: 140) |
| 21-H1 | VH | QVQLVESGGGVVQPGRSLRLSCAASGFTFSSYGMHWVRQAPGKGLEWVAVISYDGSNKYYADSVKGRFTISR DNSKNTLYLQMNSLRAEDTAVYYCAKEGELRGAFDIWGQGTTVTVSS (SEQ ID NO: 141) |
| | VL | DIVMTQSPLSLPVTPGEPASISCTSSQSLLHSIGYNFVDWYLQKPGQSPQLLIYSASNRASGVPDRFSGSGS GTDFTLKISRVEAEDVGVYYCMQALQRTLYTFGQGTKVESK (SEQ ID NO: 142) |
| 27-G3 | VH | QVQLVQSGAEVKKPGASVKLSCTASGYTFTSYYMHWVRQAPGQGLEWMGIIDPTGGSTSYAQKFQGRVTMTR DTSTSTVYMELSSLRSEDTAVYYCASAGVGNTFDYWGQGTLVTVSS (SEQ ID NO: 143) |
| | VL | NFMLTQPHSVSASPGKTVTISCTRSSGSIARNYVQWYQQRPGRSPNILIFEDKQRPSGVPDRFSGSIDSSSN SASLTISGLKTEDEADYYCQSYDSSNQWVFGGGTKLTVL (SEQ ID NO: 144) |
| 8-D4 | VH | EVQLVQSGAEVKKPGESLKISCKGSGYSFTSYWIGWVRQMPGKGLEWMGIIYPGDSDTRYSPSFQGQVTISA DKSISTAYLQWSSLKASDTAMYYCARNPSLYSSPTDYWGQGTLVTVSS (SEQ ID NO: 145) |
| | VL | QSVLTQPPSASGTPGQRVTISCSGSSSNIGSNTVNWYQQLPGTAPKLLIYNNNQRPSGVPDRFSGSKSGTSA SLAITGLQSEDEADYYCAAWDDSLNGVVFGGGTKVTVL (SEQ ID NO: 146) |
| 23-H7 | VH | QVQLVQSGAEVKLPGASMKVSCKASGYTFSTYYMHWVRQAPGQGPEWMGVIDPSGGTTSYAQKFHDRIAMTR DTSTSTAYLELSSLRSEDMAVYYCARGGFADAVDYWGQGTLVTVSS (SEQ ID NO: 147) |
| | VL | NFMLTQPHSVSGSPGKTVTISCTRNSGSIAGNYVQWYQQRPGSAPTTVIYEDNQRPSGVPDRFSGSIDSSSN SASLTISGLKTEDEADYYCQSYDASHLHVIFGGGTKVTVL (SEQ ID NO: 148) |
| 24-B8 | VH | QVQLVQSGAEVKKPGSSVKVSCKASGGTFSNYAISWVRQAPGQGLEWMGGIIPILDTTNYAQKFQGRVTITA DESTAYMELNSLRSEDTAVYYCVREEGFDYWGQGTLVTVSS (SEQ ID NO: 149) |
| | VL | QSVLTQPSSLSASPGASASLTCTLRSGINVGAYNIYWYQQKPGSPPQFVLRYNSDSDNQQGSGVPSRFSGSK DASANAGILLISGLQSEDEAEYYCMIWRSSAWVFGGGTKLTVL (SEQ ID NO: 150) |
| 21-F1 | VH | QVQLVESGGGVVQPGRSLRLSCGASGFTFDTYGMHWVRQAPGRGPEWVAVISNDGSKKYYADSVKGRFTISR DNSKNTVYLQMNSLRAEDTGVYYCGRVTEPYMVTPLMLFRMAIDNWGQGTLVTVSS (SEQ ID NO: 151) |
| | VL | SYVLTQPPSMSVAPGETARITCGGGNFGTKSVHWYQQRSGRAPVLVVYANDDRPSGIPERFSGSKSGDTATL TISRVEAGDEADYFCQVWDSSADLRGVVFGGGTQLTVL (SEQ ID NO: 152) |
| 16-C6 | VH | QVQLQESGGGLVQAGGSLRLSCAASGRTFSSYAMGWFRQVLGKERELVAAISRSGGSTYYADSVKGRFTVSR DNVKNTVYLQMNSLKPEDTAGYYCAASNEGGTWYGSSWYRPSSYEHWGQGTQVTVSS (SEQ ID NO: 153) |
| | VL | N/A |
| 16-G6 | VH | QVQLQQSGGGLVQAGGSLRLSCAASGRTFSSYAMGWFRQVLGKERELVAAISRSGGSTYYADSVKGRFTISR DNVKNTVYLQMNSLKPEDTAGYYCAASNEGGTWYGSSWYRPSSYEYWGQGTQVTVSS (SEQ ID NO: 154) |
| | VL | N/A |
| 21-F2 | VH | QVQLVQSGAEVKKPGASVTVSCKTSGYIFTNYDINWVRQAPGQGLEWVGWVNPNSGKVGYAQKFQGRVIMTR SDSESTAYMELTNLTSDDTAVYYCARGHTDFWGQGTLVTVSS (SEQ ID NO: 155) |
| | VL | QSVLTQPPSVSEAPRQRVTISCSGSSSNIGNNAVNWYQQLPGRAPKLLIYYDDLLPSGVSDRFSGSKSGTSA SLAISGLQSEDEADYYCAAWDDSLNGVVFGGGTQLTVL (SEQ ID NO: 156) |

TABLE 2-continued

HCVR/LCVR sequences of exemplary anti-SARS-COV-2 S antibodies

| Clone | | Heavy Chain variable (VH) and Light Chain variable (LH) sequences |
|---|---|---|
| 21-F2 optimized | VH | QVQLVQSGAEVKKPGASVTVSCKTSGYIFTNYDINWVRQAPGQGLEWVGWVNPNSGKVGYAQKFQGRVIMTR SDSESTAYMELTQLTSDDTAVYYCARGHTDFWGQGTLVTVSS (SEQ ID NO: 214) |
| | VL | QSVLTQPPSVSEAPRQRVTISCSGSSSNIGNNAVNWYQQLPGRAPKLLIYYDDLLPSGVSDRFSGSKSGTSA SLAISGLQSEDEADYYCAAWDDSLNGVVFGGGTQLTVL (SEQ ID NO: 156) |
| 22-D9 | VH | QVQLVQSGAEVKKPGSSVNVSCKTSGGTFNTYSINWVRQAPGQGLEWMGEIIPIFDKPNYAQKFQGRVTITA DESTSTAYMELTSLRSDDTAVYYCARGTGYYYGMDVWGQGTTVTVSS (SEQ ID NO: 157) |
| | VL | QSVLTQPPSVSGAPRQTVTISCFGSRSNIGNYPVNWYHQVPGKAPKVVVYYDDLLPSGISDRFSGYKSGTSA SLTISGLRSEDEADYYCATWDDSLNVWVFGGGTKLTVL (SEQ ID NO: 158) |
| 22-D9 optimized | VH | QVQLVQSGAEVKKPGSSVKVSCKTSGGTFNTYSINWVRQAPGQGLEWMGEIIPIFDKPNYAQKFQGRVTITA DESTSTAYMELTSLRSDDTAVYYCARGTGYYYGMDVWGQGTTVTVSS (SEQ ID NO: 215) |
| | VL | QSVLTQPPSVSGAPRQTVTISCFGSRSNIGNYPVNWYHQVPGKAPKVVVYYDDLLPSGISDRFSGYKSGTSA SLTISGLRSEDEADYYCATWDDSLNVWVFGGGTKLTVL (SEQ ID NO: 158) |
| 13-A1 | VH | EVQLVQSGAEVKKPGESLKISCKGSGYSFTSYWIGWVRQMPGKGLEWMGIIYPGDSDTRYSPSFQGQVTISA DKSISTAYLQWSSLKASDTAMYYCARYLSSEGMDVWGKGTTVTVSS (SEQ ID NO: 159) |
| | VL | QSVLTQPPSASGTPGQRVTISCSGRSSNIGSNPVNWYQQLPGTAPKLLIYNNIQRPSGVPDRFSGSKSGTSA SLAISGLQSEDEAVYYCASWDDSLNEGVFGGGTQLTVL (SEQ ID NO: 160) |
| 22-E8 | VH | QVQLVQSGAEVKKPGSSVKVSCKASGGTFSSYAISWVRQAPGQGLEWMGGIIPIFGTTNYAQKFQGRVTITA DESTSTAYMELSSLRSEDTAVYYCARDHGYYYGMDVWGQGTTVTVSS (SEQ ID NO: 161) |
| | VL | QSVLTQPSSVSAAPRQRVTLSCSGGDSNIGQNGVNWYLHVPGKAPRLVVYYDYLVSAGMSARFSGSRSGTSA SLAISGLQSEDEGVYYCASWDDSLSAWVFGGGTKLTVL (SEQ ID NO: 162) |
| 5-B6 | VH | QVQLVQSGAEVKKPGSSVKVSCKASGGTFSSYAISWVRQAPGQGLEWVGGIIPMFNSASYAQKFQGKVTITA DKATNTAYMELSSLRSEDTAVYYCARESSGYYYVSNWFDPWGQGTLVTVSS (SEQ ID NO: 163) |
| | VL | QSVLTQPSSVSGAPGQRVTISCTGSSSNIGAGYDVHWYQQIPGTAPRLLIYANSGRASGVPDRFSGSKSGTS ASLAITGLQAEDEADYYCQSYDSSLSGVVFGGGTKLTVL (SEQ ID NO: 164) |
| 13-H3 | VH | EVQLVQSGAEVKKPGESLKISCKGSGYSFTSYWIGWVRQMPGKGLEWMGITYPGDSDTRYSPSFQGQVTISA DKSISTAYLQWSSLKASDTAMYYCARGSHYGDYDYWGQGTLVTVSS (SEQ ID NO: 165) |
| | VL | QSVLTQPPSVSAAPGQKVTISCSGSSSNIGNNYVSWYQQLPGTAPKLLIYDNNKRPSGIPDRFSGSKSGTSA TLGITGLQTGDEADYYCGTWDSSLSAGVFGGGTKLTVL (SEQ ID NO: 166) |
| 27-B4 | VH | QVQLQQSGPGLVKPSQTLSLTCAISGDSVSSNSAAWNWIRQSPSRGLEWLGRTYYRSKWYNDYAVSVKNRIT INPDTSKNQFSLQLNSVTPEDTAVYYCARTIGWYDSWGQGTLVTVSS (SEQ ID NO: 167) |
| | VL | SYELMQPPSVSVSPGQTARITCSGDALPKQFANWYQQKPGQAPVLLVYRDSERPSGIPERFSGSTSGTTVTL TISGVQAEDEADYYCQSADSSATYEVFGGGTKVTVL (SEQ ID NO: 168) |
| 8-H1 | VH | EVQLVQSGAEVKKPGESLKISCKGSGYSFTSYWIGWVRQMPGKGLEWMGITYPGDSDTRYSPSFQGQVTISA DKSISTAYLQWSSLKASDTAIYYCARROSGSGYDYWGQGTLVTVSS (SEQ ID NO: 169) |
| | VL | QSVLTQPPSASGTPGQRVTISCSGSSSNVGSNSVSWYQQFPGTAPKLLIYTNNQRPSGVPDRFSGSKSGASA SLAISGPQSEDEADYYCAAWDDSLNGWVFGGGTKLTVL (SEQ ID NO: 170) |
| 8-H5 | VH | EVQLVQSGAEVKKPGESLKISCKGSGYSFTSYWIGWVRQMPGKGLEWMGITYPGDSDTRYSPSFQGQVTISA DKSISTAYLQWSSLKASDTAMYYCARWSEGNGFDYWGQGTMVTVSS (SEQ ID NO: 171) |
| | VL | QSVLTQPPSTSGTPGQWVTISCSGSSSNIGSNSVSWYQQLPGMAPKLLIYRNDQRPSGVPDRFSASKSGTSA SLAISGLQSEDEADYYCAAWDDSLNGVVFGGGTKLTVL (SEQ ID NO: 172) |
| 8-A2 | VH | DTSISTAYMELSRLTSDDTAVYYCLAVAGTGGDAFDIWGQGTTVTVSS (SEQ ID NO: 173) |
| | VL | DIQMTQSPSTLSASVGDRVTITCRASQSISSWLAWYQQKPGKAPKLLIYAASSLESGVPSRFSGSGSGTDFT LTISSLQPEDFATYYCQQHSFPLTFGGGTKVDIK (SEQ ID NO: 174) |
| 23-A11 | VH | QVQLVESGGGVVQPGRSLRLSCAASGFTFSSYGMHWVRQAPGKGLEWVAVISYDGSNKYYADSVKGRFTISR DNSKNTLYLQMNSLRAEDTAVYYCAKEGELRGAFDIWGQGTMVTVSS (SEQ ID NO: 175) |
| | VL | SYVLTQPPSVSVAPGKTARITCGGDNIESKYVHWYQQKPGQAPVLVIYYDTDRPSGIPERFSGANSGNSATL TISRVEAGDEADYYCQVWDRTSGHFVFGPGTKVTVL (SEQ ID NO: 176) |
| 22-F7 | VH | QVQLVESGGGVVQPGRSLRLSCAASGFSFTNYGMHWVRQAPGKGLEWVAVISYDGSIKYYEDSLKGRFTVSR DNSKKTLYLQMNSLRAEDTAVYYCTRERGTGIDYWGLGTLVTVSS (SEQ ID NO: 177) |
| | VL | QSALTQPASVSGYPGQSITLSCTGTKSDIGAYNYVSWYQQHPGKAPKLMVYDVSNRPSGLSNRFSGSKSDNT ASLTISGLQAEDEAHYYCSSYTTSGTVVFGGGTKVTVL (SEQ ID NO: 178) |
| 30-C5 | VH | QVQLVESGGGVVQPGRSLRLSCAASGFTFSNYGMHWVRQAPGKGLEWVAVISYDGSIEYYADSVKGRFTISR DNSSNTLYLQMNSLRAEDTAVYYCARDEDGAFDIWGQGTTVTVSS (SEQ ID NO: 179) |
| | VL | DIVMTQSPESLAVSLGERATINCKSSESVSYSSSNKNYLSWYQQIPGQPPKLLIYWASTRESGVPDRFSGSG SGTDFTLTISSLQAEDVAVYYCQQYYSSPLTFGGGTKVEIK (SEQ ID NO: 180) |
| 22-B10 | VH | QVQLVESGGDVVQPGTSLRLSCAASGFTFSDYPLHWVRQAPGKGLEWLAVISYDGWTKYYADSVKGRFTISR DNSKNTLSLQMDSLRPEDTAVYYCVRGTDYGDSWGQGTLVTVSS (SEQ ID NO: 181) |
| | VL | QSVVTQPPSVSAAPGQKVTISCSGSSSNIGNNYVSWYQQFPGTAPKFLIYENNKRPSGIPDRFSGSKSGTSA TLGITGLQTGDEADYYCGTWDNSLSAWVFGGGTKVTVL (SEQ ID NO: 182) |

TABLE 2-continued

HCVR/LCVR sequences of exemplary anti-SARS-COV-2 S antibodies

| Clone | | Heavy Chain variable (VH) and Light Chain variable (LH) sequences |
|---|---|---|
| 22-E7 | VH | QVQLVESGGGVVQPGTSLRLSCAASGFTFNNYPMFWVRQAPGKGLEWLALISYDGNHKVYADSVKGRFTISR DNAKNTLYLQMHSLRAEDTALYYCASDLSGAEDSWGQGTLVTVSS (SEQ ID NO: 183) |
| | VL | QSALTQPASVSGSPGQSITISCTGTSSDVGGYNYVSWYQQHPGKAPKLLIYEVSNRPSGVSNRFSGSKSGNT ASLTISGLQAEDEADYYCSSYTSSSTWVFGGGTKLTVL (SEQ ID NO: 184) |
| 6-A4 | VH | QVQLVESGGGVVQPARSLRLSCAASGFTLSDYPMHWVRQAPGKGLEWVALMSYDGSLKFYADSVKGRSTISR DISENTMYLQMNSLRAEDTAVYYCARGNSDGDFDYWGRGTLVTVSS (SEQ ID NO: 185) |
| | VL | SYVLTQPPSVSVAPGQTATITCGGRDIGSRSVHWYQQTPGQAPVLVVYDDTARPSEIRARFSGFNSGNTATL TISRVEAGDEATYYCQAWDSSTVVFGGGTKLTVL (SEQ ID NO: 186) |
| 6-E1 | VH | QVQLVESGGGVVQPGTSLRLSCAASGFSFNTFPMHWVRQTPGKGLEWVASISYDGSFKFYADSVKGRFTISR DNSKNTLILQLNSLRAEDTAVYYCASPGDSDWADFENWGQGTTVTVSS (SEQ ID NO: 187) |
| | VL | QSVLTQPPSVSGAPGQRVTISCTGSSSNIGAGYDVHWYQQLPGTAPKLLIYGNSNRPSGVPDRFSGSKSGTS ASLAITGLQAEDEADYYCQSYDSSLSGYVFGTGTKVTVL (SEQ ID NO: 188) |
| 6-F2 | VH | QVQLVESGGGVVQPGRSLRLSCEASGFNFSLYGMHWVRQAPGKGLEWMAVISYDGSQKYYADSVKGRFTISR DNSKNTMYLQMNSLRAEDTAVYYCVKGEGSLDYWGQGTLVTVSS (SEQ ID NO: 189) |
| | VL | QSALTQPASASGSPGQSVTISCTGTTSDVGGYGYVSWYQHPGKAPQLLIYEVAKRPSGVPDRFSGSKSGNT ASLTISGLQAEDEADYYCVSYTLSSLVVFGGGTKLTVL (SEQ ID NO: 190) |
| 15-E4 | VH | QVQLQESGGGLVQSGGSLKLSCAASGSIPSVNVMGWYRQAPGKQRELVAAVTSDGRTNYADSVKGRFTVSRD NAKNTVALQMDSLKPEDTAVYYCLITNQDHNTLGVGKGTLVTVSS (SEQ ID NO: 196) |
| | VL | N/A |
| 2-A6 | VH | QVTLRESGPALVKPTQTLTLTCTFSGFSLNTRGMSVSWIRQPPGKALEWLALIDWEDDKFYRTSLMTRLTIS KDIFKNQVVLTMTNVDPVDTGTYYCARTYSVGVKYFGMDVWGQGTTVTVSS (SEQ ID NO: 191) |
| | VL | SSELTQDPAVSVALGQTVRITCQGDSLRNYYASWYRQEPGQAPILLIYGGNYRPSGIPDRFSGSSSGNTASL TITGAQAEDEADYYCNSRDSSGNHVVFGGGTKLTVL (SEQ ID NO: 192) |
| 15-C8 | VH | QVQLQESGGGLVQSGGSRRLSCAVSGNVTSITLMGWYRHAPGKQREAVGIINDDDRTRYEDSMKGRFTISRD PAKNMLYLQMTNLKPEDTAVYYCSAKAGGNFYMGQGTQVTVSS (SEQ ID NO: 193) |
| | VL | N/A |
| 15-F7 | VH | QVQLQESGGGLVQSGGSLKLSCAASGSIPSVNVMGWYRQAPGKQRELVAAVTSDGRTNYADSVKGRFTVSRD NAKNTVALQMDSLKPEDTAVYYCLITNSDHNTLGVGKGTLVTVSS (SEQ ID NO: 194) |
| | VL | N/A |
| 15-H3 | VH | QVQLQQSGGGLVQSGGSLKLSCAASGSIPSVNVMGWYRQAPGKQRELVAAVTSDGRTSYADSVKGRFTVSRD NAKNTVALQMDSLKPEDTAVYYCLITNSDHNTLGVGKGTLVTVSS (SEQ ID NO: 195) |
| | VL | N/A |

N/A = not applicable (VHHs that do not comprise a light chain)

The sequences defining the CDRs presented in Table 1 have been determined according to the IMGT definition. The skilled person would understand that the sequences defining the CDRs may vary depending on the definition (nomenclature) used to identify the regions in the variable heavy and light chains. As an example, the sequences defining the CDRs of the variable region of the heavy chain of clone 26-G2 as determined according to various definitions is presented below.

| Definition | HCDR1 | HCDR2 | HCDR3 |
|---|---|---|---|
| IMGT | GYSFTSYW (SEQ ID NO: 1) | IYPGDSDT (SEQ ID NO: 2) | ARLGDYSGMDV (SEQ ID NO: 3) |
| Chothia | GYSFTSY (SEQ ID NO: 204) | YPGDSD (SEQ ID NO: 205) | LGDYSGMDV (SEQ ID NO: 206) |
| Kabat | SYWIG (SEQ ID NO: 207) | IIYPGDSDTRYSPSFQG (SEQ ID NO: 208) | LGDYSGMDV (SEQ ID NO: 206) |
| AbM | GYSFTSYWIG (SEQ ID NO: 209) | IIYPGDSDTR (SEQ ID NO: 210) | LGDYSGMDV (SEQ ID NO: 206) |
| Contact | TSYWIG (SEQ ID NO: 211) | WMGIIYPGDSDTR (SEQ ID NO: 212) | ARLGDYSGMD (SEQ ID NO: 213) |

Thus, the present disclosure encompasses antibodies or antigen-binding fragments thereof comprising CDRs of the variable heavy and light chains of the antibodies or antigen-binding fragments depicted in Table 2 as determined according to any of the nomenclatures/definitions (e.g., IMGT, Chothia, Kabat, AbM, Contact).

In some embodiments, an antibody or antigen-binding fragment thereof is provided comprising HCDR1 of SEQ ID NO:1, a HCDR2 of SEQ ID NO:3 and a HCDR3 selected from SEQ ID Nos: 3, 34, 62, 73, 79 and 82. In related embodiments, the antibody or antigen-binding fragment thereof comprises a HCVR sequence selected from SEQ ID Nos:131, 145, 159, 165, 169 and 171.

In some embodiments, an antibody or antigen-binding fragment thereof is provided comprising a HCDR1 of SEQ ID NO:6, a HCDR2 selected from SEQ ID Nos: 7, 16 and 30 and a HCDR3 selected from SEQ ID Nos: 8, 17 and 31. In related embodiments, the antibody or antigen-binding fragment thereof comprises a HCVR sequence selected from SEQ ID Nos:133, 137 and 143.

In some embodiments, an antibody or antigen-binding fragment thereof is provided comprising a HCDR1 of SEQ ID NO:11, a HCDR2 of SEQ ID NO:12 and a HCDR3 of SEQ ID NO:13 or SEQ ID NO:84. In related embodiments, the antibody or antigen-binding fragment thereof comprises a HCVR sequence selected from SEQ ID Nos:135 and 173.

In some embodiments, an antibody or antigen-binding fragment thereof is provided comprising a HCDR1 of SEQ ID NO:20, a HCDR2 of SEQ ID NO:21 and a HCDR3 of SEQ ID NO:22. In related embodiments, the antibody or antigen-binding fragment thereof comprises a HCVR sequence of SEQ ID NO:139.

In some embodiments, an antibody or antigen-binding fragment thereof is provided comprising a HCDR1 of SEQ ID NO:25, a HCDR2 of SEQ ID NO:26 and a HCDR3 of SEQ ID NO:27. In related embodiments, the antibody or antigen-binding fragment thereof comprises a HCVR sequence of SEQ ID NO:141 or 175.

In some embodiments, an antibody or antigen-binding fragment thereof is provided comprising a HCDR1 of SEQ ID NO:36, a HCDR2 of SEQ ID NO:16 and a HCDR3 of SEQ ID NO:17. In related embodiments, the antibody or antigen-binding fragment thereof comprises a HCVR sequence of SEQ ID NO:147.

In some embodiments, an antibody or antigen-binding fragment thereof is provided comprising a HCDR1 of SEQ ID NO:39, a HCDR2 of SEQ ID NO:40 and a HCDR3 of SEQ ID NO:41. In related embodiments, the antibody or antigen-binding fragment thereof comprises a HCVR sequence of SEQ ID NO:149.

In some embodiments, an antibody or antigen-binding fragment thereof is provided comprising a HCDR1 of SEQ ID NO:45, a HCDR2 of SEQ ID NO:46 and a HCDR3 of SEQ ID NO:47. In related embodiments, the antibody or antigen-binding fragment thereof comprises a HCVR sequence of SEQ ID NO:151.

In some embodiments, an antibody or antigen-binding fragment thereof is provided comprising a HCDR1 of SEQ ID NO:50, a HCDR2 of SEQ ID NO:51 and a HCDR3 of SEQ ID NO:52 or SEQ ID NO:53. In related embodiments, the antibody or antigen-binding fragment thereof comprises a HCVR sequence of SEQ ID No:153 or 154.

In some embodiments, an antibody or antigen-binding fragment thereof is provided comprising a HCDR1 of SEQ ID NO:54, a HCDR2 of SEQ ID NO:55, and a HCDR3 of SEQ ID NO:56. In related embodiments, the antibody or antigen-binding fragment thereof comprises a HCVR sequence of SEQ ID NO:155 or 214.

In some embodiments, an antibody or antigen-binding fragment thereof is provided comprising a HCDR1 of SEQ ID NO:57, a HCDR2 of SEQ ID NO:58, and a HCDR3 of SEQ ID NO:59. In related embodiments, the antibody or antigen-binding fragment thereof comprises a HCVR sequence of SEQ ID NO:157 or 215.

In some embodiments, an antibody or antigen-binding fragment thereof is provided comprising a HCDR1 of SEQ ID NO:64, a HCDR2 of SEQ ID NO:65 or 69, and a HCDR3 of SEQ ID NO:66 or 70. In related embodiments, the antibody or antigen-binding fragment thereof comprises a HCVR sequence of SEQ ID NO:161 or 163.

In some embodiments, an antibody or antigen-binding fragment thereof is provided comprising a HCDR1 of SEQ ID NO:74, a HCDR2 of SEQ ID NO:75, and a HCDR3 of SEQ ID NO:76. In related embodiments, the antibody or antigen-binding fragment thereof comprises a HCVR sequence of SEQ ID NO:167.

In some embodiments, an antibody or antigen-binding fragment thereof is provided comprising a HCDR1 of SEQ ID NO:89, a HCDR2 of SEQ ID NO:90, and a HCDR3 of SEQ ID NO:91. In related embodiments, the antibody or antigen-binding fragment thereof comprises a HCVR sequence of SEQ ID NO:177.

In some embodiments, an antibody or antigen-binding fragment thereof is provided comprising a HCDR1 of SEQ ID NO:94, a HCDR2 of SEQ ID NO:95, and a HCDR3 of SEQ ID NO:96. In related embodiments, the antibody or antigen-binding fragment thereof comprises a HCVR sequence of SEQ ID NO:179.

In some embodiments, an antibody or antigen-binding fragment thereof is provided comprising a HCDR1 of SEQ ID NO:99, a HCDR2 of SEQ ID NO:100, and a HCDR3 of SEQ ID NO:101. In related embodiments, the antibody or antigen-binding fragment thereof comprises a HCVR sequence of SEQ ID NO:181.

In some embodiments, an antibody or antigen-binding fragment thereof is provided comprising a HCDR1 of SEQ ID NO:103, a HCDR2 of SEQ ID NO:104, and a HCDR3 of SEQ ID NO:105. In related embodiments, the antibody or antigen-binding fragment thereof comprises a HCVR sequence of SEQ ID NO:183.

In some embodiments, an antibody or antigen-binding fragment thereof is provided comprising a HCDR1 of SEQ ID NO:108, a HCDR2 of SEQ ID NO:109, and a HCDR3 of SEQ ID NO:110. In related embodiments, the antibody or antigen-binding fragment thereof comprises a HCVR sequence of SEQ ID NO:185.

In some embodiments, an antibody or antigen-binding fragment thereof is provided comprising a HCDR1 of SEQ ID NO:113, a HCDR2 of SEQ ID NO:114, and a HCDR3 of SEQ ID NO:115. In related embodiments, the antibody or antigen-binding fragment thereof comprises a HCVR sequence of SEQ ID NO:187.

In some embodiments, an antibody or antigen-binding fragment thereof is provided comprising a HCDR1 of SEQ ID NO:117, a HCDR2 of SEQ ID NO:118, and a HCDR3 of SEQ ID NO:119. In related embodiments, the antibody or antigen-binding fragment thereof comprises a HCVR sequence of SEQ ID NO:189.

In some embodiments, an antibody or antigen-binding fragment thereof is provided comprising a HCDR1 of SEQ ID NO:122, a HCDR2 of SEQ ID NO:123, and a HCDR3 of SEQ ID NO:124. In related embodiments, the antibody or antigen-binding fragment thereof comprises a HCVR sequence of SEQ ID NO:194,195 or 196.

In some embodiments, an antibody or antigen-binding fragment thereof is provided comprising a HCDR1 of SEQ ID NO:125, a HCDR2 of SEQ ID NO:126, and a HCDR3 of SEQ ID NO:127. In related embodiments, the antibody or antigen-binding fragment thereof comprises a HCVR sequence of SEQ ID NO:191.

In some embodiments, an antibody or antigen-binding fragment thereof is provided comprising a HCDR1 of SEQ ID NO:128, a HCDR2 of SEQ ID NO:129, and a HCDR3 of SEQ ID NO:130. In related embodiments, the antibody or antigen-binding fragment thereof comprises a HCVR sequence of SEQ ID NO:193.

In some embodiments, an antibody or antigen-binding fragment thereof is provided comprising an LCDR1 of SEQ ID NO:4, an LCDR2 of GND or NNI, and an LCDR3 of SEQ ID NO:5 or 63. In related embodiments, the antibody or antigen-binding fragment thereof comprises an LCVR sequence of SEQ ID NO:132 or 160.

In some embodiments, an antibody or antigen-binding fragment thereof is provided comprising an LCDR1 of SEQ ID NO:9, an LCDR2 of DNN or ENN, and an LCDR3 of SEQ ID NO:10 or 102. In related embodiments, the antibody or antigen-binding fragment thereof comprises an LCVR sequence of any one of SEQ ID NOs:134, 166 and 182.

In some embodiments, an antibody or antigen-binding fragment thereof is provided comprising an LCDR1 of SEQ ID NO:14, an LCDR2 of YDN or YDD and an LCDR3 of SEQ ID NO:15 or 5. In related embodiments, the antibody or antigen-binding fragment thereof comprises an LCVR sequence of SEQ ID NO:136 or 156.

In some embodiments, an antibody or antigen-binding fragment thereof is provided comprising an LCDR1 of SEQ ID NO:18, an LCDR2 of EDN and an LCDR3 of SEQ ID NO:19. In related embodiments, the antibody or antigen-binding fragment thereof comprises an LCVR sequence of SEQ ID NO:138.

In some embodiments, an antibody or antigen-binding fragment thereof is provided comprising an LCDR1 of SEQ ID NO:23, an LCDR2 of DDN and an LCDR3 of SEQ ID NO:24. In related embodiments, the antibody or antigen-binding fragment thereof comprises an LCVR sequence of SEQ ID NO:140.

In some embodiments, an antibody or antigen-binding fragment thereof is provided comprising an LCDR1 of SEQ ID NO:28, an LCDR2 of SAS and an LCDR3 of SEQ ID NO:29. In related embodiments, the antibody or antigen-binding fragment thereof comprises an LCVR sequence of SEQ ID NO:142.

In some embodiments, an antibody or antigen-binding fragment thereof is provided comprising an LCDR1 of SEQ ID NO:32, an LCDR2 of EDK and an LCDR3 of SEQ ID NO:33. In related embodiments, the antibody or antigen-binding fragment thereof comprises an LCVR sequence of SEQ ID NO:144.

In some embodiments, an antibody or antigen-binding fragment thereof is provided comprising an LCDR1 of SEQ ID NO:35, an LCDR2 of NNN and an LCDR3 of SEQ ID NO:5. In related embodiments, the antibody or antigen-binding fragment thereof comprises an LCVR sequence of SEQ ID NO:146.

In some embodiments, an antibody or antigen-binding fragment thereof is provided comprising an LCDR1 of SEQ ID NO:37, an LCDR2 of EDN and an LCDR3 of SEQ ID NO:38. In related embodiments, the antibody or antigen-binding fragment thereof comprises an LCVR sequence of SEQ ID NO:148.

In some embodiments, an antibody or antigen-binding fragment thereof is provided comprising an LCDR1 of SEQ ID NO:42, an LCDR2 of SEQ ID NO:43 and an LCDR3 of SEQ ID NO:44. In related embodiments, the antibody or antigen-binding fragment thereof comprises an LCVR sequence of SEQ ID NO:150.

In some embodiments, an antibody or antigen-binding fragment thereof is provided comprising an LCDR1 of SEQ ID NO:48, an LCDR2 of AND and an LCDR3 of SEQ ID NO:49. In related embodiments, the antibody or antigen-binding fragment thereof comprises an LCVR sequence of SEQ ID NO:152.

In some embodiments, an antibody or antigen-binding fragment thereof is provided comprising an LCDR1 of SEQ ID NO:60, an LCDR2 of YDD and an LCDR3 of SEQ ID NO:61. In related embodiments, the antibody or antigen-binding fragment thereof comprises an LCVR sequence of SEQ ID NO:158.

In some embodiments, an antibody or antigen-binding fragment thereof is provided comprising an LCDR1 of SEQ ID NO:67, an LCDR2 of YDY and an LCDR3 of SEQ ID NO:68. In related embodiments, the antibody or antigen-binding fragment thereof comprises an LCVR sequence of SEQ ID NO:162.

In some embodiments, an antibody or antigen-binding fragment thereof is provided comprising an LCDR1 of SEQ ID NO:71, an LCDR2 of ANS or GNS and an LCDR3 of SEQ ID NO:72 or 116. In related embodiments, the antibody or antigen-binding fragment thereof comprises an LCVR sequence of SEQ ID NO:164 or 188.

In some embodiments, an antibody or antigen-binding fragment thereof is provided comprising an LCDR1 of SEQ ID NO:77, an LCDR2 of RDS and an LCDR3 of SEQ ID NO:78. In related embodiments, the antibody or antigen-binding fragment thereof comprises an LCVR sequence of SEQ ID NO:168.

In some embodiments, an antibody or antigen-binding fragment thereof is provided comprising an LCDR1 of SEQ ID NO:80, an LCDR2 of TNN and an LCDR3 of SEQ ID NO:81. In related embodiments, the antibody or antigen-binding fragment thereof comprises an LCVR sequence of SEQ ID NO:170.

In some embodiments, an antibody or antigen-binding fragment thereof is provided comprising an LCDR1 of SEQ ID NO:83, an LCDR2 of RND and an LCDR3 of SEQ ID NO:5. In related embodiments, the antibody or antigen-binding fragment thereof comprises an LCVR sequence of SEQ ID NO:172.

In some embodiments, an antibody or antigen-binding fragment thereof is provided comprising an LCDR1 of SEQ ID NO:85, an LCDR2 of AAS and an LCDR3 of SEQ ID NO:86. In related embodiments, the antibody or antigen-binding fragment thereof comprises an LCVR sequence of SEQ ID NO:174

In some embodiments, an antibody or antigen-binding fragment thereof is provided comprising an LCDR1 of SEQ ID NO:87, an LCDR2 of YDT and an LCDR3 of SEQ ID NO:88. In related embodiments, the antibody or antigen-binding fragment thereof comprises an LCVR sequence of SEQ ID NO:176.

In some embodiments, an antibody or antigen-binding fragment thereof is provided comprising an LCDR1 of SEQ ID NO:92, an LCDR2 of DVS and an LCDR3 of SEQ ID NO:93. In related embodiments, the antibody or antigen-binding fragment thereof comprises an LCVR sequence of SEQ ID NO:178.

In some embodiments, an antibody or antigen-binding fragment thereof is provided comprising an LCDR1 of SEQ ID NO:97, an LCDR2 of WAS and an LCDR3 of SEQ ID NO:98. In related embodiments, the antibody or antigen-binding fragment thereof comprises an LCVR sequence of SEQ ID NO:180.

In some embodiments, an antibody or antigen-binding fragment thereof is provided comprising an LCDR1 of SEQ ID NO:106, an LCDR2 of EVS and an LCDR3 of SEQ ID NO:107. In related embodiments, the antibody or antigen-binding fragment thereof comprises an LCVR sequence of SEQ ID NO:184.

In some embodiments, an antibody or antigen-binding fragment thereof is provided comprising an LCDR1 of SEQ ID NO:111 an LCDR2 of DDT and an LCDR3 of SEQ ID NO:112. In related embodiments, the antibody or antigen-binding fragment thereof comprises an LCVR sequence of SEQ ID NO:186.

In some embodiments, an antibody or antigen-binding fragment thereof is provided comprising an LCDR1 of SEQ ID NO:120 an LCDR2 of EVA and an LCDR3 of SEQ ID NO:121. In related embodiments, the antibody or antigen-binding fragment thereof comprises an LCVR sequence of SEQ ID NO:190.

In related embodiments, an antibody or antigen-binding fragment thereof is provided comprising a HCVR comprising HCDR1, HCDR2 and HCDR3 a described above and an LCVR comprising LCDR1, LCDR2 and LCDR3 as described above.

In some embodiments, an antibody or antigen-binding fragment thereof is provided that specifically binds the RBD of SARS-CoV-2 S1 and comprises:
  a HCVR of SEQ ID NO:131 and an LCVR of SEQ ID NO:132;
  a HCVR of SEQ ID NO:133 and an LCVR of SEQ ID NO:134;
  a HCVR of SEQ ID NO:135 and an LCVR of SEQ ID NO:136;
  a HCVR of SEQ ID NO:137 and an LCVR of SEQ ID NO:138;
  a HCVR of SEQ ID NO:139 and an LCVR of SEQ ID NO:140;
  a HCVR of SEQ ID NO:141 and an LCVR of SEQ ID NO:142;
  a HCVR of SEQ ID NO:143 and an LCVR of SEQ ID NO:144;
  a HCVR of SEQ ID NO:145 and an LCVR of SEQ ID NO:146;
  a HCVR of SEQ ID NO:147 and an LCVR of SEQ ID NO:148;
  a HCVR of SEQ ID NO:149 and an LCVR of SEQ ID NO:150;
  a HCVR of SEQ ID NO:151 and an LCVR of SEQ ID NO:152;
  a HCVR of SEQ ID NO:153;
  a HCVR of SEQ ID NO:154;
  a HCVR of SEQ ID NO:155 or 214 and an LCVR of SEQ ID NO:156;
  a HCVR of SEQ ID NO:157 or 215 and an LCVR of SEQ ID NO:158;
  a HCVR of SEQ ID NO:159 and an LCVR of SEQ ID NO:160;
  a HCVR of SEQ ID NO:161 and an LCVR of SEQ ID NO:162;
  a HCVR of SEQ ID NO:163 and an LCVR of SEQ ID NO:164;
  a HCVR of SEQ ID NO:165 and an LCVR of SEQ ID NO:166;
  a HCVR of SEQ ID NO:167 and an LCVR of SEQ ID NO:168;
  a HCVR of SEQ ID NO:169 and an LCVR of SEQ ID NO:170;
  a HCVR of SEQ ID NO:171 and an LCVR of SEQ ID NO:172;
  a HCVR of SEQ ID NO:173 and an LCVR of SEQ ID NO:174; or
  a HCVR of SEQ ID NO:175 and an LCVR of SEQ ID NO:176.

In some embodiments, an antibody or antigen-binding fragment thereof is provided that specifically binds the SARS-CoV-2 S1 subunit in a region outside the RBD and comprises:
  a HCVR of SEQ ID NO:177 and an LCVR of SEQ ID NO:178;
  a HCVR of SEQ ID NO:179 and an LCVR of SEQ ID NO:180;
  a HCVR of SEQ ID NO:181 and an LCVR of SEQ ID NO:182;
  a HCVR of SEQ ID NO:183 and an LCVR of SEQ ID NO:184;
  a HCVR of SEQ ID NO:185 and an LCVR of SEQ ID NO:186;
  a HCVR of SEQ ID NO:187 and an LCVR of SEQ ID NO:188; or
  a HCVR of SEQ ID NO:189 and an LCVR of SEQ ID NO:190.

In some embodiments, an antibody or antigen-binding fragment thereof is provided that specifically binds the SARS-CoV-2 S2 subunit and comprises:
  a HCVR of SEQ ID NO:191 and an LCVR of SEQ ID NO:192;
  a HCVR of SEQ ID NO:193;
  a HCVR of SEQ ID NO:194;
  a HCVR of SEQ ID NO:195; or
  a HCVR of SEQ ID NO:196.

Antigen-Binding Fragments of Antibodies

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen (e.g., SARS-CoV-2 Spike protein) to form a complex. The terms "antigen-binding fragment" of an antibody, or "antibody fragment", as used herein, refers to one or more fragments of an antibody that retain the ability to specifically bind to SARS-CoV-2 Spike protein. An antibody fragment may include a Fab fragment, a F(ab')2 fragment, a Fv fragment, a dAb fragment, a fragment containing a CDR, or an isolated CDR. In certain embodiments, the term "antigen-binding fragment" refers to a polypeptide fragment of a multi-specific antigen-binding molecule. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a VH domain associated with a VL domain, the VH and VL domains may be situated relative to one another in any suitable arrangement. For example, the variable region may be dimeric and contain VH-VH, VH-VL or VL-VL dimers. Alternatively, the antigen-binding fragment of an antibody may contain a monomeric VH or VL domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) VH-CH1; (ii) VH-CH2; (iii) VH-CH3; (iv) VH-CH1-CH2; (v) VH-CH1-CH2-CH3, (vi) VH-CH2-CH3; (vii) VH-CL; (viii) VL-CH1; (ix) VL-CH2; (x) VL-CH3; (xi) VL-CH1-CH2; (xii) VL-CH1-CH2-CH3; (xiii) VL-CH2-CH3, and (xiv) VL-CL. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric VH or VL domain (e.g., by disulfide bond(s)).

As with full antibody molecules, antigen-binding fragments may be mono-specific or multi-specific (e.g., bi-specific), as described below.

Multi-Specific Antibodies or Antigen-Binding Fragments

Antibodies or antigen-binding fragments thereof described herein may be monospecific, bispecific, or multi-specific. Multi-specific antibodies or antigen-binding fragments thereof may be specific for different epitopes of one target polypeptide or may contain antigen-binding domains specific for more than one target polypeptide. See, e.g., Tutt et al., 1991, *J. Immunol.* 147:60-69; Kufer et al., 2004, *Trends Biotechnol.* 22:238-244.

Any of the multi-specific antigen-binding molecules of the disclosure, or variants thereof, may be constructed using standard molecular biological techniques (e.g., recombinant DNA and protein expression technology), as will be known to a person of ordinary skill in the art.

In some embodiments, SARS-CoV-2 Spike protein-specific antibodies or antigen-binding fragments thereof are generated in a bispecific format (a "bispecific") in which variable regions binding to distinct domains of SARS-CoV-2 Spike protein are linked together to confer dual-domain specificity within a single binding molecule. Appropriately designed bispecifics may enhance overall SARS-CoV-2 Spike protein inhibitory efficacy through increasing both specificity and binding avidity. Variable regions with specificity for individual domains, (e.g., segments of the N-terminal domain), or that can bind to different regions within one domain, are paired on a structural scaffold that allows each region to bind simultaneously to the separate epitopes, or to different regions within one domain. In one example for a bispecific, heavy chain variable regions (VH or VH) from a binder with specificity for one domain are recombined with light chain variable regions (VL or VL) from a series of binders with specificity for a second domain to identify non-cognate VL partners that can be paired with an original VH without disrupting the original specificity for that VH. In this way, a single VL segment (e.g., VL1) can be combined with two different VH domains (e.g., VH1 and VH2) to generate a bi-specific comprised of two binding "arms" (VH1-VL1 and VH2-VL1). Use of a single VL segment reduces the complexity of the system and thereby simplifies and increases efficiency in cloning, expression, and purification processes used to generate the bispecific (See, for example, US2010/0331527).

Alternatively, antibodies or antigen-binding fragments thereof that bind more than one domains and a second target, such as, but not limited to, for example, a second different anti-SARS-CoV-2 Spike protein antibody, may be prepared in a bispecific format using techniques described herein, or other techniques known to those skilled in the art. Antibody variable regions binding to distinct regions may be linked together with variable regions that bind to relevant sites on, for example, the extracellular domain of SARS-CoV-2 Spike protein, to confer dual-antigen specificity within a single binding molecule. Appropriately designed bispecifics of this nature serve a dual function. Variable regions with specificity for the extracellular domain are combined with a variable region with specificity for outside the extracellular domain and are paired on a structural scaffold that allows each variable region to bind to the separate antigens.

An exemplary bispecific antibody format that can be used in the context of the present disclosure involves the use of a first immunoglobulin (Ig) CH3 domain and a second Ig CH3 domain, wherein the first and second Ig CH3 domains differ from one another by at least one amino acid, and wherein at least one amino acid difference reduces binding of the bispecific antibody to Protein A as compared to a bispecific antibody lacking the amino acid difference. In one embodiment, the first Ig CH3 domain binds Protein A and the second Ig CH3 domain contains a mutation that reduces or abolishes Protein A binding such as an H95R modification (by IMGT exon numbering; H435R by EU numbering). The second CH3 may further comprise a Y96F modification (by IMGT; Y436F by EU). Further modifications that may be found within the second CH3 include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bispecific antibody format described above are contemplated within the scope of the present disclosure.

Other exemplary bispecific formats that can be used in the context of the present disclosure include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al. (2012) Site-specific DNA-antibody conjugates for specific and sensitive immuno-PCR, *PNAS* 109 (10) 3731-3736; DOI: 10.1073/pnas.1120682109), U.S. Pat. Nos. 4,496,689; 4,301,144; 4,670,417; 4,791,192 or 4,179,337.

The antibody or antigen-binding fragment thereof may further comprise one or more modifications that confer additional biological properties to the antibody or antigen-binding fragment thereof such as increased protease resistance, reduced plasma protein binding, increased plasma half-life, increased intracellular penetration, increased storage stability, increased expression, reduced aggregation, etc. Such modifications include, for example, covalent attachment of molecules/moiety to the antibody or antigen-binding fragment thereof such as fatty acids (e.g., $C_6$-$C_{18}$), attachment of proteins such as albumin (see, e.g., U.S. Pat. No. 7,268,113); sugars/polysaccharides (glycosylation), biotinylation or PEGylation (see, e.g., U.S. Pat. Nos. 7,256,258 and 6,528,485). The antibody or antigen-binding fragment thereof may also be mutated to remove a glycosylation site, e.g., by mutating one or more asparagine residues in the sequence of the heavy and/or light chain(s) of the antibody or antigen-binding fragment thereof. In an embodiment, the antibody or antigen-binding fragment thereof is an optimized version of antibody 21-F2 disclosed herein (or an antigen-binding fragment thereof) comprising a mutation at a glycosylation site, and comprises a VH chain comprising the sequence of SEQ ID NO:214. In another embodiment, the antibody or antigen-binding fragment thereof is an optimized version of antibody 22-D9 disclosed herein (or an antigen-binding fragment thereof) comprising a mutation at a glycosylation site, and comprises a VH chain comprising the sequence of SEQ ID NO:215.

The above description of modification of the antibody or antigen-binding fragment thereof does not limit the scope of the approaches nor the possible modifications that can be engineered. Thus, in another aspect, the present disclosure provides a conjugate comprising the antibody or antigen-binding fragment thereof described herein and one or more additional molecules or agents (hereinafter secondary molecules or agents). The antibody or antigen-binding fragment thereof may be conjugated to any type of synthetic or natural secondary molecules or agents, such as peptides. proteins, saccharides/polysaccharides, lipids, naturally-occurring or synthetic polymers/co-polymers, etc. to modify one or more properties of the antibody or antigen-binding fragment thereof.

In an embodiment, the conjugate comprises a covalent link or bond between the antibody or antigen-binding fragment thereof and the molecule conjugated thereto. The molecule may be conjugated directly to the antibody or antigen-binding fragment thereof, or indirectly via a linker. The linker may be a polypeptide linker comprising one or more amino acids or another type of chemical linker (e.g., a carbohydrate linker, a lipid linker, a fatty acid linker, a polyether linker, PEG, etc.

In another embodiment, the molecule may be conjugated/attached to the side chain of one the amino acids of the antibody or antigen-binding fragment thereof. Methods for conjugating moieties to side chains of amino acids are well known in the art. For example, chemical groups that react with primary amines (—$NH_2$) present in the side-chain of lysine residues such as isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters may be used to conjugate the molecule to the antigenic peptide. Most of these groups conjugate to amines by either acylation or alkylation. Cysteine residues present in the antibody or antigen-binding fragment thereof may also be used to attach the molecule.

In an embodiment, the antibody or antigen-binding fragment thereof is labelled or conjugated with one or more moieties. The antibody or antigen-binding fragment thereof may be labeled with one or more labels such as a biotin label, a fluorescent label, an enzyme label, a coenzyme label, a chemiluminescent label, or a radioactive isotope label. In an embodiment, the antibody or antigen-binding fragment thereof is labelled with a detectable label, for example a fluorescent moiety (fluorophore). Useful detectable labels include fluorescent compounds (e.g., fluorescein isothiocyanate, Texas red, rhodamine, fluorescein, Alexa Fluor® dyes, and the like), radiolabels, enzymes (e.g., horseradish peroxidase, alkaline phosphatase and others commonly used in a protein detection assays), streptavidin/biotin, and colorimetric labels such as colloidal gold, colored glass or plastic beads (e.g., polystyrene, polypropylene, latex, etc.). Chemiluminescent compounds may also be used. Such labelled antibodies or antigen-binding fragments thereof may be useful, for example, for the detection of SARS-CoV-2 and/or SARS-CoV-2-infected cells in vivo or in vitro, e.g., by flow cytometry, immunohistochemistry, etc. The antibody or antigen-binding fragment thereof can also be conjugated to detectable or affinity tags that facilitate detection and/or purification of the antibody or antigen-binding fragment thereof. Such tags are well known in the art. Examples of detectable or affinity tags include polyhistidine tags (His-tags), polyarginine tags, polyaspartate tags, polycysteine tags, polyphenylalanine tags, glutathione S-transferase (GST) tags, maltose binding protein (MBP) tags, calmodulin binding peptide (CBP) tags, Streptavidin/Biotin-based tags, HaloTag®, Profinity eXact® tags, epitope tags (such as FLAG, hemagglutinin (HA), HSV, S/S1, c-myc, KT3, T7, V5, E2, and Glu-Glu epitope tags), reporter tags such as β-galactosidase (β-gal), alkaline phosphatase (AP), chloramphenicol acetyl transferase (CAT), and horseradish peroxidase (HRP) tags (see, e.g., Kimple et al., *Curr Protoc Protein Sci.* 2013; 73: Unit-9.9).

Antibody Combinations or Cocktails

In some embodiments, a pharmaceutical combination (or "cocktail") is provided comprising two or more antibodies or antigen-binding fragments thereof as herein described. In some aspects, the combination is an additive or synergistic combination. In a further embodiment, the combination is a synergistic combination.

By "synergistic combination" it is meant that the combined action of two or more antibodies (or antigen-binding fragments thereof) generates a result that is greater than the sum of their individual effects as measured, e.g., by a lowering in $IC_{50}$ value in a live-virus cell-based neutralization assay. Synergy occurs when the combined action of two or more antibodies (or antigen-binding fragments thereof) is greater than would have been predicted based on the performance of the antibodies (or antigen-binding fragments thereof) when used alone.

By "additive combination" it is meant that the combined action of two or more antibodies (or antigen-binding fragments thereof) generates a result that corresponds to the additive effect of their individual components as measured by additive $IC_{50}$ values from the live-virus cell-based neutralization assay.

In an embodiment, the combination of antibodies has broad neutralization or inhibitor activity against SARS-CoV-2. In some preferred embodiments, the antibodies of the combination bind to distinct (e.g., non-overlapping) epitopes on the Spike protein (see FIG. 1E for a Venn diagram showing the blocking relationships between the bins) herein named bin1, 1a, 1b, 1c, 2, 3, 4, 5 (RBD), binC (S1 non-RBD non-NTD), and binS2 (S2 subunit). In some embodiments, antibodies falling within the following non-overlapping bins are combined and provide additive or synergistic effects; 1+3+5+S2; 1+4+5+S2; 1a+3+5+C+S2; 1a+4+5+C+S2; 2+4+5+C+S2.

In some embodiments, the pharmaceutical combination comprises (i) an antibody or antigen-binding fragment thereof comprising a heavy chain variable region and a light chain variable region each comprising a CDR1, CDR2 and CDR3 of clone 23-H7 (i.e., comprising HCDR1, HCDR2 and HCDR3 of SEQ ID NOs: 36, 16 and 17 and LCDR1 of SEQ ID NO:37, LCDR2 of EDN and LCDR3 of SEQ ID NO:38) and (ii) one or more antibodies or antigen-binding fragments thereof, each comprising a heavy chain variable region and a light chain variable region, each heavy chain variable region and light chain variable region comprising a CDR1, CDR2 and CDR3 of clone 2-A6, 8-A2, 23-A11, 30-C5, 22-D9 (or 22-D9-optimized), 21-F2 (or 21-F2-optimized), 23-H7, 22-F7, or 22-E7. In some embodiments, the combination comprises (i) an antibody or antigen-binding fragment thereof comprising heavy chain and light chain variable regions of SEQ ID NOs:147 and 148 (23-H7) and (ii) one or more antibodies or antigen-binding fragments thereof, each comprising a heavy and light chain variable region of SEQ ID NOs: 191 and 192 (2-A6), SEQ ID NOs:173 and 174 (8-A2), SEQ ID NOs:175 and 176 (23-A11), SEQ ID NOs:179 and 180 (30-C05), SEQ ID NOs: 157 and 158 (22-D9), SEQ ID NOs:215 and 158 (22-D9-optimized), SEQ ID NOs: 155 and 156 (21-F2), SEQ ID NOs: 214 and 156 (21-F2-optimized) or SEQ ID NOs:183 and 184 (22-E7).

In some embodiments, a combination of two antibodies or antigen-binding fragments thereof is provided, one antibody or antigen-binding fragment thereof comprising a heavy chain variable region and a light chain variable region each comprising a CDR1, CDR2 and CDR3 of clone 23-H7 and the other comprising a heavy chain variable region and a light chain variable region each comprising a CDR1, CDR2 and CDR3 of one of 2-A6, 8-A2, 23-A11, 30-C5, 22-D9 (or 22-D9-optimized), 21-F2 (or 21-F2-optimized), 22-F7 and 22-E7. In a particular embodiment, a combination of two antibodies comprises (i) an antibody or antigen-binding fragment thereof comprising a heavy chain variable region and a light chain variable region each comprising a CDR1, CDR2 and CDR3 of clone 23-H7 and (ii) an antibody or antigen-binding fragment thereof comprising a heavy chain variable region and a light chain variable region each comprising a CDR1, CDR2 and CDR3 of clone 21-F2 (or 21-F2-optimized).

In some embodiments, a combination of three antibodies or antigen-binding fragments thereof is provided, one antibody or antigen-binding fragment thereof comprising a heavy chain variable region and a light chain variable region each comprising a CDR1, CDR2 and CDR3 of clone 23-H7 and the other two each comprising a heavy chain variable region and a light chain variable region each comprising a CDR1, CDR2 and CDR3, or VL/VH, of:
  22-D9 (or 22-D9-optimized) and one of 30-C5, 23-A11, 8-A2, and 2-A6;
  21-F2 (or 21-F2-optimized) and one of 30-C5, 23-A11, 8-A2, and 2-A6; or
  22-E7 and one of 21-F2 (or 21-F2-optimized) and 22-D9 (or 22-D9-optimized).

In a particular embodiment, a combination of three antibodies comprises (i) an antibody or antigen-binding fragment thereof comprising a heavy chain variable region and a light chain variable region each comprising a CDR1, CDR2 and CDR3 of clone 23-H7 (ii) an antibody or antigen-binding fragment thereof comprising a heavy chain variable region and a light chain variable region each comprising a CDR1, CDR2 and CDR3 of clone 21-F2 (or 21-F2-optimized) and (iii) an antibody or antigen-binding fragment thereof comprising a heavy chain variable region and a light chain variable region each comprising a CDR1, CDR2 and CDR3 of clone 22-E7 or 22-F7.

In some embodiments, a combination of four antibodies or antigen-binding fragments thereof is provided, one antibody or antigen-binding fragment thereof comprising a heavy chain variable region and a light chain variable region each comprising a CDR1, CDR2 and CDR3 of clone 23-H7 and the other three each comprising a heavy chain variable region and a light chain variable region each comprising a CDR1, CDR2 and CDR3, or VL/VH, of:
  22-D9 (or 22-D9-optimized), 30-C05 and one of 23-A11, 8-A2 and 2-A6;
  22-D9 (or 22-D9-optimized), 23-A11 and 22-E7
  22-D9 (or 22-D9-optimized), 2-A6 and 22-E7
  21-F2 (or 21-F2-optimized), 2-A6 and one of 22-E7 and 30-C05
  21-F2 (or 21-F2-optimized), 8-A2 and one of 22-E7 and 30-C05
  21-F2 (or 21-F2-optimized), 23-A11 and one of 22-E7 and 30-C05; or
  22-E7, 22-D9 (or 22-D9-optimized) and 8-A2.

In a particular embodiment, a combination of four antibodies comprises (i) an antibody or antigen-binding fragment thereof comprising a heavy chain variable region and a light chain variable region each comprising a CDR1, CDR2 and CDR3, or VL/VH, of clone 23-H7 (ii) an antibody or antigen-binding fragment thereof comprising a heavy chain variable region and a light chain variable region each comprising a CDR1, CDR2 and CDR3, or VL/VH, of clone 21-F2 (or 21-F2-optimized) (iii) an antibody or antigen-binding fragment thereof comprising a heavy chain variable region and a light chain variable region each comprising CDR1, CDR2 and CDR3, or VL/VH, of 8-A2 or 23-A11 and (iv) an antibody or antigen-binding fragment thereof comprising a heavy chain variable region and a light chain variable region each comprising a CDR1, CDR2 and CDR3, or VL/VH, of clone 22-E7 or 22-F7.

In another particular embodiment, a combination of four antibodies comprises (i) an antibody or antigen-binding fragment thereof comprising a heavy chain variable region and a light chain variable region each comprising a CDR1, CDR2 and CDR3, or VL/VH, of clone 23-H7 (ii) an antibody or antigen-binding fragment thereof comprising a heavy chain variable region and a light chain variable region each comprising a CDR1, CDR2 and CDR3, or VL/VH, of clone 21-F2 (or 21-F2-optimized) (iii) an antibody or antigen-binding fragment thereof comprising a heavy chain variable region and a light chain variable region each comprising a CDR1, CDR2 and CDR3, or VL/VH, of 8-A2 or 23-A11 and (iv) an antibody or antigen-binding fragment thereof comprising a heavy chain variable region and a light chain variable region each comprising a CDR1, CDR2 and CDR3, or VL/VH, of clone 2-A6.

In another particular embodiment, a combination of four antibodies comprises (i) an antibody or antigen-binding fragment thereof comprising a heavy chain variable region and a light chain variable region each comprising a CDR1, CDR2 and CDR3, or VL/VH, of clone 23-H7 (ii) an antibody or antigen-binding fragment thereof comprising a heavy chain variable region and a light chain variable region each comprising a CDR1, CDR2 and CDR3, or VL/VH, of clone 21-F2 (or 21-F2-optimized) (iii) an antibody or antigen-binding fragment thereof comprising a heavy chain variable region and a light chain variable region each comprising a CDR1, CDR2 and CDR3, or VL/VH, of 22-E7 or 22-F7 and (iv) an antibody or antigen-binding fragment thereof comprising a heavy chain variable region and a light chain variable region each comprising a CDR1, CDR2 and CDR3, or VL/VH, of clone 2-A6.

In some embodiments, a combination of five antibodies or antigen-binding fragments thereof is provided, one antibody or antigen-binding fragment thereof comprising a heavy chain variable region and a light chain variable region each comprising a CDR1, CDR2 and CDR3, or VL/VH, of clone 23-H7 and the other four each comprising a heavy chain variable region and a light chain variable region each comprising a CDR1, CDR2 and CDR3, or VL/VH, of:

22-D9 (or 22-D9-optimized), 30-C5, 2-A6 and one of 23-A11 and 8-A2
22-D9 (or 22-D9-optimized), 2-A6, 22-E7 and one of 23-A11 and 8-A2
21-F2 (or 21-F2-optimized), 8-A2, 22-E7 and 2-A6
21-F2 (or 21-F2-optimized), 23-A11, 22-E7 and 2-A6
21-F2 (or 21-F2-optimized), 23-A11, 30-C05 and 2-A6
21-F2 (or 21-F2-optimized), 30-C05, 8-A2 and 2-A6
22-E7, 21-F2 (or 21-F2-optimized), 8-A2 and 2-A6.

In a particular embodiment, a combination of five antibodies comprises (i) an antibody or antigen-binding fragment thereof comprising a heavy chain variable region and a light chain variable region each comprising a CDR1, CDR2 and CDR3, or VL/VH, of clone 23-H7 (ii) an antibody or antigen-binding fragment thereof comprising a heavy chain variable region and a light chain variable region each comprising a CDR1, CDR2 and CDR3, or VL/VH, of clone 21-F2 (or 21-F2-optimized) (iii) an antibody or antigen-binding fragment thereof comprising a heavy chain variable region and a light chain variable region each comprising a CDR1, CDR2 and CDR3, or VL/VH, of 8-A2 or 23-A11 (iv) an antibody or antigen-binding fragment thereof comprising a heavy chain variable region and a light chain variable region each comprising a CDR1, CDR2 and CDR3, or VL/VH, of 22-E7 or 22-F7 and (v) an antibody or antigen-binding fragment thereof comprising a heavy chain variable region and a light chain variable region each comprising a CDR1, CDR2 and CDR3, or VL/VH, of clone 2-A6.

In some embodiments, the pharmaceutical combination comprises (i) an antibody or antigen-binding fragment thereof comprising a heavy chain variable region and a light chain variable region each comprising a CDR1, CDR2 and CDR3, or VL/VH, of clone 22-D9 (or 22-D9-optimized) (i.e., comprising heavy chain CDR1, CDR2 and CDR3 of SEQ ID Nos:57-59 and light chain CDR1 of SEQ ID NO:60, CDR2 of YDD and CDR3 of SEQ ID NO:61) and (ii) one or more antibodies or antigen-binding fragments thereof, each comprising a heavy chain variable region and a light chain variable region, each heavy chain variable region and light chain variable region comprising a CDR1, CDR2 and CDR3, or VL/VH, of clone 2-A6, 8-A2, 23-A11, 30-C05, or 22-E7. In some preferred embodiments, the pharmaceutical combination has two antibodies or antigen-binding fragments thereof, the first antibody or antigen-binding fragment thereof comprising a heavy chain variable region and a light chain variable region each comprising a CDR1, CDR2 and CDR3, or VL/VH, of clone 22-D9 (or 22-D9-optimized) and the second antibody or antigen-binding fragment thereof comprising a heavy chain variable region and a light chain variable region, each comprising a CDR1, CDR2 and CDR3, or VL/VH, of clone 2-A6, 8-A2, 23-A11, 30-C05, or 22-E7. In some embodiments, the pharmaceutical combination comprises (i) an antibody or antigen-binding fragment thereof comprising a heavy chain variable region and a light chain variable region each comprising a CDR1, CDR2 and CDR3, or VL/VH, of clone 21-F2 (or 21-F2-optimized) (i.e., comprising heavy chain CDR1, CDR2 and CDR3 of SEQ ID Nos:54-56 and light chain CDR1 of SEQ ID NO:14, CDR2 of YDD and CDR3 of SEQ ID NO:5) and (ii) one or more antibodies or antigen-binding fragments thereof, each comprising a heavy chain variable region and a light chain variable region, each heavy chain variable region and light chain variable region comprising a CDR1, CDR2 and CDR3, or VL/VH, of clone 2-A6, 8-A2, 23-A11, 30-C05, or 22-E7. In some preferred embodiments, the pharmaceutical combination has two antibodies or antigen-binding fragments thereof, the first antibody or antigen-binding fragment thereof comprising a heavy chain variable region and a light chain variable region each comprising a CDR1, CDR2 and CDR3, or VL/VH, of clone 21-F2 (or 21-F2-optimized) and the second antibody or antigen-binding fragment thereof comprising a heavy chain variable region and a light chain variable region, each comprising a CDR1, CDR2 and CDR3, or VL/VH, of clone 2-A6, 8-A2, 23-A11, 30-C05, or 22-E7.

In some embodiments, the pharmaceutical combination comprises (i) an antibody or antigen-binding fragment thereof comprising a heavy chain variable region and a light chain variable region each comprising a CDR1, CDR2 and CDR3, or VL/VH, of clone 27-A11 (i.e., comprising heavy chain CDR1, CDR2 and CDR3 of SEQ ID NOs:6-8 and light chain CDR1 of SEQ ID NO:9, CDR2 of DNN and CDR3 of SEQ ID NO:10) and (ii) one or more antibodies or antigen-binding fragments thereof, each comprising a heavy chain variable region and a light chain variable region, each heavy chain variable region and light chain variable region comprising a CDR1, CDR2 and CDR3, or VL/VH, of clone 21-F2 (or 21-F2-optimized), 2-A6, 8-A2, or 22-E7.

In some embodiments, a combination of two antibodies or antigen-binding fragments thereof is provided, one antibody or antigen-binding fragment thereof comprising a heavy chain variable region and a light chain variable region each comprising a CDR1, CDR2 and CDR3, or VL/VH, of clone 27-A11 and the other comprising a heavy chain variable region and a light chain variable region each comprising a CDR1, CDR2 and CDR3, or VL/VH, of one of 21-F2 (or 21-F2-optimized), 2-A6, 8-A2, or 22-E7.

In some embodiments, a combination of three antibodies or antigen-binding fragments thereof is provided, a first antibody or antigen-binding fragment thereof comprising a heavy chain variable region and a light chain variable region each comprising a CDR1, CDR2 and CDR3, or VL/VH, of clone 27-A11 and the other two each comprising a heavy chain variable region and a light chain variable region each comprising a CDR1, CDR2 and CDR3, or VL/VH, of 21-F2 (or 21-F2-optimized) and one of 22-E7, 8-A2 and 2-A6.

In some embodiments, a combination of four antibodies or antigen-binding fragments thereof is provided, a first antibody or antigen-binding fragment thereof comprising a heavy chain variable region and a light chain variable region each comprising a CDR1, CDR2 and CDR3, or VL/VH, of clone 27-A11 and the other three each comprising a heavy chain variable region and a light chain variable region each comprising a CDR1, CDR2 and CDR3, or VL/VH, of 21-F2 (or 21-F2-optimized), 22-E7, and one of 8-A2 and 2-A6.

In some embodiments, a combination of five antibodies or antigen-binding fragments thereof is provided, a first antibody or antigen-binding fragment thereof comprising a heavy chain variable region and a light chain variable region each comprising a CDR1, CDR2 and CDR3, or VL/VH, of clone 27-A11 and the other four each comprising a heavy chain variable region and a light chain variable region each comprising a CDR1, CDR2 and CDR3, or VL/VH, of 21-F2 (or 21-F2-optimized), 22-E7, 8-A2 and 2-A6.

One or more antibodies of the combination may be administered prior to, concurrent with, or after the administration of one or more other antibodies of the combination. In embodiments wherein antibodies of the combination are administered sequentially, the antibodies are administered such that a therapeutically effective amount of each antibody of the combination in a subject overlaps for a period of time in the subject. For example, a first antibody of the combination may be deemed to be administered prior to a second antibody of the combination if the first antibody is administered 72 hours before, 60 hours before, 48 hours before, 36 hours before, 24 hours before, 12 hours before, 6 hours before, 2 hours before, 1 hour before, 30 minutes before, 15 minutes before, 5 minutes before, or less than one minute before the second antibody of the combination is administered. Concurrent administration includes, e.g., administration of antibodies of the combination to a subject in a single dosage form (wherein antibodies of the combination are co-formulated), or in separate dosage forms administered to the subject within about 30 minutes or less of each other. If administered in separate dosage forms, each dosage form may be administered via the same route or by different route. Administration of an antibody of a combination "prior to", "concurrent with," or "after" (as those terms are defined herein above) administration of another antibody of the combination is considered administration of the pharmaceutical combination.

In related embodiments, one or more antibodies or antigen-binding fragments as described herein is combined with an additional therapeutic agent used to treat a viral disease such as COVID-19 (e.g., to reduce viral load or ameliorate one or more symptoms or syndromes associated with SARS-CoV-2 infection). In some embodiments, the additional therapeutic agent is an anti-inflammatory drug (e.g., corticosteroids, preferably administered at a total daily dose equivalency to dexamethasone 6 mg) to prevent or treat a systemic inflammatory response associated with SARS-CoV-2 infection), and/or an antiviral agent (e.g., remdesivir, ivermectin, lopinavir/ritonavir) and/or immune-based therapies such as COVID-19 convalescent plasma and/or immunomodulators such as an interleukin (IL)-1 inhibitor, a beta interferon, an alpha interferon and antibodies that disrupt interaction of IL-6 with its receptor.

In some embodiments, pharmaceutical compositions comprising one or more antibodies of the combination are for administration to a subject by the subcutaneous, intravenous, intradermal, intrapulmonary, intraperitoneal, oral, intranasal, pulmonary, intramuscular or intracranial route.

Epitopes

The anti-SARS-CoV-2 Spike protein antibodies and antigen-binding fragments thereof as herein described interact with one or more amino acids found within one or more domains of the SARS-CoV-2 Spike protein, including the N-terminal S1 domain and C-terminal S2 domain. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within any of the domains of the SARS-CoV-2 Spike protein molecule (e.g., a linear epitope in a domain). Alternatively, the epitope may consist of a plurality of non-contiguous amino acids (or amino acid sequences) located within either or both of the aforementioned domains of the Spike protein molecule (e.g., a conformational epitope).

In certain aspects, an antibody or antigen-binding fragment thereof as herein described interacts with one or more amino acid residues in the receptor binding domain of SARS-CoV-2 Spike protein selected from amino acid residues 345 to 490 of SEQ ID NO: 197, preferably including at least 1, at least 2, at least 3, at least 4, at least 5, at least 6, at least 7, at least 8, at least 9, at least 10 or at least 11 of the following amino acid residues: Thr345, Arg346, Tyr351, Lys444, Asn450, Leu452, Arg466, Ile468, Thr470, Glu471, Gly482 and Phe490.

In other aspects, an antibody or antigen-binding fragment thereof as herein described interacts with one or more amino acid residues in the receptor binding domain of SARS-CoV-2 Spike protein selected from amino acid residues 417 to 505 of SEQ ID NO:197, preferably including at least 1, at least 2, at least 3, at least 4, at least 5, or at least 6 of the following amino acid residues: Lys417, Glu484, Phe486, Asn487, Tyr489, Asn493, and Tyr505.

Also provided herein are anti-SARS-CoV-2 antibodies or antigen-binding fragments thereof that bind to the same epitope, or a portion of the epitope, as any of the specific exemplary antibodies described herein and/or that compete for binding to SARS-CoV-2 Spike protein with any of the specific exemplary antibodies described herein. In some embodiments, provided herein are anti-SARS-CoV-2 antibodies or antigen-binding fragments thereof that bind to an epitope within the receptor binding domain (RBD) selected from an epitope defined herein as "bin1", "bin1a", "bin2", "bin3", "bin4" or "bin5". In other embodiments, provided herein are anti-SARS-CoV-2 antibodies or antigen-binding fragment thereof that bind outside the RBD selected from an epitope defined herein as "binC" or bin"S2".

One can easily determine whether an antibody or antigen-binding fragment thereof binds to the same epitope as, or competes for binding with, a reference anti-SARS-CoV-2 Spike protein antibody by using routine methods known in the art. For example, to determine if a test antibody binds to the same epitope as a reference anti-SARS-CoV-2 antibody of the present disclosure, the reference antibody is allowed to bind to a SARS-CoV-2 Spike protein or peptide under saturating conditions. Next, the ability of a test antibody to bind to the SARS-CoV-2 Spike protein molecule is assessed. If the test antibody is able to bind to SARS-CoV-2 Spike protein following saturation binding with the reference anti-SARS-CoV-2 Spike protein antibody, it can be concluded that the test antibody binds to a different epitope than the reference anti-SARS-CoV-2 Spike protein antibody. On the other hand, if the test antibody is not able to bind to the SARS-CoV-2 Spike protein following saturation binding with the reference anti-SARS-CoV-2 spike protein antibody, then the test antibody may bind to the same epitope as the epitope bound by the reference anti-SARS-CoV-2 Spike protein antibody of the disclosure.

To determine if an antibody competes for binding with a reference anti-SARS-CoV-2 Spike protein antibody, the above-described binding methodology is performed in two orientations: In a first orientation, the reference antibody is allowed to bind to a SARS-CoV-2 Spike protein under saturating conditions followed by assessment of binding of the test antibody to the SARS-CoV-2 Spike protein molecule. In a second orientation, the test antibody is allowed to bind to a SARS-CoV-2 Spike protein molecule under saturating conditions followed by assessment of binding of the reference antibody to the SARS-CoV-2 Spike protein molecule. If, in both orientations, only the first (saturating) antibody is capable of binding to the SARS-CoV-2 Spike protein molecule, then it is concluded that the test antibody and the reference antibody compete for binding to SARS-CoV-2 Spike protein. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other as well.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, biolayer interferometry, flow cytometry or any other quantitative or qualitative antibody-binding assay available in the art.

Nucleic Acids and Cells

A further aspect of the present disclosure provides nucleic acids encoding the antibody or antigen-binding fragment described herein, e.g., encoding the light and heavy chains of the antibody or antigen-binding fragment. The isolated nucleic acid may be a synthetic DNA, an mRNA (e.g., a non-naturally occurring mRNA), or a cDNA, for example.

The nucleic acid may be inserted within a plasmid, vector, or transcription or expression cassette. The nucleic acids encoding the antibody or antigen-binding fragment described herein may be made and the expressed antibodies or antigen-binding fragments described may be tested using conventional techniques well known in the art. In some embodiments, the nucleic acid encoding the antibody or antigen-binding fragment described herein can be maintained in the vector in a host cell. In some embodiments, the nucleic acid is an expression vector. In some embodiments, the nucleic acid sequence encoding the antibody can be maintained in the vector in a host cell. In embodiment, the nucleic acid(s) (DNA, mRNA) encoding the antibody or antigen-binding fragment described herein of the disclosure is comprised within a vesicle such as lipid nanoparticles (e.g., liposomes) or any other suitable vehicle. In an embodiment, the nucleic acid(s) is/are mRNA and is/are encapsulated into nanoparticulate delivery vehicles (see, e.g., Van Hoecke and Roose (2019) How mRNA therapeutics are entering the monoclonal antibody field, J. Transl. Med. 17, 54. doi.org/10.1186/s12967-019-1804-8; Sanz and Álvarez-Vallina (2021) Engineered mRNA and the Rise of Next-Generation Antibodies, Antibodies 10(4):37. doi.org/10.3390/antib10040037).

In another aspect, the present disclosure provides a cell, for example a recombinant host cell, expressing the antibody or antigen-binding fragment described herein. Methods of preparing antibodies or antigen-binding fragments comprise expressing the encoding nucleic acid(s) in a host cell under conditions to produce the antibodies or antigen-binding fragments, and recovering the antibodies or antigen-binding fragments. The process of recovering the antibodies or antigen-binding fragments may comprise isolation and/or purification of the antibodies or antigen-binding fragments. The method of production may comprise formulating the antibodies or antigen-binding fragments into a composition including at least one additional component, such as a pharmaceutically acceptable excipient. In another aspect, provided herein is a cell expressing one or more antibodies of the disclosure.

The term "recombinant host cell" (or simply "host cell"), as used herein, is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. Preferably host cells include prokaryotic and eukaryotic cells selected from any of the Kingdoms of life. To produce the antibody or antigen-binding fragment thereof recombinantly, the nucleic acid or nucleic acids encoding the light and heavy chains of the antibody or antigen-binding fragment thereof are introduced in a cell which is able to produce the recombinant antibody. Examples thereof include CHO-K1 (ATCC CCL-61), DUkXB11 (ATCC CCL-9096), Pro-5 (ATCC CCL-1781), CHO-S(Life Technologies®, Cat #11619), rat myeloma cell YB2/3HL.P2.G11.16Ag.20 (also called YB2/0), mouse myeloma cell NSO, mouse myeloma cell SP2/0-Ag14 (ATCC No. CRL1581), mouse P3-X63-Ag8653 cell (ATCC No. CRL1580), CHO cell in which a dihydrofolate reductase gene is defective, lectin resistance-acquired Lec13, CHO cell in which α1,6-fucosyltransaferse gene is defective, rat YB2/3HL.P2.G11.16Ag.20 cell (ATCC No. CRL1662), CHO-3E7 cells (expressing a truncated but functional form of EBNA1, U.S. Pat. No. 8,637,315) or the like. After introduction of the expression vector, transformants which stably express a recombinant antibody are selected by culturing them in a medium for animal cell culture containing an agent such as G418 sulfate or the like. Examples of the medium for animal cell culture include RPM11640 medium (manufactured by Invitrogen®), GIT medium (manufactured by Nihon Pharmaceutical®), EX-CELL301® medium (manufactured by JRH®), IMDM medium (manufactured by Invitrogen®), Hybridoma-SFM medium (manufactured by Invitrogen®), media obtained by adding various additives such as FBS to these media, or the like. The recombinant antibody can be produced and accumulated in a culture supernatant by culturing the obtained transformants in a medium. The expression level and antigen binding activity of the recombinant antibody in the culture supernatant can be measured by ELISA or the like. Also, in the transformant, the expression level of the recombinant antibody can be increased by using DHFR amplification system or the like. The recombinant antibody can be purified from the culture supernatant of the transformant by using a protein A column. In addition, the recombinant antibody can be purified by combining the protein purification methods such as gel filtration, ion-exchange chromatography, ultrafiltration or the like. The molecular weight of the H chain or the L chain of the purified recombinant antibody or the antibody molecule as a whole is determined by polyacrylamide gel electrophoresis, Western blotting, or the like.

Suitable vectors comprising nucleic acid(s) encoding the antibody or antigen-binding fragment described herein can be chosen or constructed, containing appropriate regulatory sequences, including promoter sequences, terminator sequences, polyadenylation sequences, enhancer sequences, marker genes and other sequences as appropriate. Vectors may be plasmids, phage, phagemids, adenoviral, AAV, lentiviral, for example. Techniques and protocols for manipulation of nucleic acid, for example in preparation of nucleic acid constructs, mutagenesis, sequencing, introduction of DNA into cells, and gene expression, are well known in the art.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome.

Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions.

Introducing such nucleic acids into a host cell can be accomplished using techniques well known in the art. For eukaryotic cells, suitable techniques may include calcium phosphate transfection, DEAE-Dextran, electroporation, liposome-mediated transfection, and transduction using retroviruses or other viruses, for example. For bacterial cells, suitable techniques may include calcium chloride transformation, electroporation, and transfection using bacteriophage. The introduction may be followed by causing or allowing expression from the nucleic acid, e.g. by culturing host cells under conditions for expression of the gene. In one embodiment, the nucleic acid of the disclosure is integrated into the genome, e.g., chromosome, of the host cell. Integration may be promoted by inclusion of sequences which promote recombination with the genome, in accordance with standard techniques.

Therapeutic Compositions

Also provided are therapeutic compositions comprising the anti-SARS-CoV-2 Spike protein antibodies or antigen-binding fragments thereof, or nucleic acids encoding such antibodies or antigen-binding fragments thereof, as described herein. Pharmaceutical compositions are generally administered with suitable carriers, excipients, and other agents that are incorporated into formulations to provide e.g. improved transfer, delivery, tolerance, and include formulations described in Remington's Pharmaceutical Sciences, Mack Publishing Company, Easton, Pa., which formulations include, for example, powders, pastes, ointments, jellies, waxes, oils, lipids, lipid (cationic or anionic) containing vesicles, DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) *J Pharm Sci Technol* 52:238-311.

The carrier/excipient can be suitable for administration of the antibody or an antigen-binding fragment thereof, or the nucleic acid(s) encoding the antibody or antigen-binding fragment thereof, by any conventional administration route, for example, for oral, intravenous, parenteral, subcutaneous, intramuscular, intracranial, intraorbital, ophthalmic, intraventricular, intracapsular, intraspinal, intrathecal, epidural, intracisternal, intraperitoneal, intranasal or pulmonary (e.g., aerosol) administration. In an embodiment, the carrier/excipient is adapted for administration of the antibody or an antigen-binding fragment thereof by the intravenous or subcutaneous route. In an embodiment, the carriers/excipients are adapted for administration of the antibody or an antigen-binding fragment thereof, or the nucleic acid(s) encoding the antibody or antigen-binding fragment thereof, by the intravenous route. In another embodiment, the carriers/excipients are adapted for administration of the antibody or an antigen-binding fragment thereof, or the nucleic acid(s) encoding the antibody or antigen-binding fragment thereof, by the subcutaneous route.

An "excipient" as used herein has its normal meaning in the art and is any ingredient that is not an active ingredient (drug) itself. Excipients include for example binders, lubricants, diluents, fillers, thickening agents, disintegrants, plasticizers, coatings, barrier layer formulations, lubricants, stabilizing agent, release-delaying agents and other components. "Pharmaceutically acceptable excipient" as used herein refers to any excipient that does not interfere with effectiveness of the biological activity of the active ingredients (the antibody or an antigen-binding fragment thereof, or the nucleic acid(s) encoding the antibody or antigen-binding fragment thereof) and that is not toxic to the subject, i.e., is a type of excipient and/or is for use in an amount which is not toxic to the subject. Excipients are well known in the art, and the present system is not limited in these respects. In certain embodiments, one or more formulations of the dosage form include excipients, including for example and without limitation, one or more binders (binding agents), thickening agents, surfactants, diluents, release-delaying agents, colorants, flavoring agents, fillers, disintegrants/dissolution promoting agents, lubricants, plasticizers, silica flow conditioners, glidants, anti-caking agents, anti-tacking agents, stabilizing agents, anti-static agents, swelling agents and any combinations thereof. As those of skill would recognize, a single excipient can fulfill more than two functions at once, e.g., can act as both a binding agent and a thickening agent. As those of skill will also recognize, these terms are not necessarily mutually exclusive. Examples of commonly used excipient include water, saline, phosphate buffered saline, dextrose, glycerol, ethanol, and the like, as well as combinations thereof. In many cases, it will be preferable to include isotonic agents, for example, sugars, polyalcohols, such as mannitol, sorbitol, or sodium chloride in the composition. Additional examples of pharmaceutically acceptable substances are wetting agents or auxiliary substances, such as emulsifying agents, preservatives, or buffers, which increase the shelf life or effectiveness.

In an embodiment, the antibody or antigen-binding fragment thereof defined herein, or the nucleic acid(s) encoding the antibody or antigen-binding fragment thereof, is/are encapsulated in a vesicle or vesicle-like particle, such as a lipid vesicle (e.g., liposome). The term "lipid vesicle" (or "lipid-based vesicle") as used herein encompasses macromolecular structures which as the main constituent include lipid or lipid derivatives. Suitable examples hereof are liposomes and micelles including detergent micelles/lipid emulsion, liposomes prepared from palmitoyloleoylphosphatidylcholine, hydrogenated soy phosphatdylcholine, and solid lipid nanoparticles prepared from steric acid or tripalmitin. The term liposome is used herein in accordance with its usual meaning, referring to microscopic lipid vesicles composed of a bilayer of phospholipids or any similar amphipathic lipids encapsulating an internal aqueous medium. The liposomes may be unilamellar vesicles such as small unilamellar vesicles (SUVs), which typically have a diameter of less than 0.2 µm (e.g., between 0.02 and 0.2 µm), and large unilamellar vesicles (LUVs), and multilamellar vesicles (MLV), which typically have a diameter greater than 0.45 µm (in some cases greater than 1 µm). No particular limitation is imposed on the liposomal membrane structure in the present disclosure. The term liposomal membrane refers to the bilayer of phospholipids separating the internal aqueous medium from the external aqueous medium.

The dose of antibody may vary depending upon, e.g., the age and the size of a subject to be administered, target disease, conditions, and route of administration. Antibodies as described herein (e.g., administered prophylactically or therapeutically) may be administered at a single dose of about 0.1 to about 60 mg/kg body weight, more preferably about 5 to about 60, about 10 to about 50, or about 20 to about 50 mg/kg body weight. Depending on the severity of the condition, the frequency and the duration of the treatment can be adjusted. In certain embodiments, the antibody or antigen-binding fragment can be administered as an initial dose of at least about 0.1 mg to about 800 mg, about 1 to about 500 mg, about 5 to about 300 mg, or about 10 to about 200 mg, to about 100 mg, or to about 50 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical compositions including but not limited to encapsulation in liposomes, microparticles, microcapsules, recombinant cells capable of expressing the mutant viruses, receptor mediated endocytosis (see, e.g., Wu et al. (1987) *J. Biol. Chem.* 262:4429-4432). Methods of introduction include, but are not limited to, intradermal, transdermal (e.g., using a microinjection device), intramuscular, intraperitoneal, intravenous, subcutaneous, intranasal, intrapulmonary, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer (1990) Science 249:1527-1533).

The use of nanoparticles to deliver the antibodies of the present disclosure is also contemplated herein. Antibody-conjugated nanoparticles may be used both for therapeutic and diagnostic applications. Antibody-conjugated nanoparticles and methods of preparation and use are described in detail by Arruebo, et al. (2009) Antibody-conjugated nanoparticles for biomedical applications, *J. Nanomat.*, 439389, doi: 10.1155/2009/439389), incorporated herein by reference. Nanoparticles may be developed and conjugated to antibodies contained in pharmaceutical compositions to target virally infected cells. Nanoparticles for drug delivery have also been described in, for example, U.S. Pat. No. 8,257,740, or U.S. Pat. No. 8,246,995.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

Injectable preparations comprising one or more antibodies or antibody fragments thereof may include dosage forms for intravenous, subcutaneous, intracutaneous, intranasal (e.g., nasal spray or drop), intracranial, intraperitoneal and intramuscular injections, and drip infusions. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant (e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

The pharmaceutical composition can be delivered subcutaneously or intravenously with a standard needle and syringe. In addition, with respect to subcutaneous delivery, a pen delivery device (reusable or disposable) can be used to deliver the pharmaceutical composition.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the antibody contained is generally about 5 to about 500 mg per dosage form in a unit dose; especially in the form of injection, it is preferred that the antibody is contained in about 5 to about 100 mg and in about 10 to about 250 mg for the other dosage forms.

According to certain embodiments, a single dose of an anti-SARS-CoV Spike protein antibody(ies) or antigen-binding fragment(s) thereof, or nucleic acid(s) encoding such antibody(ies) or antigen-binding fragment(s), as herein described (or a single dose of a pharmaceutical combination as herein described) may be administered to a subject in need thereof. According to certain embodiments of the present disclosure, multiple doses of the antibody(ies), antigen-binding fragment(s) or nucleic acid(s) (or multiple doses of a pharmaceutical as herein described) may be administered to a subject over a defined time course. The methods comprise sequentially administering to a subject multiple doses of the antibody(ies), antigen-binding fragment(s) or nucleic acid(s) (or multiple doses of a pharmaceutical combination as herein described). By, "sequentially administering" it is meant that each dose of antibody(ies), antigen-binding fragment(s) or nucleic acid(s) (or each dose of a pharmaceutical combination) is administered to the subject at a different point in time, e.g., on different days separated by a predetermined interval (e.g., hours, days, weeks or months). The present disclosure includes methods which comprise sequentially administering to the patient a single initial dose of antibody(ies), antigen-binding fragment(s) or nucleic acid(s), followed by one or more secondary doses of the antibody(ies), antigen-binding fragment(s) or nucleic acid(s), and optionally followed by one or more tertiary doses of the antibody(ies), antigen-binding fragment(s) or nucleic acid(s).

The terms "initial dose," "secondary doses," and "tertiary doses," refer to the temporal sequence of administration of the antibody. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of antibody, but generally may differ from one another in terms of frequency of administration. In certain embodiments, however, the amount of antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present disclosure, each secondary and/or tertiary dose is administered 1 to 48 hours after the immediately preceding dose. The phrase "the immediately preceding dose," as used herein, means, in a sequence of multiple administrations, the dose of antibody which is administered to a patient prior to the administration of the very next dose in the sequence with no intervening doses.

The methods according to this aspect of the disclosure may comprise administering to a patient any number of secondary and/or tertiary doses of antibody(ies), antigen-binding fragment(s) or nucleic acid(s). For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In certain embodiments of the disclosure, the frequency at which the secondary and/or tertiary doses are administered to a patient can vary over the course of the treatment regimen. The frequency of administration may also be adjusted during the course of treatment by a physician depending on the needs of the individual patient following clinical examination.

Therapeutic Uses

The antibodies, antigen-binding fragments thereof (including combinations thereof) and nucleic acids encoding same (or pharmaceutical compositions) as herein described may be useful for the treatment, and/or prevention of a syndrome or condition associated with a betacoronavirus, such as a sarbecovirus, e.g., SARS-CoV-2, infection or a related disease (Coronavirus disease 2019, COVID-19). In some embodiments, the antibodies, antigen-binding fragments thereof and nucleic acids may be useful in preventing infection with a betacoronavirus, such as a sarbecovirus, e.g., SARS-CoV-2, and/or reducing viral load in a subject infected with a betacoronavirus, such as a sarbecovirus, e.g., SARS-CoV-2. In one embodiment, antibodies, antigen-binding fragments thereof and nucleic acids of the present disclosure may be administered at a therapeutic dose to a patient with a betacoronavirus, such as a sarbecovirus, e.g., SARS-CoV-2 infection.

In another aspect, the present disclosure provides a method for preventing a betacoronavirus, such as a sarbecovirus, e.g., SARS-CoV-2 infection or a related disease (Coronavirus disease 2019, COVID-19), in a subject in need thereof, the method comprising administering to the subject an effective amount of the antibody or antigen-binding fragment thereof, of one more nucleic acids encoding the antibody antigen-binding fragment thereof, or pharmaceutical composition described herein. The present disclosure also provides the use of the antibody or antigen-binding fragment thereof, of one more nucleic acids encoding the antibody antigen-binding fragment thereof, or pharmaceutical composition described herein, for preventing a betacoronavirus, such as a sarbecovirus, e.g., SARS-CoV-2 infection or a related disease (e.g., COVID-19) in a subject. The present disclosure also provides the use of the antibody or antigen-binding fragment thereof, of one more nucleic acids encoding the antibody antigen-binding fragment thereof, or pharmaceutical composition described herein, for the manufacture of a medicament for preventing a betacoronavirus, such as a sarbecovirus, e.g., SARS-CoV-2 infection or a related disease (e.g., COVID-19) in a subject.

In another aspect, the present disclosure provides a method for reducing the risk of developing a betacoronavirus-related disease, such as a sarbecovirus-related disease (e.g., COVID-19), or the severity of a betacoronavirus-related disease, such as a sarbecovirus-related disease (e.g., COVID-19), in a subject in need thereof, the method comprising administering to the subject an effective amount of the antibody or antigen-binding fragment thereof, of one more nucleic acids encoding the antibody antigen-binding fragment thereof, or pharmaceutical composition described herein. The present disclosure also provides the use of the antibody or antigen-binding fragment thereof, of one more nucleic acids encoding the antibody antigen-binding fragment thereof, or pharmaceutical composition described herein, for reducing the risk of developing a betacoronavirus-related disease, such as a sarbecovirus-related disease (e.g., COVID-19), or the severity of a betacoronavirus-related disease, such as a sarbecovirus-related disease (e.g., COVID-19), in a subject. The present disclosure also provides the antibody or antigen-binding fragment thereof, of one more nucleic acids encoding the antibody antigen-binding fragment thereof, or pharmaceutical composition described herein, for use in reducing the risk of developing a betacoronavirus-related disease, such as a sarbecovirus-related disease (e.g., COVID-19), or the severity of a betacoronavirus-related disease, such as a sarbecovirus-related disease (e.g., COVID-19), in a subject.

In another aspect, the present disclosure provides a method (in vitro or in vivo) for blocking the entry of a betacoronavirus, such as a sarbecovirus, e.g., SARS-CoV-2 in a cell, such as an ACE2-expressing cell, comprising contacting the cell and/or virus with an effective amount of the antibody or antigen-binding fragment thereof, of one or more nucleic acids encoding the antibody antigen-binding fragment thereof, or pharmaceutical composition described herein. The present disclosure provides the use of the antibody or antigen-binding fragment thereof, of one or more nucleic acids encoding the antibody antigen-binding fragment thereof, or pharmaceutical composition described herein, for blocking the entry of a betacoronavirus, such as a sarbecovirus, e.g., SARS-CoV-2 in a cell, such as an ACE2-expressing cell. The present disclosure provides the use of the antibody or antigen-binding fragment thereof, of one or more nucleic acids encoding the antibody antigen-binding fragment thereof, or pharmaceutical composition described herein for the manufacture of a medicament for blocking the entry of a betacoronavirus, such as a sarbecovirus, e.g., SARS-CoV-2 in a cell, such as an ACE2-expressing cell. The present disclosure provides the antibody or antigen-binding fragment thereof, of one or more nucleic acids encoding the antibody antigen-binding fragment thereof, or pharmaceutical composition described herein, for use in blocking the entry of a betacoronavirus, such as a sarbecovirus, e.g., SARS-CoV-2 in a cell, such as an ACE2-expressing cell.

In another aspect, the present disclosure provides a method (in vitro or in vivo) for inducing complement-dependent cytotoxicity (CDC), antibody-dependent cellular phagocytosis (ADCP) and/or antibody-dependent cellular cytotoxicity (ADCC) against a betacoronavirus-, such as a sarbecovirus-, e.g., SARS-CoV-2-infected cell, comprising contacting the cell and/or virus with an effective amount of the antibody or antigen-binding fragment thereof, of one more nucleic acids encoding the antibody antigen-binding fragment thereof, or pharmaceutical composition described herein. The present disclosure provides the use of the antibody or antigen-binding fragment thereof, of one more nucleic acids encoding the antibody antigen-binding fragment thereof, or pharmaceutical composition described herein, for inducing complement-dependent cytotoxicity (CDC), antibody-dependent cellular phagocytosis (ADCP) and/or antibody-dependent cellular cytotoxicity (ADCC) against a betacoronavirus-, such as a sarbecovirus-, e.g., SARS-CoV-2-infected cell. The present disclosure provides the use of the antibody or antigen-binding fragment thereof, of one more nucleic acids encoding the antibody antigen-binding fragment thereof, or pharmaceutical composition described herein for the manufacture of a medicament for inducing complement-dependent cytotoxicity (CDC), antibody-dependent cellular phagocytosis (ADCP) and/or antibody-dependent cellular cytotoxicity (ADCC) against a betacoronavirus-, such as a sarbecovirus-, e.g., SARS-CoV-2-infected cell. The present disclosure provides the antibody or antigen-binding fragment thereof, of one more nucleic acids encoding the antibody antigen-binding fragment thereof, or pharmaceutical composition described herein, for use in inducing complement-dependent cytotoxicity (CDC), antibody-dependent cellular phagocytosis (ADCP) and/or antibody-dependent cellular cytotoxicity (ADCC) against a betacoronavirus-, such as a sarbecovirus-, e.g., SARS-CoV-2-infected cell.

In another aspect, the disclosure provides a method of preventing or treating a disease or disorder caused by SARS-CoV-2 by administering to a person at risk of suffering from the disease or disorder or suffering from a disease or disorder caused by SARS-CoV-2, a therapeutically effective amount of the antibody or antigen-binding fragment thereof, of one more nucleic acids encoding the antibody antigen-binding fragment thereof, or pharmaceutical composition described herein. In some embodiments, the antibody or antigen-binding fragment thereof, of one more nucleic acids encoding the antibody antigen-binding fragment thereof, or pharmaceutical composition described herein can be administered individually. In some embodiments, the antibody or antigen-binding fragment thereof, of one more nucleic acids encoding the antibody antigen-binding fragment thereof, or pharmaceutical composition described herein can be administered in combination with one or more other antibodies, antigen-binding fragments or nucleic acids of the disclosure, e.g., as a cocktail comprising more than one antibodies, antibody fragments or nucleic acids. In some embodiments, the disease or disorder is COVID-19. The antibody or antigen-binding fragment thereof, of one more nucleic acids encoding the antibody antigen-binding fragment thereof, or pharmaceutical composition described herein (e.g., a monoclonal antibody) or a combination thereof can be administered at a dose sufficient to neutralize the SARS-CoV-2. In some embodiments, the method also includes administering an anti-viral drug, a viral entry inhibitor, or a viral attachment inhibitor.

In some embodiments, the antibody or antigen-binding fragment thereof, or nucleic acids encoding the antibody or antigen-binding fragment thereof, or pharmaceutical composition described herein, can be administered prior to or after exposure to SARS-CoV-2.

In certain embodiments, antibodies, antigen-binding fragments thereof and nucleic acids described herein are useful to treat a subject suffering from the severe and acute respiratory syndrome caused by SARS-CoV-2. In some embodiments, the antibodies, antigen-binding fragments thereof and nucleic acids are useful in decreasing viral titer or reducing viral load in a host subject. In one embodiment, the antibodies, antigen-binding fragments thereof and nucleic acids are useful in preventing or reducing inflammation in the lung of a subject with COVID-19. In one embodiment, the antibodies, antigen-binding fragments thereof and nucleic acids are useful in preventing or reducing interstitial, peribronchiolar or perivascular inflammation, alveolar damage and pleural changes in a subject with COVID-19.

One or more antibodies, antigen-binding fragments thereof and nucleic acids described herein may be administered to relieve or prevent or decrease the severity of at least one symptom of SARS-CoV-2 infection including, but not limited to fever, cough, shortness of breath, pneumonia, diarrhea, organ failure (e.g., kidney failure and renal dysfunction), neurological complications, septic shock and death. It is also contemplated herein to use one or more antibodies, antigen-binding fragments thereof and nucleic acids described herein prophylactically to subjects at risk of being infected by SARS-CoV-2 and/or of developing a SARS-CoV-2-related disease (COVID-19), or a severe form of the disease, such as immunocompromised individuals, elderly adults (more than 65 years of age), healthcare workers, family members in close proximity to a COVID-19 patient, adults or children with contact with persons with confirmed or suspected COVID-19 infection, and patients with one or more co-morbidities including but not limited to cardiovascular disease (including coronary artery disease, cardiomyopathies, heart failure), type 2 diabetes, obesity (BMI≥30 kg/m$^2$), high blood pressure, chronic kidney disease (CKD), chronic obstructive pulmonary disease (COPD), and sickle cell disease.

In a further embodiment of the disclosure the antibodies, antigen-binding fragments thereof and nucleic acids described herein are used for the preparation of a pharmaceutical composition or medicament for treating patients suffering from a betacoronavirus, such as a sarbecovirus, e.g., SARS-CoV-2, infection or a related disease. In another embodiment of the disclosure, the antibodies, antigen-binding fragments thereof and nucleic acids described herein are used as adjunct therapy with any other agent or any other therapy known to those skilled in the art useful for treating or ameliorating a betacoronavirus, such as a sarbecovirus, e.g., SARS-CoV-2, infection or a related disease (e.g., COVID-19).

In an embodiment, the methods and uses defined herein are for the prevention, treatment and/or management of infections by the Wuhan original SARS-CoV-2 strain. In another embodiment, the methods and uses defined herein are for the prevention, treatment and/or management of infections by variants of the Wuhan original SARS-CoV-2 strain, such as the B.1.1.7 (also known as VOC-202012/01 or alpha (α)), 501Y.V2 (also known as B.1.351 or beta (β)), P.1 (also known as B.1.1.28.1 or gamma (γ)), B.1.617.2 (also known as delta (δ)), or B.1.1.529 (Omicron (o)) variant, as well as other variants of concern (VOC) such as B.1.429, B.1.526, B.1.525, and A.23.1 (see, e.g., www.cdc.gov/coronavirus/2019-ncov/cases-updates/variant-surveillance/variant-info.html). In an embodiment, the methods and uses defined herein are for the prevention, treatment and/or management of infections by the SARS-CoV-2 delta (δ) variant. In an embodiment, the methods and uses defined herein are for the prevention, treatment and/or management of infections by the SARS-CoV-2 Omicron (o) variant.

Diagnostic Uses of the Antibodies or Antigen-Binding Fragments Thereof

The anti-SARS-Cov2 Spike protein antibodies or antigen-binding fragments thereof described herein may be used to detect and/or measure a betacoronavirus, such as a sarbecovirus, e.g., SARS-CoV-2, in a sample, e.g., for diagnostic purposes. Some embodiments contemplate the use of one or more of the antibodies or antigen-binding fragments thereof in assays to detect a disease or disorder such as viral infection. Exemplary diagnostic assays for SARS-CoV-2 may comprise, e.g., contacting a sample, obtained from a patient, with an anti-SARS-CoV-2 Spike protein antibody or antigen-binding fragment thereof described herein, wherein the antibody or antigen-binding fragment thereof is labeled with a detectable label or reporter molecule or used as a capture ligand to selectively isolate SARS-CoV-2 from patient samples. Alternatively, an unlabeled anti-SARS-CoV-2 Spike protein antibody or antigen-binding fragment thereof can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure SARS-CoV-2 in a sample include enzyme-linked immunosorbent assay (ELISA), radioimmunoassay (RIA), bead-based flow cytometry and fluorescence-activated cell sorting (FACS).

Samples that can be used in SARS-CoV-2 diagnostic assays according to the present disclosure include any tissue or fluid sample obtainable from a patient (e.g., blood, plasma, saliva, nasal secretion), which contains detectable quantities of either SARS-CoV-2 Spike protein, or fragments thereof, under normal or pathological conditions. Generally, levels of SARS-CoV-2 Spike protein in a particular sample obtained from a healthy patient (e.g., a patient not afflicted with a disease associated with SARS-CoV-2) will be measured to initially establish a baseline, or standard, level of SARS-CoV-2. This baseline level of SARS-CoV-2 can then be compared against the levels of SARS-CoV-2 measured in samples obtained from individuals suspected of having a SARS-CoV-2-associated condition, or symptoms associated with such condition.

The antibodies or antigen-binding fragments thereof specific for SARS-CoV-2 Spike protein may contain no additional labels or moieties, or they may contain an N-terminal, internal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

EXAMPLES

The present disclosure is illustrated in further details by the following non-limiting examples.

Example 1: Materials and Methods

Recombinant Proteins

Various targets were used as panning, screening and analytical reagents for ELISA and Octet binding assays and purchased from different vendors. SARS-CoV-2 Spike trimer, RBD-hFc, RBD (tagless), human ACE2-hFc, and SARS-CoV-1 Spike trimer were obtained from U-Protein Express (UPE, Utrecht, Netherlands). SARS-CoV-2 Spike trimer (cat #A33-11-02-SMT1) was obtained from the National Research Council (Quebec, Canada). SARS CoV-2 full-length spike protein and B.1.1.7, B.1.351, and P.1 mutations were purchased form Cube Biotech (cat #28702, 28717, 28720, and 28723). Various Spike protein subunits including S1-mFc, S1-hFc, S2-hFc, NTD-hFc, S1-S2-His, S1-His, and mutants S1-His(D614G), Beta B.1.351 lineage S1-His(K417N, E484K, N501Y, D614G), S1-His(HV69-70del, N501Y, D614G), Alpha S1-His(HV69-70del, Y144del, N501Y, A570D, D614G, P681H) and RBD single point mutants (A435S, F342L, G476S, K458R, N354D, N439K, S477N, V367F, V483A, W436R, E484K, K417N, Y453F, N501Y) were purchased from Sino Biological.

Benchmark Abs were generated from published sequences and expressed in the human IgG1 framework resembling the one used for the Ab candidates: B385 (PDB ID: 7BZ5), CB64, CR3022[23] H4[5], REGN10933 & REGN10987[6], or as VHH-hFc1: VHH-7224, SB1425, SB6826 and acquired from UPE. Negative control antibodies bococizumab (hIgG1) and caplacizumab (VHH-hFc) were also acquired from UPE. Anti-hKappa and anti-hLamda were purchased from SouthernBiotech (Birmingham, AL, USA). Antibodies destined for in vitro work were produced in-house in HEK293 cells as both FAb fragments and full-length IgGs. FAbs were purified by a CH1 matrix VHH-based purification resin, while IgGs were purified by protein A chromatography. Antibodies destined for animal studies were produced in CHO cells. All FAbs and IgGs were subjected to an additional purification step in-house using gel filtration and formulated in PBS.

Library Panning

The libraries employed here were previously generated by ImmunoPrecise Antibodies (Naïve Human Library #0899, Autoimmune Patient Library #0845, and Llama VHH Library #3566). Briefly, B lymphocytes were isolated from previously generated phage display libraries (Naïve Human Library, Autoimmune Patient Library, and Llama VHH Library), and antibody variable region sequences were amplified by real-time PCR (RT-PCR). The fragments were ligated into the pHENIX-His8-VSV vector and transformed into Escherichia coli TG1 cells. Library rescue was conducted prior to each round of antigen panning by inoculating bacterial cells into TYAG medium followed by the addition of helper phage to induce phage production. Phage particles were isolated by PEG/NaCl precipitation and filtered using a 0.45 µm filter.

Either magnetic Protein A or polystyrene beads were coated with the antigen of interest and washed to remove any unbound protein. Purified phage particles were blocked in PBS supplemented with 5% (v/v) skim milk and any bead-reactive antibodies were depleted by pre-incubation with uncoated beads. The resulting phages were then incubated with the antigen-coated beads, followed by washing in PBS-Tween™ to remove any unbound phage particles. Depending on the panning strategy, either the bead-bound (for positive antigen selection) or unbound (for negative selection) phage particles were incubated with TG1 cells followed by subsequent rescue by helper phage superinfection as described above. The output phages of each round were also screened by ELISA for their reactivity to the antigen of interest and relevant controls. Eleven unique panning strategies were conducted in parallel using varying combinations of S1, S2, and RBD subunits of the SARS-CoV-2 Spike protein, and a fully assembled, stabilized Spike trimer of the related SARS-CoV-1 for target enrichment (UPE/Cube). Depletion panning with human ACE2, CR3022-bound Spike (where CR3022 represents an anti-SARS-CoV-1 antibody from the literature with cross-reactivity to SARS-CoV-2[23,27]) and irrelevant non-target proteins further increased target specificity and reduced off-target reactivity.

ELISA Screening

HIS-tagged recombinant DNA spike proteins (wild-type or carrying VOC mutations) were diluted to final concentrations 1.5 µg/mL in carbonate binding buffer and were added to Greiner Bio-One High Bind ELISA plates in 50 µL/well and incubated overnight at 4° C. If additional capture step was performed it was conducted in PBS for 1 hour at room temperature. Plates were blocked with 1% (w/v) BSA in PBS for 60 min. Coated plates were washed with PBS-T before serial dilutions of recombinant antibodies were added in duplicate in PBS supplemented with 1% (w/v) BSA and incubated at room temperature (RT) for 60 min. After washing with PBS-T, secondary goat-anti-human-IgG-HRP for detection was added and incubated for 60 min at RT. Following final washing, 50 µL TMB substrate was added for 10 min and the reaction was stopped by adding 50 µL 2M $H_2SO_4$. Absorbance was read at 450 nm on an Envision multimode plate reader and data was processed in GraphPad Prism.

Interaction Analysis by Octet

All label-free interaction analysis was performed on an Octet HTX biolayer interferometry-based detection system (ForteBio/Sartorius, Göttingen, Germany) equipped with various sensor types; AR (amine-reactive), SAX (streptavidin-coated), or AHC (anti-human-Fc capture) sensors. Experiments were conducted at 25° C. in a run buffer of PBS containing 0.05% Tween™-20 and 0.5 mg/mL BSA.

Binding affinity estimates. Different assay formats were used to estimate the binding affinities of Ab/target bimolecular interactions. In one assay format, Fab was titrated as monovalent analyte (typically as a 3-fold series with a top concentration of 3 µM, and at least one concentration in duplicate) over AHC sensors coated with human-Fc-fused targets RBD-hFc, S1-hFc or S2-hFc as ligands (Sino Biological). In the reverse format, tagless RBD or S1-His (D614G) were titrated as monovalent analytes over Ab-coated AHC sensors. Global affinity estimates were determined using the Kinetics module of Fortebio's Data Analysis HT software version 12.0.1.55. Data were processed by subtracting the responses of a buffer analyte sample and fitting these referenced data globally to a simple 1:1 Langmuir binding model to deduce the $K_D$ value from the ratio of the kinetic rate constants ($K_D=k_d/k_a$), where $k_d$ and $k_a$ are the dissociation and association rate constants, respectively. Interactions showing square-shaped binding curves were alternatively fit to a steady-state (equilibrium) isotherm; affinities deduced from kinetic and equilibrium fitting routines were equivalent. Additionally, the solution affinity of the 23-H7-Fab/RBD binding interaction was determined by titrating 23-H7 Fab (1,000 to 1.4 nM, as a 7-membered three-fold series) into RBD fixed at 5 nM, allowing these solutions to equilibrate (an hour at room temperature) and then probing for free RBD in these samples using SAX sensors coated with biotinylated-23-H7-IgG. All samples were measured on duplicate sensors. An apparent solution affinity (or $IC_{50}$ value) was determined by fitting the reference-subtracted responses (from a buffer analyte sample) to a non-linear regression, inhibition dose-response curve (four-parameter least-squares fit) model in GraphPad Prism software version 9.

Pairwise epitope binning. Combinatorial pairwise Ab competition or "epitope binning" assays were performed on the Octet using various assay formats. To perform a "classical sandwich" assay format, Abs were covalently coupled onto AR sensors using standard coupling conditions to generate the ligands (surface-immobilized Abs) and used to capture S1-His(D614G) monovalent target (typically 5 μg/mL, 65 nM) followed by an Ab analyte typically at 10 μg/mL (133 nM binding sites). Alternatively, reaction surfaces were generated by coating SAX sensors with 5 μg/mL biotinylated Abs. Ligands were regenerated with 75 mM phosphoric acid. "Waterfall" experiments were conducted on freshly Ab-coated SAX sensors (single use, not regenerated) using 5 μg/mL S1-His(D614G) followed by an Ab titration spanning 6,000 to 25 nM binding sites as a six-membered three-fold series, with one concentration (667 nM) in duplicate. Data were analyzed in the Epitope Binning molecule of Fortebio's Data Analysis HT software version 12.0.1.55. Heat maps were curated manually in Excel by merging the results from different experiments.

Multi-Ab epitope binning. To perform a "tandem cocktail" multi-ab binning experiment, SAX sensors were coated with 5 μg/mL biotinylated 23-H7 (bin 2) and used to tether 5 μg/mL Spike trimer. Three Ab analytes from non-overlapping bins were associated in consecutive analyte binding steps, each step building upon the complex formed in the previous steps. For example, bin 4 Ab was used in step1, bin 4+C was used in step 2, and bin 4+C+S2 was used in step 3, thereby maintaining saturating levels of the Ab analyte applied in the previously applied steps to eventually saturate the 23-H7-tethered Spike with three Ab analytes (from bins 4, C and S2). The responses of each newly applied Ab analyte to "Ab-saturated" 23-H7-tethered Spike were compared with the responses of that Ab analyte to the "naked" 23-H7-tethered Spike. Data were processed in ForteBio's Data Acquisition software version 12.0.1.8 by Y-aligning to zero at each association step.

Alternatively, multi-Ab binnings were performed in a "premix" assay format. To prepare the reaction surfaces for these experiments, SAX sensors were coated with 5 μg/ml biotinylated Abs from different bins (e.g., 2, 4, C, or S2) or with controls; biotinylated ACE2-hFc or mouse anti-His mAb (R&D systems). Spike trimer (1 μM binding sites) was premixed with Abs from different epitope bins, either individually, or as 2-, 3-, or 4-membered cocktails using Abs at saturating concentrations (10 μM binding sites). Samples of premixed Spike/Ab complexes, Spike alone or buffer were used as analytes for binding to the Ab-coated sensors (or control surfaces) to probe for free binding sites in these mixtures. Binding responses were compared with those of Spike alone and determined to be blocked if their responses were significantly suppressed to baseline levels (like the buffer blank).

Mutant screening by Octet. AHC sensors were coated with 10 μg/mL human Abs, benchmark control Abs, and ACE2-hFc to provide reaction surfaces for testing the binding of a panel of recombinant mutant proteins as His-tagged S1 or RBD subunits as monovalent analytes, tested at 10 μg/mL.

Cell-Associated Spike Screening

To produce cell-associated Spike protein trimers, synthetic genes encoding for SARS-CoV-2 surface glycoprotein variants, including B.1.1.7 (Alpha), B.1.351 (Beta), P.1 (Gamma), B.1.429, B.1.526 (Iota), B.1.617 (Delta), B.1.621 (Mu), C.37 (Lambda) and B.1.1.529 (Omicron) lineages, as well as the A (Wuhan-1) and B (D614G) parental lineages, obtained from GeneArt, were cloned into a standard mammalian expression vector. To induce expression of spike trimers in a cell context, HEK293F cells were transiently transfected using the FectoPRO™ transfection system according to the manufacturer specifications (PolyPlus Transfection, Illkirch, France) with SARS-CoV-2 surface glycoprotein expression vector. Cells were harvested 48 hours post-transfection, washed and dispensed to 96-well cell culture plates at a concentration of $1.0 \times 10^5$ cells per well, and serial dilutions of test or control Abs were added in a final volume of 30 μL per well in duplicate. After 1 hour at 4° C. protected from light, the wells were washed, and Ab binding was detected with Donkey F(ab')$_2$ anti-human IgG conjugated to phycoerythrin (PE, Abcam cat. #ab102439). Following fixation using paraformaldehyde, cells were analyzed using an iQue High-Throughput Flow Cytometer (Sartorius, Gottingen, Germany). EC50 values were calculated in GraphPad Prism.

Pseudovirus Neutralization

The production of VSV virus particles expressing the SARS-CoV-2 Spike protein has been previously described[28]. Briefly, the SARS-CoV-2 Spike protein was cloned into the pCAGGS expression vector system and transfected into HEK-293T cells. Cells were then infected with the VSVΔG pseudotyped virus further modified to encode the *Photinus pyralis* luciferase reporter protein. After 24 hours supernatants were collected and titrated on African green monkey VeroE6 cells. In neutralization assays Abs were diluted in DMEM supplemented with 1% (v/v) fetal calf serum (Bodinco), 100 U/ml penicillin, and 100 μg/ml streptomycin before being added to an equal volume of pseudotyped virus particles and incubated at room temperature for 1 hour. The mixture was then added to a confluent monolayer of VeroE6 cells in a 96-well tissue culture plate and incubated for 24 hours. Following this incubation luciferase activity was measured in the presence of D-luciferin substrate (Promega) using a Centro LB960 plate luminometer (Berthold). Neutralization was calculated as the ratio of luciferase activity in the presence of Abs normalized to a negative control well containing only pseudotyped virus and no Abs.

Authentic Virus Neutralization

Authentic virus neutralization assays were performed at ViroClinics Biosciences (Rotterdam, The Netherlands) using the SARS-CoV-2 virus (BetaCoV/Munich/BavPat1/2020) carrying the D614G mutation. In short, two-fold serial dilutions of the samples provided were incubated with a fixed amount of virus (200 TCID$_{50}$/well or 4000 TCID$_{50}$/mL) for 1 hour at 37° C. with a starting Ab concentration of 100 μg/mL. Next, the virus-Ab mixtures were transformed to plates with VeroE6 cell culture monolayers and after the incubation period of 5-6 days at 37° C. Cytopathic effect (CPE) in the monolayer was measured and scored by the vitality marker WST8 and neutralization titers were calculated according to the Reed-Muench method[29].

In Vivo Hamster Challenge Model of Infection

All animal studies were performed at ViroClinics Xplore (Schaijk, The Netherlands) and conducted according to European Union Directive 2010/63/EU and the standards of Dutch law for animal experimentation. Groups of 5 male Syrian Hamsters (*Mesocricetus auratus*) aged 9 to 10 weeks at the start of the experiment were randomly assigned to experimental groups. Antibody or mock (PBS) treatment were administered as a single intraperitoneal injection at the indicated time. All animals were challenged at day 0 with a single intranasal administration of $10^{2.0}$ TCID50 SARS-CoV-2 (BetaCoV/Munich/BavPat1/2020) in a volume of 100 μL equally divided between nostrils. On day 4 post-challenge all animals were euthanized by abdominal exsanguination under isoflurane anesthesia (3-5%).

Animal Study Tissue Collection

Animals were weighed and throat swabs were collected daily post infection. At the time of euthanasia, lung lobes were inspected and observed percentage of affected lung tissue was estimated, samples of the left nasal turbinates, trachea and the entire left lung (often with presence of the primary bronchi) were preserved in 10% formaldehyde for histopathology and samples of the right lung parenchyma and right nasal turbinates were collected. Throat swabs and right lung and nasal turbinate tissues were frozen for subsequent virological assessment by quantitative PCR and virus titration.

Viral Load Quantification from In Vivo Samples

For determination of replication competent virus levels, quadruplicate ten-fold serial dilutions were used to determine the virus titers in confluent layers of Vero E6 cells. In short, serial dilutions of the samples (throat swabs and tissue homogenates) were prepared and incubated on Vero E6 monolayers for 1 hour at 37° C. Vero E6 monolayers are washed and incubated for 5 or 6 days at 37° C. Viability was measured by scoring using the vitality marker WST8. Viral titers (log10 TCID50/ml or/g) were calculated using the method of Spearman-Karber. For detection of viral RNA levels in the samples, RNA was extracted from samples using Magnapure LC total nucleic acid isolation kit (Roche). RNA amplification and quantification were carried out using a 7500 Real-Time PCR System (Applied biosystems) specific primers (E_Sarbeco_F: ACAGGTACGTTAATAGT-TAATAGCGT, SEQ ID NO: 200 and E_Sarbeco_R:ATAT-TGCAGCAGTACGCACACA, SEQ ID NO: 201) and probe (E_Sarbeco_P1: ACACTAGCCATCCT-TACTGCGCTTCG, SEQ ID NO: 202) as described previously[31] and RNA copies (log10 copies/ml or/g) were calculated.

Histopathological Evaluation of Tissue from In Vivo Studies

After fixation with 10% neutral-buffered formalin, lung, nasal turbinate and trachea tissues were sectioned, paraffin embedded, micro-sectioned to 3 μm on glass slides and stained with hematoxylin and eosin for histopathological evaluation. The stained tissues were examined using an Olympus BX45 light microscope with magnification steps of 40×, 100×, 200×, and 400× for scoring. Severity of inflammation was scored based on inflammatory cell infiltration in tracheas and bronchi (0=no inflammatory cells, 1=few inflammatory cells, 2=moderate number of inflammatory cells, 3=many inflammatory cells).

Assessment of Antibody-Dependent Cellular Phagocytosis (ADCP) and Antibody-Dependent Cellular Cytotoxicity (ADCC) Activity Triggered by Antibodies To assess cellular binding, SARS-CoV-2-S CHO-K1 target cells (Promega) incubated with a four-fold dilution series of mAbs 21-F2-optimized, 2-A6, 22-D9-optimized, 22-F7, 23-H7, and control NISTmAb from 150 μg/mL to 10 μg/mL in duplo were examined using an anti-human IgG-PE-conjugated antibody on an iQue High-Throughput Flow Cytometer (Sartorius, Gottingen, Germany). In presence of Jurkat ADCC reporter cells at a ratio of 4:1, or of THP-1 ADCP reporter cells (Promega) at a ratio of 3:2 to SARS-CoV-2-S CHO-K1 target cells, a four-fold dilution series from 230 pg/mL to 15 μg/mL ADCC reporter or from 150 pg/mL to 10 μg/mL ADCP reporter were incubated with the mAbs-treated CHO-K1 cells in triplo. For each condition, samples without the addition CHO-K1 cells, were inspected for effects of mAbs on effector cells. After 6 h at 37° C., Bio-Glo™ substrate was added to the antibody-cell mixtures and after 5 to 10 min luminescence was assessed on an Envision spectrophotometer.

Statistical Analysis

All treatment groups were compared with the mock group. The treatment groups were compared on the development of weight, throat swab real time PCR and throat swab virus titration. Mixed model analyses were conducted in SAS with Proc Mixed. A Dunnet correction for multiple testing was applied. For the virology and histopathology variables measured on day 4 post-challenge a two-sided p-value was calculated for Fisher's Exact Test for categorical variables and the Wilcoxon Rank Sum Exact Test for continuous and ordinal variables. Since the statistical analysis of these variables was explorative in nature, no correction for multiple testing was used. For values below the lower limit of detection the lower limit of detection was reported.

Example 2: Phage Display Library Panning Enriched for a Panel of Anti-Spike Abs with Diverse Binding Profiles To enrich for fully human Abs specific for the Spike protein, pre-existing human scFv repertoires derived from healthy donors and auto-immune diseased individuals were subjected to four rounds of phage panning against a panel of purified recombinant protein targets using eleven unique panning strategies in parallel (FIG. 1A). As determined by ELISA, except for one panning strategy, polyclonal phage outputs showed target-specific binding, with diverse reactivity profiles between the phage outputs from the different panning approaches, suggesting enrichment of phages displaying epitope-diverse Ab fragments. Approximately 700 clones with diverse binding profiles were selected for monoclonal scFv expression and subsequent isolation of periplasmic fractions. Upon confirming their target-specificity by ELISA, the top 279 periplasmic fractions were selected for initial in vitro pseudovirus-based neutralization assays. Sixty sequence-unique scFv clones showing diverse reactivity profiles and distinct neutralization capacity were selected for Fv-model based in silico developability profiling using BioLuminate (Schrödinger) and subsequent recombinant eukaryotic expression as full-length human IgG1 antibodies. Following Protein A purification and purity/integrity analysis by SDS-PAGE, antibodies were subjected to more in-depth characterization.

Figure 1B:
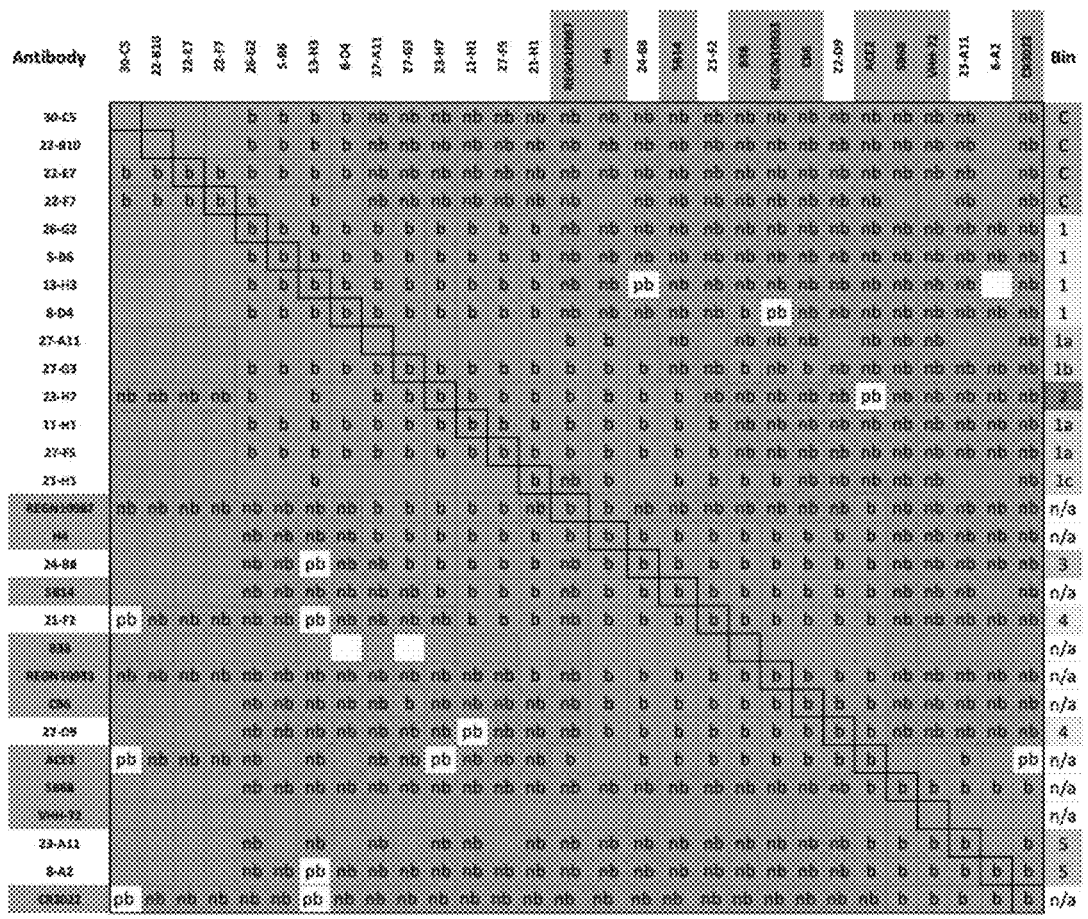

Example 3: High-Throughput Epitope Binning Assays Facilitated the Identification of Multiple Distinct Epitope Bins An integral part of the triage workflow involved the early implementation of label-free biosensor screenings of the down-selected Abs to assess their pairwise and combinatorial blockade of S-protein by one another, ACE2, and a panel of nine RBD-specific Abs from the literature with known epitopes (REGN10987/imdevimab, REGN10933/casirivimab, CB6/etesevimab, B38, H4, SB14, SB68, VHH-72 and CR3022), as sequences became publicly available. An example heat map resulting from a merged high-throughput binning analysis of our human library-derived clones combined with those from the literature using S1-His(D614G) as target, is shown in FIG. 1B and highlights the identification of several epitope clusters or "bins" of Abs sharing similar blocking profiles. The inter-bin blocking relationships revealed a series of both overlapping and non-overlapping bins, as shown in the simplified Venn Diagram in FIG. 1E.

Figure 1C:
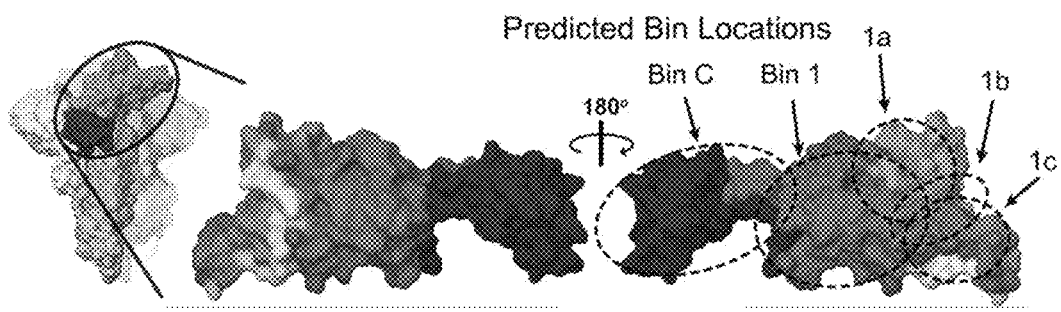

Literature clones (CR3022, REGN10987, REGN10933, CB6) served as "structural benchmarks" to infer the approximate locations of our deduced bins onto the Spike protein, as shown for bin C, bin 1, and its sub-bins a-c (FIG. 1C). All S1-non-RBD binders fell into bin C, while the RBD binders were distributed across five bins (1-5). Neither bin C nor bin 1 blocked ACE2 or any of the structural benchmarks. Some bin-1-like clones did not block bin C but showed nuanced interference with binding of some of the benchmarks, so were assigned to sub-bins 1a, 1b, and 1c (FIGS. 1F-H).

Figure 1D:
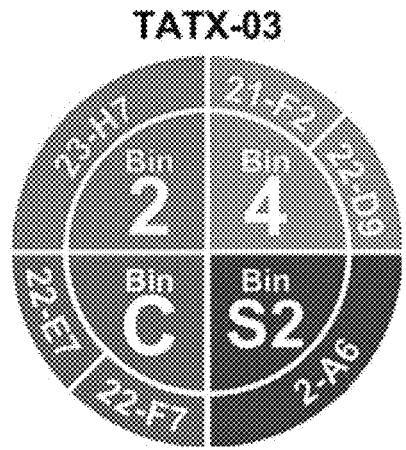
Figure 1E:
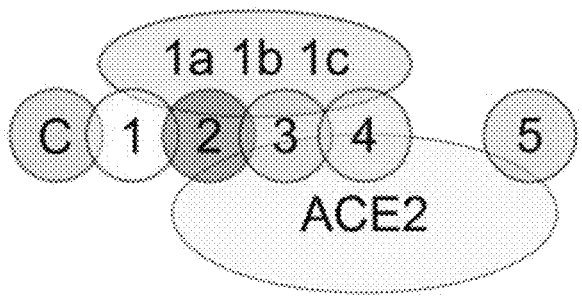
Figure 1F:
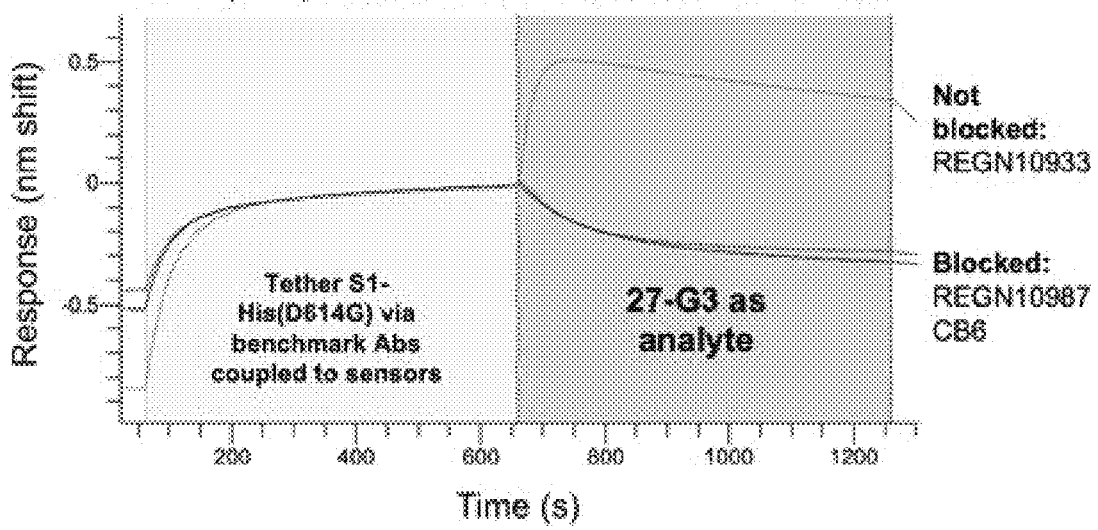
Figure 1G:
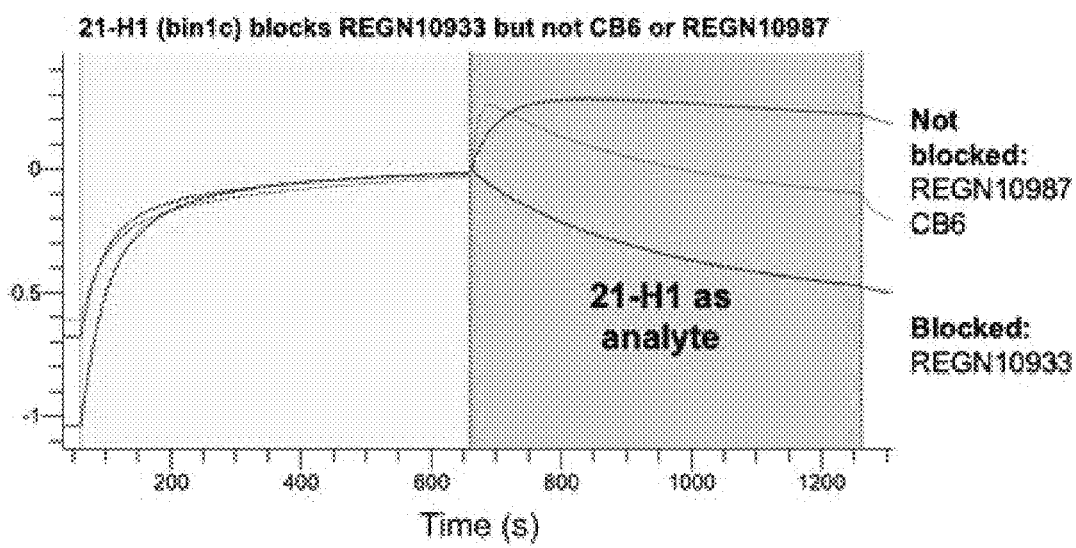
Figure 1H:
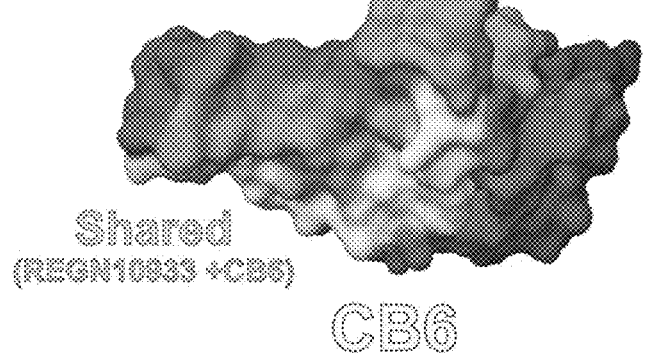
Figure 1I:
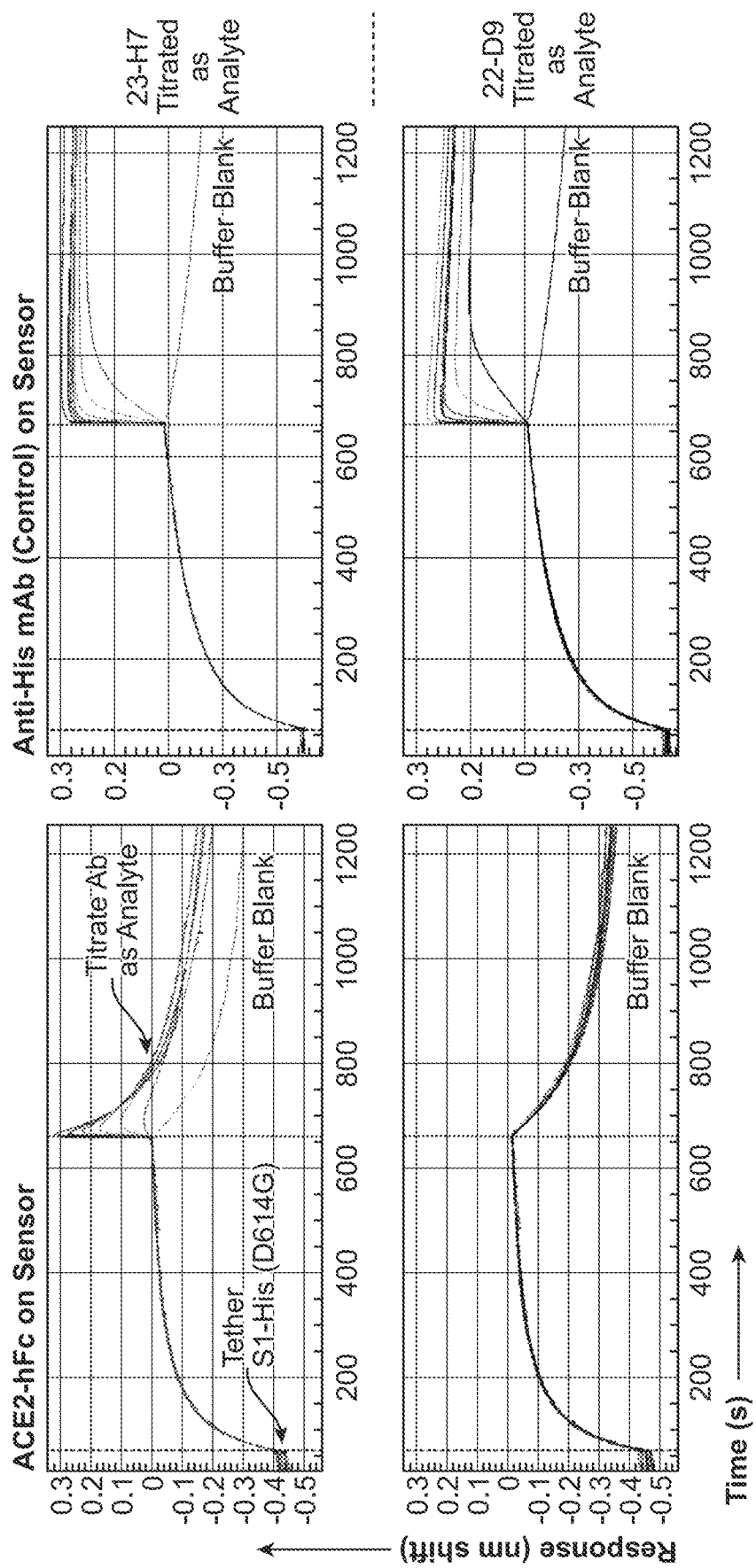

Bin 2 co-located with REGN10987 and uniquely kinetically perturbed/partially blocked ACE2 (FIG. 1I). Bin 4 (FIG. 1I) and bin 5 both blocked ACE2 but not one another; bin 4 co-located with REGN10933 and CB6, while bin 5 co-located with the "cryptic" epitope of CR3022, VHH-72 and SB68. Bin 3, like bin 4, also interfered with ACE2 binding and co-located with REGN10933 and CB6, but additionally blocked bin 2, appearing to be a "broader" blocker than bin 4.

While the bin-definition may constitute an over-simplification of a much more nuanced epitope landscape with crosstalk between otherwise discrete bins, it guided the identification of clones from distinct non-overlapping bins that could be curated into cocktails, such as the four-bin combination that formed the basis of the TATX-03 cocktail (FIG. 1D).

Figure 2A:
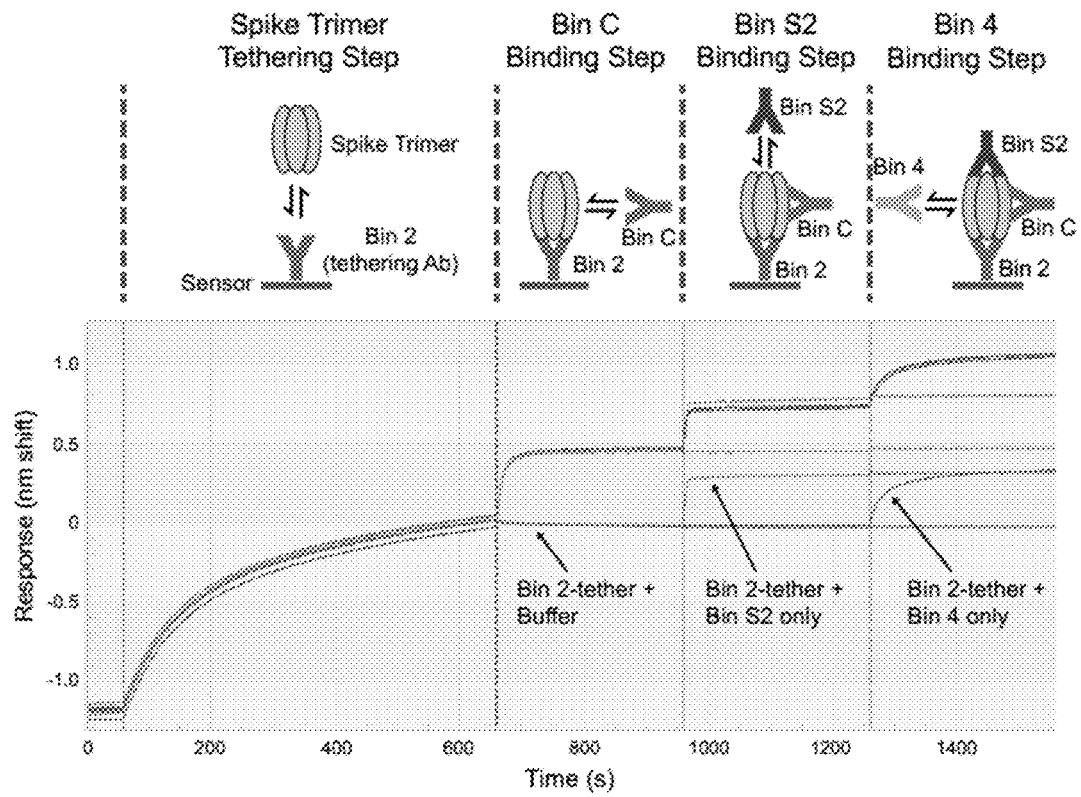
FIGS. 2A-H show multi-Ab epitope binning results using complementary assay formats. Binning results verifying the simultaneous saturation of Spike trimer protein with up to four Abs targeting distinct non-overlapping epitopes.
Figure 2B:
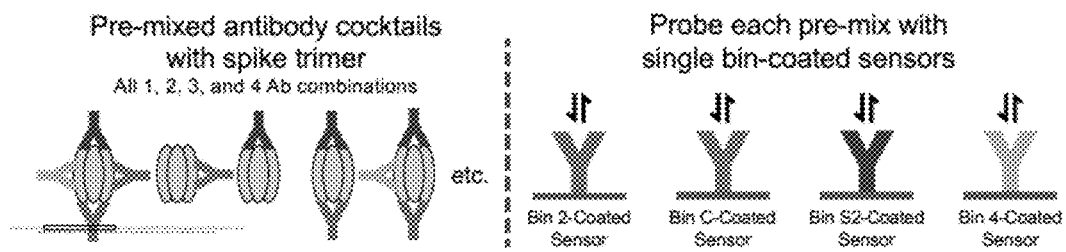
Figure 2C:
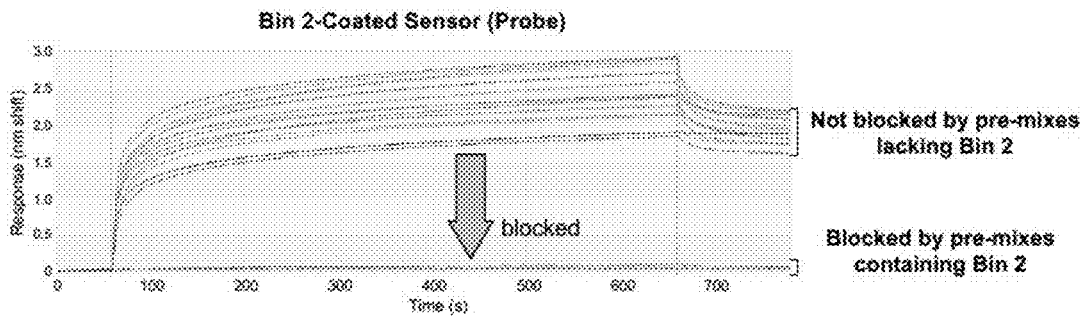
Figure 2D:
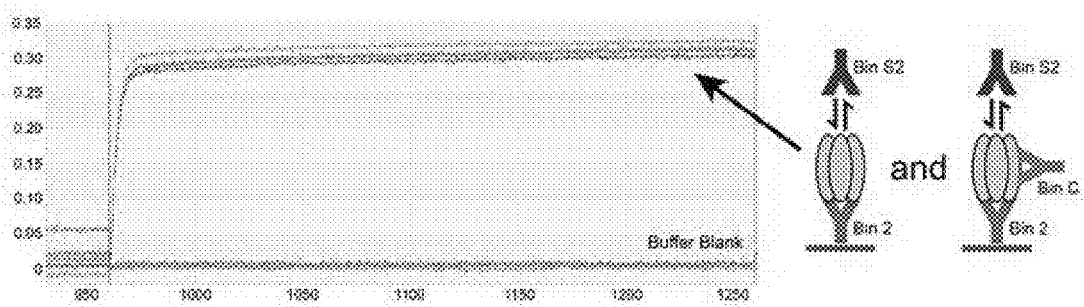
Figure 2E:
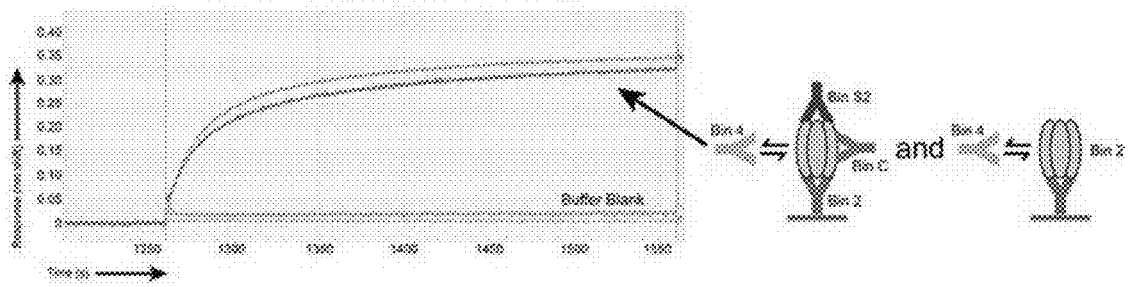
Figure 2F:
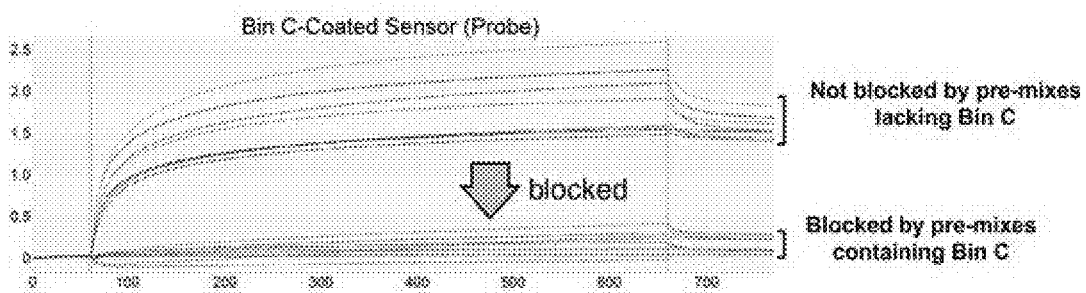
Figure 2G:
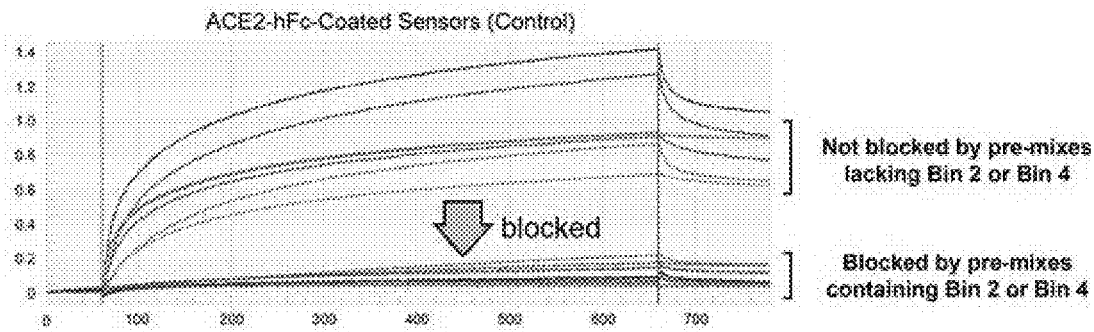
Figure 2H:
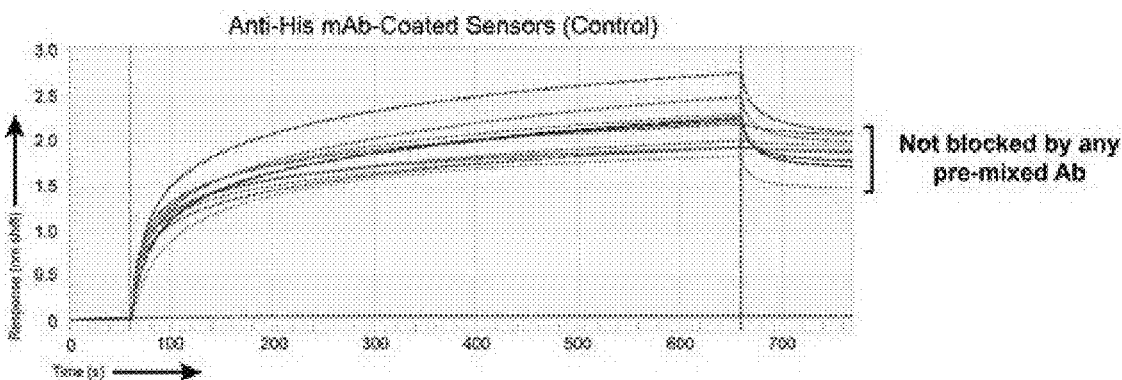

Example 4: Multi-Ab Epitope Binning Experiments Confirmed that Up to Four Abs can Co-Exist on the Spike Trimer Having identified antibody pairs that could co-exist on recombinant monomeric S1-subunit as judged by the pairwise binning matrix, the analysis was extended to higher-order binning experiments using a fully assembled recombinant Spike trimer to test whether it could physically accommodate Abs from up to four distinct non-overlapping bins as present in TATX-03 (2, 4, C, and S2). The results from assays performed in complementary formats, a tandem cocktail assay (FIGS. 2A, D and E) and a premix assay (FIGS. 2C, F, G and H), confirmed that Abs from these four bins could access their epitopes without interfering with one another's binding, thereby validating this bin combination for use in functional studies.

While the tandem binning assay had relied upon avid interactions between bivalent full length IgGs and trimeric Spike, the binding affinities of the Abs to recombinant targets under monovalent conditions was assessed using complementary assay orientations on the Octet. Most of the Abs showed weak affinities with apparent $K_D$ values ranging from 0.1-1 μM as characterized by square-shaped sensorgrams that were adequately described by an equilibrium analysis. However, clone 23-H7 (bin 2) uniquely bound RBD (or S1) with a high affinity, giving an apparent $K_D$ value of approximately 4.6 nM, regardless of the assay orientation used (FIGS. 3A-D, Table 3).

TABLE 3

Octet affinity estimates using various assay orientations

Figure 3A:
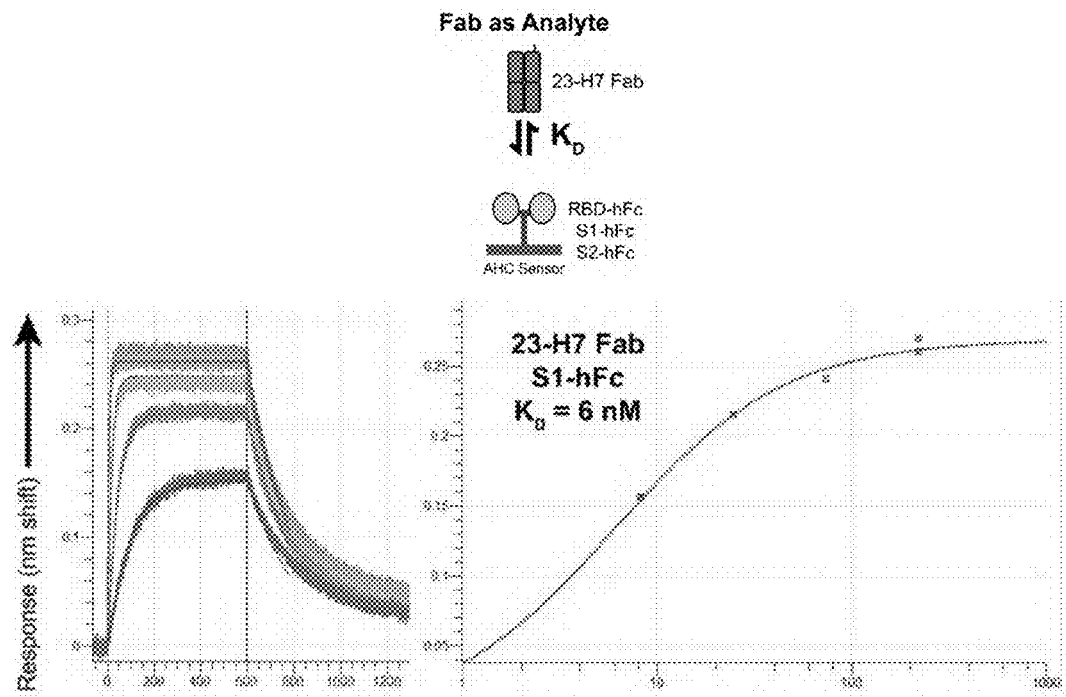
Figure 3B:
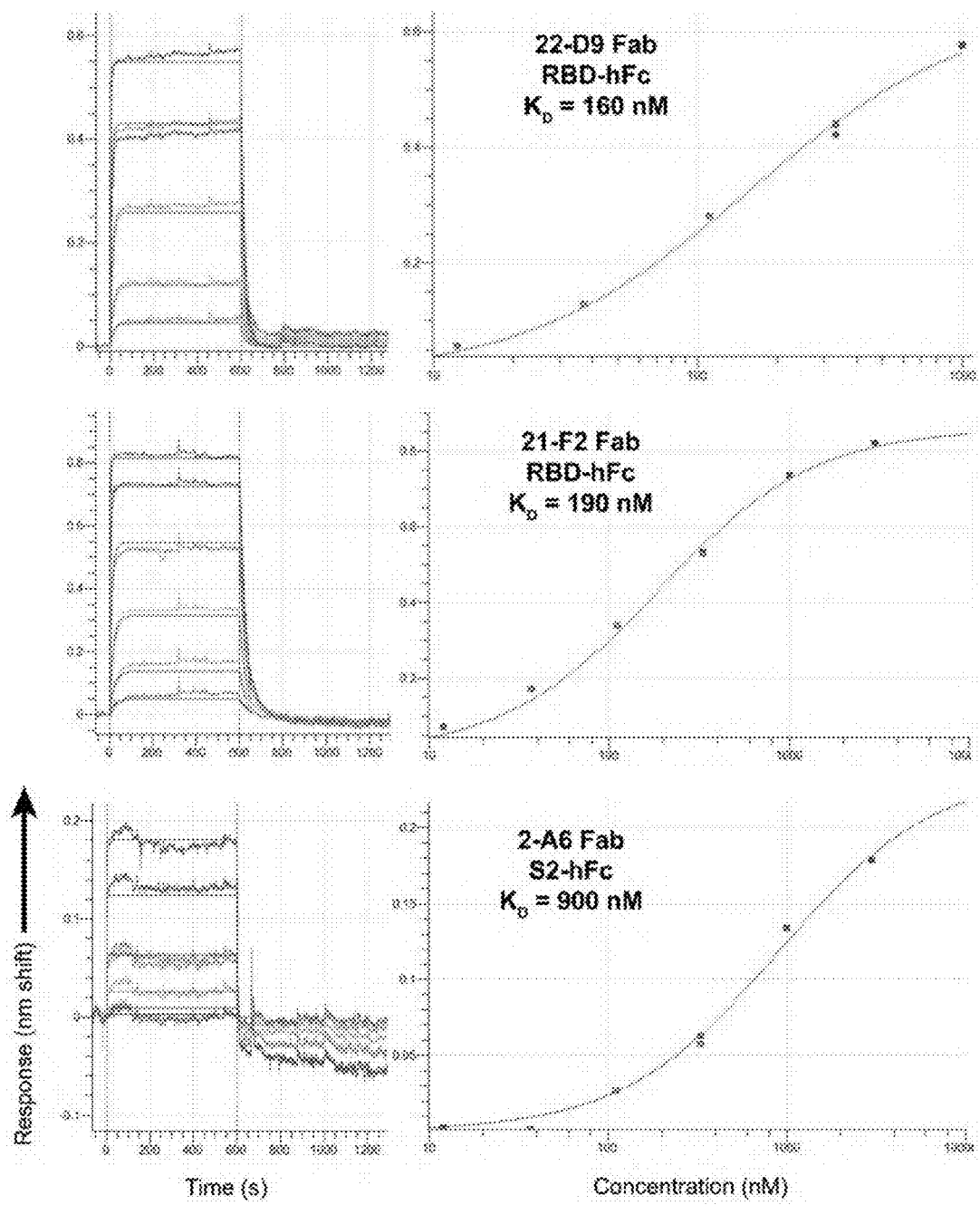
Figure 3C:
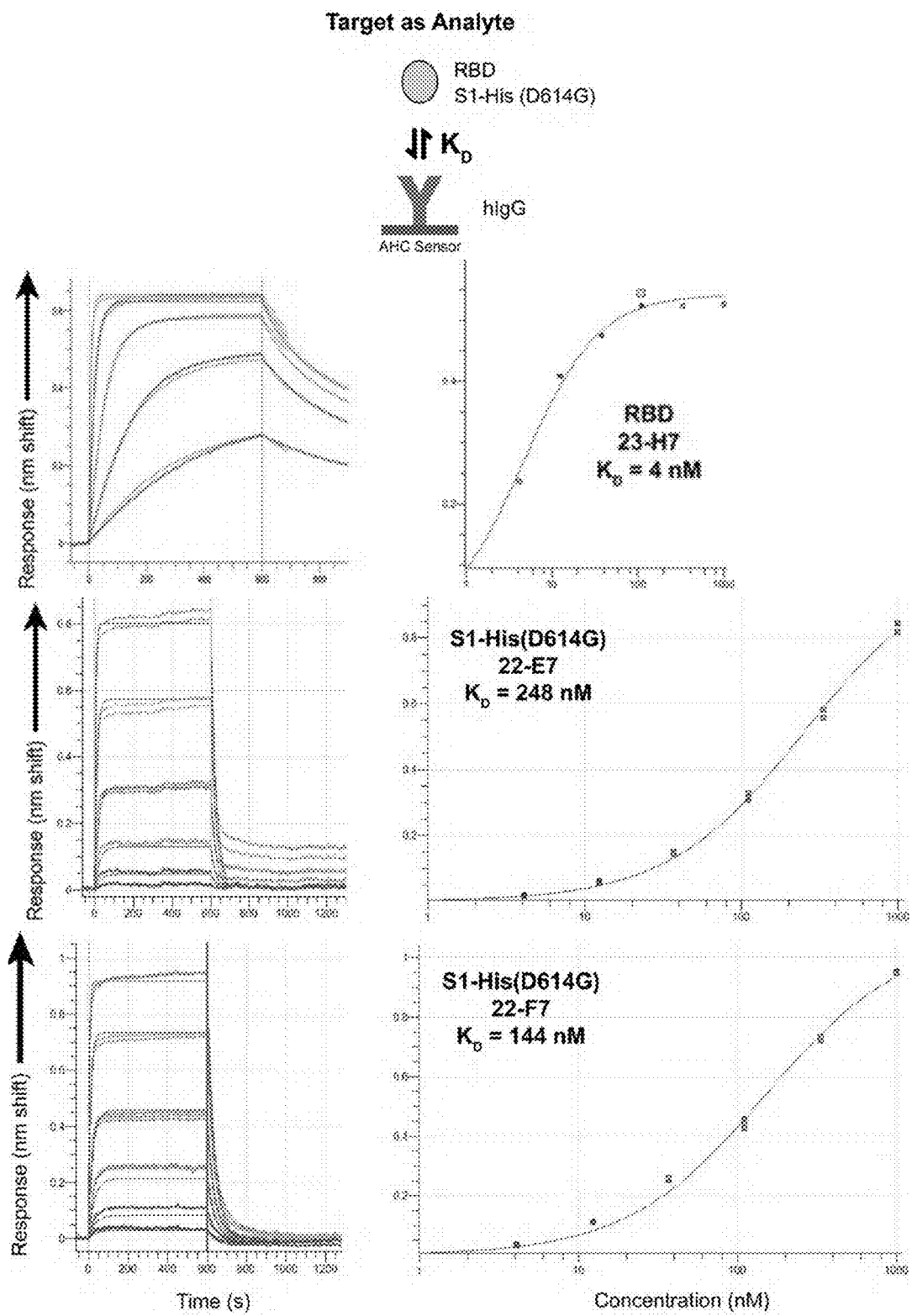
Figure 3D:
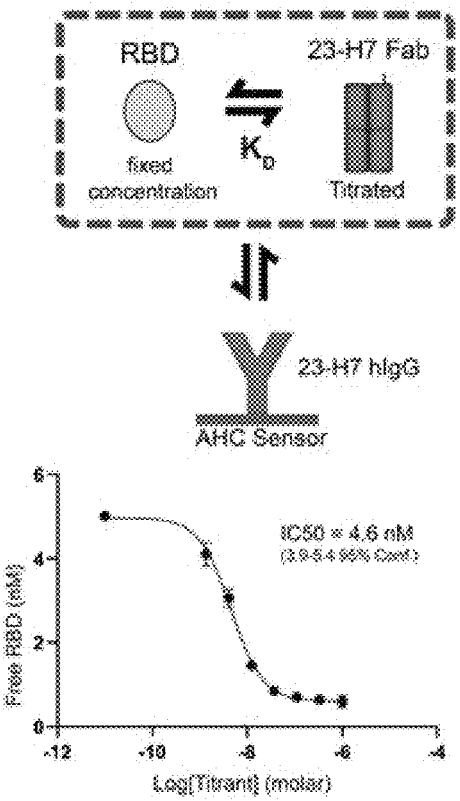

| Clone ID | Bin | Ligand | Analyte | Orientation | $k_a$ (1/Ms) | $k_d$ (1/s) | $K_D$ (nM) |
|---|---|---|---|---|---|---|---|
| 23-H7 | 2 | RBD-hFc | FAb | FIG. 3A | $2.60 \times 10^5$ | $3.35 \times 10^{-3}$ | 13 |
|  |  |  |  |  | $2.90 \times 10^5$ | $2.63 \times 10^{-3}$ | 9 (n = 2) |
| 23-H7 | 2 | S1-hFc | FAb | FIG. 3A | $2.47 \times 10^5$ | $3.55 \times 10^{-3}$ | 14 |
|  |  |  |  |  | $7.07 \times 10^5$ | $4.28 \times 10^{-3}$ | 6 (n = 2) |
| 23-H7 | 2 | 23-H7 | RBD | FIG. 3C | $4.19 \times 10^5$ | $1.71 \times 10^{-3}$ | 4 |
|  |  |  |  |  | $4.44 \times 10^5$ | $1.81 \times 10^{-3}$ | 4 (n = 2) |
| 23-H7 | 2 | 23-H7 | S1-D614G-His | FIG. 3C | $3.12 \times 10^5$ | $4.82 \times 10^{-3}$ | 15 |
| 23-H7 | 2 | 23-H7 (probe) | RBD (titrated with 23-H7 FAb) | FIG. 3D | n/d | n/d | 4.6 (3.9-5.4, 95%)** |
| 22-D9 | 4 | RBD-hFc | FAb | FIG. 3A | n/d | n/d | 163 |
| 22-D9 | 4 | 22-D9 | S1-D614G-His | FIG. 3C | n/d | n/d | 245, 249 (n = 2) |
| 21-F2 | 4 | RBD-hFc | FAb | FIG. 3A | n/d | n/d | 162, 195 (n = 2) |
| 22-E7 | C | 22-E7 | S1-D614G-His | FIG. 3C | n/d | n/d | 207 (+/−37) n = 3 |
| 22-F7 | C | 22-F7 | S1-D614G-His | FIG. 3C | n/d | n/d | 144 |
| 2-A6 | S2 | S2-hFc | FAb | FIG. 3A | n/d | n/d | 913 |

Ligand and analyte refer to the binding partner used "on sensor" or "in solution", respectively.

n/d = kinetics not determined for steady-state analysis or solution affinity measurements

**solution affinity estimate (with 95% confidence interval)

Example 5: Some Ab Combinations Show Synergistic Neutralization In Vitro

Twenty candidate Abs which had been assigned to epitope bins were subsequently tested individually and as 2-, 3-, 4-, and 5-Ab cocktails in a cell-based pseudovirus neutralization assay using a mini-checkerboard format. The number of combinations screened was reduced by first pairing Abs across bins, identifying synergistic pairs and using those to anchor higher-order cocktails. Results are provided below in Table 4.

TABLE 4

Determination of Synergistic combinations

| Clone ID | #Abs in cocktail | Bin | Pseudovirus $IC_{50}$ (μg/mL)# | Live Virus $IC_{50}$ (μg/mL)## | Synergistic effect |
|---|---|---|---|---|---|
| 23-H7 | 1 | 2 | 0.84 | non** | n/a**** |
| 27-A11 | 1 | 1a | 12.75 | non | n/a |
| 22-D9 | 1 | 4 | 4.99 | non | n/a |
| 21-F2 | 1 | 4 | 0.84 | 10.5 | n/a |
| 22-E7 | 1 | C | part.* | non | n/a |
| 30-C5 | 1 | C | part. | non | n/a |
| 23-A11 | 1 | 5 | non | non | n/a |
| 8-A2 | 1 | 5 | non | non | n/a |
| 2-A6 | 1 | S2 | non | non | n/a |
| 11-H1 | 1 | 1a | non | non | n/a |
| 22-E8 | 1 | 4 | 11.20 | non | n/a |
| 24-B8 | 1 | 3 | 6.26 | non | n/a |
| 22-F7 | 1 | C | 12.63 | non | n/a |
| 5-B6 | 1 | 1 | non | non | n/a |
| 8-D4 | 1 | 1 | part. | non | n/a |
| 13-A1 | 1 | 4 | part. | non | n/a |
| 26-G2 | 1 | 1 | Part. | n/d*** | n/a |
| 21-H1 | 1 | 1a | Non | n/d | n/a |
| 23H7 + 22-D9 | 2 | 2 + 4 | 0.93 | 4.3 | Y****** |
| 23H7 + 21-F2 | 2 | 2 + 4 | 0.69 | 2.3 | Y |
| 23H7 + 22-E7 | 2 | 2 + C | 0.89 | Non | Y(p)***** |
| 23H7 + 30-C5 | 2 | 2 + C | 1.06 | n/d | Y(p) |
| 23-H7 + 23-A11 | 2 | 2 + 5 | 0.88 | n/d | Y(p) |
| 23-H7 + 8-A2 | 2 | 2 + 5 | 0.45 | n/d | Y(p) |
| 23-H7 + 2-A6 | 2 | 2 + S2 | 0.69 | Non | N******* |
| 22-D9 + 22-E7 | 2 | 4 + C | 18.28 | Non | N |
| 22-D9 + 30-C5 | 2 | 4 + C | 8.80 | n/d | N |
| 22-D9 + 23-A11 | 2 | 4 + 5 | 9.52 | n/d | N |
| 22-D9 + 8-A2 | 2 | 4 + 5 | 9.91 | n/d | N |
| 22-D9 + 2-A6 | 2 | 4 + S2 | 12.49 | n/d | N |
| 21-F2 + 22-E7 | 2 | 4 + C | 1.68 | 14.9 | N |
| 21-F2 + 30-C5 | 2 | 4 + C | 1.97 | n/d | N |
| 21-F2 + 23-A11 | 2 | 4 + 5 | 2.07 | n/d | N |
| 21-F2 + 8-A2 | 2 | 4 + 5 | 1.94 | n/d | N |
| 21-F2 + 2-A6 | 2 | 4 + S2 | 2.23 | n/d | N |
| 27-A11 + 21-F2 | 2 | 1a + 4 | 0.89 | n/d | Y(p) |
| 27-A11 + 22-E7 | 2 | 1a + C | 5.3 | n/d | Y(p) |
| 27-A11 + 8-A2 | 2 | 1a + 5 | 8.71 | n/d | Y(p) |
| 27-A11 + 2-A6 | 2 | 1a + S2 | Non | n/d | N |
| 23-H7 + 22-D9 + 22-E7 | 3 | 2 + 4 + C | 1.43 | 7.4 | Y |
| 23-H7 + 22-D9 + 30-C5 | 3 | 2 + 4 + C | 1.15 | n/d | Y(p) |
| 23-H7-22-D9 + 23-A11 | 3 | 2 + 4 + 5 | 0.91 | n/d | Y(p) |
| 23-H7 + 22-D9 + 8-A2 | 3 | 2 + 4 + 5 | 1.14 | n/d | Y(p) |
| 23-H7 + 22-D9 + 2-A6 | 3 | 2 + 4 + S2 | 1.48 | n/d | Y(p) |
| 23-H7 + 21-F2 + 22-E7 | 3 | 2 + 4 + C | 1.06 | 1.9 | Y |
| 23-H7 + 21-F2 + 30-C5 | 3 | 2 + 4 + C | 0.82 | n/d | Y(p) |
| 23-H7 + 21-F2 + 23-A11 | 3 | 2 + 4 + 5 | 0.79 | n/d | Y(p) |
| 23-H7 + 21-F2 + 8-A2 | 3 | 2 + 4 + 5 | 0.74 | n/d | Y(p) |
| 23-H7 + 21-F2 + 2-A6 | 3 | 2 + 4 + S2 | 1.09 | n/d | Y(p) |
| 27-A11 + 21-F2 + 22-E7 | 3 | 1a + 4 + C | 1.52 | n/d | Y(p) |
| 27-A11 + 21-F2 + 8-A2 | 3 | 1a + 4 + 5 | 1.27 | n/d | Y(p) |
| 27-A11 + 21-F2 + 2-A6 | 3 | 1a + 4 + S2 | 1.08 | n/d | Y(p) |
| 23-H7 + 22-D9 + 22-E7 + 23-A11 | 4 | 2 + 4 + C + 5 | 1.41 | 19.4 | Y |

TABLE 4-continued

Determination of Synergistic combinations

| Clone ID | #Abs in cocktail | Bin | Pseudovirus IC$_{50}$ (µg/mL)# | Live Virus IC$_{50}$ (µg/mL)## | Synergistic effect |
|---|---|---|---|---|---|
| 23-H7 + 22-D9 + 22-E7 + 8-A2 | 4 | 2 + 4 + C + 5 | 1.18 | 8.8 | Y |
| 23-H7 + 22-D9 + 22-E7 + 2-A6 | 4 | 2 + 4 + C + S2 | 0.93 | 14.8 | Y |
| 23-H7 + 22-D9 + 30-C5 + 23-A11 | 4 | 2 + 4 + C + 5 | 0.93 | n/d | Y(p) |
| 23-H7 + 22-D9 + 30-C5 + 8-A2 | 4 | 2 + 4 + C + 5 | 1.05 | n/d | Y(p) |
| 23-H7 + 22-9 + 30-C5 + 2-A6 | 4 | 2 + 4 + C + S2 | 1.10 | n/d | Y(p) |
| 23-H7 + 21-F2 + 22-E7 + 23-A11 | 4 | 2 + 4 + C + 5 | 1.28 | 2.6 | Y |
| 23-H7 + 21-F2 + 22-E7 + 8-A2 | 4 | 2 + 4 + C + 5 | 1.27 | 2.6 | Y |
| 23-H7 + 21-F2 + 22-E7 + 2-A6 | 4 | 2 + 4 + C + S2 | 0.88 | 1.9 | Y |
| 23-H7 + 21-F2 + 30-C5 + 23-A11 | 4 | 2 + 4 + C + 5 | 1.30 | n/d | Y(p) |
| 23-H7 + 21-F2 + 30-C5 + 8-A2 | 4 | 2 + 4 + C + 5 | 0.8 | n/d | Y(p) |
| 23-H7 + 21-F2 + 30-C5 + 2-A6 | 4 | 2 + 4 + C + S2 | 0.93 | n/d | Y(p) |
| 27-A11 + 21-F2 + 22-E7 + 8-A2 | 4 | 1a + 4 + C + 5 | 1.18 | n/d | Y(p) |
| 27-A11 + 21-F2 + 22-E7 + 2-A6 | 4 | 1a + 4 + C + S2 | 0.88 | n/d | Y(p) |
| 23-H7 + 22-D9 + 22-E7 + 23-A11 + 2-A6 | 5 | 2 + 4 + C + 5 + S2 | 1.48 | 5.2 | Y |
| 23-H7 + 22-D9 + 22-E7 + 8-A2 + 2-A6 | 5 | 2 + 4 + C + 5 + S2 | 0.95 | 15.7 | Y |
| 23-H7 + 22-D9 + 30-C5 + 23-A11 + 2-A6 | 5 | 2 + 4 + C + 5 + S2 | 1.12 | n/d | Y(p) |
| 23-H7 + 22-D9 + 30 C5 + 8-A2 + 2-A6 | 5 | 2 + 4 + C + 5 + S2 | 1.20 | n/d | Y(p) |
| 23-H7 + 21-F2 + 22-E7 + 23-A11 + 2-A6 | 5 | 2 + 4 + C + 5 + S2 | 0.94 | 4.4 | Y |
| 23-H7 + 21-F2 + 22-E7 + 8-A2 + 2-A6 | 5 | 2 + 4 + C + 5 + S2 | 0.99 | 4.4 | Y |
| 23-H7 + 21-F2 + 30-C5 + 23-A11 + 2-A6 | 5 | 2 + 4 + C + 5 + S2 | 1.24 | n/d | Y(p) |
| 23-H7 + 21-F2 + 30-C5 + 8-A2 + 2-A6 | 5 | 2 + 4 + C + 5 + S2 | 0.92 | n/d | Y(p) |
| 27-A11 + 21-F2 + 22-E7 + 8-A2 + 2-A6 | 5 | 1a + 4 + C + 5 + S2 | 1.80 | 14.9 | N |

*part. = <100% neutralization at highest assay concentration
**non = non-neutralizing at highest tested concentration (42 ug/mL in pseudovirus and 100 µg/mL in live virus)
***n/d = not determined-sample was not tested in indicated assay
****n/a = not applicable-single Ab measurements cannot show synergy
*****y(p)-synergy determination from pseudovirus neutralization only
******y = synergy in both live virus and pseudovirus neutralization assays
*******n = no synergy observed#

Figure 4A:
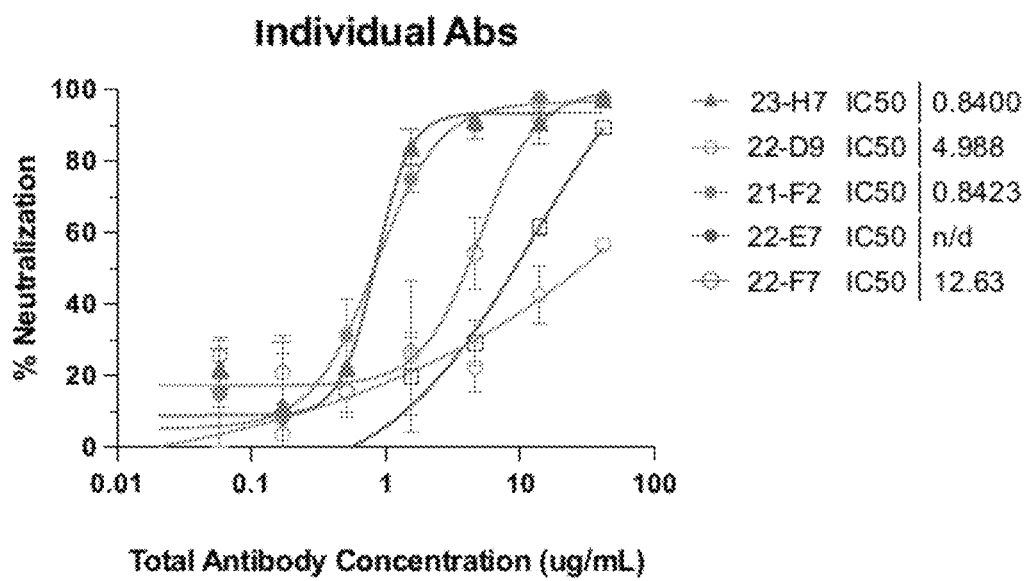
Figure 4B:
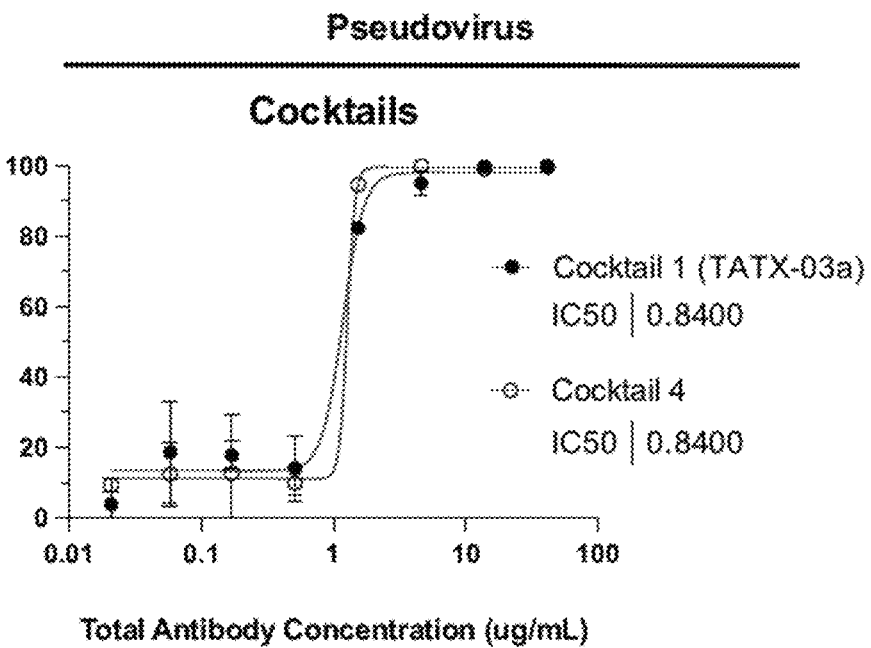
Figure 4C:
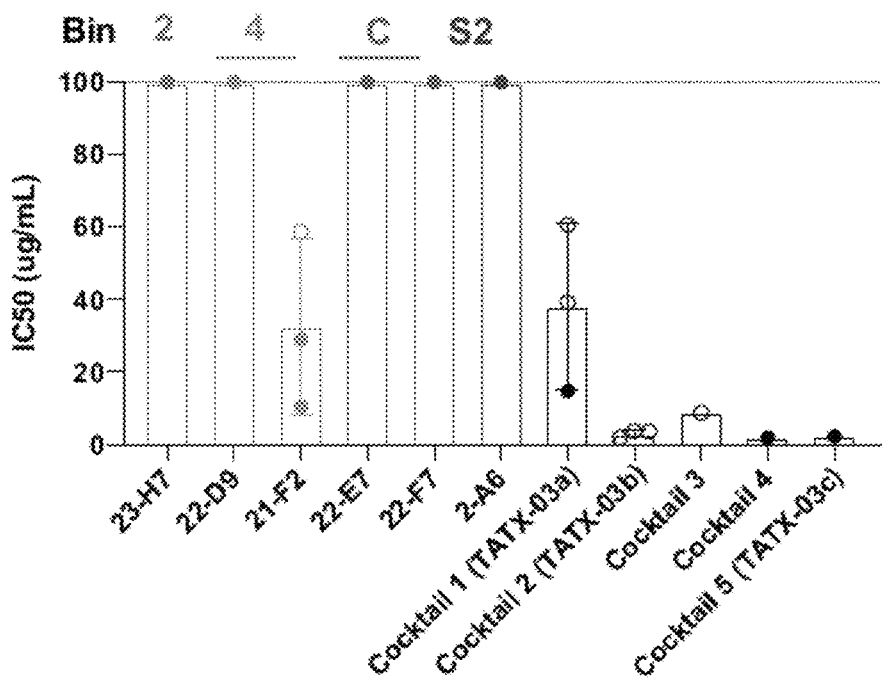

The TATX-03 four-bin combination, represented by six leads (23-H7 from bin 2, 22-D9 or 21-F2 from bin 4, 22-E7 or 22-F7 from bin C, and 2-A6 from bin S2) which showed varying neutralization capacity individually in the pseudovirus assay (FIG. 4A), demonstrated synergistic activity in various multi-Ab combinations (FIG. 4B). In authentic virus-based neutralization assays, all individual Abs, except 21-F2, showed a lack of neutralization within the assay window when tested at a top concentration of 100 µg/mL (FIG. 4C). However, multiple 4- and 5-Ab combinations showed potent neutralization at the same total antibody concentration, indicating that synergistic effects improved neutralization of authentic virus (FIG. 4C). These in vitro data resulted in the prioritization of two 4 Ab-cocktails, number 1 (TATX-03a) and 2 (TATX-03b), for in vivo efficacy evaluation.

Figure 5A:
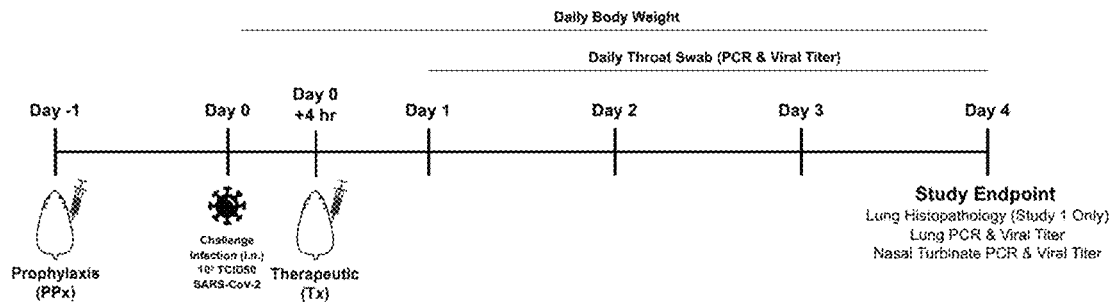
Figure 5B:
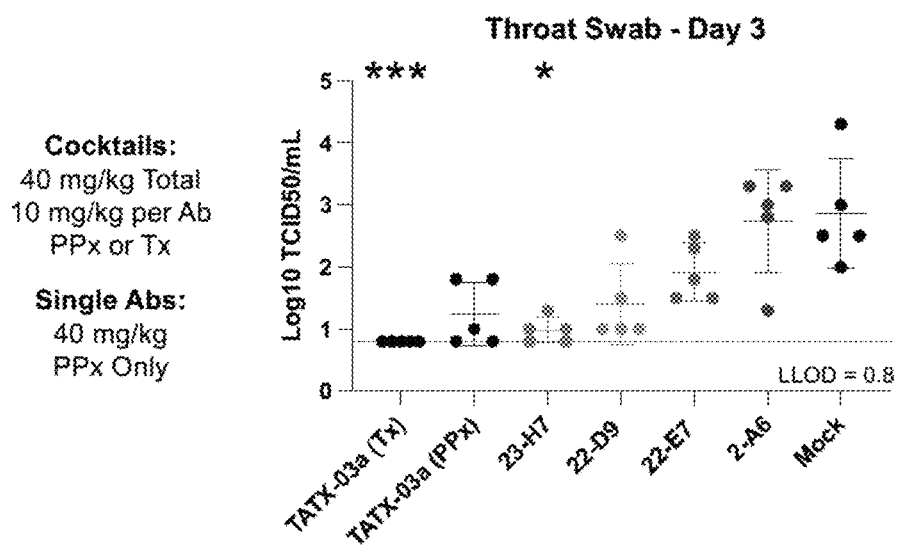

Example 6: Multi-Ab Cocktail TATX-03 Reduces Viral Titer in Hamster Challenge Model To determine the in vivo efficacy of TATX-03, two blends and their individual constituent Abs were tested in a Syrian hamster model of acute SARS-CoV-2 infection[15,16]. Blends TATX-03a and TATX-03b were tested in separate studies, with all Abs (or PBS mock) administered as a single intraperitoneal (i.p.) dose either 24-hours pre-challenge (prophylaxis, PPx) or 4 hours post-challenge (therapeutic, Tx) with SARS-CoV-2 (D614G Mutant BetaCoV/Munich/BavPat1/2020) (FIG. 5A). Infection was confirmed by RT-PCR analysis on day 1 post-challenge throat swab samples and average daily weight loss was similar for all groups for the duration of the study (FIGS. 5E-F). All animals survived to endpoint at day 4 post-challenge.

Figure 5C:
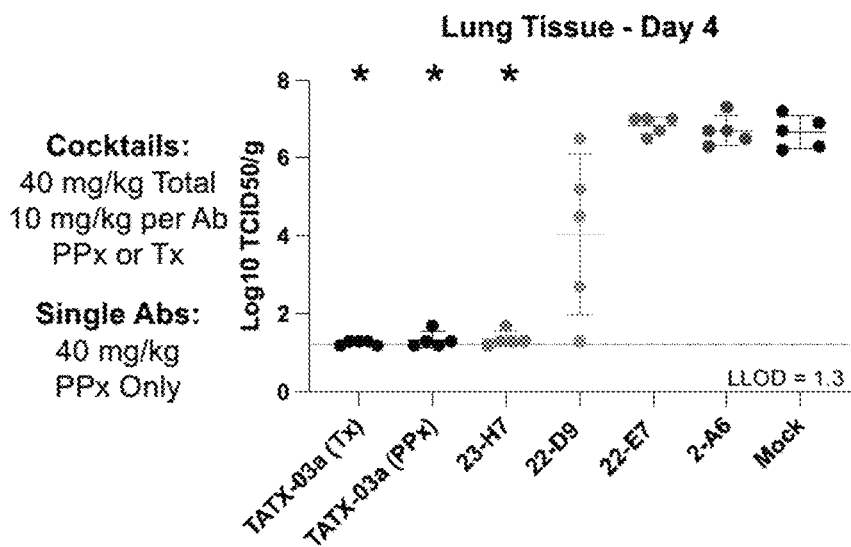
Figure 5D:
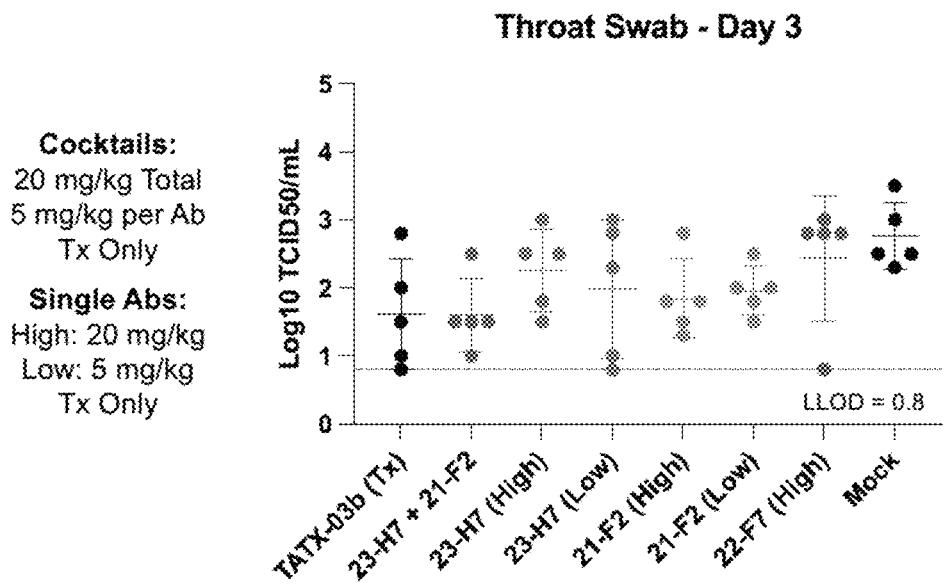
Figure 5E:
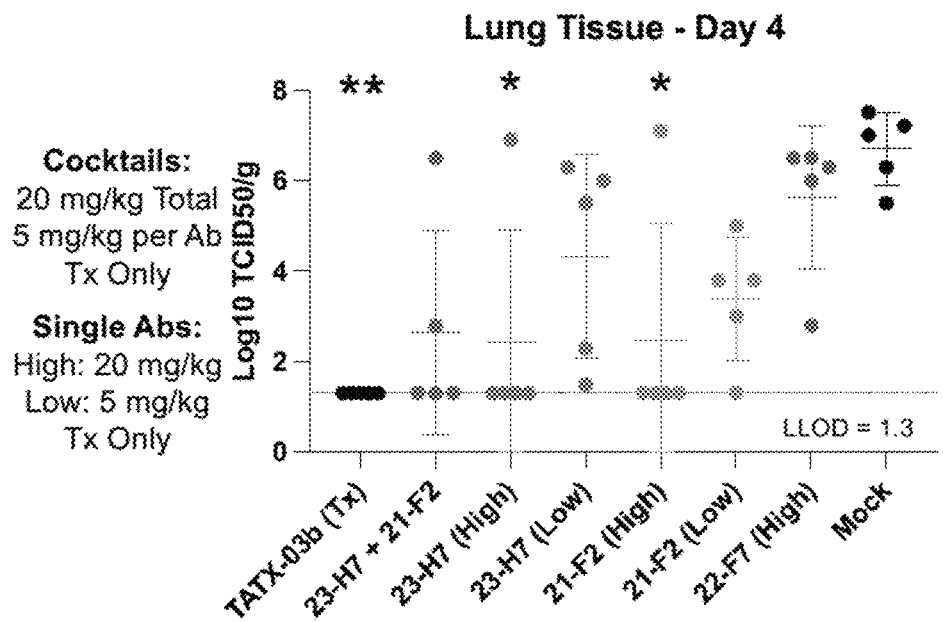
Figure 5F:
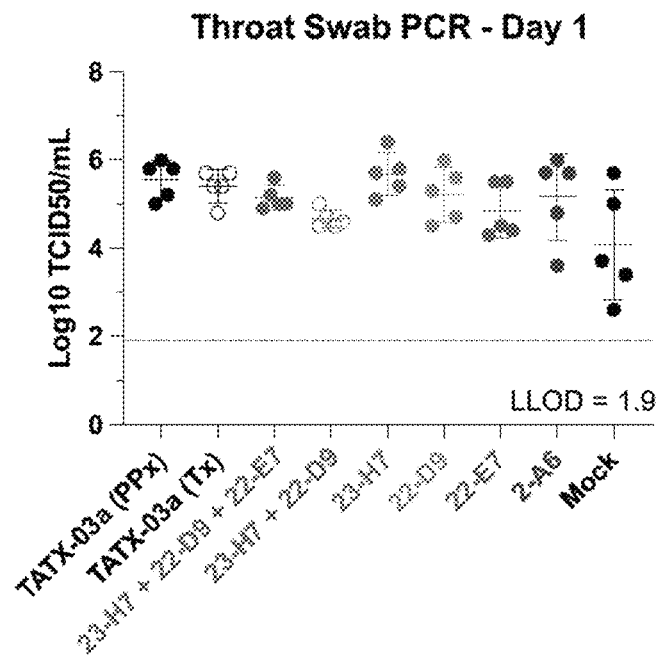
Figure 5G:
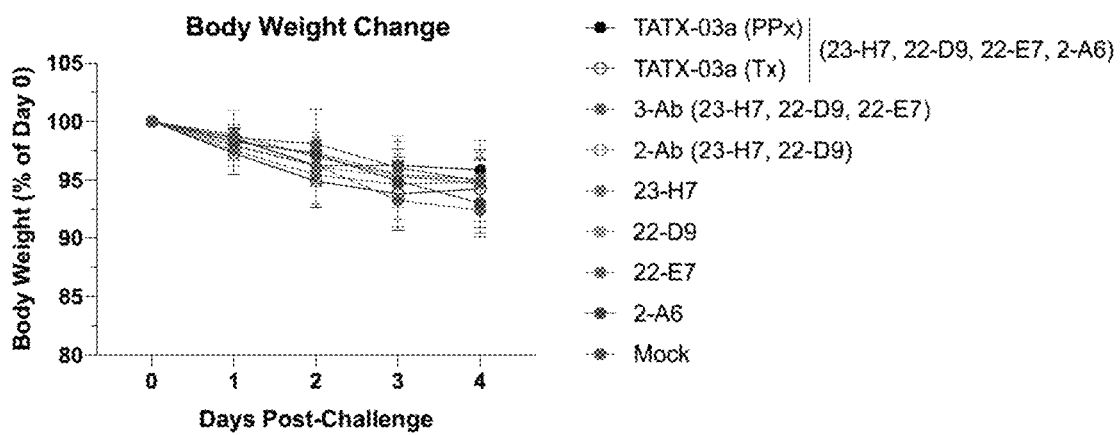
Figure 5H:
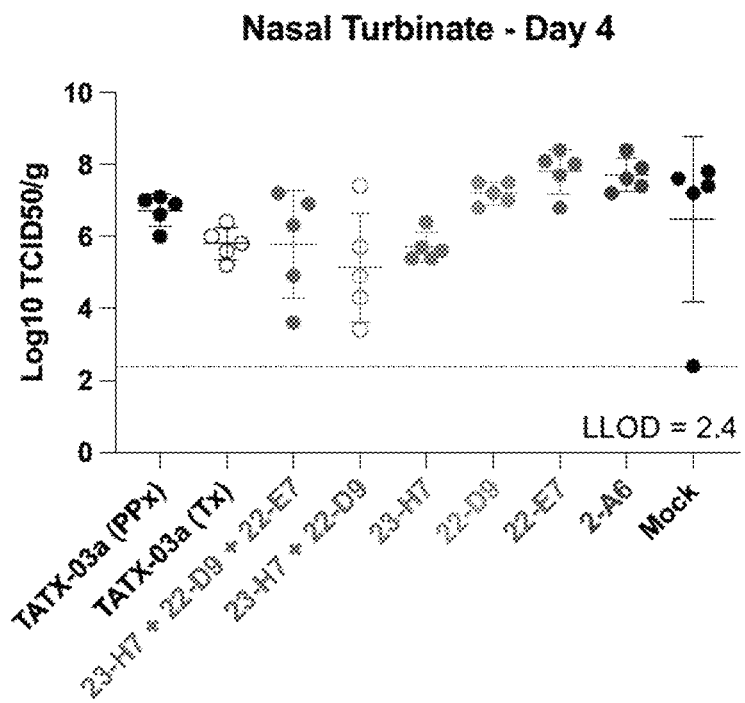
Figure 5I:
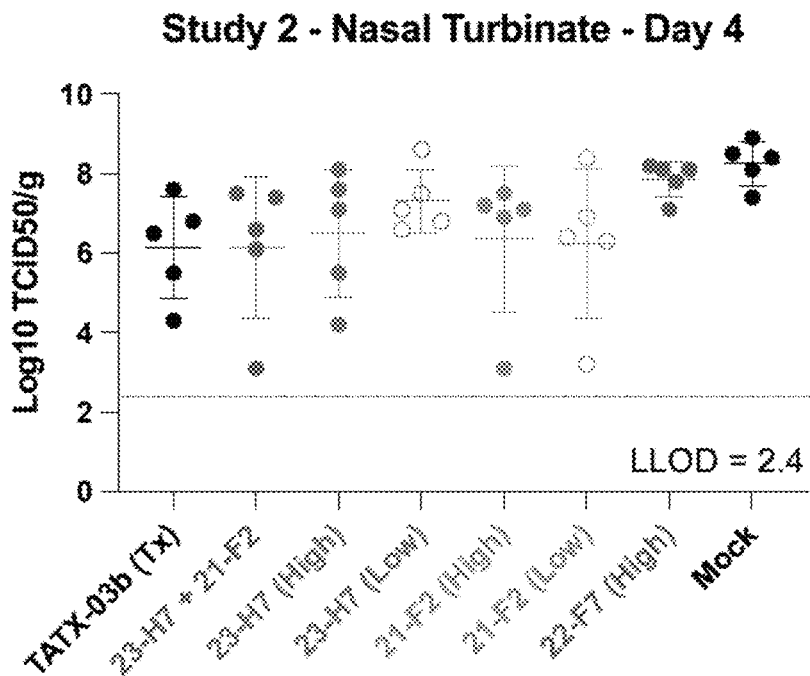
Figure 6A:
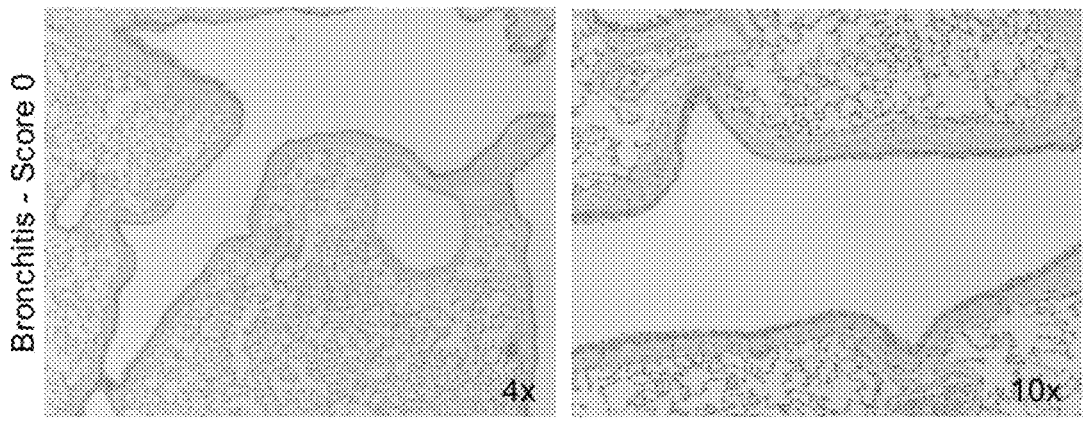
Figure 6B:
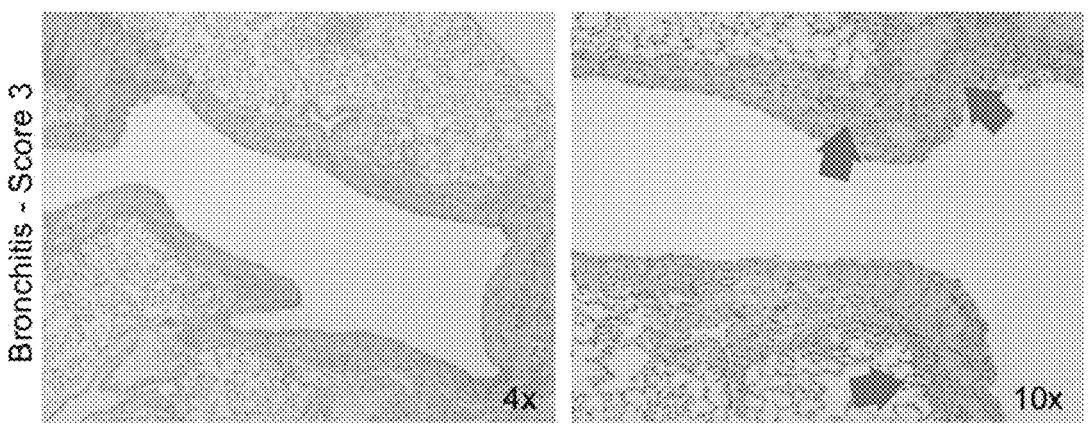
Figure 6C:
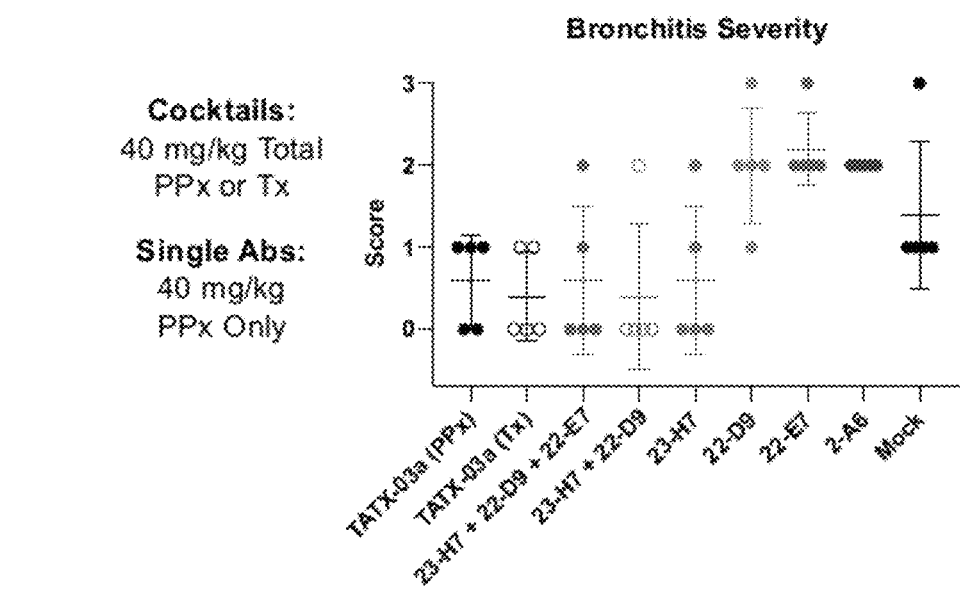
Figure 6D:
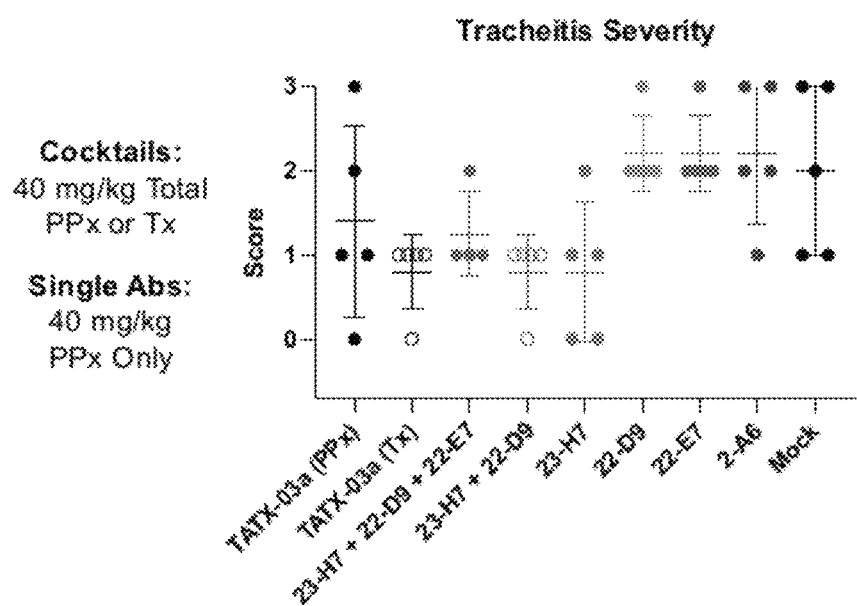

The first study tested the TATX-03a blend (23-H7, 22-D9, 22-E7, 2-A6), composed of Abs that were non-neutralizing individually but neutralized synergistically as a cocktail in authentic virus in vitro (FIG. 5C). All animals (5/5) receiving therapeutic administration of the TATX-03a cocktail (40 mg/kg bw which equals 10 mg/kg bw/Ab) showed day 3 throat swab virus titers at or below the lowest limit of detection (LLOD), with animals treated with TATX-03a prophylaxis showing clear reductions in day 3 throat swab virus titer compared to mock (FIG. 5B). At the day 4 endpoint both TATX-03 treated groups demonstrated significantly reduced virus titers in whole lung tissue compared to mock (FIG. 5C), with 100% (5/5) of the animals in the therapeutic group and 80% (4/5) of the prophylactically treated animals showing viral titers below LLOD. In line with previous reports of discordant reductions in viral load between lung and nasal turbinate in this model of infection[17], all but one animal across both studies harbored detectable viral titers in the nasal turbinate at the day 4 endpoint (FIGS. 5G-H), which is believed to be due to prominent local infections following intranasal inoculation with a significant bolus of virus. Table 5 summarizes the various replication-competent viral titers per cohort.

ity/extent of immune cell infiltration was reduced in groups treated with the TATX-03a cocktail compared to mock, resulting in reduced bronchitis and tracheitis severity scores (FIG. 6C-D). FIGS. 6A and 6B show representative images of hematoxylin and eosin-stained lung tissue with bronchitis severity score 0 and 3, respectively.

Two individual Abs demonstrated partial (22-D9) or significant (23-H7) efficacy by these measures despite their inability to neutralize authentic virus in vitro; notably, 80% (4/5) of the animals prophylactically treated with 23-H7 achieved undetectable viral load in the lung (below LLOD), with the fifth animal showing viral titer barely above LLOD.

The second blend tested in vivo, TATX-03b (23-H7, 21-F2, 22-F7, 2-A6), included the only Ab that neutralized authentic virus in vitro (FIG. 4C). To determine whether in vitro synergy could be recapitulated in vivo, Abs were administered individually either at a high dose (20 mg/kg bw) or at a low dose (5 mg/kg bw), with the latter matching their individual contributions to the TATX-03b cocktail (dosed at 20 mg/kg bw total Ab, equivalent to 5 mg/kg bw/Ab). Like TATX-03a, all animals (5/5) treated with the

TABLE 5

Efficacy results for two different 4-Ab cocktails, TATX-03a (23-H7, 22-D9, 22-E7, 2-A6) and TATX-03b (23-H7, 21-F2, 22-F7, 2-A6) in independent studies (#1 and 2). Antibodies were administered as a single i.p. injection 24-hours pre-challenge (prophylaxis, PPx) or 4-hours post-challenge (therapeutic setting, Tx) at the specified dose (representing total Ab concentration). Five animals were used per cohort. Values are reported for the replication-competent viral titers measured in throat swab at day 3, lung tissue day 4 (end point) and nasal turbinate day 4 (end point). Values represent the mean (±standard deviation) for n = 5. LLOD = lowest limit of detection. The number of animals per cohort with titers at LLOD is also reported as percent and fraction.

| | | | Dose | Replication-competent viral titer (Log10 TCID50) | | |
|---|---|---|---|---|---|---|
| Study # | Ab treatment | PPX or Tx | (mg/kg bw) | /mL Throat swab day 3 | /g Lung tissue day 4, end point | /g Nasal turbinate day 4, end point |
| 1 | 4-Ab (TATX-03a) | Tx | 40 | 0.8 (0), 100% (5/5) LLOD | 1.26 (0.05), 100% (5/5) LLOD | 6.72 (0.44) |
| 1 | 4-Ab (TATX-03a) | PPx | 40 | 1.24 (0.52), 40% (2/5) LLOD | 1.34 (0.21), 80% (4/5) LLOD | 5.8 (0.45) |
| 1 | 3-Ab (23-H7, 22-D9, 22-E7) | PPx | 40 | 0.98 (0.30), 60% (3/5) LLOD | 3.18 (2.58), 60% (3/5) LLOD | 5.78 (1.51) |
| 1 | 2-Ab (23-H7, 22-D9) | PPx | 40 | 1.08 (0.31), 40% (2/5) LLOD | 2.28 (2.30), 80% (4/5) LLOD | 5.14 (1.52) |
| 1 | 23-H7 | PPx | 40 | 0.98 (0.20), 40% (2/5) LLOD | 1.36 (0.19), 80% (4/5) LLOD | 5.7 (0.41) |
| 1 | 22-D9 | PPx | 40 | 1.4 (0.65) | 4.04 (2.06), 20% (1/5) LLOD | 7.2 (0.31) |
| 1 | 22-E7 | PPx | 40 | 1.92 (0.46) | 6.84 (0.23) | 7.8 (0.61) |
| 1 | 2-A6 | PPx | 40 | 2.74 (0.83) | 6.7 (0.37) | 7.7 (0.47) |
| 1 | Mock (PBS) | PPx | 0 | 2.86 (0.88) | 6.66 (0.42) | 6.48 (2.29), 20% (1/5) LLOD |
| 2 | 4-Ab (TATX-03b) | Tx | 20 | 1.62 (0.81) | 1.3 (0), 100% (5/5) LLOD | 6.14 (1.27) |
| 2 | 4-Ab (TATX-03b) | Tx | 5 | 2.32 (0.66) | 4.22 (2.71) | 7.48 (0.64) |
| 2 | 2-Ab (23-H7, 21-F2) | Tx | 5 | 1.6 (0.55) | 2.64 (2.25), 60% (3/5) LLOD | 6.14 (1.80) |
| 2 | 23-H7 | Tx | 20 | 2.26 (0.60) | 2.42 (2.50), 80% (4/5) LLOD | 6.5 (1.61) |
| 2 | 23-H7 | Tx | 5 | 1.98 (1.02) | 4.32 (2.25) | 7.32 (0.79) |
| 2 | 21-F2 | Tx | 20 | 1.84 (0.58) | 2.46 (2.59), 80% (4/5) LLOD | 6.36 (1.84) |
| 2 | 21-F2 | Tx | 5 | 1.96 (0.36) | 3.38 (1.36), 20% (1/5) LLOD | 6.24 (1.90) |
| 2 | 22-F7 | Tx | 20 | 2.44, 20% (1/5) LLOD | 5.62 | 7.86 |
| 2 | Mock (PBS) | Tx | 0 | 2.76 LLOD = 0.8 | 6.70 LLOD = 1.3 | 8.26 LLOD = 2.4 |

Histopathological analysis of airway tissues harvested at the day 4 endpoint showed relatively minimal changes in gross pathology (as expected with the study endpoint coinciding with the acute phase of disease), however, the sever- TATX-03b showed undetectable viral titers in lung at the day 4 endpoint. Only high dose monotherapy with 23-H7 or 21-F2 resulted in viral titer reduction in lung comparable to the cocktail in 80% (4/5) of the animals, while viral titer reduction was clearly less pronounced in animals treated with the corresponding low dose monotherapy (FIG. 5E, Table 5). This indicates that the cocktail's efficacy cannot not solely be attributed to the presence of 23-H7 or 21-F2 individually, strongly suggesting a synergistic effect. When dosed as a 2-Ab cocktail (23-H7, 21-F2) at 5 mg/kg bw total Ab concentration (equivalent to 2.5 mg/kg bw/Ab), viral load in the lung at the day 4 endpoint was reduced to undetectable levels in 60% (3/5) of animals, which was more efficacious than either individual Ab when administered at 5 mg/kg bw, consistent with a synergistic effect (FIG. 5E).

Example 7: Cocktail Formulation Overcomes Escape of Individual Abs by Variants of Concern (VOCs)

Figure 7A:
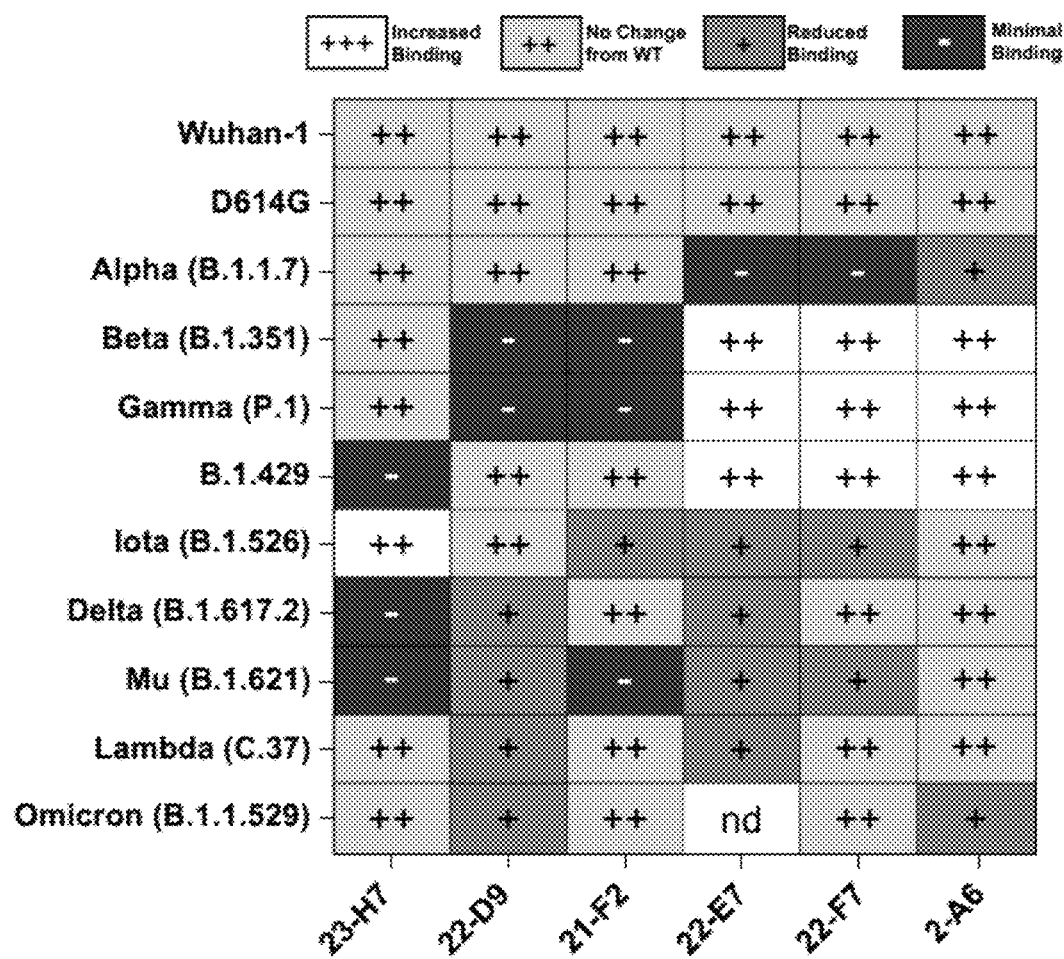
FIGS. 7A-H show the results of cell-based reactivity and pseudovirus neutralization screening against variants of concern (VOCs).
Figure 7B:
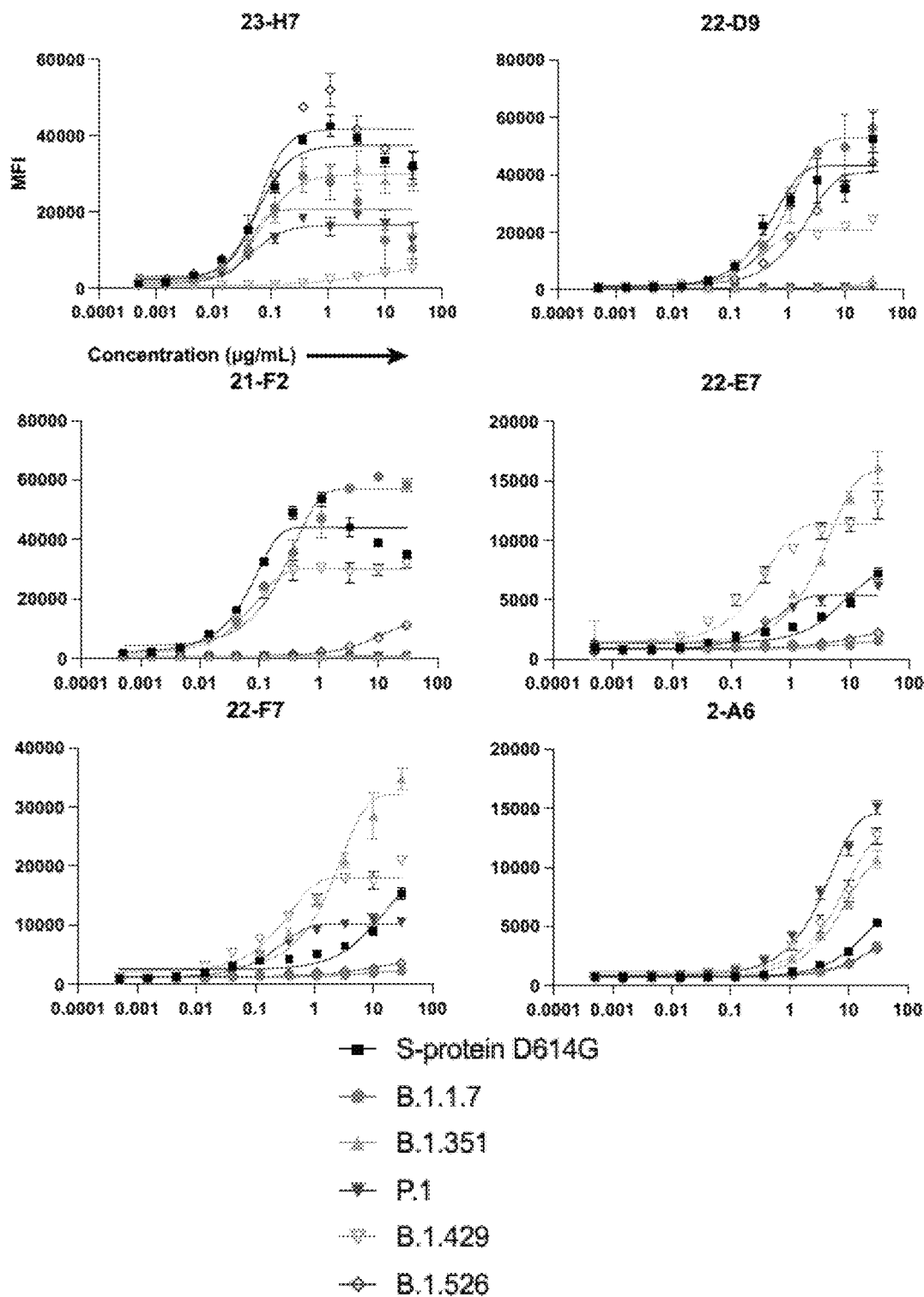
Figure 7C:
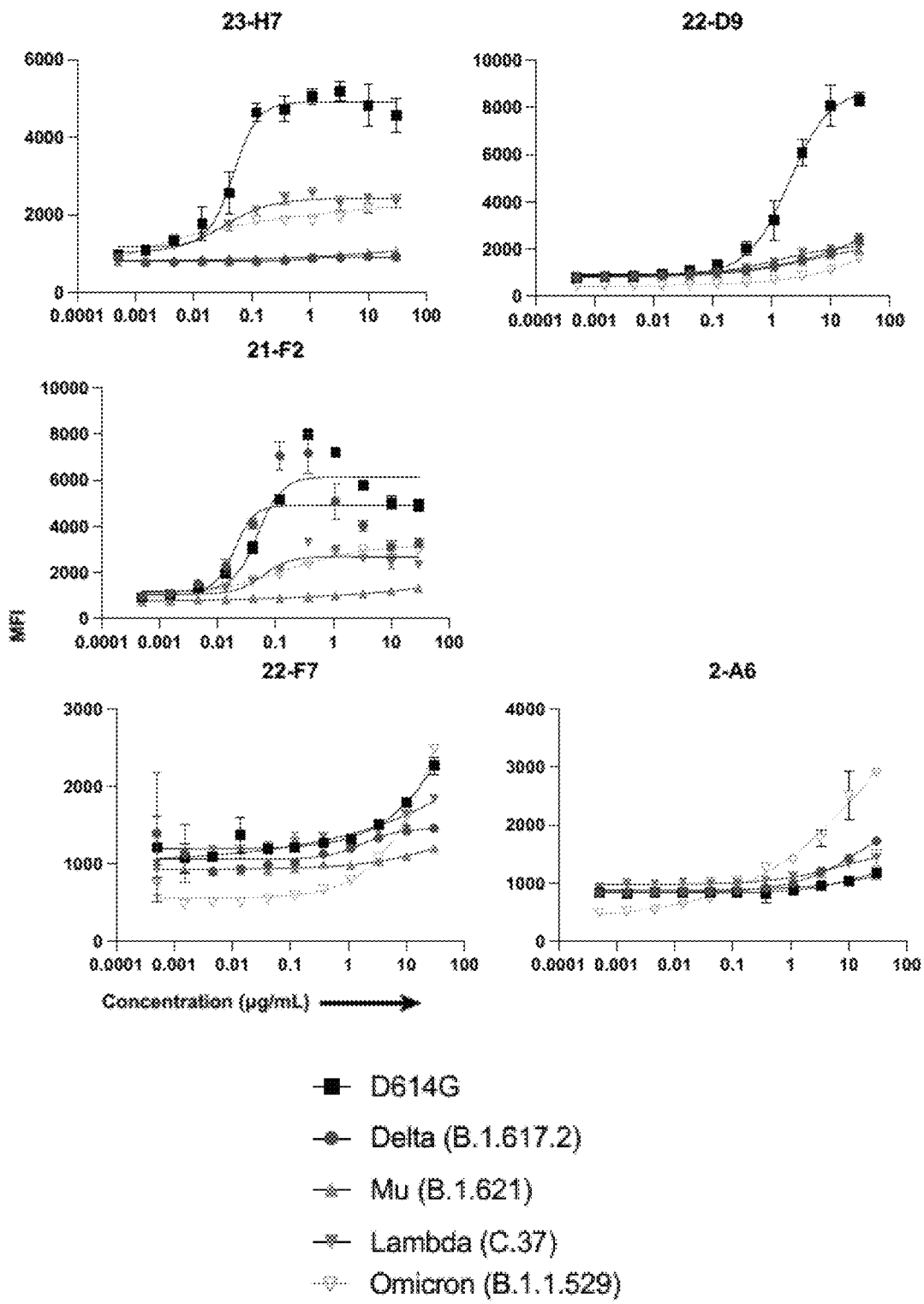
Figure 7D:
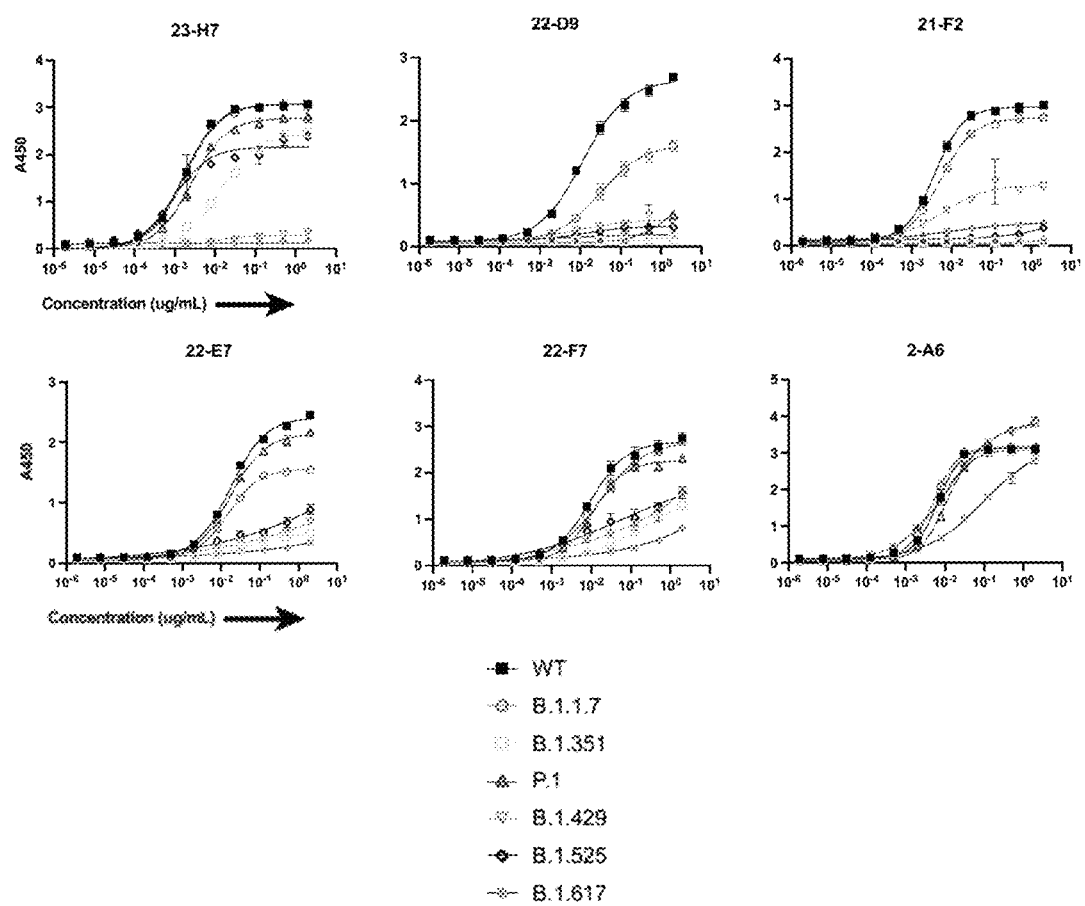
Figure 7E:
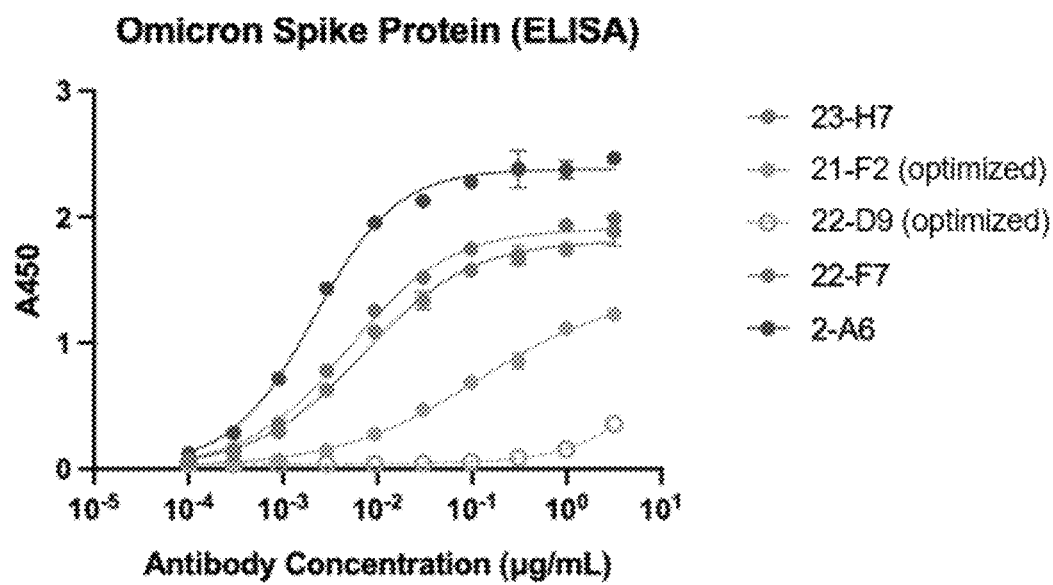
Figure 7F:
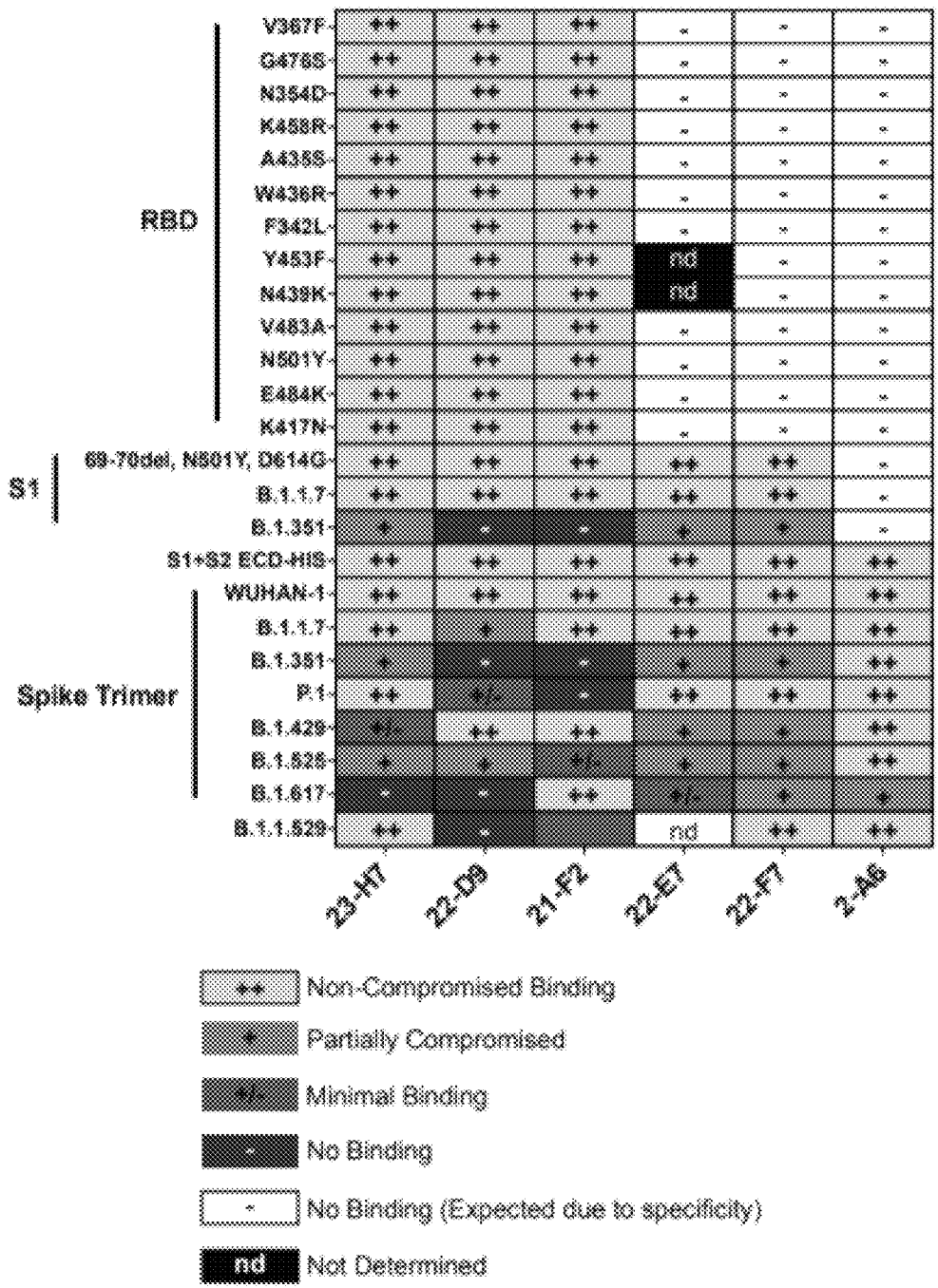

To determine whether the components of the TATX-03 cocktail were resistant to SARS-CoV-2 VOCs, individual Abs were screened against a panel of cell-associated Spike trimers harboring mutations from the B.1.1.7 (Alpha), B.1.351 (Beta), P.1 (Gamma), B.1.429, B.1.526 (Iota), B.1.617 (Delta), B.1.621 (Mu), C.37 (Lambda) and B.1.1.529 (Omicron) lineages, as well as the A (Wuhan-1) and B (D614G) parental lineages for reference. These data revealed a bin-dependent susceptibility to viral variants (FIGS. 7A-C), which generally was in line with the data obtained from ELISA-based reactivity screening towards plate-adsorbed recombinant Spike variants (FIGS. 7D-E). Bin 2 (23-H7) was resistant to all cell-associated Spike trimer variants tested except for the Mu variant (B.1.621) and those carrying the L452R mutation (B.1.429 and B.1.617.2), which results in reduced, but not totally abrogated, binding of Bin 2. The other, non-23-H7, Abs in the cocktail all bound to B.1.429. Bin 4 Abs, 22-D9 and 21-F2, were similarly incapable to bind to B.1.351. In addition, while both 22-D9 and 21-F2 showed no binding to the P.1 variant in the context of cell-associated spike, 22-D9 retained low-level binding to P.1 by ELISA. Bin C Abs 22-E7 and 22-F7, were uniformly incapable to bind to B.1.1.7, whereas no difference was observed towards other mutants. Bin S2 showed uniform binding of 2-A6 to all tested mutant trimer constructs, being unaffected by any of the mutations in the S2 subunit. Bin C (22-E7 and 22-F7) and bin S2 (2-A6) clones both showed some reactivity discrepancies towards cell-associated spike compared to their binding profiles against plate-immobilized soluble recombinant spike counterparts as revealed by ELISA, which is likely due to the trimer being cleavable on cells. Such cleavage represents a more "native" conformation in contrast to the more artificial cleavage-resistant stabilized forms of the soluble recombinant constructs. The susceptibility of the antibodies of the cocktail to Omicron spike protein mutations was assessed by ELISA using an immobilized recombinant spike trimer carrying the lineage-defining mutations. All antibodies were screened individually (FIG. 7E), showing the susceptibility of 22-D9 and partial reduction in binding of 21-F2 (both from bin 4) relative to the wild type control spike protein. FIG. 7F summarizes the relative reactivities of each antibody constituent in the cocktail towards SARS-CoV-2 spike-protein fragments and against trimer spike-proteins representing the indicated viral variants. Overall, no two bins represented in the TATX-03 cocktail could be simultaneously escaped by the variants tested.

Figure 7G:
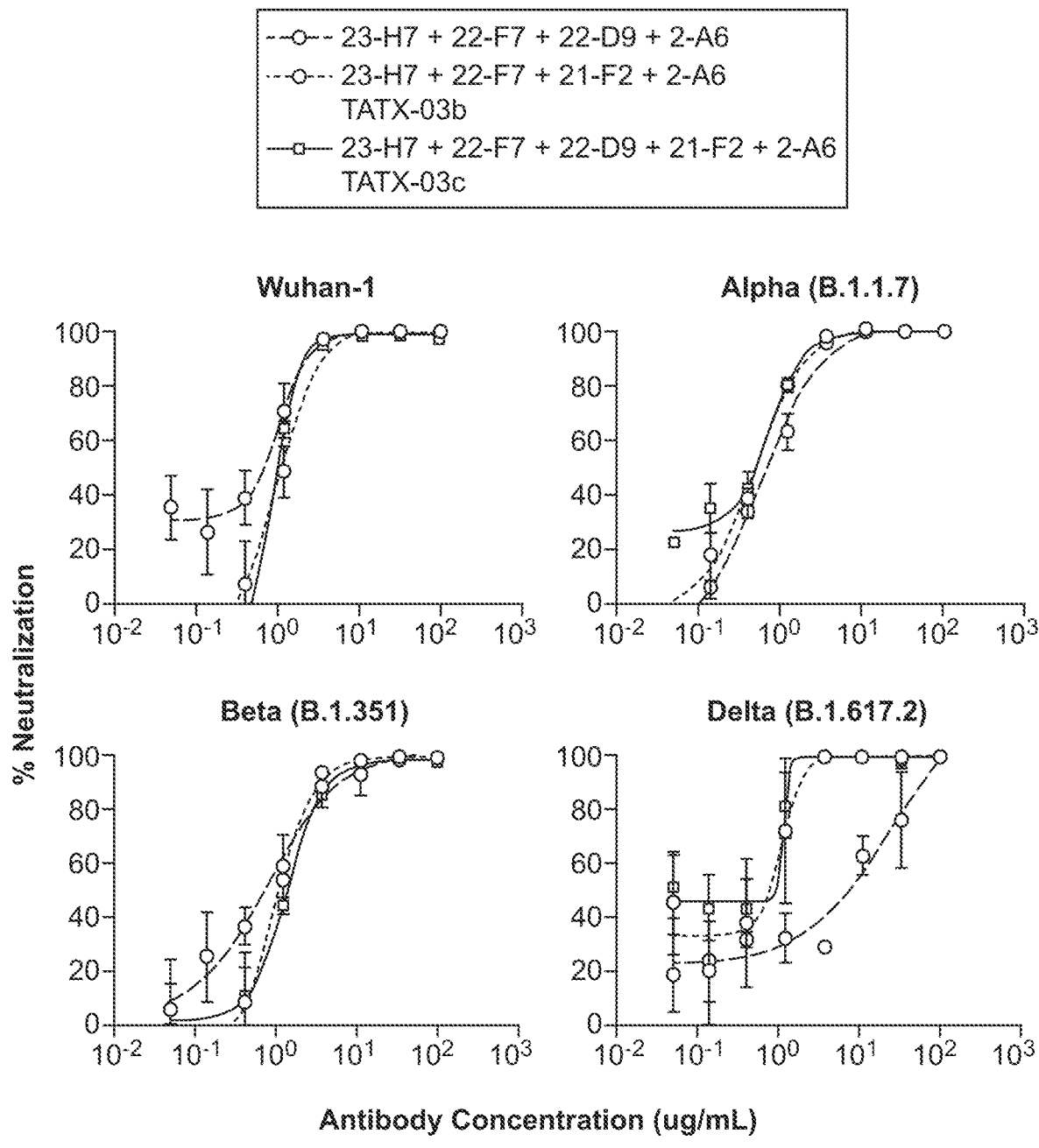
Figure 7H:
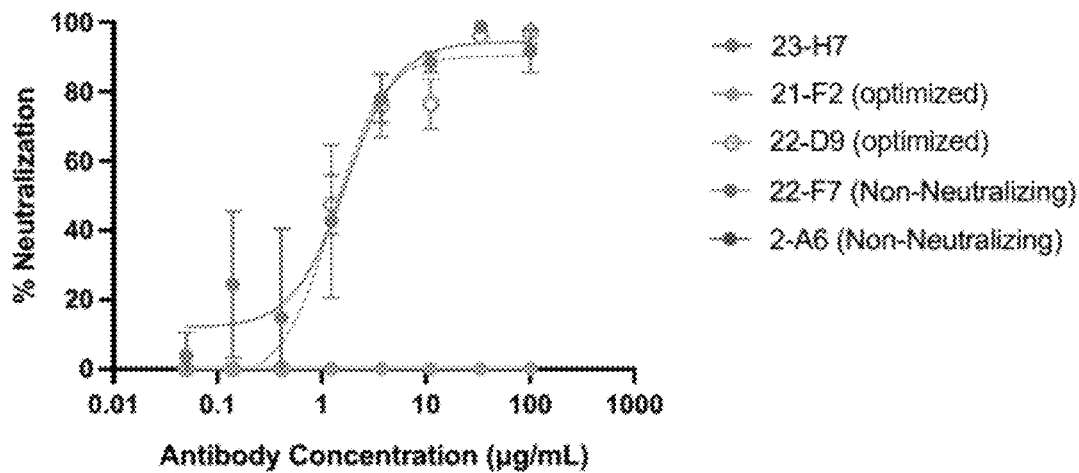
Figure 7H:
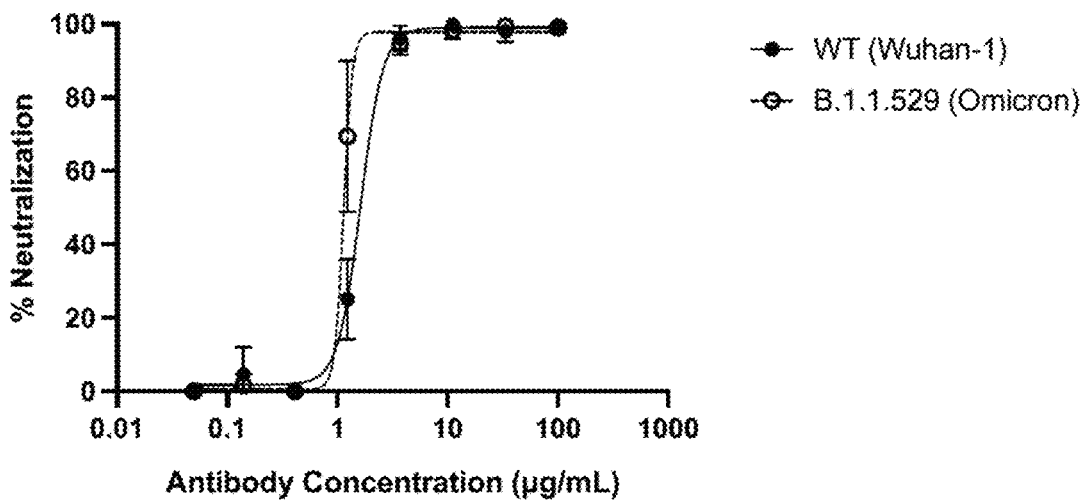

To assess the functional consequence of mutant susceptibility, it was tested whether TATX-03 could retain neutralization potency in pseudovirus assays adapted to the Alpha, Beta, B.1.617.2 (Delta) and Omicron variants. In addition to the two TATX-03 4-Ab cocktails, a 5-Ab version of TATX-03 (TATX-03c) was tested which included two bin 4 antibodies (21-F2 and 22-D9) to potentially capitalize on subtle differences in their binding specificities identified by the epitope binning experiments and VOCs screenings. All analyzed multi-Ab cocktails retained potent neutralization against the tested pseudotyped viruses including Omicron (FIGS. 7G-H) with only one 4-Ab combination showing partial susceptibility to the Delta variant.

Example 8: ADCP and ADCC Activity of Antibodies

Figure 8A:
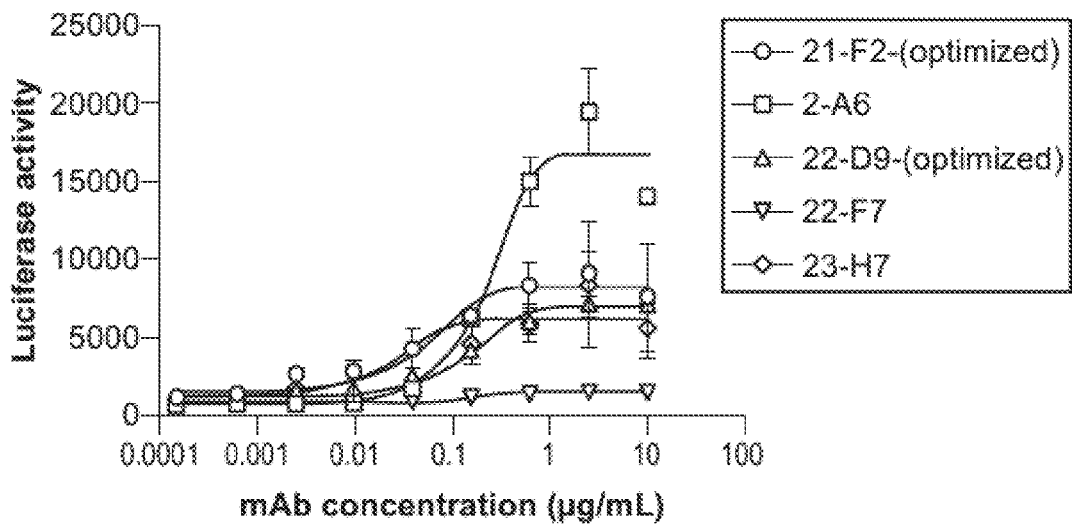
FIGS. 8A-C show the results of an in vitro antibody-dependent cellular phagocytosis (ADCP) reporter cell activity screening of mAbs in presence of SARS-CoV-2-expressing cells.

In contrast to 22-F7 and 2-A6, which showed weak binding, antibodies 23-H7, 21-F2-optimized and 22-D9-optimized revealed a clear correlation of their concentration with the amount of binding to SARS-CoV2-S CHO-K1 target cells on guidance of an anti-human IgG-PE-conjugated antibody. In a next step, cytotoxicity reporter cells were added and co-incubated, and a dose-dependent activation, except in the case of 22-F7-treated CHO-K1 cells, of FcγR ADCP reporter cells was observed, most likely as a result from the antibody binding and clustering (FIG. 8A, N=2). Intriguingly, antibody 2-A6, which showed only weak binding to SARS-CoV2-S CHO-K1 cells, yielded the highest absolute ADCP activation signals.

Figure 9A:
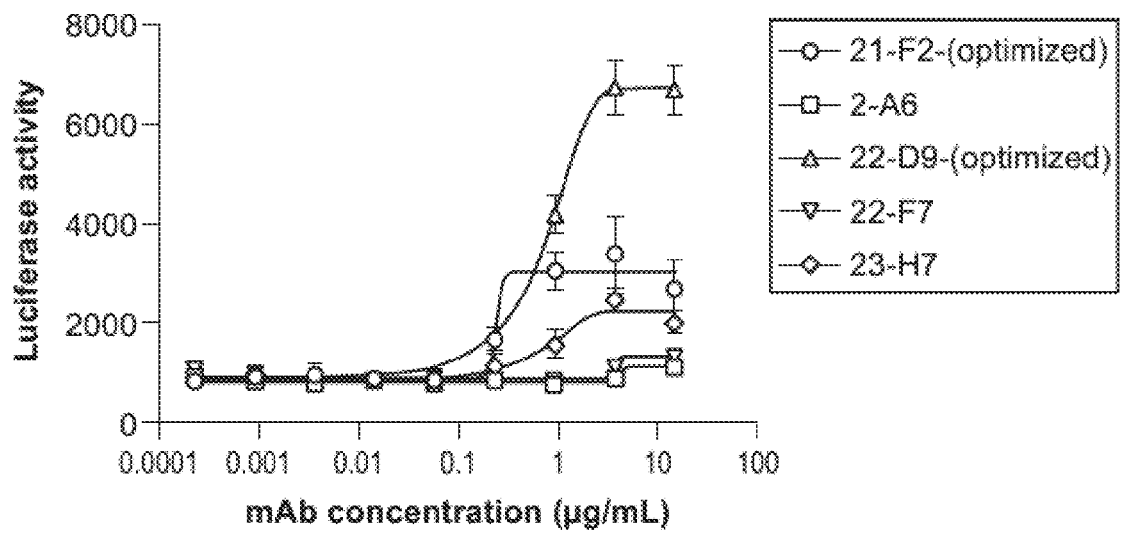
FIGS. 9A-C show the results of an in vitro antibody-dependent cellular cytotoxicity (ADCC) reporter cell activity screening of mAbs in presence of SARS-CoV-2 expressing cells.

Similarly, co-incubation of 23-H7, 21-F2-optimized and 22-D9-optimized-treated SARS-CoV2-S CHO-K1 cells revealed an evident dose-dependent activation of FcγR ADCC reporter cells, while other mAbs, 2-A6 and 22-F7, showed no activation (FIG. 9A, N=2).

Figure 8B:
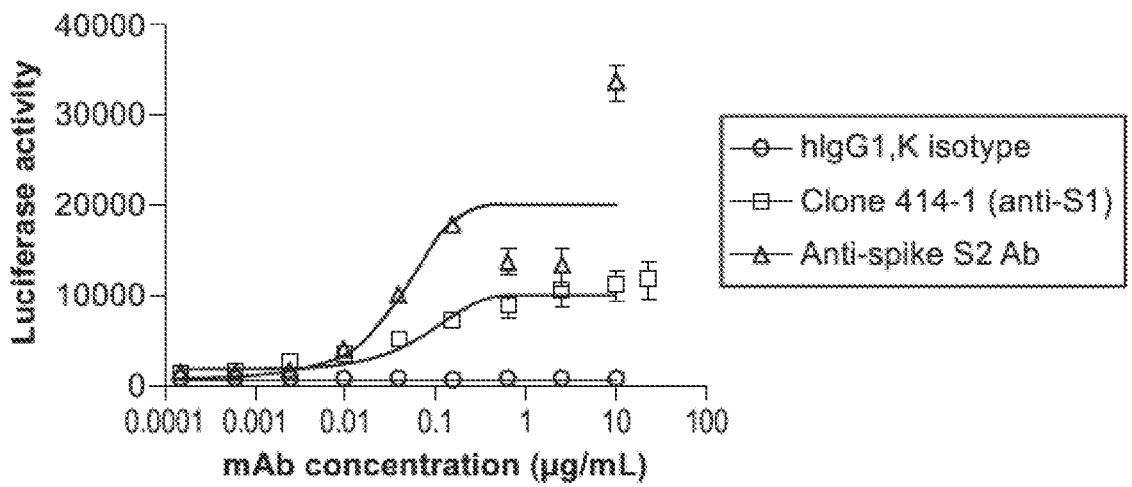
Figure 8C:
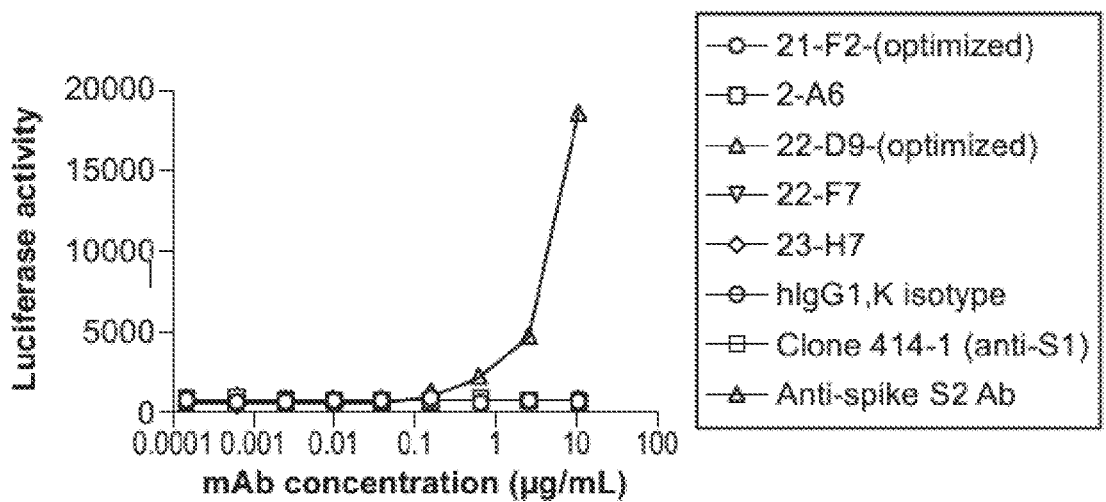
Figure 9B:
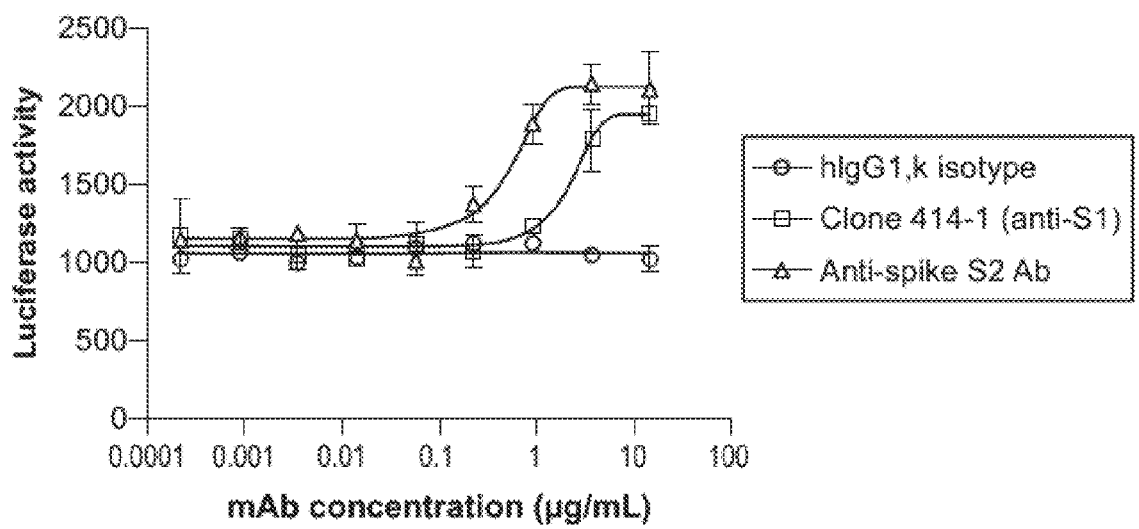
Figure 9C:
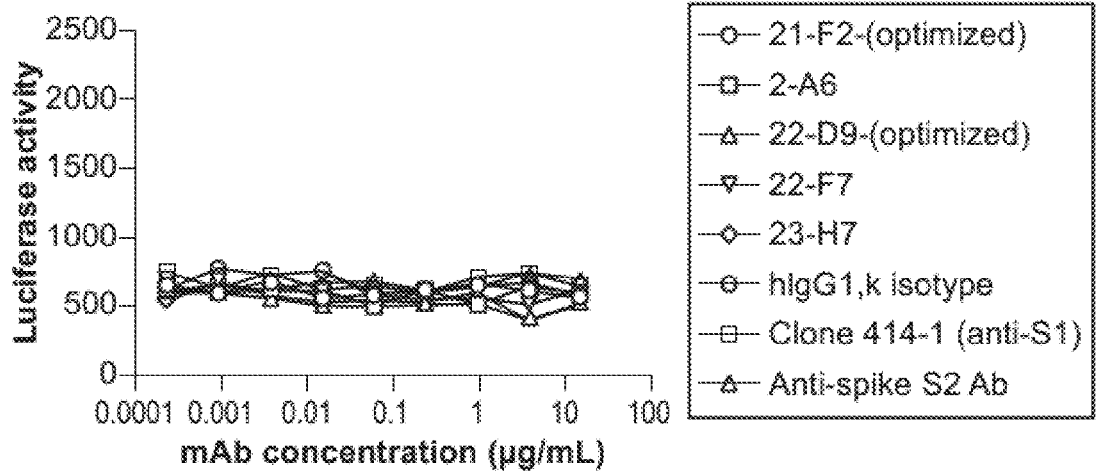

Activation of FcγR reporter cells was not detected following incubation with any of the cocktail antibodies in the absence of target-expressing CHO-K1 cells (FIGS. 8C and 9C), and control mAb NISTmAb (hIgG1,κ isotype) did not give ADCP (FIG. 8B) or ADCC (FIG. 9B) activation in the presence of target and effector cells, thus confirming the specificity of the assays.

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

REFERENCES

1. Li, W., Moore, M., Vasilieva, N. et al. Angiotensin-converting enzyme 2 is a functional receptor for the SARS coronavirus. Nature 426, 450-454 (2003).
2. Yi, C., Sun, X., Ye, J. et al. Key residues of the receptor binding motif in the spike protein of SARS-CoV-2 that interact with ACE2 and neutralizing antibodies. Cell Mol Immunol 17, 621-630 (2020). https://doi.org/10.1038/s41423-020-0458-z
3. Ge, J., Wang, R., Ju, B. et al. Antibody neutralization of SARS-CoV-2 through ACE2 receptor mimicry. Nat Commun 12, 250 (2021). https://doi.org/10.1038/s41467-020-20501-9
4. Shi, R., Shan, C., Duan, X. et al. A human neutralizing antibody targets the receptor-binding site of SARS-CoV-2. Nature 584, 120-124 (2020). https://doi.org/10.1038/s41586-020-2381-y 5. Wu, Y., Wang, F., Shen, C., et al. A noncompeting pair of human neutralizing antibodies block COVID-19 virus binding to its receptor ACE2. Science 368, 1274-1278 (2020) http://doi.org/10.1126/science.abc2241
6. Hansen, J., Baum, A., Pascal, K. E., et al. Studies in humanized mice and convalescent humans yield a SARS-CoV-2 antibody cocktail. Science 369, 1010-1014 (2020). http://doi.org/10.1126/science.abd0827
7. Schäfer, A. et al. Antibody potency, effector function, and combinations in protection and therapy for SARS-CoV-2 infection in vivo. J. Exp. Med. 218, e20201993 (2021).
8. Weisblum, Y., Schmidt, F., Zhang, F., et al. Escape from neutralizing antibodies by SARS-CoV-2 spike protein variants. eLife 9, e61312 (2020) http://doi.org/10.7554/eLife.61312
9. Chen, J., Gao, K., Wang, R. & Wei, G.-W. Revealing the threat of emerging SARS-CoV-2 mutations to antibody therapies. bioRxiv 2021.04.12.439473 (2021) doi: 10.1101/2021.04.12.439473.
10. Starr, T. N., Greaney, A. J., Dingens, A. S. & Bloom, J. D. Complete map of SARS-CoV-2 RBD mutations that escape the monoclonal antibody LY-CoV555 and its cocktail with LY-CoV016. BioRxiv Prepr. Serv. Biol. (2021) doi:10.1101/2021.02.17.431683.
11. Wec, A. Z., Bornholdt, Z. A., He, S., et al. Development of a Human Antibody Cocktail that Deploys Multiple Functions to Confer Pan-Ebolavirus Protection. Cell Host & Microbe 25, 39-48.e5 (2019) https://doi.org/10.1016/j.chom.2018.12.004
12. Simoes, E. A. F., Forleo-Neto, E., Geba, G. P., et al. Suptavumab for the Prevention of Medically Attended Respiratory Syncytial Virus Infection in Preterm Infants, Clinical Infectious Diseases, ciaa951 (2020) https://doi.org/10.1093/cid/ciaa951
13. de Kruif, J., Bakker, A. B. H., Marissen, W. E., et al. A Human Monoclonal Antibody Cocktail as a Novel Component of Rabies Postexposure Prophylaxis. Annual Review of Medicine 58:1, 359-368 (2007) https://doi.org/10.1146/annurev.med.58.061705.145053
14. Snow, D. M., Cobb, R. R., Martinez, J., et al. A Monoclonal Antibody Combination against both Serotypes A and B Botulinum Toxin Prevents Inhalational Botulism in a Guinea Pig Model. Toxins 2021, 13, 31. https://doi.org/10.3390/toxins13010031
15. Rosenke, K. et al. Defining the Syrian hamster as a highly susceptible preclinical model for SARS-CoV-2 infection. Emerg. Microbes Infect. 9, 2673-2684 (2020).
16. Sia, S. F. et al. Pathogenesis and transmission of SARS-CoV-2 in golden hamsters. Nature 583, 834-838 (2020).
17. Zhou, D. et al. Robust SARS-CoV-2 infection in nasal turbinates after treatment with systemic neutralizing antibodies. Cell Host Microbe 29, 551-563.e5 (2021).
18. Ku, Z. et al. Molecular determinants and mechanism for antibody cocktail preventing SARS-CoV-2 escape. Nat. Commun. 12, 469 (2021).
19. Zost, S. J. et al. Potently neutralizing and protective human antibodies against SARS-CoV-2. Nature 584, 443-449 (2020).
20. Baum, A. et al. Antibody cocktail to SARS-CoV-2 spike protein prevents rapid mutational escape seen with individual antibodies. Science 369, 1014-1018 (2020).
21. Baum, A. et al. REGN-COV2 antibodies prevent and treat SARS-CoV-2 infection in rhesus macaques and hamsters. Science 370, 1110-1115 (2020).
22. Abdiche, Y. N. et al. Antibodies Targeting Closely Adjacent or Minimally Overlapping Epitopes Can Displace One Another. PloS One 12, e0169535 (2017).
23. Yuan, M. et al. A highly conserved cryptic epitope in the receptor binding domains of SARS-CoV-2 and SARS-CoV. Science 368, 630-633 (2020).
24. Wrapp, D. et al. Structural Basis for Potent Neutralization of Betacoronaviruses by Single-Domain Camelid Antibodies. Cell 181, 1004-1015.e15 (2020).
25. Walter, J. D. et al. Sybodies targeting the SARS-CoV-2 receptor-binding domain. bioRxiv 2020.04.16.045419 (2020) doi:10.1101/2020.04.16.045419.
26. Ahmad, J., Jiang, J., Boyd, L. F., Natarajan, K. & Margulies, D. H. Synthetic nanobody—SARS-CoV-2 receptor-binding domain structures identify distinct epitopes. bioRxiv 2021.01.27.428466 (2021) doi: 10.1101/2021.01.27.428466.
27. Meulen, J. ter et al. Human Monoclonal Antibody Combination against SARS Coronavirus: Synergy and Coverage of Escape Mutants. PLOS Med. 3, e237 (2006).
28. Wang, C. et al. A human monoclonal antibody blocking SARS-CoV-2 infection. Nat. Com. 2251(2021) doi: 10.1038/s41467-020-16256-y.
29. Reed, L. J. & Muench, H. A simple method of estimating fifty percent endpoints. Am. J. Epidemiol. 27, 493-497 (1938).
30. Walser, M. et al. Highly potent anti-SARS-CoV-2 multi-DARPin therapeutic candidates. bioRxiv 2020.08.25.256339 (2020) doi:10.1101/2020.08.25.256339.
31. Corman, V. M. et al. Detection of 2019 novel coronavirus (2019-nCoV) by real-time RT-PCR. Eurosurveillance 25, 2000045 (2020)

What is claimed is:

1. A nucleic acid comprising a sequence encoding the light and heavy chains of an antibody or antigen binding fragment thereof, or a nucleic acid pair comprising a first nucleic acid comprising a sequence encoding the light chain of the antibody or antigen binding fragment thereof and a second nucleic acid comprising a sequence encoding the heavy chain of the antibody or antigen binding fragment thereof, wherein the antibody or antigen-binding fragment thereof specifically binds to severe acute respiratory syndrome coronavirus 2 (SARS-CoV-2) Spike protein, wherein the antibody or antigen-binding fragment comprises one of the following combinations of heavy chain complementarity determining regions (CDRs) (HCDR1, HCDR2 and HCDR3) and light chain CDRs (LCDR1, LCDR2 and LCDR3):

- (i) an HCDR1 comprising the amino acid sequence of SEQ ID NO: 36, an HCDR2 comprising the amino acid sequence of SEQ ID NO: 16, an HCDR3 comprising the amino acid sequence of SEQ ID NO: 17, an LCDR1 comprising the amino acid sequence of SEQ ID NO: 37, an LCDR2 comprising the amino acid sequence EDN, and an LCDR3 comprising the amino acid sequence of SEQ ID NO: 38;
- (ii) an HCDR1 comprising the amino acid sequence of SEQ ID NO: 125, an HCDR2 comprising the amino acid sequence of SEQ ID NO: 126, an HCDR3 comprising the amino acid sequence of SEQ ID NO: 127, an LCDR1 comprising the amino acid sequence of SEQ ID NO: 198, an LCDR2 comprising the amino acid sequence GGN, and an LCDR3 comprising the amino acid sequence of SEQ ID NO: 199;
- (iii) an HCDR1 comprising the amino acid sequence of SEQ ID NO: 57, an HCDR2 comprising the amino acid sequence of SEQ ID NO: 58, an HCDR3 comprising the amino acid sequence of SEQ ID NO: 59, an LCDR1 comprising the amino acid sequence of SEQ ID NO: 60, an LCDR2 comprising the amino acid sequence YDD, and an LCDR3 comprising the amino acid sequence of SEQ ID NO: 61;
- (iv) an HCDR1 comprising the amino acid sequence of SEQ ID NO: 103, an HCDR2 comprising the amino acid sequence of SEQ ID NO: 104, an HCDR3 comprising the amino acid sequence of SEQ ID NO: 105, an LCDR1 comprising the amino acid sequence of SEQ ID NO: 106, an LCDR2 comprising the amino acid sequence EVS, and an LCDR3 comprising the amino acid sequence of SEQ ID NO: 107;
- (v) an HCDR1 comprising the amino acid sequence of SEQ ID NO: 54, an HCDR2 comprising the amino acid sequence of SEQ ID NO: 55, an HCDR3 comprising the amino acid sequence of SEQ ID NO: 56, an LCDR1 comprising the amino acid sequence of SEQ ID NO: 14, an LCDR2 comprising the amino acid sequence YDD, and an LCDR3 comprising the amino acid sequence of SEQ ID NO: 5;
- (vi) an HCDR1 comprising the amino acid sequence of SEQ ID NO: 89, an HCDR2 comprising the amino acid sequence of SEQ ID NO: 90, an HCDR3 comprising the amino acid sequence of SEQ ID NO: 91, an LCDR1 comprising the amino acid sequence of SEQ ID NO: 92, an LCDR2 comprising the amino acid sequence DVS, and an LCDR3 comprising the amino acid sequence of SEQ ID NO: 93;
- (vii) an HCDR1 comprising the amino acid sequence of SEQ ID NO: 1, an HCDR2 comprising the amino acid sequence of SEQ ID NO: 2, an HCDR3 comprising the amino acid sequence of SEQ ID NO: 3, an LCDR1 comprising the amino acid sequence of SEQ ID NO: 4, an LCDR2 comprising the amino acid sequence GND, and an LCDR3 comprising the amino acid sequence of SEQ ID NO: 5;
- (viii) an HCDR1 comprising the amino acid sequence of SEQ ID NO: 6, an HCDR2 comprising the amino acid sequence of SEQ ID NO: 7, an HCDR3 comprising the amino acid sequence of SEQ ID NO: 8, an LCDR1 comprising the amino acid sequence of SEQ ID NO: 9, an LCDR2 comprising the amino acid sequence DNN, and an LCDR3 comprising the amino acid sequence of SEQ ID NO: 10;
- (ix) an HCDR1 comprising the amino acid sequence of SEQ ID NO: 11, an HCDR2 comprising the amino acid sequence of SEQ ID NO: 12, an HCDR3 comprising the amino acid sequence of SEQ ID NO: 13, an LCDR1 comprising the amino acid sequence of SEQ ID NO: 14, an LCDR2 comprising the amino acid sequence YDN, and an LCDR3 comprising the amino acid sequence of SEQ ID NO: 15;
- (x) an HCDR1 comprising the amino acid sequence of SEQ ID NO: 6, an HCDR2 comprising the amino acid sequence of SEQ ID NO: 16, an HCDR3 comprising the amino acid sequence of SEQ ID NO: 17, an LCDR1 comprising the amino acid sequence of SEQ ID NO: 18, an LCDR2 comprising the amino acid sequence EDN, and an LCDR3 comprising the amino acid sequence of SEQ ID NO: 19;
- (xi) an HCDR1 comprising the amino acid sequence of SEQ ID NO: 20, an HCDR2 comprising the amino acid sequence of SEQ ID NO: 21, an HCDR3 comprising the amino acid sequence of SEQ ID NO: 22, an LCDR1 comprising the amino acid sequence of SEQ ID NO: 23, an LCDR2 comprising the amino acid sequence DDN, and an LCDR3 comprising the amino acid sequence of SEQ ID NO: 24;
- (xii) an HCDR1 comprising the amino acid sequence of SEQ ID NO: 25, an HCDR2 comprising the amino acid sequence of SEQ ID NO: 26, an HCDR3 comprising the amino acid sequence of SEQ ID NO: 27, an LCDR1 comprising the amino acid sequence of SEQ ID NO: 28, an LCDR2 comprising the amino acid sequence SAS, and an LCDR3 comprising the amino acid sequence of SEQ ID NO: 29;
- (xiii) an HCDR1 comprising the amino acid sequence of SEQ ID NO: 6, an HCDR2 comprising the amino acid sequence of SEQ ID NO: 30, an HCDR3 comprising the amino acid sequence of SEQ ID NO: 31, an LCDR1 comprising the amino acid sequence of SEQ ID NO: 32, an LCDR2 comprising the amino acid sequence EDK, and an LCDR3 comprising the amino acid sequence of SEQ ID NO: 33;
- (xiv) an HCDR1 comprising the amino acid sequence of SEQ ID NO: 1, an HCDR2 comprising the amino acid sequence of SEQ ID NO: 2, an HCDR3 comprising the amino acid sequence of SEQ ID NO: 34, an LCDR1 comprising the amino acid sequence of SEQ ID NO: 35, an LCDR2 comprising the amino acid sequence NNN, and an LCDR3 comprising the amino acid sequence of SEQ ID NO: 5;
- (xv) an HCDR1 comprising the amino acid sequence of SEQ ID NO: 39, an HCDR2 comprising the amino acid sequence of SEQ ID NO: 40, an HCDR3 comprising the amino acid sequence of SEQ ID NO: 41, an LCDR1 comprising the amino acid sequence of SEQ ID NO: 42, an LCDR2 comprising the amino acid sequence of SEQ ID NO: 43, and an LCDR3 comprising the amino acid sequence of SEQ ID NO: 44;
- (xvi) an HCDR1 comprising the amino acid sequence of SEQ ID NO: 45, an HCDR2 comprising the amino acid sequence of SEQ ID NO: 46, an HCDR3 comprising the amino acid sequence of SEQ ID NO: 47, an LCDR1 comprising the amino acid sequence of SEQ ID NO: 48, an LCDR2 comprising the amino acid sequence AND, and an LCDR3 comprising the amino acid sequence of SEQ ID NO: 49;

(xvii) an HCDR1 comprising the amino acid sequence of SEQ ID NO: 1, an HCDR2 comprising the amino acid sequence of SEQ ID NO: 2, an HCDR3 comprising the amino acid sequence of SEQ ID NO: 62, an LCDR1 comprising the amino acid sequence of SEQ ID NO: 4, an LCDR2 comprising the amino acid sequence NNI, and an LCDR3 comprising the amino acid sequence of SEQ ID NO: 63;

(xviii) an HCDR1 comprising the amino acid sequence of SEQ ID NO: 64, an HCDR2 comprising the amino acid sequence of SEQ ID NO: 65, an HCDR3 comprising the amino acid sequence of SEQ ID NO: 66, an LCDR1 comprising the amino acid sequence of SEQ ID NO: 67, an LCDR2 comprising the amino acid sequence YDY, and an LCDR3 comprising the amino acid sequence of SEQ ID NO: 68;

(xix) an HCDR1 comprising the amino acid sequence of SEQ ID NO: 64, an HCDR2 comprising the amino acid sequence of SEQ ID NO: 69, an HCDR3 comprising the amino acid sequence of SEQ ID NO: 70, an LCDR1 comprising the amino acid sequence of SEQ ID NO: 71, an LCDR2 comprising the amino acid sequence ANS, and an LCDR3 comprising the amino acid sequence of SEQ ID NO: 72;

(xx) an HCDR1 comprising the amino acid sequence of SEQ ID NO: 1, an HCDR2 comprising the amino acid sequence of SEQ ID NO: 2, an HCDR3 comprising the amino acid sequence of SEQ ID NO: 73, an LCDR1 comprising the amino acid sequence of SEQ ID NO: 9, an LCDR2 comprising the amino acid sequence DNN, and an LCDR3 comprising the amino acid sequence of SEQ ID NO: 10;

(xxi) an HCDR1 comprising the amino acid sequence of SEQ ID NO: 74, an HCDR2 comprising the amino acid sequence of SEQ ID NO: 75, an HCDR3 comprising the amino acid sequence of SEQ ID NO: 76, an LCDR1 comprising the amino acid sequence of SEQ ID NO: 77, an LCDR2 comprising the amino acid sequence RDS, and an LCDR3 comprising the amino acid sequence of SEQ ID NO: 78;

(xxii) an HCDR1 comprising the amino acid sequence of SEQ ID NO: 1, an HCDR2 comprising the amino acid sequence of SEQ ID NO: 2, an HCDR3 comprising the amino acid sequence of SEQ ID NO: 79, an LCDR1 comprising the amino acid sequence of SEQ ID NO: 80, an LCDR2 comprising the amino acid sequence TNN, and an LCDR3 comprising the amino acid sequence of SEQ ID NO: 81;

(xxiii) an HCDR1 comprising the amino acid sequence of SEQ ID NO: 1, an HCDR2 comprising the amino acid sequence of SEQ ID NO: 2, an HCDR3 comprising the amino acid sequence of SEQ ID NO: 82, an LCDR1 comprising the amino acid sequence of SEQ ID NO: 83, an LCDR2 comprising the amino acid sequence RND, and an LCDR3 comprising the amino acid sequence of SEQ ID NO: 5;

(xxiv) an HCDR1 comprising the amino acid sequence of SEQ ID NO: 11, an HCDR2 comprising the amino acid sequence of SEQ ID NO: 12, an HCDR3 comprising the amino acid sequence of SEQ ID NO: 84, an LCDR1 comprising the amino acid sequence of SEQ ID NO: 85, an LCDR2 comprising the amino acid sequence AAS, and an LCDR3 comprising the amino acid sequence of SEQ ID NO: 86;

(xxv) an HCDR1 comprising the amino acid sequence of SEQ ID NO: 25, an HCDR2 comprising the amino acid sequence of SEQ ID NO: 26, an HCDR3 comprising the amino acid sequence of SEQ ID NO: 27, an LCDR1 comprising the amino acid sequence of SEQ ID NO: 87, an LCDR2 comprising the amino acid sequence YDT, and an LCDR3 comprising the amino acid sequence of SEQ ID NO: 88;

(xxvi) an HCDR1 comprising the amino acid sequence of SEQ ID NO: 94, an HCDR2 comprising the amino acid sequence of SEQ ID NO: 95, an HCDR3 comprising the amino acid sequence of SEQ ID NO: 96, an LCDR1 comprising the amino acid sequence of SEQ ID NO: 97, an LCDR2 comprising the amino acid sequence WAS, and an LCDR3 comprising the amino acid sequence of SEQ ID NO: 98;

(xxvii) an HCDR1 comprising the amino acid sequence of SEQ ID NO: 99, an HCDR2 comprising the amino acid sequence of SEQ ID NO: 100, an HCDR3 comprising the amino acid sequence of SEQ ID NO: 101, an LCDR1 comprising the amino acid sequence of SEQ ID NO: 9, an LCDR2 comprising the amino acid sequence ENN, and an LCDR3 comprising the amino acid sequence of SEQ ID NO: 102;

(xxviii) an HCDR1 comprising the amino acid sequence of SEQ ID NO: 108, an HCDR2 comprising the amino acid sequence of SEQ ID NO: 109, an HCDR3 comprising the amino acid sequence of SEQ ID NO: 110, an LCDR1 comprising the amino acid sequence of SEQ ID NO: 111, an LCDR2 comprising the amino acid sequence DDT, and an LCDR3 comprising the amino acid sequence of SEQ ID NO: 112;

(xxix) an HCDR1 comprising the amino acid sequence of SEQ ID NO: 113, an HCDR2 comprising the amino acid sequence of SEQ ID NO: 114, an HCDR3 comprising the amino acid sequence of SEQ ID NO: 115, an LCDR1 comprising the amino acid sequence of SEQ ID NO: 71, an LCDR2 comprising the amino acid sequence GNS, and an LCDR3 comprising the amino acid sequence of SEQ ID NO: 116; or (xxx) an HCDR1 comprising the amino acid sequence of SEQ ID NO: 117, an HCDR2 comprising the amino acid sequence of SEQ ID NO: 118, an HCDR3 comprising the amino acid sequence of SEQ ID NO: 119, an LCDR1 comprising the amino acid sequence of SEQ ID NO: 120, an LCDR2 comprising the amino acid sequence EVA, and an LCDR3 comprising the amino acid sequence of SEQ ID NO: 121.

2. The nucleic acid or nucleic acid pair according to claim 1, wherein the antibody or antigen-binding fragment comprises one of the following heavy chain variable region (VH)/light chain variable region (VL) pairs:

(i) a VH comprising the amino acid sequence of SEQ ID NO: 147 and a VL comprising an LCDR1 comprising the amino acid sequence of SEQ ID NO: 37, an LCDR2 comprising the amino acid sequence EDN, and an LCDR3 comprising the amino acid sequence of SEQ ID NO: 38;

(ii) a VH comprising the amino acid sequence of SEQ ID NO: 191 and a VL comprising an LCDR1 comprising the amino acid sequence of SEQ ID NO: 198, an LCDR2 comprising the amino acid sequence GGN, and an LCDR3 comprising the amino acid sequence of SEQ ID NO: 199;

(iii) a VH comprising the amino acid sequence of SEQ ID NO: 157 or 215 and a VL comprising an LCDR1 comprising the amino acid sequence of SEQ ID NO: 60, an LCDR2 comprising the amino acid sequence YDD, and an LCDR3 comprising the amino acid sequence of SEQ ID NO: 61;

(iv) a VH comprising the amino acid sequence of SEQ ID NO: 183 and a VL comprising an LCDR1 comprising the amino acid sequence of SEQ ID NO: 106, an LCDR2 comprising the amino acid sequence EVS, and an LCDR3 comprising the amino acid sequence of SEQ ID NO: 107;

(v) a VH comprising the amino acid sequence of SEQ ID NO: 155 or 214 and a VL comprising an LCDR1 comprising the amino acid sequence of SEQ ID NO: 14, an LCDR2 comprising the amino acid sequence YDD, and an LCDR3 comprising the amino acid sequence of SEQ ID NO: 5;

(vi) a VH comprising the amino acid sequence of SEQ ID NO: 177 and a VL comprising an LCDR1 comprising the amino acid sequence of SEQ ID NO: 92, an LCDR2 comprising the amino acid sequence DVS, and an LCDR3 comprising the amino acid sequence of SEQ ID NO: 93;

(vii) a VH comprising the amino acid sequence of SEQ ID NO: 131 and a VL comprising an LCDR1 comprising the amino acid sequence of SEQ ID NO: 4, an LCDR2 comprising the amino acid sequence GND, and an LCDR3 comprising the amino acid sequence of SEQ ID NO: 5;

(viii) a VH comprising the amino acid sequence of SEQ ID NO: 133 and a VL comprising an LCDR1 comprising the amino acid sequence of SEQ ID NO: 9, an LCDR2 comprising the amino acid sequence DNN, and an LCDR3 comprising the amino acid sequence of SEQ ID NO: 10;

(ix) a VH comprising the amino acid sequence of SEQ ID NO: 135 and a VL comprising an LCDR1 comprising the amino acid sequence of SEQ ID NO: 14, an LCDR2 comprising the amino acid sequence YDN, and an LCDR3 comprising the amino acid sequence of SEQ ID NO: 15;

(x) a VH comprising the amino acid sequence of SEQ ID NO: 137 and a VL comprising an LCDR1 comprising the amino acid sequence of SEQ ID NO: 18, an LCDR2 comprising the amino acid sequence EDN, and an LCDR3 comprising the amino acid sequence of SEQ ID NO: 19;

(xi) a VH comprising the amino acid sequence of SEQ ID NO: 139 and a VL comprising an LCDR1 comprising the amino acid sequence of SEQ ID NO: 23, an LCDR2 comprising the amino acid sequence DDN, and an LCDR3 comprising the amino acid sequence of SEQ ID NO: 24;

(xii) a VH comprising the amino acid sequence of SEQ ID NO: 141 and a VL comprising an LCDR1 comprising the amino acid sequence of SEQ ID NO: 28, an LCDR2 comprising the amino acid sequence SAS, and an LCDR3 comprising the amino acid sequence of SEQ ID NO: 29;

(xiii) a VH comprising the amino acid sequence of SEQ ID NO: 143 and a VL comprising an LCDR1 comprising the amino acid sequence of SEQ ID NO: 32, an LCDR2 comprising the amino acid sequence EDK, and an LCDR3 comprising the amino acid sequence of SEQ ID NO: 33;

(xiv) a VH comprising the amino acid sequence of SEQ ID NO: 145 and a VL comprising an LCDR1 comprising the amino acid sequence of SEQ ID NO: 35, an LCDR2 comprising the amino acid sequence NNN, and an LCDR3 comprising the amino acid sequence of SEQ ID NO: 5;

(xv) a VH comprising the amino acid sequence of SEQ ID NO: 149 and a VL comprising an LCDR1 comprising the amino acid sequence of SEQ ID NO: 42, an LCDR2 comprising the amino acid sequence of SEQ ID NO: 43, and an LCDR3 comprising the amino acid sequence of SEQ ID NO: 44;

(xvi) a VH comprising the amino acid sequence of SEQ ID NO: 151 and a VL comprising an LCDR1 comprising the amino acid sequence of SEQ ID NO: 48, an LCDR2 comprising the amino acid sequence AND, and an LCDR3 comprising the amino acid sequence of SEQ ID NO: 49;

(xvii) a VH comprising the amino acid sequence of SEQ ID NO: 159 and a VL comprising an LCDR1 comprising the amino acid sequence of SEQ ID NO: 4, an LCDR2 comprising the amino acid sequence NNI, and an LCDR3 comprising the amino acid sequence of SEQ ID NO: 63;

(xviii) a VH comprising the amino acid sequence of SEQ ID NO: 161 and a VL comprising an LCDR1 comprising the amino acid sequence of SEQ ID NO: 67, an LCDR2 comprising the amino acid sequence YDY, and an LCDR3 comprising the amino acid sequence of SEQ ID NO: 68;

(xix) a VH comprising the amino acid sequence of SEQ ID NO: 163 and a VL comprising an LCDR1 comprising the amino acid sequence of SEQ ID NO: 71, an LCDR2 comprising the amino acid sequence ANS, and an LCDR3 comprising the amino acid sequence of SEQ ID NO: 72;

(xx) a VH comprising the amino acid sequence of SEQ ID NO: 165 and a VL comprising an LCDR1 comprising the amino acid sequence of SEQ ID NO: 9, an LCDR2 comprising the amino acid sequence DNN, and an LCDR3 comprising the amino acid sequence of SEQ ID NO: 10;

(xxi) a VH comprising the amino acid sequence of SEQ ID NO: 167 and a VL comprising an LCDR1 comprising the amino acid sequence of SEQ ID NO: 77, an LCDR2 comprising the amino acid sequence RDS, and an LCDR3 comprising the amino acid sequence of SEQ ID NO: 78;

(xxii) a VH comprising the amino acid sequence of SEQ ID NO: 169 and a VL comprising an LCDR1 comprising the amino acid sequence of SEQ ID NO: 80, an LCDR2 comprising the amino acid sequence TNN, and an LCDR3 comprising the amino acid sequence of SEQ ID NO: 81;

(xxiii) a VH comprising the amino acid sequence of SEQ ID NO: 171 and a VL comprising an LCDR1 comprising the amino acid sequence of SEQ ID NO: 83, an LCDR2 comprising the amino acid sequence RND, and an LCDR3 comprising the amino acid sequence of SEQ ID NO: 5;

(xxiv) a VH comprising the amino acid sequence of SEQ ID NO: 173 and a VL comprising an LCDR1 comprising the amino acid sequence of SEQ ID NO: 85, an LCDR2 comprising the amino acid sequence AAS, and an LCDR3 comprising the amino acid sequence of SEQ ID NO: 86;

(xxv) a VH comprising the amino acid sequence of SEQ ID NO: 175 and a VL comprising an LCDR1 comprising the amino acid sequence of SEQ ID NO: 87, an LCDR2 comprising the amino acid sequence YDT, and an LCDR3 comprising the amino acid sequence of SEQ ID NO: 88;

(xxvi) a VH comprising the amino acid sequence of SEQ ID NO: 179 and a VL comprising an LCDR1 comprising the amino acid sequence of SEQ ID NO: 97, an LCDR2 comprising the amino acid sequence WAS, and an LCDR3 comprising the amino acid sequence of SEQ ID NO: 98;

(xxvii) a VH comprising the amino acid sequence of SEQ ID NO: 181 and a VL comprising an LCDR1 comprising the amino acid sequence of SEQ ID NO: 9, an LCDR2 comprising the amino acid sequence ENN, and an LCDR3 comprising the amino acid sequence of SEQ ID NO: 102;

(xxviii) a VH comprising the amino acid sequence of SEQ ID NO: 185 and a VL comprising an LCDR1 comprising the amino acid sequence of SEQ ID NO: 111, an LCDR2 comprising the amino acid sequence DDT, and an LCDR3 comprising the amino acid sequence of SEQ ID NO: 112;

(xxix) a VH comprising the amino acid sequence of SEQ ID NO: 187 and a VL comprising an LCDR1 comprising the amino acid sequence of SEQ ID NO: 71, an LCDR2 comprising the amino acid sequence GNS, and an LCDR3 comprising the amino acid sequence of SEQ ID NO: 116; or (xxx) a VH comprising the amino acid sequence of SEQ ID NO: 189 and a VL comprising an LCDR1 comprising the amino acid sequence of SEQ ID NO: 120, an LCDR2 comprising the amino acid sequence EVA, and an LCDR3 comprising the amino acid sequence of SEQ ID NO: 121.

3. The nucleic acid or nucleic acid pair according to claim 1, wherein the antibody or antigen-binding fragment comprises one of the following VH/VL pairs:

(i) a VH comprising an HCDR1 comprising the amino acid sequence of SEQ ID NO: 36, an HCDR2 comprising the amino acid sequence of SEQ ID NO: 16, and an HCDR3 comprising the amino acid sequence of SEQ ID NO: 17, and a VL comprising the amino acid sequence of SEQ ID NO: 148;

(ii) a VH comprising an HCDR1 comprising the amino acid sequence of SEQ ID NO: 125, an HCDR2 comprising the amino acid sequence of SEQ ID NO: 126, and an HCDR3 comprising the amino acid sequence of SEQ ID NO: 127, and a VL comprising the amino acid sequence of SEQ ID NO: 192;

(iii) a VH comprising an HCDR1 comprising the amino acid sequence of SEQ ID NO: 57, an HCDR2 comprising the amino acid sequence of SEQ ID NO: 58, and an HCDR3 comprising the amino acid sequence of SEQ ID NO: 59, and a VL comprising the amino acid sequence of SEQ ID NO: 158;

(iv) a VH comprising an HCDR1 comprising the amino acid sequence of SEQ ID NO: 103, an HCDR2 comprising the amino acid sequence of SEQ ID NO: 104, and an HCDR3 comprising the amino acid sequence of SEQ ID NO: 105, and a VL comprising the amino acid sequence of SEQ ID NO: 184;

(v) a VH comprising an HCDR1 comprising the amino acid sequence of SEQ ID NO: 54, an HCDR2 comprising the amino acid sequence of SEQ ID NO: 55, and an HCDR3 comprising the amino acid sequence of SEQ ID NO: 56, and a VL comprising the amino acid sequence of SEQ ID NO: 156;

(vi) a VH comprising an HCDR1 comprising the amino acid sequence of SEQ ID NO: 89, an HCDR2 comprising the amino acid sequence of SEQ ID NO: 90, and an HCDR3 comprising the amino acid sequence of SEQ ID NO: 91, and a VL comprising the amino acid sequence of SEQ ID NO: 178;

(vii) a VH comprising an HCDR1 comprising the amino acid sequence of SEQ ID NO: 1, an HCDR2 comprising the amino acid sequence of SEQ ID NO: 2, and an HCDR3 comprising the amino acid sequence of SEQ ID NO: 3, and a VL comprising the amino acid sequence of SEQ ID NO: 132;

(viii) a VH comprising an HCDR1 comprising the amino acid sequence of SEQ ID NO: 6, an HCDR2 comprising the amino acid sequence of SEQ ID NO: 7, and an HCDR3 comprising the amino acid sequence of SEQ ID NO: 8, and a VL comprising the amino acid sequence of SEQ ID NO: 134;

(ix) a VH comprising an HCDR1 comprising the amino acid sequence of SEQ ID NO: 11, an HCDR2 comprising the amino acid sequence of SEQ ID NO: 12, and an HCDR3 comprising the amino acid sequence of SEQ ID NO: 13, and a VL comprising the amino acid sequence of SEQ ID NO: 136;

(x) a VH comprising an HCDR1 comprising the amino acid sequence of SEQ ID NO: 6, an HCDR2 comprising the amino acid sequence of SEQ ID NO: 16, and an HCDR3 comprising the amino acid sequence of SEQ ID NO: 17, and a VL comprising the amino acid sequence of SEQ ID NO: 138;

(xi) a VH comprising an HCDR1 comprising the amino acid sequence of SEQ ID NO: 20, an HCDR2 comprising the amino acid sequence of SEQ ID NO: 21, and an HCDR3 comprising the amino acid sequence of SEQ ID NO: 22, and a VL comprising the amino acid sequence of SEQ ID NO: 140;

(xii) a VH comprising an HCDR1 comprising the amino acid sequence of SEQ ID NO: 25, an HCDR2 comprising the amino acid sequence of SEQ ID NO: 26, and an HCDR3 comprising the amino acid sequence of SEQ ID NO: 27, and a VL comprising the amino acid sequence of SEQ ID NO: 142;

(xiii) a VH comprising an HCDR1 comprising the amino acid sequence of SEQ ID NO: 6, an HCDR2 comprising the amino acid sequence of SEQ ID NO: 30, and an HCDR3 comprising the amino acid sequence of SEQ ID NO: 31, and a VL comprising the amino acid sequence of SEQ ID NO: 144;

(xiv) a VH comprising an HCDR1 comprising the amino acid sequence of SEQ ID NO: 1, an HCDR2 comprising the amino acid sequence of SEQ ID NO: 2, and an HCDR3 comprising the amino acid sequence of SEQ ID NO: 34, and a VL comprising the amino acid sequence of SEQ ID NO: 146;

(xv) a VH comprising an HCDR1 comprising the amino acid sequence of SEQ ID NO: 39, an HCDR2 comprising the amino acid sequence of SEQ ID NO: 40, and an HCDR3 comprising the amino acid sequence of SEQ ID NO: 41, and a VL comprising the amino acid sequence of SEQ ID NO: 150;

(xvi) a VH comprising an HCDR1 comprising the amino acid sequence of SEQ ID NO: 45, an HCDR2 comprising the amino acid sequence of SEQ ID NO: 46, and an HCDR3 comprising the amino acid sequence of SEQ ID NO: 47, and a VL comprising the amino acid sequence of SEQ ID NO: 152;

(xvii) a VH comprising an HCDR1 comprising the amino acid sequence of SEQ ID NO: 1, an HCDR2 comprising the amino acid sequence of SEQ ID NO: 2, and an HCDR3 comprising the amino acid sequence of SEQ ID NO: 62, and a VL comprising the amino acid sequence of SEQ ID NO: 160;

(xviii) a VH comprising an HCDR1 comprising the amino acid sequence of SEQ ID NO: 64, an HCDR2 comprising the amino acid sequence of SEQ ID NO: 65, and an HCDR3 comprising the amino acid sequence of SEQ ID NO: 66, and a VL comprising the amino acid sequence of SEQ ID NO: 162;

(xix) a VH comprising an HCDR1 comprising the amino acid sequence of SEQ ID NO: 64, an HCDR2 comprising the amino acid sequence of SEQ ID NO: 69, and an HCDR3 comprising the amino acid sequence of SEQ ID NO: 70, and a VL comprising the amino acid sequence of SEQ ID NO: 164;

(xx) a VH comprising an HCDR1 comprising the amino acid sequence of SEQ ID NO: 1, an HCDR2 comprising the amino acid sequence of SEQ ID NO: 2, and an HCDR3 comprising the amino acid sequence of SEQ ID NO: 73, and a VL comprising the amino acid sequence of SEQ ID NO: 166;

(xxi) a VH comprising an HCDR1 comprising the amino acid sequence of SEQ ID NO: 74, an HCDR2 comprising the amino acid sequence of SEQ ID NO: 75, and an HCDR3 comprising the amino acid sequence of SEQ ID NO: 76, and a VL comprising the amino acid sequence of SEQ ID NO: 168;

(xxii) a VH comprising an HCDR1 comprising the amino acid sequence of SEQ ID NO: 1, an HCDR2 comprising the amino acid sequence of SEQ ID NO: 2, and an HCDR3 comprising the amino acid sequence of SEQ ID NO: 79, and a VL comprising the amino acid sequence of SEQ ID NO: 170;

(xxiii) a VH comprising an HCDR1 comprising the amino acid sequence of SEQ ID NO: 1, an HCDR2 comprising the amino acid sequence of SEQ ID NO: 2, and an HCDR3 comprising the amino acid sequence of SEQ ID NO: 82, and a VL comprising the amino acid sequence of SEQ ID NO: 172;

(xxiv) a VH comprising an HCDR1 comprising the amino acid sequence of SEQ ID NO: 11, an HCDR2 comprising the amino acid sequence of SEQ ID NO: 12, and an HCDR3 comprising the amino acid sequence of SEQ ID NO: 84, and a VL comprising the amino acid sequence of SEQ ID NO: 174;

(xxv) a VH comprising an HCDR1 comprising the amino acid sequence of SEQ ID NO: 25, an HCDR2 comprising the amino acid sequence of SEQ ID NO: 26, and an HCDR3 comprising the amino acid sequence of SEQ ID NO: 27, and a VL comprising the amino acid sequence of SEQ ID NO: 176;

(xxvi) a VH comprising an HCDR1 comprising the amino acid sequence of SEQ ID NO: 94, an HCDR2 comprising the amino acid sequence of SEQ ID NO: 95, and an HCDR3 comprising the amino acid sequence of SEQ ID NO: 96, and a VL comprising the amino acid sequence of SEQ ID NO: 180;

(xxvii) a VH comprising an HCDR1 comprising the amino acid sequence of SEQ ID NO: 99, an HCDR2 comprising the amino acid sequence of SEQ ID NO: 100, and an HCDR3 comprising the amino acid sequence of SEQ ID NO: 101, and a VL comprising the amino acid sequence of SEQ ID NO: 182;

(xxviii) a VH comprising an HCDR1 comprising the amino acid sequence of SEQ ID NO: 108, an HCDR2 comprising the amino acid sequence of SEQ ID NO: 109, and an HCDR3 comprising the amino acid sequence of SEQ ID NO: 110, and a VL comprising the amino acid sequence of SEQ ID NO: 186;

(xxix) a VH comprising an HCDR1 comprising the amino acid sequence of SEQ ID NO: 113, an HCDR2 comprising the amino acid sequence of SEQ ID NO: 114, and an HCDR3 comprising the amino acid sequence of SEQ ID NO: 115, and a VL comprising the amino acid sequence of SEQ ID NO: 188; or (xxx) a VH comprising an HCDR1 comprising the amino acid sequence of SEQ ID NO: 117, an HCDR2 comprising the amino acid sequence of SEQ ID NO: 118, and an HCDR3 comprising the amino acid sequence of SEQ ID NO: 119, and a VL comprising the amino acid sequence of SEQ ID NO: 190.

4. The nucleic acid or nucleic acid pair according to claim 1, wherein the antibody or antigen-binding fragment thereof comprises one of the following VH/VL pairs: a VH comprising the amino acid sequence of SEQ ID No:131 and a VL comprising the amino acid sequence of SEQ ID No: 132; a VH comprising the amino acid sequence of SEQ ID No:133 and a VL comprising the amino acid sequence of SEQ ID No: 134; a VH comprising the amino acid sequence of SEQ ID No:135 and a VL comprising the amino acid sequence of SEQ ID No: 136; a VH comprising the amino acid sequence of SEQ ID No:137 and a VL comprising the amino acid sequence of SEQ ID No: 138; a VH comprising the amino acid sequence of SEQ ID No:139 and a VL comprising the amino acid sequence of SEQ ID No: 140; a VH comprising the amino acid sequence of SEQ ID No:141 and a VL comprising the amino acid sequence of SEQ ID No: 142; a VH comprising the amino acid sequence of SEQ ID No:143 and a VL comprising the amino acid sequence of SEQ ID No: 144; a VH comprising the amino acid sequence of SEQ ID No:145 and a VL comprising the amino acid sequence of SEQ ID No: 146; a VH comprising the amino acid sequence of SEQ ID No:147 and a VL comprising the amino acid sequence of SEQ ID No: 148; a VH comprising the amino acid sequence of SEQ ID No:149 and a VL comprising the amino acid sequence of SEQ ID No: 150; a VH comprising the amino acid sequence of SEQ ID No:151 and a VL comprising the amino acid sequence of SEQ ID No: 152; a VH comprising the amino acid sequence of SEQ ID No:153 and a VL comprising the amino acid sequence of SEQ ID No: 154; a VH comprising the amino acid sequence of SEQ ID No:155 or 214 and a VL comprising the amino acid sequence of SEQ ID No: 156; a VH comprising the amino acid sequence of SEQ ID No:157 or 215 and a VL comprising the amino acid sequence of SEQ ID No: 158; a VH comprising the amino acid sequence of SEQ ID No:159 and a VL comprising the amino acid sequence of SEQ ID No: 160; a VH comprising the amino acid sequence of SEQ ID No:161 and a VL comprising the amino acid sequence of SEQ ID No: 162; a VH comprising the amino acid sequence of SEQ ID No:163 and a VL comprising the amino acid sequence of SEQ ID No: 164; a VH comprising the amino acid sequence of SEQ ID No:165 and a VL comprising the amino acid sequence of SEQ ID No: 166; a VH comprising the amino acid sequence of SEQ ID No:167 and a VL comprising the amino acid sequence of SEQ ID No: 168; a VH comprising the amino acid sequence of SEQ ID No:169 and a VL comprising the amino acid sequence of SEQ ID No: 170; a VH comprising the amino acid sequence of SEQ ID No:171 and a VL comprising the amino acid sequence of SEQ ID No: 172; a VH comprising the amino acid sequence of SEQ ID No:173 and a VL comprising the amino acid sequence of SEQ ID No: 174; a VH comprising the amino acid sequence of SEQ ID No:175 and a VL comprising the amino acid sequence of SEQ ID No: 176; a VH comprising the amino acid sequence of SEQ ID No:177 and a VL comprising the amino acid sequence of SEQ ID No: 178; a VH comprising the amino acid sequence of SEQ ID No:179 and a VL comprising the amino acid sequence of SEQ ID No: 180; a VH comprising the amino acid sequence of SEQ ID No:181 and a VL comprising the amino acid sequence of SEQ ID No: 182; a VH comprising the amino acid sequence of SEQ ID No:183 and a VL comprising the amino acid sequence of SEQ ID No: 184; a VH comprising the amino acid sequence of SEQ ID No:185 and a VL comprising the amino acid sequence of SEQ ID No: 186; a VH comprising the amino acid sequence of SEQ ID No:187 and a VL comprising the amino acid sequence of SEQ ID No: 188; a VH comprising the amino acid sequence of SEQ ID No:189 and a VL comprising the amino acid sequence of SEQ ID No: 190; or a VH comprising the amino acid sequence of SEQ ID No:191 and a VL comprising the amino acid sequence of SEQ ID No: 192.

5. The nucleic acid or nucleic acid pair according to claim 1, wherein the antibody or antigen-binding fragment thereof comprises one of the following combinations of heavy chain complementarity determining regions (CDRs) (HCDR1, HCDR2 and HCDR3) and light chain CDRs (LCDR1, LCDR2 and LCDR3):

(i) an HCDR1 comprising the amino acid sequence of SEQ ID NO: 36, an HCDR2 comprising the amino acid sequence of SEQ ID NO: 16, an HCDR3 comprising the amino acid sequence of SEQ ID NO: 17, an LCDR1 comprising the amino acid sequence of SEQ ID NO: 37, an LCDR2 comprising the amino acid sequence EDN, and an LCDR3 comprising the amino acid sequence of SEQ ID NO: 38;

(ii) an HCDR1 comprising the amino acid sequence of SEQ ID NO: 125, an HCDR2 comprising the amino acid sequence of SEQ ID NO: 126, an HCDR3 comprising the amino acid sequence of SEQ ID NO: 127, an LCDR1 comprising the amino acid sequence of SEQ ID NO: 198, an LCDR2 comprising the amino acid sequence GGN, and an LCDR3 comprising the amino acid sequence of SEQ ID NO: 199;

(iii) an HCDR1 comprising the amino acid sequence of SEQ ID NO: 57, an HCDR2 comprising the amino acid sequence of SEQ ID NO: 58, an HCDR3 comprising the amino acid sequence of SEQ ID NO: 59, an LCDR1 comprising the amino acid sequence of SEQ ID NO: 60, an LCDR2 comprising the amino acid sequence YDD, and an LCDR3 comprising the amino acid sequence of SEQ ID NO: 61;

(iv) an HCDR1 comprising the amino acid sequence of SEQ ID NO: 103, an HCDR2 comprising the amino acid sequence of SEQ ID NO: 104, an HCDR3 comprising the amino acid sequence of SEQ ID NO: 105, an LCDR1 comprising the amino acid sequence of SEQ ID NO: 106, an LCDR2 comprising the amino acid sequence EVS, and an LCDR3 comprising the amino acid sequence of SEQ ID NO: 107;

(v) an HCDR1 comprising the amino acid sequence of SEQ ID NO: 54, an HCDR2 comprising the amino acid sequence of SEQ ID NO: 55, an HCDR3 comprising the amino acid sequence of SEQ ID NO: 56, an LCDR1 comprising the amino acid sequence of SEQ ID NO: 14, an LCDR2 comprising the amino acid sequence YDD, and an LCDR3 comprising the amino acid sequence of SEQ ID NO: 5; or (vi) an HCDR1 comprising the amino acid sequence of SEQ ID NO: 89, an HCDR2 comprising the amino acid sequence of SEQ ID NO: 90, an HCDR3 comprising the amino acid sequence of SEQ ID NO: 91, an LCDR1 comprising the amino acid sequence of SEQ ID NO: 92, an LCDR2 comprising the amino acid sequence DVS, and an LCDR3 comprising the amino acid sequence of SEQ ID NO: 93.

6. The nucleic acid or nucleic acid pair according to claim 1, wherein the antibody or antigen-binding fragment thereof comprises one of the following VH/VL pairs: a VH comprising the amino acid sequence of SEQ ID No:147 and a VL comprising the amino acid sequence of SEQ ID No: 148; a VH comprising the amino acid sequence of SEQ ID No:191 and a VL comprising the amino acid sequence of SEQ ID No: 192; a VH comprising the amino acid sequence of SEQ ID No:157 or 215 and a VL comprising the amino acid sequence of SEQ ID No: 158; a VH comprising the amino acid sequence of SEQ ID No:183 and a VL comprising the amino acid sequence of SEQ ID No: 184; a VH comprising the amino acid sequence of SEQ ID No:155 or 214 and a VL comprising the amino acid sequence of SEQ ID No: 156; or a VH comprising the amino acid sequence of SEQ ID No:177 and a VL comprising the amino acid sequence of SEQ ID No: 178.

7. The nucleic acid or nucleic acid pair according to claim 6, wherein the antibody or antigen-binding fragment thereof comprises a VH comprising the amino acid sequence of SEQ ID No:147 and a VL comprising the amino acid sequence of SEQ ID No: 148.

8. The nucleic acid or nucleic acid pair according to claim 6, wherein the antibody or antigen-binding fragment thereof comprises a VH comprising the amino acid sequence of SEQ ID No:191 and a VL comprising the amino acid sequence of SEQ ID No: 192.

9. The nucleic acid or nucleic acid pair according to claim 6, wherein the antibody or antigen-binding fragment thereof comprises a VH comprising the amino acid sequence of SEQ ID No:157 or 215 and a VL comprising the amino acid sequence of SEQ ID No: 158.

10. The nucleic acid or nucleic acid pair according to claim 6, wherein the antibody or antigen-binding fragment thereof comprises a VH comprising the amino acid sequence of SEQ ID No:183 and a VL comprising the amino acid sequence of SEQ ID No: 184.

11. The nucleic acid or nucleic acid pair according to claim 6, wherein the antibody or antigen-binding fragment thereof comprises a VH comprising the amino acid sequence of SEQ ID No:155 or 214 and a VL comprising the amino acid sequence of SEQ ID No: 156.

12. The nucleic acid or nucleic acid pair according to claim 6, wherein the antibody or antigen-binding fragment thereof comprises a VH comprising the amino acid sequence of SEQ ID No:177 and a VL comprising the amino acid sequence of SEQ ID No: 178.

13. The nucleic acid or nucleic acid pair according to claim 1, wherein the antibody or antigen-binding fragment thereof is a bispecific antibody.

14. The nucleic acid or nucleic acid pair according to claim 1, which is/are in the form of mRNA.

15. A nucleic acid combination comprising at least two of the nucleic acids or nucleic acid pairs according to claim 1, wherein the at least two nucleic acids or nucleic acid pairs encode the heavy and light chains of at least two of the antibodies or antigen-binding fragments thereof defined in claim 1.

16. The nucleic acid combination of claim 15, wherein the at least two antibodies or antigen-binding fragments thereof comprise:

(i) an antibody or antigen-binding fragment thereof comprising the following combination of CDRs: an HCDR1 comprising the amino acid sequence of SEQ ID NO: 36, an HCDR2 comprising the amino acid sequence of SEQ ID NO: 16, an HCDR3 comprising the amino acid sequence of SEQ ID NO: 17, an LCDR1 comprising the amino acid sequence of SEQ ID NO: 37, an LCDR2 comprising the amino acid sequence EDN, and an LCDR3 comprising the amino acid sequence of SEQ ID NO: 38; and (ii) at least one additional antibody or antigen-binding fragment thereof comprising one of the following combinations of CDRs:
  (a) an HCDR1 comprising the amino acid sequence of SEQ ID NO: 125, an HCDR2 comprising the amino acid sequence of SEQ ID NO: 126, an HCDR3 comprising the amino acid sequence of SEQ ID NO: 127, an LCDR1 comprising the amino acid sequence of SEQ ID NO: 198, an LCDR2 comprising the amino acid sequence GGN, and an LCDR3 comprising the amino acid sequence of SEQ ID NO: 199;
  (b) an HCDR1 comprising the amino acid sequence of SEQ ID NO: 89, an HCDR2 comprising the amino acid sequence of SEQ ID NO: 90, an HCDR3 comprising the amino acid sequence of SEQ ID NO: 91, an LCDR1 comprising the amino acid sequence of SEQ ID NO: 92, an LCDR2 comprising the amino acid sequence DVS, and an LCDR3 comprising the amino acid sequence of SEQ ID NO: 93;
  (c) an HCDR1 comprising the amino acid sequence of SEQ ID NO: 57, an HCDR2 comprising the amino acid sequence of SEQ ID NO: 58, an HCDR3 comprising the amino acid sequence of SEQ ID NO: 59, an LCDR1 comprising the amino acid sequence of SEQ ID NO: 60, an LCDR2 comprising the amino acid sequence YDD, and an LCDR3 comprising the amino acid sequence of SEQ ID NO: 61;
  (d) an HCDR1 comprising the amino acid sequence of SEQ ID NO: 54, an HCDR2 comprising the amino acid sequence of SEQ ID NO: 55, an HCDR3 comprising the amino acid sequence of SEQ ID NO: 56, an LCDR1 comprising the amino acid sequence of SEQ ID NO: 14, an LCDR2 comprising the amino acid sequence YDD, and an LCDR3 comprising the amino acid sequence of SEQ ID NO: 5; or
  (e) an HCDR1 comprising the amino acid sequence of SEQ ID NO: 103, an HCDR2 comprising the amino acid sequence of SEQ ID NO: 104, an HCDR3 comprising the amino acid sequence of SEQ ID NO: 105, an LCDR1 comprising the amino acid sequence of SEQ ID NO: 106, an LCDR2 comprising the amino acid sequence EVS, and an LCDR3 comprising the amino acid sequence of SEQ ID NO: 107.

17. The nucleic acid combination of claim 15, wherein the at least two antibodies or antigen-binding fragments thereof comprise:
  (i) an antibody or antigen-binding fragment thereof comprising the following combination of CDRs: an HCDR1 comprising the amino acid sequence of SEQ ID NO: 57, an HCDR2 comprising the amino acid sequence of SEQ ID NO: 58, an HCDR3 comprising the amino acid sequence of SEQ ID NO: 59, an LCDR1 comprising the amino acid sequence of SEQ ID NO: 60, an LCDR2 comprising the amino acid sequence YDD, and an LCDR3 comprising the amino acid sequence of SEQ ID NO: 61; and (ii) at least one additional antibody or antigen-binding fragment thereof comprising one of the following combinations of CDRs:
    (a) an HCDR1 comprising the amino acid sequence of SEQ ID NO: 125, an HCDR2 comprising the amino acid sequence of SEQ ID NO: 126, an HCDR3 comprising the amino acid sequence of SEQ ID NO: 127, an LCDR1 comprising the amino acid sequence of SEQ ID NO: 198, an LCDR2 comprising the amino acid sequence GGN, and an LCDR3 comprising the amino acid sequence of SEQ ID NO: 199;
    (b) an HCDR1 comprising the amino acid sequence of SEQ ID NO: 36, an HCDR2 comprising the amino acid sequence of SEQ ID NO: 16, an HCDR3 comprising the amino acid sequence of SEQ ID NO: 17, an LCDR1 comprising the amino acid sequence of SEQ ID NO: 37, an LCDR2 comprising the amino acid sequence EDN, and an LCDR3 comprising the amino acid sequence of SEQ ID NO: 38;
    (c) an HCDR1 comprising the amino acid sequence of SEQ ID NO: 89, an HCDR2 comprising the amino acid sequence of SEQ ID NO: 90, an HCDR3 comprising the amino acid sequence of SEQ ID NO: 91, an LCDR1 comprising the amino acid sequence of SEQ ID NO: 92, an LCDR2 comprising the amino acid sequence DVS, and an LCDR3 comprising the amino acid sequence of SEQ ID NO: 93;
    (d) an HCDR1 comprising the amino acid sequence of SEQ ID NO: 54, an HCDR2 comprising the amino acid sequence of SEQ ID NO: 55, an HCDR3 comprising the amino acid sequence of SEQ ID NO: 56, an LCDR1 comprising the amino acid sequence of SEQ ID NO: 14, an LCDR2 comprising the amino acid sequence YDD, and an LCDR3 comprising the amino acid sequence of SEQ ID NO: 5; or
    (e) an HCDR1 comprising the amino acid sequence of SEQ ID NO: 103, an HCDR2 comprising the amino acid sequence of SEQ ID NO: 104, an HCDR3 comprising the amino acid sequence of SEQ ID NO: 105, an LCDR1 comprising the amino acid sequence of SEQ ID NO: 106, an LCDR2 comprising the amino acid sequence EVS, and an LCDR3 comprising the amino acid sequence of SEQ ID NO: 107.

18. The nucleic acid combination of claim 15, wherein the at least two antibodies or antigen-binding fragments thereof comprise:
  (i) an antibody or antigen-binding fragment thereof comprising the following combination of CDRs: an HCDR1 comprising the amino acid sequence of SEQ ID NO: 54, an HCDR2 comprising the amino acid sequence of SEQ ID NO: 55, an HCDR3 comprising the amino acid sequence of SEQ ID NO: 56, an LCDR1 comprising the amino acid sequence of SEQ ID NO: 14, an LCDR2 comprising the amino acid sequence YDD, and an LCDR3 comprising the amino acid sequence of SEQ ID NO: 5; and (ii) at least one additional antibody or antigen-binding fragment thereof comprising one of the following combinations of CDRs:
    (a) an HCDR1 comprising the amino acid sequence of SEQ ID NO: 125, an HCDR2 comprising the amino acid sequence of SEQ ID NO: 126, an HCDR3 comprising the amino acid sequence of SEQ ID NO: 127, an LCDR1 comprising the amino acid sequence of SEQ ID NO: 198, an LCDR2 comprising the amino acid sequence GGN, and an LCDR3 comprising the amino acid sequence of SEQ ID NO: 199;

(b) an HCDR1 comprising the amino acid sequence of SEQ ID NO: 36, an HCDR2 comprising the amino acid sequence of SEQ ID NO: 16, an HCDR3 comprising the amino acid sequence of SEQ ID NO: 17, an LCDR1 comprising the amino acid sequence of SEQ ID NO: 37, an LCDR2 comprising the amino acid sequence EDN, and an LCDR3 comprising the amino acid sequence of SEQ ID NO: 38;

(c) an HCDR1 comprising the amino acid sequence of SEQ ID NO: 89, an HCDR2 comprising the amino acid sequence of SEQ ID NO: 90, an HCD R3 comprising the amino acid sequence of SEQ ID NO: 91, an LCDR1 comprising the amino acid sequence of SEQ ID NO: 92, an LCDR2 comprising the amino acid sequence DVS, and an LCDR3 comprising the amino acid sequence of SEQ ID NO: 93;

(d) an HCDR1 comprising the amino acid sequence of SEQ ID NO: 57, an HCDR2 comprising the amino acid sequence of SEQ ID NO: 58, an HCDR3 comprising the amino acid sequence of SEQ ID NO: 59, an LCDR1 comprising the amino acid sequence of SEQ ID NO: 60, an LCDR2 comprising the amino acid sequence YDD, and an LCDR3 comprising the amino acid sequence of SEQ ID NO: 61; or (e) an HCDR1 comprising the amino acid sequence of SEQ ID NO: 103, an HCDR2 comprising the amino acid sequence of SEQ ID NO: 104, an HCDR3 comprising the amino acid sequence of SEQ ID NO: 105, an LCDR1 comprising the amino acid sequence of SEQ ID NO: 106, an LCDR2 comprising the amino acid sequence EVS, and an LCDR3 comprising the amino acid sequence of SEQ ID NO: 107.

19. The nucleic acid combination of claim 15, wherein the at least two antibodies or antigen-binding fragments thereof comprise:
(i) an antibody or antigen-binding fragment thereof comprising the following combination of CDRs: an HCDR1 comprising the amino acid sequence of SEQ ID NO: 125, an HCDR2 comprising the amino acid sequence of SEQ ID NO: 126, an HCDR3 comprising the amino acid sequence of SEQ ID NO: 127, an LCDR1 comprising the amino acid sequence of SEQ ID NO: 198, an LCDR2 comprising the amino acid sequence GGN, and an LCDR3 comprising the amino acid sequence of SEQ ID NO: 199; and
(ii) at least one additional antibody or antigen-binding fragment thereof comprising one of the following combinations of CDRs:
(a) an HCDR1 comprising the amino acid sequence of SEQ ID NO: 36, an HCDR2 comprising the amino acid sequence of SEQ ID NO: 16, an HCDR3 comprising the amino acid sequence of SEQ ID NO: 17, an LCDR1 comprising the amino acid sequence of SEQ ID NO: 37, an LCDR2 comprising the amino acid sequence EDN, and an LCDR3 comprising the amino acid sequence of SEQ ID NO: 38;
(b) an HCDR1 comprising the amino acid sequence of SEQ ID NO: 89, an HCDR2 comprising the amino acid sequence of SEQ ID NO: 90, an HCDR3 comprising the amino acid sequence of SEQ ID NO: 91, an LCDR1 comprising the amino acid sequence of SEQ ID NO: 92, an LCDR2 comprising the amino acid sequence DVS, and an LCDR3 comprising the amino acid sequence of SEQ ID NO: 93;
(c) an HCDR1 comprising the amino acid sequence of SEQ ID NO: 57, an HCDR2 comprising the amino acid sequence of SEQ ID NO: 58, an HCDR3 comprising the amino acid sequence of SEQ ID NO: 59, an LCDR1 comprising the amino acid sequence of SEQ ID NO: 60, an LCDR2 comprising the amino acid sequence YDD, and an LCDR3 comprising the amino acid sequence of SEQ ID NO: 61;
(d) an HCDR1 comprising the amino acid sequence of SEQ ID NO: 54, an HCDR2 comprising the amino acid sequence of SEQ ID NO: 55, an HCDR3 comprising the amino acid sequence of SEQ ID NO: 56, an LCDR1 comprising the amino acid sequence of SEQ ID NO: 14, an LCDR2 comprising the amino acid sequence YDD, and an LCDR3 comprising the amino acid sequence of SEQ ID NO: 5; or
(e) an HCDR1 comprising the amino acid sequence of SEQ ID NO: 103, an HCDR2 comprising the amino acid sequence of SEQ ID NO: 104, an HCDR3 comprising the amino acid sequence of SEQ ID NO: 105, an LCDR1 comprising the amino acid sequence of SEQ ID NO: 106, an LCDR2 comprising the amino acid sequence EVS, and an LCDR3 comprising the amino acid sequence of SEQ ID NO: 107.

20. The nucleic acid combination of claim 15, wherein the at least two antibodies or antigen-binding fragments thereof comprise:
(i) an antibody or antigen-binding fragment thereof comprising the following combination of CDRs: an HCDR1 comprising the amino acid sequence of SEQ ID NO: 89, an HCDR2 comprising the amino acid sequence of SEQ ID NO: 90, an HCDR3 comprising the amino acid sequence of SEQ ID NO: 91, an LCDR1 comprising the amino acid sequence of SEQ ID NO: 92, an LCDR2 comprising the amino acid sequence DVS, and an LCDR3 comprising the amino acid sequence of SEQ ID NO: 93; and
(ii) at least one additional antibody or antigen-binding fragment thereof comprising one of the following combinations of CDRs:
(a) an HCDR1 comprising the amino acid sequence of SEQ ID NO: 36, an HCDR2 comprising the amino acid sequence of SEQ ID NO: 16, an HCDR3 comprising the amino acid sequence of SEQ ID NO: 17, an LCDR1 comprising the amino acid sequence of SEQ ID NO: 37, an LCDR2 comprising the amino acid sequence EDN, and an LCDR3 comprising the amino acid sequence of SEQ ID NO: 38;
(b) an HCDR1 comprising the amino acid sequence of SEQ ID NO: 125, an HCDR2 comprising the amino acid sequence of SEQ ID NO: 126, an HCDR3 comprising the amino acid sequence of SEQ ID NO: 127, an LCDR1 comprising the amino acid sequence of SEQ ID NO: 198, an LCDR2 comprising the amino acid sequence GGN, and an LCDR3 comprising the amino acid sequence of SEQ ID NO: 199;
(c) an HCDR1 comprising the amino acid sequence of SEQ ID NO: 57, an HCDR2 comprising the amino acid sequence of SEQ ID NO: 58, an HCDR3 comprising the amino acid sequence of SEQ ID NO: 59, an LCDR1 comprising the amino acid sequence of SEQ ID NO: 60, an LCDR2 comprising the amino acid sequence YDD, and an LCDR3 comprising the amino acid sequence of SEQ ID NO: 61;
(d) an HCDR1 comprising the amino acid sequence of SEQ ID NO: 54, an HCDR2 comprising the amino acid sequence of SEQ ID NO: 55, an HCDR3 comprising the amino acid sequence of SEQ ID NO: 56, an LCDR1 comprising the amino acid sequence of SEQ ID NO: 14, an LCDR2 comprising the amino acid sequence YDD, and an LCDR3 comprising the amino acid sequence of SEQ ID NO: 5; or (e) an HCDR1 comprising the amino acid sequence of SEQ ID NO: 103, an HCDR2 comprising the amino acid sequence of SEQ ID NO: 104, an HCDR3 comprising the amino acid sequence of SEQ ID NO: 105, an LCDR1 comprising the amino acid sequence of SEQ ID NO: 106, an LCDR2 comprising the amino acid sequence EVS, and an LCDR3 comprising the amino acid sequence of SEQ ID NO: 107.

21. The nucleic acid combination of claim 15, wherein the at least two antibodies or antigen-binding fragments thereof comprise:

(i) an antibody or antigen-binding fragment thereof comprising the following combination of CDRs: an HCDR1 comprising the amino acid sequence of SEQ ID NO: 103, an HCDR2 comprising the amino acid sequence of SEQ ID NO: 104, an HCDR3 comprising the amino acid sequence of SEQ ID NO: 105, an LCDR1 comprising the amino acid sequence of SEQ ID NO: 106, an LCDR2 comprising the amino acid sequence EVS, and an LCDR3 comprising the amino acid sequence of SEQ ID NO: 107; and (ii) at least one additional antibody or antigen-binding fragment thereof comprising one of the following combinations of CDRs:

(a) an HCDR1 comprising the amino acid sequence of SEQ ID NO: 36, an HCDR2 comprising the amino acid sequence of SEQ ID NO: 16, an HCDR3 comprising the amino acid sequence of SEQ ID NO: 17, an LCDR1 comprising the amino acid sequence of SEQ ID NO: 37, an LCDR2 comprising the amino acid sequence EDN, and an LCDR3 comprising the amino acid sequence of SEQ ID NO: 38;

(b) an HCDR1 comprising the amino acid sequence of SEQ ID NO: 89, an HCDR2 comprising the amino acid sequence of SEQ ID NO: 90, an HCDR3 comprising the amino acid sequence of SEQ ID NO: 91, an LCDR1 comprising the amino acid sequence of SEQ ID NO: 92, an LCDR2 comprising the amino acid sequence DVS, and an LCDR3 comprising the amino acid sequence of SEQ ID NO: 93;

(c) an HCDR1 comprising the amino acid sequence of SEQ ID NO: 57, an HCDR2 comprising the amino acid sequence of SEQ ID NO: 58, an HCDR3 comprising the amino acid sequence of SEQ ID NO: 59, an LCDR1 comprising the amino acid sequence of SEQ ID NO: 60, an LCDR2 comprising the amino acid sequence YDD, and an LCDR3 comprising the amino acid sequence of SEQ ID NO: 61;

(d) an HCDR1 comprising the amino acid sequence of SEQ ID NO: 54, an HCDR2 comprising the amino acid sequence of SEQ ID NO: 55, an HCDR3 comprising the amino acid sequence of SEQ ID NO: 56, an LCDR1 comprising the amino acid sequence of SEQ ID NO: 14, an LCDR2 comprising the amino acid sequence YDD, and an LCDR3 comprising the amino acid sequence of SEQ ID NO: 5; or (e) an HCDR1 comprising the amino acid sequence of SEQ ID NO: 125, an HCDR2 comprising the amino acid sequence of SEQ ID NO: 126, an HCDR3 comprising the amino acid sequence of SEQ ID NO: 127, an LCDR1 comprising the amino acid sequence of SEQ ID NO: 198, an LCDR2 comprising the amino acid sequence GGN, and an LCDR3 comprising the amino acid sequence of SEQ ID NO: 199.

22. The nucleic acid combination of claim 15, wherein the at least two antibodies or antigen-binding fragments thereof comprise:

(i) a first antibody or antigen-binding fragment thereof comprising the following combination of CDRs: an HCDR1 comprising the amino acid sequence of SEQ ID NO: 36, an HCDR2 comprising the amino acid sequence of SEQ ID NO: 16, an HCDR3 comprising the amino acid sequence of SEQ ID NO: 17, an LCDR1 comprising the amino acid sequence of SEQ ID NO: 37, an LCDR2 comprising the amino acid sequence EDN, and an LCDR3 comprising the amino acid sequence of SEQ ID NO: 38;

(ii) a second antibody or antigen-binding fragment thereof comprising the following combinations of CDRs: an HCDR1 comprising the amino acid sequence of SEQ ID NO: 125, an HCDR2 comprising the amino acid sequence of SEQ ID NO: 126, an HCDR3 comprising the amino acid sequence of SEQ ID NO: 127, an LCDR1 comprising the amino acid sequence of SEQ ID NO: 198, an LCDR2 comprising the amino acid sequence GGN, and an LCDR3 comprising the amino acid sequence of SEQ ID NO: 199;

(iii) a third antibody or antigen-binding fragment thereof comprising one of the following combinations of CDRs:

(a) an HCDR1 comprising the amino acid sequence of SEQ ID NO: 54, an HCDR2 comprising the amino acid sequence of SEQ ID NO: 55, an HCDR3 comprising the amino acid sequence of SEQ ID NO: 56, an LCDR1 comprising the amino acid sequence of SEQ ID NO: 14, an LCDR2 comprising the amino acid sequence YDD, and an LCDR3 comprising the amino acid sequence of SEQ ID NO: 5; or (b) an HCDR1 comprising the amino acid sequence of SEQ ID NO: 57, an HCDR2 comprising the amino acid sequence of SEQ ID NO: 58, an HCDR3 comprising the amino acid sequence of SEQ ID NO: 59, an LCDR1 comprising the amino acid sequence of SEQ ID NO: 60, an LCDR2 comprising the amino acid sequence YDD, and an LCDR3 comprising the amino acid sequence of SEQ ID NO: 61; and (iv) a fourth antibody or antigen-binding fragment thereof comprising one of the following combinations of CDRs:

(a) an HCDR1 comprising the amino acid sequence of SEQ ID NO: 103, an HCDR2 comprising the amino acid sequence of SEQ ID NO: 104, an HCDR3 comprising the amino acid sequence of SEQ ID NO: 105, an LCDR1 comprising the amino acid sequence of SEQ ID NO: 106, an LCDR2 comprising the amino acid sequence EVS, and an LCDR3 comprising the amino acid sequence of SEQ ID NO: 107; or (b) an HCDR1 comprising the amino acid sequence of SEQ ID NO: 89, an HCDR2 comprising the amino acid sequence of SEQ ID NO: 90, an HCDR3 comprising the amino acid sequence of SEQ ID NO: 91, an LCDR1 comprising the amino acid sequence of SEQ ID NO: 92, an LCDR2 comprising the amino acid sequence DVS, and an LCDR3 comprising the amino acid sequence of SEQ ID NO: 93.

23. The nucleic acid combination of claim 22, wherein the at least two antibodies or antigen-binding fragments thereof comprise:

(i) the first antibody or antigen-binding fragment thereof comprises a VH comprising the sequence of SEQ ID NO:147 and a VL comprising the sequence of SEQ ID NO:148;

(ii) the second antibody or antigen-binding fragment thereof comprises a VH comprising the sequence of SEQ ID NO:191 and a VL comprising the sequence of SEQ ID NO:192;

(iii) the third antibody or antigen-binding fragment thereof comprises a VH comprising the sequence of SEQ ID NO:155 or 214 and a VL comprising the sequence of SEQ ID NO:156, or a VH comprising the sequence of SEQ ID NO:157 or 215 and a VL comprising the sequence of SEQ ID NO:158; and (iv) the fourth antibody or antigen-binding fragment thereof comprises a VH comprising the sequence of SEQ ID NO:183 and a VL comprising the sequence of SEQ ID NO:184, or a VH comprising the sequence of SEQ ID NO:177 and a VL comprising the sequence of SEQ ID NO:178.

24. The nucleic acid combination of claim 22, wherein:

(i) the first antibody or antigen-binding fragment thereof comprises an HCDR1 comprising the amino acid sequence of SEQ ID NO: 36, an HCDR2 comprising the amino acid sequence of SEQ ID NO: 16, an HCDR3 comprising the amino acid sequence of SEQ ID NO: 17, an LCDR1 comprising the amino acid sequence of SEQ ID NO: 37, an LCDR2 comprising the amino acid sequence EDN, and an LCDR3 comprising the amino acid sequence of SEQ ID NO: 38;

(ii) the second antibody or antigen-binding fragment thereof comprises an HCDR1 comprising the amino acid sequence of SEQ ID NO: 125, an HCDR2 comprising the amino acid sequence of SEQ ID NO: 126, an HCDR3 comprising the amino acid sequence of SEQ ID NO: 127, an LCDR1 comprising the amino acid sequence of SEQ ID NO: 198, an LCDR2 comprising the amino acid sequence GGN, and an LCDR3 comprising the amino acid sequence of SEQ ID NO: 199;

(iii) the third antibody or antigen-binding fragment thereof comprises an HCDR1 comprising the amino acid sequence of SEQ ID NO: 54, an HCDR2 comprising the amino acid sequence of SEQ ID NO: 55, an HCDR3 comprising the amino acid sequence of SEQ ID NO: 56, an LCDR1 comprising the amino acid sequence of SEQ ID NO: 14, an LCDR2 comprising the amino acid sequence YDD, and an LCDR3 comprising the amino acid sequence of SEQ ID NO: 5; and (iv) the fourth antibody or antigen-binding fragment thereof comprises an HCDR1 comprising the amino acid sequence of SEQ ID NO: 89, an HCDR2 comprising the amino acid sequence of SEQ ID NO: 90, an HCDR3 comprising the amino acid sequence of SEQ ID NO: 91, an LCDR1 comprising the amino acid sequence of SEQ ID NO: 92, an LCDR2 comprising the amino acid sequence DVS, and an LCDR3 comprising the amino acid sequence of SEQ ID NO: 93.

25. The nucleic acid combination of claim 15, wherein the at least two antibodies or antigen-binding fragments thereof comprise:

(i) a first antibody or antigen-binding fragment thereof comprising the following combination of CDRs: an HCDR1 comprising the amino acid sequence of SEQ ID NO: 36, an HCDR2 comprising the amino acid sequence of SEQ ID NO: 16, an HCDR3 comprising the amino acid sequence of SEQ ID NO: 17, an LCDR1 comprising the amino acid sequence of SEQ ID NO: 37, an LCDR2 comprising the amino acid sequence EDN, and an LCDR3 comprising the amino acid sequence of SEQ ID NO: 38;

(ii) a second antibody or antigen-binding fragment thereof comprising the following combinations of CDRs: an HCDR1 comprising the amino acid sequence of SEQ ID NO: 125, an HCDR2 comprising the amino acid sequence of SEQ ID NO: 126, an HCDR3 comprising the amino acid sequence of SEQ ID NO: 127, an LCDR1 comprising the amino acid sequence of SEQ ID NO: 198, an LCDR2 comprising the amino acid sequence GGN, and an LCDR3 comprising the amino acid sequence of SEQ ID NO: 199;

(iii) a third antibody or antigen-binding fragment thereof comprising the following combinations of CDRs: an HCDR1 comprising the amino acid sequence of SEQ ID NO: 54, an HCDR2 comprising the amino acid sequence of SEQ ID NO: 55, an HCDR3 comprising the amino acid sequence of SEQ ID NO: 56, an LCDR1 comprising the amino acid sequence of SEQ ID NO: 14, an LCDR2 comprising the amino acid sequence YDD, and an LCDR3 comprising the amino acid sequence of SEQ ID NO: 5;

(iv) a fourth antibody or antigen-binding fragment thereof comprising the following combinations of CDRs: an HCDR1 comprising the amino acid sequence of SEQ ID NO: 57, an HCDR2 comprising the amino acid sequence of SEQ ID NO: 58, an HCDR3 comprising the amino acid sequence of SEQ ID NO: 59, an LCDR1 comprising the amino acid sequence of SEQ ID NO: 60, an LCDR2 comprising the amino acid sequence YDD, and an LCDR3 comprising the amino acid sequence of SEQ ID NO: 61; and (v) a fifth antibody or antigen-binding fragment thereof comprising comprising one of the following combinations of CDRs:

(a) an HCDR1 comprising the amino acid sequence of SEQ ID NO: 103, an HCDR2 comprising the amino acid sequence of SEQ ID NO: 104, an HCDR3 comprising the amino acid sequence of SEQ ID NO: 105, an LCDR1 comprising the amino acid sequence of SEQ ID NO: 106, an LCDR2 comprising the amino acid sequence EVS, and an LCDR3 comprising the amino acid sequence of SEQ ID NO: 107; or (b) an HCDR1 comprising the amino acid sequence of SEQ ID NO: 89, an HCDR2 comprising the amino acid sequence of SEQ ID NO: 90, an HCDR3 comprising the amino acid sequence of SEQ ID NO: 91, an LCDR1 comprising the amino acid sequence of SEQ ID NO: 92, an LCDR2 comprising the amino acid sequence DVS, and an LCDR3 comprising the amino acid sequence of SEQ ID NO: 93.

26. A pharmaceutical composition comprising at least one nucleic acid or nucleic acid pair according to claim 1 and a pharmaceutically acceptable carrier.

27. The pharmaceutical composition according to claim 26, comprising lipid nanoparticles comprising the nucleic acid or nucleic acid pair.

28. A pharmaceutical composition comprising the nucleic acid combination according to claim 15 and a pharmaceutically acceptable carrier.

29. The pharmaceutical composition according to claim 28, comprising lipid nanoparticles comprising the at least two nucleic acids or nucleic acid pairs.

30. The pharmaceutical composition of claim 26, wherein the at least one nucleic acid or nucleic acid pair encodes the heavy and light chains of at least one the following antibodies or antigen-binding fragments thereof:
- (i) an antibody or antigen-binding fragment thereof comprising an HCDR1 comprising the amino acid sequence of SEQ ID NO: 36, an HCDR2 comprising the amino acid sequence of SEQ ID NO: 16, an HCDR3 comprising the amino acid sequence of SEQ ID NO: 17, an LCDR1 comprising the amino acid sequence of SEQ ID NO: 37, an LCDR2 comprising the amino acid sequence EDN, and an LCDR3 comprising the amino acid sequence of SEQ ID NO: 38;
- (ii) an antibody or antigen-binding fragment thereof comprising an HCDR1 comprising the amino acid sequence of SEQ ID NO: 125, an HCDR2 comprising the amino acid sequence of SEQ ID NO: 126, an HCDR3 comprising the amino acid sequence of SEQ ID NO: 127, an LCDR1 comprising the amino acid sequence of SEQ ID NO: 198, an LCDR2 comprising the amino acid sequence GGN, and an LCDR3 comprising the amino acid sequence of SEQ ID NO: 199;
- (iii) an antibody or antigen-binding fragment thereof comprising an HCDR1 comprising the amino acid sequence of SEQ ID NO: 57, an HCDR2 comprising the amino acid sequence of SEQ ID NO: 58, an HCDR3 comprising the amino acid sequence of SEQ ID NO: 59, an LCDR1 comprising the amino acid sequence of SEQ ID NO: 60, an LCDR2 comprising the amino acid sequence YDD, and an LCDR3 comprising the amino acid sequence of SEQ ID NO: 61;
- (iv) an antibody or antigen-binding fragment thereof comprising an HCDR1 comprising the amino acid sequence of SEQ ID NO: 103, an HCDR2 comprising the amino acid sequence of SEQ ID NO: 104, an HCDR3 comprising the amino acid sequence of SEQ ID NO: 105, an LCDR1 comprising the amino acid sequence of SEQ ID NO: 106, an LCDR2 comprising the amino acid sequence EVS, and an LCDR3 comprising the amino acid sequence of SEQ ID NO: 107;
- (v) an antibody or antigen-binding fragment thereof comprising an HCDR1 comprising the amino acid sequence of SEQ ID NO: 54, an HCDR2 comprising the amino acid sequence of SEQ ID NO: 55, an HCDR3 comprising the amino acid sequence of SEQ ID NO: 56, an LCDR1 comprising the amino acid sequence of SEQ ID NO: 14, an LCDR2 comprising the amino acid sequence YDD, and an LCDR3 comprising the amino acid sequence of SEQ ID NO: 5; and
- (vi) an antibody or antigen-binding fragment thereof comprising an HCDR1 comprising the amino acid sequence of SEQ ID NO: 89, an HCDR2 comprising the amino acid sequence of SEQ ID NO: 90, an HCDR3 comprising the amino acid sequence of SEQ ID NO: 91, an LCDR1 comprising the amino acid sequence of SEQ ID NO: 92, an LCDR2 comprising the amino acid sequence DVS, and an LCDR3 comprising the amino acid sequence of SEQ ID NO: 93.

* * * * *

SEQUENCE LISTING

```
Sequence total quantity: 215
SEQ ID NO: 1            moltype = AA  length = 8
FEATURE                 Location/Qualifiers
source                  1..8
                        mol_type = protein
                        organism = Homo sapiens
SEQUENCE: 1
GYSFTSYW                                                                 8

SEQ ID NO: 2            moltype = AA  length = 8
FEATURE                 Location/Qualifiers
source                  1..8
                        mol_type = protein
                        organism = Homo sapiens
SEQUENCE: 2
IYPGDSDT                                                                 8
```

```
SEQ ID NO: 3              moltype = AA  length = 11
FEATURE                   Location/Qualifiers
source                    1..11
                          mol_type = protein
                          organism = Homo sapiens
SEQUENCE: 3
ARLGDYSGMD V                                                          11

SEQ ID NO: 4              moltype = AA  length = 8
FEATURE                   Location/Qualifiers
source                    1..8
                          mol_type = protein
                          organism = Homo sapiens
SEQUENCE: 4
SSNIGSNP                                                              8

SEQ ID NO: 5              moltype = AA  length = 11
FEATURE                   Location/Qualifiers
source                    1..11
                          mol_type = protein
                          organism = Homo sapiens
SEQUENCE: 5
AAWDDSLNGV V                                                          11

SEQ ID NO: 6              moltype = AA  length = 13
FEATURE                   Location/Qualifiers
source                    1..13
                          mol_type = protein
                          organism = Homo sapiens
SEQUENCE: 6
GYTFTSYYSE QID                                                        13

SEQ ID NO: 7              moltype = AA  length = 8
FEATURE                   Location/Qualifiers
source                    1..8
                          mol_type = protein
                          organism = Homo sapiens
SEQUENCE: 7
IDPSGGST                                                              8

SEQ ID NO: 8              moltype = AA  length = 14
FEATURE                   Location/Qualifiers
source                    1..14
                          mol_type = protein
                          organism = Homo sapiens
SEQUENCE: 8
ARSRDGYIDD AFDI                                                       14

SEQ ID NO: 9              moltype = AA  length = 8
FEATURE                   Location/Qualifiers
source                    1..8
                          mol_type = protein
                          organism = Homo sapiens
SEQUENCE: 9
SSNIGNNY                                                              8

SEQ ID NO: 10             moltype = AA  length = 11
FEATURE                   Location/Qualifiers
source                    1..11
                          mol_type = protein
                          organism = Homo sapiens
SEQUENCE: 10
GTWDSSLSAG V                                                          11

SEQ ID NO: 11             moltype = AA  length = 8
FEATURE                   Location/Qualifiers
source                    1..8
                          mol_type = protein
                          organism = Homo sapiens
SEQUENCE: 11
GYTFTGYY                                                              8

SEQ ID NO: 12             moltype = AA  length = 8
FEATURE                   Location/Qualifiers
source                    1..8
                          mol_type = protein
                          organism = Homo sapiens
SEQUENCE: 12
```

-continued

```
INPNSGGT                                                                         8

SEQ ID NO: 13           moltype = AA   length = 17
FEATURE                 Location/Qualifiers
source                  1..17
                        mol_type = protein
                        organism = Homo sapiens SEQUENCE: 13
ARDKLPFSVG ATHGMDV                                                              17

SEQ ID NO: 14           moltype = AA   length = 8
FEATURE                 Location/Qualifiers
source                  1..8
                        mol_type = protein
                        organism = Homo sapiens SEQUENCE: 14
SSNIGNNA                                                                         8

SEQ ID NO: 15           moltype = AA   length = 11
FEATURE                 Location/Qualifiers
source                  1..11
                        mol_type = protein
                        organism = Homo sapiens SEQUENCE: 15
ASWDDRLDSP V                                                                    11

SEQ ID NO: 16           moltype = AA   length = 8
FEATURE                 Location/Qualifiers
source                  1..8
                        mol_type = protein
                        organism = Homo sapiens SEQUENCE: 16
IDPSGGTT                                                                         8

SEQ ID NO: 17           moltype = AA   length = 11
FEATURE                 Location/Qualifiers
source                  1..11
                        mol_type = protein
                        organism = Homo sapiens SEQUENCE: 17
ARGGFADAVD Y                                                                    11

SEQ ID NO: 18           moltype = AA   length = 8
FEATURE                 Location/Qualifiers
source                  1..8
                        mol_type = protein
                        organism = Homo sapiens SEQUENCE: 18
SGSIASNY                                                                         8

SEQ ID NO: 19           moltype = AA   length = 9
FEATURE                 Location/Qualifiers
source                  1..9
                        mol_type = protein
                        organism = Homo sapiens SEQUENCE: 19
QSYDSGNVI                                                                        9

SEQ ID NO: 20           moltype = AA   length = 8
FEATURE                 Location/Qualifiers
source                  1..8
                        mol_type = protein
                        organism = Homo sapiens SEQUENCE: 20
GYTFTSYA                                                                         8

SEQ ID NO: 21           moltype = AA   length = 8
FEATURE                 Location/Qualifiers
source                  1..8
                        mol_type = protein
                        organism = Homo sapiens SEQUENCE: 21
INAGNGNT                                                                         8

SEQ ID NO: 22           moltype = AA   length = 20
FEATURE                 Location/Qualifiers
source                  1..20
                        mol_type = protein
                        organism = Homo sapiens
```

```
SEQUENCE: 22
AREGMITFGG VIVTNYGMDV                                                         20

SEQ ID NO: 23          moltype = AA  length = 6
FEATURE                Location/Qualifiers
source                 1..6
                       mol_type = protein
                       organism = Homo sapiens
SEQUENCE: 23
NIGSES                                                                         6

SEQ ID NO: 24          moltype = AA  length = 9
FEATURE                Location/Qualifiers
source                 1..9
                       mol_type = protein
                       organism = Homo sapiens
SEQUENCE: 24
QAWDGSTVV                                                                      9

SEQ ID NO: 25          moltype = AA  length = 8
FEATURE                Location/Qualifiers
source                 1..8
                       mol_type = protein
                       organism = Homo sapiens
SEQUENCE: 25
GFTFSSYG                                                                       8

SEQ ID NO: 26          moltype = AA  length = 8
FEATURE                Location/Qualifiers
source                 1..8
                       mol_type = protein
                       organism = Homo sapiens
SEQUENCE: 26
ISYDGSNK                                                                       8

SEQ ID NO: 27          moltype = AA  length = 12
FEATURE                Location/Qualifiers
source                 1..12
                       mol_type = protein
                       organism = Homo sapiens
SEQUENCE: 27
AKEGELRGAF DI                                                                 12

SEQ ID NO: 28          moltype = AA  length = 11
FEATURE                Location/Qualifiers
source                 1..11
                       mol_type = protein
                       organism = Homo sapiens
SEQUENCE: 28
QSLLHSIGYN F                                                                  11

SEQ ID NO: 29          moltype = AA  length = 10
FEATURE                Location/Qualifiers
source                 1..10
                       mol_type = protein
                       organism = Homo sapiens
SEQUENCE: 29
MQALQRTLYT                                                                    10

SEQ ID NO: 30          moltype = AA  length = 8
FEATURE                Location/Qualifiers
source                 1..8
                       mol_type = protein
                       organism = Homo sapiens
SEQUENCE: 30
IDPTGGST                                                                       8

SEQ ID NO: 31          moltype = AA  length = 11
FEATURE                Location/Qualifiers
source                 1..11
                       mol_type = protein
                       organism = Homo sapiens
SEQUENCE: 31
ASAGVGNTFD Y                                                                  11

SEQ ID NO: 32          moltype = AA  length = 8
FEATURE                Location/Qualifiers
source                 1..8
                       mol_type = protein
```

-continued

```
SEQUENCE: 32
SGSIARNY                                                                8

SEQ ID NO: 33           moltype = AA   length = 10
FEATURE                 Location/Qualifiers
source                  1..10
                        mol_type = protein
                        organism = Homo sapiens
SEQUENCE: 33
QSYDSSNQWV                                                             10

SEQ ID NO: 34           moltype = AA   length = 13
FEATURE                 Location/Qualifiers
source                  1..13
                        mol_type = protein
                        organism = Homo sapiens
SEQUENCE: 34
ARNPSLYSSP TDY                                                         13

SEQ ID NO: 35           moltype = AA   length = 8
FEATURE                 Location/Qualifiers
source                  1..8
                        mol_type = protein
                        organism = Homo sapiens
SEQUENCE: 35
SSNIGSNT                                                                8

SEQ ID NO: 36           moltype = AA   length = 8
FEATURE                 Location/Qualifiers
source                  1..8
                        mol_type = protein
                        organism = Homo sapiens
SEQUENCE: 36
GYTFSTYY                                                                8

SEQ ID NO: 37           moltype = AA   length = 8
FEATURE                 Location/Qualifiers
source                  1..8
                        mol_type = protein
                        organism = Homo sapiens
SEQUENCE: 37
SGSIAGNY                                                                8

SEQ ID NO: 38           moltype = AA   length = 11
FEATURE                 Location/Qualifiers
source                  1..11
                        mol_type = protein
                        organism = Homo sapiens
SEQUENCE: 38
QSYDASHLHV I                                                           11

SEQ ID NO: 39           moltype = AA   length = 8
FEATURE                 Location/Qualifiers
source                  1..8
                        mol_type = protein
                        organism = Homo sapiens
SEQUENCE: 39
GGTFSNYA                                                                8

SEQ ID NO: 40           moltype = AA   length = 8
FEATURE                 Location/Qualifiers
source                  1..8
                        mol_type = protein
                        organism = Homo sapiens
SEQUENCE: 40
IIPILDTT                                                                8

SEQ ID NO: 41           moltype = AA   length = 8
FEATURE                 Location/Qualifiers
source                  1..8
                        mol_type = protein
                        organism = Homo sapiens
SEQUENCE: 41
VREEGFDY                                                                8

SEQ ID NO: 42           moltype = AA   length = 9
FEATURE                 Location/Qualifiers
source                  1..9
```

```
                        mol_type = protein
                        organism = Homo sapiens
SEQUENCE: 42
SGINVGAYN                                                               9

SEQ ID NO: 43           moltype = AA  length = 7
FEATURE                 Location/Qualifiers
source                  1..7
                        mol_type = protein
                        organism = Homo sapiens
SEQUENCE: 43
YNSDSDN                                                                 7

SEQ ID NO: 44           moltype = AA  length = 9
FEATURE                 Location/Qualifiers
source                  1..9
                        mol_type = protein
                        organism = Homo sapiens
SEQUENCE: 44
MIWRSSAWV                                                               9

SEQ ID NO: 45           moltype = AA  length = 8
FEATURE                 Location/Qualifiers
source                  1..8
                        mol_type = protein
                        organism = Homo sapiens
SEQUENCE: 45
GFTFDTYG                                                                8

SEQ ID NO: 46           moltype = AA  length = 8
FEATURE                 Location/Qualifiers
source                  1..8
                        mol_type = protein
                        organism = Homo sapiens
SEQUENCE: 46
ISNDGSKK                                                                8

SEQ ID NO: 47           moltype = AA  length = 21
FEATURE                 Location/Qualifiers
source                  1..21
                        mol_type = protein
                        organism = Homo sapiens
SEQUENCE: 47
GRVTEPYMVT PLMLFRMAID N                                                21

SEQ ID NO: 48           moltype = AA  length = 6
FEATURE                 Location/Qualifiers
source                  1..6
                        mol_type = protein
                        organism = Homo sapiens
SEQUENCE: 48
NFGTKS                                                                  6

SEQ ID NO: 49           moltype = AA  length = 13
FEATURE                 Location/Qualifiers
source                  1..13
                        mol_type = protein
                        organism = Homo sapiens
SEQUENCE: 49
QVWDSSADLR GVV                                                         13

SEQ ID NO: 50           moltype = AA  length = 8
FEATURE                 Location/Qualifiers
source                  1..8
                        mol_type = protein
                        organism = Homo sapiens
SEQUENCE: 50
GRTFSSYA                                                                8

SEQ ID NO: 51           moltype = AA  length = 8
FEATURE                 Location/Qualifiers
source                  1..8
                        mol_type = protein
                        organism = Homo sapiens
SEQUENCE: 51
ISRSGGST                                                                8

SEQ ID NO: 52           moltype = AA  length = 22
FEATURE                 Location/Qualifiers
```

```
                        source          1..22
                                        mol_type = protein
                                        organism = Homo sapiens
SEQUENCE: 52
AASNEGGTWY GSSWYRPSSY EH                                                22

SEQ ID NO: 53           moltype = AA   length = 22
FEATURE                 Location/Qualifiers
source                  1..22
                        mol_type = protein
                        organism = Homo sapiens
SEQUENCE: 53
AASNEGGTWY GSSWYRPSSY EY                                                22

SEQ ID NO: 54           moltype = AA   length = 8
FEATURE                 Location/Qualifiers
source                  1..8
                        mol_type = protein
                        organism = Homo sapiens
SEQUENCE: 54
GYIFTNYD                                                                 8

SEQ ID NO: 55           moltype = AA   length = 8
FEATURE                 Location/Qualifiers
source                  1..8
                        mol_type = protein
                        organism = Homo sapiens
SEQUENCE: 55
VNPNSGKV                                                                 8

SEQ ID NO: 56           moltype = AA   length = 7
FEATURE                 Location/Qualifiers
source                  1..7
                        mol_type = protein
                        organism = Homo sapiens
SEQUENCE: 56
ARGHTDF                                                                  7

SEQ ID NO: 57           moltype = AA   length = 8
FEATURE                 Location/Qualifiers
source                  1..8
                        mol_type = protein
                        organism = Homo sapiens
SEQUENCE: 57
GGTFNTYS                                                                 8

SEQ ID NO: 58           moltype = AA   length = 8
FEATURE                 Location/Qualifiers
source                  1..8
                        mol_type = protein
                        organism = Homo sapiens
SEQUENCE: 58
IIPIFDKP                                                                 8

SEQ ID NO: 59           moltype = AA   length = 12
FEATURE                 Location/Qualifiers
source                  1..12
                        mol_type = protein
                        organism = Homo sapiens
SEQUENCE: 59
ARGTGYYYGM DV                                                           12

SEQ ID NO: 60           moltype = AA   length = 8
FEATURE                 Location/Qualifiers
source                  1..8
                        mol_type = protein
                        organism = Homo sapiens
SEQUENCE: 60
RSNIGNYP                                                                 8

SEQ ID NO: 61           moltype = AA   length = 11
FEATURE                 Location/Qualifiers
source                  1..11
                        mol_type = protein
                        organism = Homo sapiens
SEQUENCE: 61
ATWDDSLNVW V                                                            11

SEQ ID NO: 62           moltype = AA   length = 10
```

-continued

```
FEATURE                 Location/Qualifiers
source                  1..10
                        mol_type = protein
                        organism = Homo sapiens
SEQUENCE: 62
ARYLSSEGMD                                                                      10

SEQ ID NO: 63           moltype = AA  length = 11
FEATURE                 Location/Qualifiers
source                  1..11
                        mol_type = protein
                        organism = Homo sapiens
SEQUENCE: 63
ASWDDSLNEG V                                                                    11

SEQ ID NO: 64           moltype = AA  length = 8
FEATURE                 Location/Qualifiers
source                  1..8
                        mol_type = protein
                        organism = Homo sapiens
SEQUENCE: 64
GGTFSSYA                                                                        8

SEQ ID NO: 65           moltype = AA  length = 8
FEATURE                 Location/Qualifiers
source                  1..8
                        mol_type = protein
                        organism = Homo sapiens
SEQUENCE: 65
IIPIFGTT                                                                        8

SEQ ID NO: 66           moltype = AA  length = 12
FEATURE                 Location/Qualifiers
source                  1..12
                        mol_type = protein
                        organism = Homo sapiens
SEQUENCE: 66
ARDHGYYYGM DV                                                                   12

SEQ ID NO: 67           moltype = AA  length = 8
FEATURE                 Location/Qualifiers
source                  1..8
                        mol_type = protein
                        organism = Homo sapiens
SEQUENCE: 67
DSNIGQNG                                                                        8

SEQ ID NO: 68           moltype = AA  length = 11
FEATURE                 Location/Qualifiers
source                  1..11
                        mol_type = protein
                        organism = Homo sapiens
SEQUENCE: 68
ASWDDSLSAW V                                                                    11

SEQ ID NO: 69           moltype = AA  length = 8
FEATURE                 Location/Qualifiers
source                  1..8
                        mol_type = protein
                        organism = Homo sapiens
SEQUENCE: 69
IIPMFNSA                                                                        8

SEQ ID NO: 70           moltype = AA  length = 16
FEATURE                 Location/Qualifiers
source                  1..16
                        mol_type = protein
                        organism = Homo sapiens
SEQUENCE: 70
ARESSGYYYV SNWFDP                                                               16

SEQ ID NO: 71           moltype = AA  length = 9
FEATURE                 Location/Qualifiers
source                  1..9
                        mol_type = protein
                        organism = Homo sapiens
SEQUENCE: 71
SSNIGAGYD                                                                       9
```

```
SEQ ID NO: 72          moltype = AA   length = 11
FEATURE                Location/Qualifiers
source                 1..11
                       mol_type = protein
                       organism = Homo sapiens
SEQUENCE: 72
QSYDSSLSGV V                                                              11

SEQ ID NO: 73          moltype = AA   length = 11
FEATURE                Location/Qualifiers
source                 1..11
                       mol_type = protein
                       organism = Homo sapiens
SEQUENCE: 73
ARGSHYGDYD Y                                                              11

SEQ ID NO: 74          moltype = AA   length = 10
FEATURE                Location/Qualifiers
source                 1..10
                       mol_type = protein
                       organism = Homo sapiens
SEQUENCE: 74
GDSVSSNSAA                                                                10

SEQ ID NO: 75          moltype = AA   length = 7
FEATURE                Location/Qualifiers
source                 1..7
                       mol_type = protein
                       organism = Homo sapiens
SEQUENCE: 75
TYYRSKW                                                                   7

SEQ ID NO: 76          moltype = AA   length = 9
FEATURE                Location/Qualifiers
source                 1..9
                       mol_type = protein
                       organism = Homo sapiens
SEQUENCE: 76
ARTIGWYDS                                                                 9

SEQ ID NO: 77          moltype = AA   length = 6
FEATURE                Location/Qualifiers
source                 1..6
                       mol_type = protein
                       organism = Homo sapiens
SEQUENCE: 77
ALPKQF                                                                    6

SEQ ID NO: 78          moltype = AA   length = 11
FEATURE                Location/Qualifiers
source                 1..11
                       mol_type = protein
                       organism = Homo sapiens
SEQUENCE: 78
QSADSSATYE V                                                              11

SEQ ID NO: 79          moltype = AA   length = 11
FEATURE                Location/Qualifiers
source                 1..11
                       mol_type = protein
                       organism = Homo sapiens
SEQUENCE: 79
ARRQSGSGYD Y                                                              11

SEQ ID NO: 80          moltype = AA   length = 8
FEATURE                Location/Qualifiers
source                 1..8
                       mol_type = protein
                       organism = Homo sapiens
SEQUENCE: 80
SSNVGSNS                                                                  8

SEQ ID NO: 81          moltype = AA   length = 11
FEATURE                Location/Qualifiers
source                 1..11
                       mol_type = protein
                       organism = Homo sapiens
SEQUENCE: 81
AAWDDSLNGW V                                                              11
```

```
SEQ ID NO: 82              moltype = AA   length = 11
FEATURE                    Location/Qualifiers
source                     1..11
                           mol_type = protein
                           organism = Homo sapiens
SEQUENCE: 82
ARWSEGNGFD Y                                                                11

SEQ ID NO: 83              moltype = AA   length = 8
FEATURE                    Location/Qualifiers
source                     1..8
                           mol_type = protein
                           organism = Homo sapiens
SEQUENCE: 83
SSNIGSNS                                                                    8

SEQ ID NO: 84              moltype = AA   length = 13
FEATURE                    Location/Qualifiers
source                     1..13
                           mol_type = protein
                           organism = Homo sapiens
SEQUENCE: 84
LAVAGTGGDA FDI                                                              13

SEQ ID NO: 85              moltype = AA   length = 6
FEATURE                    Location/Qualifiers
source                     1..6
                           mol_type = protein
                           organism = Homo sapiens
SEQUENCE: 85
QSISSW                                                                      6

SEQ ID NO: 86              moltype = AA   length = 9
FEATURE                    Location/Qualifiers
source                     1..9
                           mol_type = protein
                           organism = Homo sapiens
SEQUENCE: 86
QQGHSFPLT                                                                   9

SEQ ID NO: 87              moltype = AA   length = 6
FEATURE                    Location/Qualifiers
source                     1..6
                           mol_type = protein
                           organism = Homo sapiens
SEQUENCE: 87
NIESKY                                                                      6

SEQ ID NO: 88              moltype = AA   length = 11
FEATURE                    Location/Qualifiers
source                     1..11
                           mol_type = protein
                           organism = Homo sapiens
SEQUENCE: 88
QVWDRTSGHF V                                                                11

SEQ ID NO: 89              moltype = AA   length = 8
FEATURE                    Location/Qualifiers
source                     1..8
                           mol_type = protein
                           organism = Homo sapiens
SEQUENCE: 89
GFSFTNYG                                                                    8

SEQ ID NO: 90              moltype = AA   length = 8
FEATURE                    Location/Qualifiers
source                     1..8
                           mol_type = protein
                           organism = Homo sapiens
SEQUENCE: 90
ISYDGSIK                                                                    8

SEQ ID NO: 91              moltype = AA   length = 10
FEATURE                    Location/Qualifiers
source                     1..10
                           mol_type = protein
                           organism = Homo sapiens
SEQUENCE: 91
```

TRERGTGIDY                                                                                       10

SEQ ID NO: 92          moltype = AA  length = 9
FEATURE                Location/Qualifiers
source                 1..9
                       mol_type = protein
                       organism = Homo sapiens SEQUENCE: 92
KSDIGAYNY                                                                                         9

SEQ ID NO: 93          moltype = AA  length = 10
FEATURE                Location/Qualifiers
source                 1..10
                       mol_type = protein
                       organism = Homo sapiens SEQUENCE: 93
SSYTTSGTVV                                                                                       10

SEQ ID NO: 94          moltype = AA  length = 8
FEATURE                Location/Qualifiers
source                 1..8
                       mol_type = protein
                       organism = Homo sapiens SEQUENCE: 94
GFTFSNYG                                                                                          8

SEQ ID NO: 95          moltype = AA  length = 8
FEATURE                Location/Qualifiers
source                 1..8
                       mol_type = protein
                       organism = Homo sapiens SEQUENCE: 95
ISYDGSIE                                                                                          8

SEQ ID NO: 96          moltype = AA  length = 10
FEATURE                Location/Qualifiers
source                 1..10
                       mol_type = protein
                       organism = Homo sapiens SEQUENCE: 96
ARDEDGAFDI                                                                                       10

SEQ ID NO: 97          moltype = AA  length = 12
FEATURE                Location/Qualifiers
source                 1..12
                       mol_type = protein
                       organism = Homo sapiens SEQUENCE: 97
ESVSYSSSNK NY                                                                                    12

SEQ ID NO: 98          moltype = AA  length = 9
FEATURE                Location/Qualifiers
source                 1..9
                       mol_type = protein
                       organism = Homo sapiens SEQUENCE: 98
QQYSSPLT                                                                                          9

SEQ ID NO: 99          moltype = AA  length = 8
FEATURE                Location/Qualifiers
source                 1..8
                       mol_type = protein
                       organism = Homo sapiens SEQUENCE: 99
GFTFSDYP                                                                                          8

SEQ ID NO: 100         moltype = AA  length = 8
FEATURE                Location/Qualifiers
source                 1..8
                       mol_type = protein
                       organism = Homo sapiens SEQUENCE: 100
ISYDGWTK                                                                                          8

SEQ ID NO: 101         moltype = AA  length = 9
FEATURE                Location/Qualifiers
source                 1..9
                       mol_type = protein
                       organism = Homo sapiens

```
SEQUENCE: 101
VRGTDYGDS                                                                               9

SEQ ID NO: 102         moltype = AA   length = 11
FEATURE                Location/Qualifiers
source                 1..11
                       mol_type = protein
                       organism = Homo sapiens
SEQUENCE: 102
GTWDNSLSAW V                                                                           11

SEQ ID NO: 103         moltype = AA   length = 8
FEATURE                Location/Qualifiers
source                 1..8
                       mol_type = protein
                       organism = Homo sapiens
SEQUENCE: 103
GFTFNNYP                                                                                8

SEQ ID NO: 104         moltype = AA   length = 8
FEATURE                Location/Qualifiers
source                 1..8
                       mol_type = protein
                       organism = Homo sapiens
SEQUENCE: 104
ISYDGNHK                                                                                8

SEQ ID NO: 105         moltype = AA   length = 10
FEATURE                Location/Qualifiers
source                 1..10
                       mol_type = protein
                       organism = Homo sapiens
SEQUENCE: 105
ASDLSGAEDS                                                                             10

SEQ ID NO: 106         moltype = AA   length = 9
FEATURE                Location/Qualifiers
source                 1..9
                       mol_type = protein
                       organism = Homo sapiens
SEQUENCE: 106
SSDVGGYNY                                                                               9

SEQ ID NO: 107         moltype = AA   length = 10
FEATURE                Location/Qualifiers
source                 1..10
                       mol_type = protein
                       organism = Homo sapiens
SEQUENCE: 107
SSYTSSSTWV                                                                             10

SEQ ID NO: 108         moltype = AA   length = 8
FEATURE                Location/Qualifiers
source                 1..8
                       mol_type = protein
                       organism = Homo sapiens
SEQUENCE: 108
GFTLSDYP                                                                                8

SEQ ID NO: 109         moltype = AA   length = 8
FEATURE                Location/Qualifiers
source                 1..8
                       mol_type = protein
                       organism = Homo sapiens
SEQUENCE: 109
MSYDGSLK                                                                                8

SEQ ID NO: 110         moltype = AA   length = 11
FEATURE                Location/Qualifiers
source                 1..11
                       mol_type = protein
                       organism = Homo sapiens
SEQUENCE: 110
ARGNSDGDFD Y                                                                           11

SEQ ID NO: 111         moltype = AA   length = 6
FEATURE                Location/Qualifiers
source                 1..6
                       mol_type = protein
```

-continued

```
SEQUENCE: 111
DIGSRS                                                                     6

SEQ ID NO: 112          moltype = AA  length = 9
FEATURE                 Location/Qualifiers
source                  1..9
                        mol_type = protein
                        organism = Homo sapiens
SEQUENCE: 112
QAWDSSTVV                                                                  9

SEQ ID NO: 113          moltype = AA  length = 8
FEATURE                 Location/Qualifiers
source                  1..8
                        mol_type = protein
                        organism = Homo sapiens
SEQUENCE: 113
GFSFNTFP                                                                   8

SEQ ID NO: 114          moltype = AA  length = 8
FEATURE                 Location/Qualifiers
source                  1..8
                        mol_type = protein
                        organism = Homo sapiens
SEQUENCE: 114
ISYDGSFK                                                                   8

SEQ ID NO: 115          moltype = AA  length = 13
FEATURE                 Location/Qualifiers
source                  1..13
                        mol_type = protein
                        organism = Homo sapiens
SEQUENCE: 115
ASPGDSDWAD FEN                                                            13

SEQ ID NO: 116          moltype = AA  length = 11
FEATURE                 Location/Qualifiers
source                  1..11
                        mol_type = protein
                        organism = Homo sapiens
SEQUENCE: 116
QSYDSSLSGY V                                                              11

SEQ ID NO: 117          moltype = AA  length = 8
FEATURE                 Location/Qualifiers
source                  1..8
                        mol_type = protein
                        organism = Homo sapiens
SEQUENCE: 117
GFNFSLYG                                                                   8

SEQ ID NO: 118          moltype = AA  length = 8
FEATURE                 Location/Qualifiers
source                  1..8
                        mol_type = protein
                        organism = Homo sapiens
SEQUENCE: 118
ISYDGSQK                                                                   8

SEQ ID NO: 119          moltype = AA  length = 9
FEATURE                 Location/Qualifiers
source                  1..9
                        mol_type = protein
                        organism = Homo sapiens
SEQUENCE: 119
VKGEGSLDY                                                                  9

SEQ ID NO: 120          moltype = AA  length = 9
FEATURE                 Location/Qualifiers
source                  1..9
                        mol_type = protein
                        organism = Homo sapiens
SEQUENCE: 120
TSDVGGYGY                                                                  9

SEQ ID NO: 121          moltype = AA  length = 10
FEATURE                 Location/Qualifiers
source                  1..10
```

```
SEQUENCE: 121
VSYTLSSLVV                                                                          10

SEQ ID NO: 122         moltype = AA   length = 8
FEATURE                Location/Qualifiers
source                 1..8
                       mol_type = protein
                       organism = Homo sapiens
SEQUENCE: 122
GSIPSVNV                                                                             8

SEQ ID NO: 123         moltype = AA   length = 7
FEATURE                Location/Qualifiers
source                 1..7
                       mol_type = protein
                       organism = Homo sapiens
SEQUENCE: 123
VTSDGRT                                                                              7

SEQ ID NO: 124         moltype = AA   length = 12
FEATURE                Location/Qualifiers
source                 1..12
                       mol_type = protein
                       organism = Homo sapiens
SEQUENCE: 124
LITNQDHNTL GV                                                                       12

SEQ ID NO: 125         moltype = AA   length = 10
FEATURE                Location/Qualifiers
source                 1..10
                       mol_type = protein
                       organism = Homo sapiens
SEQUENCE: 125
GFSLNTRGMS                                                                          10

SEQ ID NO: 126         moltype = AA   length = 7
FEATURE                Location/Qualifiers
source                 1..7
                       mol_type = protein
                       organism = Homo sapiens
SEQUENCE: 126
IDWEDDK                                                                              7

SEQ ID NO: 127         moltype = AA   length = 15
FEATURE                Location/Qualifiers
source                 1..15
                       mol_type = protein
                       organism = Homo sapiens
SEQUENCE: 127
ARTYSVGVKY FGMDV                                                                    15

SEQ ID NO: 128         moltype = AA   length = 8
FEATURE                Location/Qualifiers
source                 1..8
                       mol_type = protein
                       organism = Homo sapiens
SEQUENCE: 128
GNVTSITL                                                                             8

SEQ ID NO: 129         moltype = AA   length = 8
FEATURE                Location/Qualifiers
source                 1..8
                       mol_type = protein
                       organism = Homo sapiens
SEQUENCE: 129
IINDDDRT                                                                             8

SEQ ID NO: 130         moltype = AA   length = 9
FEATURE                Location/Qualifiers
source                 1..9
                       mol_type = protein
                       organism = Homo sapiens
SEQUENCE: 130
SAKAGGNFY                                                                            9

SEQ ID NO: 131         moltype = AA   length = 118
FEATURE                Location/Qualifiers
```

```
source                  1..118
                        mol_type = protein
                        organism = Homo sapiens
SEQUENCE: 131
EVQLVQSGAE VKKPGKSLKI SCKGSGYSFT SYWIGWVRQM PGKGLEWMGI IYPGDSDTRY    60
SPSFQGQVTI SADKSISTAY LQWSSLKASD TAMYYCARLG DYSGMDVWGQ GTMVTVSS     118

SEQ ID NO: 132          moltype = AA  length = 110
FEATURE                 Location/Qualifiers
source                  1..110
                        mol_type = protein
                        organism = Homo sapiens
SEQUENCE: 132
QSVLTQPPSA SGTPGQRVTI SCSGSSSNIG SNPVNWYQHL PGTAPKLLIS GNDQRPSGVP    60
DRFSGSKSGT SASLAISGLQ SEDEGDYYCA AWDDSLNGVV FGGGTQLTVL             110

SEQ ID NO: 133          moltype = AA  length = 121
FEATURE                 Location/Qualifiers
source                  1..121
                        mol_type = protein
                        organism = Homo sapiens
SEQUENCE: 133
QVQLVQSGAE VKKPGASVKV SCKASGYTFT SYYMHWVRQA PGQGLEWMGI IDPSGGSTSY    60
AQKFQGRVTL TRDTSTSTVY MELSSLRSED TAVYYCARSR DGYIDDAFDI WGQGTLVTVS   120
S                                                                  121

SEQ ID NO: 134          moltype = AA  length = 110
FEATURE                 Location/Qualifiers
source                  1..110
                        mol_type = protein
                        organism = Homo sapiens
SEQUENCE: 134
QSVLTQPPSV SAAPGQKVTI SCSGSSSNIG NNYVSWYQQL PGTAPKLLIY DNNKRPSGIP    60
DRFSGSKSGT SATLGITGLQ TGDEADYYCG TWDSSLSAGV FGGGTKLTVL             110

SEQ ID NO: 135          moltype = AA  length = 124
FEATURE                 Location/Qualifiers
source                  1..124
                        mol_type = protein
                        organism = Homo sapiens
SEQUENCE: 135
QVQLVQSGAE VKKPGASVKV SCKASGYTFT GYYMHWVRQA PGQGLEWMGR INPNSGGTNY    60
AQKFQGRVTM TRDTSISTAY MELSRLRSDD TAVYYCARDK LPFSVGATHG MDVWGQGTLV   120
TVSS                                                               124

SEQ ID NO: 136          moltype = AA  length = 110
FEATURE                 Location/Qualifiers
source                  1..110
                        mol_type = protein
                        organism = Homo sapiens
SEQUENCE: 136
QSVLTQPPSV SEAPRQRVTI SCSGSSSNIG NNAVNWYQQL PGQAPRLLIY YDNLLPSGVS    60
DRFSASTSGT SASLAISDLR SEDEADYYCA SWDDRLDSPV FGGGTKLTVL             110

SEQ ID NO: 137          moltype = AA  length = 126
FEATURE                 Location/Qualifiers
source                  1..126
                        mol_type = protein
                        organism = Homo sapiens
SEQUENCE: 137
QVQLVQSGAE VKKPGASVKV SCKASVKVSC KASGYTFTSY YMHWVRQAPG QGPEWMGVID    60
PSGGTTSYAQ KFHDRIAMTR DTSTSTAYLE LSSLRSEDTA VYYCARGGFA DAVDYWGQGT   120
LVTVSS                                                             126

SEQ ID NO: 138          moltype = AA  length = 110
FEATURE                 Location/Qualifiers
source                  1..110
                        mol_type = protein
                        organism = Homo sapiens
SEQUENCE: 138
NFMLTQPHSV SESPGKTVTI SCTRSSGSIA SNYVQWYQQR PGSSPTTVIY EDNQRPSGVP    60
DRFSGSIDSS SNSASLTISG LKTEDEADYY CQSYDSGNVI FGGGTKVTVL             110

SEQ ID NO: 139          moltype = AA  length = 127
FEATURE                 Location/Qualifiers
source                  1..127
                        mol_type = protein
                        organism = Homo sapiens
SEQUENCE: 139
```

```
EVQLVQSGAE VKKPGASVKV SCKASGYTFT SYAMHWVRQA PGQRLEWMGW INAGNGNTKY    60
SQKFQGRVTI TRDTSASTAY MELSSLRSED TAVYYCAREG MITFGGVIVT NYGMDVWGQG   120
TMVTVSS                                                            127

SEQ ID NO: 140          moltype = AA  length = 106
FEATURE                 Location/Qualifiers
source                  1..106
                        mol_type = protein
                        organism = Homo sapiens
SEQUENCE: 140
SYVLTQPPSV SVAPGQTARI TCGGNNIGSE SVHWYQQKPG QAPLLVVYDD NNRPSGIPER    60
FSGSNSGNTA TLTINRVEAG DEADYSCQAW DGSTVVFGGG TKLTVL                 106

SEQ ID NO: 141          moltype = AA  length = 119
FEATURE                 Location/Qualifiers
source                  1..119
                        mol_type = protein
                        organism = Homo sapiens
SEQUENCE: 141
QVQLVESGGG VVQPGRSLRL SCAASGFTFS SYGMHWVRQA PGKGLEWVAV ISYDGSNKYY    60
ADSVKGRFTI SRDNSKNTLY LQMNSLRAED TAVYYCAKEG ELRGAFDIWG QGTTVTVSS   119

SEQ ID NO: 142          moltype = AA  length = 113
FEATURE                 Location/Qualifiers
source                  1..113
                        mol_type = protein
                        organism = Homo sapiens
SEQUENCE: 142
DIVMTQSPLS LPVTPGEPAS ISCTSSQSLL HSIGYNFVDW YLQKPGQSPQ LLIYSASNRA    60
SGVPDRFSGS GSGTDFTLKI SRVEAEDVGV YYCMQALQRT LYTFGQGTKV ESK         113

SEQ ID NO: 143          moltype = AA  length = 118
FEATURE                 Location/Qualifiers
source                  1..118
                        mol_type = protein
                        organism = Homo sapiens
SEQUENCE: 143
QVQLVQSGAE VKKPGASVKL SCTASGYTFT SYYMHWVRQA PGQGLEWMGI IDPTGGSTSY    60
AQKFQGRVTM TRDTSTSTVY MELSSLRSED TAVYYCASAG VGNTFDYWGQ GTLVTVSS    118

SEQ ID NO: 144          moltype = AA  length = 111
FEATURE                 Location/Qualifiers
source                  1..111
                        mol_type = protein
                        organism = Homo sapiens
SEQUENCE: 144
NPMLTQPHSV SASPGKTVTI SCTRSSGSIA RNYVQWYQQR PGRSPNILIF EDKQRPSGVP    60
DRFSGSIDSS SNSASLTISG LKTEDEADYY CQSYDSSNQW VFGGGTKLTV L           111

SEQ ID NO: 145          moltype = AA  length = 120
FEATURE                 Location/Qualifiers
source                  1..120
                        mol_type = protein
                        organism = Homo sapiens
SEQUENCE: 145
EVQLVQSGAE VKKPGESLKI SCKGSGYSFT SYWIGWVRQM PGKGLEWMGI IYPGDSDTRY    60
SPSFQGQVTI SADKSISTAY LQWSSLKASD TAMYYCARNP SLYSSPTDYW GQGTLVTVSS  120

SEQ ID NO: 146          moltype = AA  length = 110
FEATURE                 Location/Qualifiers
source                  1..110
                        mol_type = protein
                        organism = Homo sapiens
SEQUENCE: 146
QSVLTQPPSA SGTPGQRVTI SCSGSSSNIG SNTVNWYQQL PGTAPKLLIY NNNQRPSGVP    60
DRFSGSKSGT SASLAITGLQ SEDEADYYCA AWDDSLNGVV FGGGTKVTVL             110

SEQ ID NO: 147          moltype = AA  length = 118
FEATURE                 Location/Qualifiers
source                  1..118
                        mol_type = protein
                        organism = Homo sapiens
SEQUENCE: 147
QVQLVQSGAE VKLPGASMKV SCKASGYTFS TYYMHWVRQA PGQGPEWMGV IDPSGGTTSY    60
AQKFHDRIAM TRDTSTSTAY LELSSLRSED MAVYYCARGG FADAVDYWGQ GTLVTVSS    118

SEQ ID NO: 148          moltype = AA  length = 112
FEATURE                 Location/Qualifiers
source                  1..112
```

```
                        mol_type = protein
                        organism = Homo sapiens
SEQUENCE: 148
NFMLTQPHSV SGSPGKTVTI SCTRNSGSIA GNYVQWYQQR PGSAPTTVIY EDNQRPSGVP   60
DRFSGSIDSS SNSASLTISG LKTEDEADYY CQSYDASHLH VIFGGGTKVT VL          112

SEQ ID NO: 149          moltype = AA   length = 115
FEATURE                 Location/Qualifiers
source                  1..115
                        mol_type = protein
                        organism = Homo sapiens
SEQUENCE: 149
QVQLVQSGAE VKKPGSSVKV SCKASGGTFS NYAISWVRQA PGQGLEWMGG IIPILDTTNY   60
AQKFQGRVTI TADESTSTAY MELNSLRSED TAVYYCVREE GFDYWGQGTL VTVSS        115

SEQ ID NO: 150          moltype = AA   length = 115
FEATURE                 Location/Qualifiers
source                  1..115
                        mol_type = protein
                        organism = Homo sapiens
SEQUENCE: 150
QSVLTQPSSL SASPGASASL TCTLRSGINV GAYNIYWYQQ KPGSPPQFVL RYNSDSDNQQ   60
GSGVPSRFSG SKDASANAGI LLISGLQSED EAEYYCMIWR SSAWVFGGGT KLTVL        115

SEQ ID NO: 151          moltype = AA   length = 128
FEATURE                 Location/Qualifiers
source                  1..128
                        mol_type = protein
                        organism = Homo sapiens
SEQUENCE: 151
QVQLVESGGG VVQPGRSLRL SCGASGFTFD TYGMHWVRQA PGRGPEWVAV ISNDGSKKYY   60
ADSVKGRFTI SRDNSKNTVY LQMNSLRAED TGVYYCGRVT EPYMVTPLML FRMAIDNWGQ   120
GTLVTVSS                                                            128

SEQ ID NO: 152          moltype = AA   length = 110
FEATURE                 Location/Qualifiers
source                  1..110
                        mol_type = protein
                        organism = Homo sapiens
SEQUENCE: 152
SYVLTQPPSM SVAPGETARI TCGGGNFGTK SVHWYQQRSG RAPVLVVYAN DDRPSGIPER   60
FSGSKSGDTA TLTISRVEAG DEADYFCQVW DSSADLRGVV FGGGTQLTVL              110

SEQ ID NO: 153          moltype = AA   length = 129
FEATURE                 Location/Qualifiers
source                  1..129
                        mol_type = protein
                        organism = Homo sapiens
SEQUENCE: 153
QVQLQESGGG LVQAGGSLRL SCAASGRTFS SYAMGWFRQV LGKERELVAA ISRSGGSTYY   60
ADSVKGRFTV SRDNVKNTVY LQMNSLKPED TAGYYCAASN EGGTWYGSSW YRPSSYEHWG   120
QGTQVTVSS                                                           129

SEQ ID NO: 154          moltype = AA   length = 129
FEATURE                 Location/Qualifiers
source                  1..129
                        mol_type = protein
                        organism = Homo sapiens
SEQUENCE: 154
QVQLQQSGGG LVQAGGSLRL SCAASGRTFS SYAMGWFRQV LGKERELVAA ISRSGGSTYY   60
ADSVKGRFTI SRDNVKNTVY LQMNSLKPED TAGYYCAASN EGGTWYGSSW YRPSSYEYWG   120
QGTQVTVSS                                                           129

SEQ ID NO: 155          moltype = AA   length = 114
FEATURE                 Location/Qualifiers
source                  1..114
                        mol_type = protein
                        organism = Homo sapiens
SEQUENCE: 155
QVQLVQSGAE VKKPGASVTV SCKTSGYIFT NYDINWVRQA PGQGLEWVGW VNPNSGKVGY   60
AQKFQGRVIM TRSDSESTAY MELTNLTSDD TAVYYCARGH TDFWGQGTLV TVSS          114

SEQ ID NO: 156          moltype = AA   length = 110
FEATURE                 Location/Qualifiers
source                  1..110
                        mol_type = protein
                        organism = Homo sapiens
SEQUENCE: 156
QSVLTQPPSV SEAPRQRVTI SCSGSSSNIG NNAVNWYQQL PGRAPKLLIY YDDLLPSGVS   60
```

```
DRFSGSKSGT SASLAISGLQ SEDEADYYCA AWDDSLNGVV FGGGTQLTVL            110

SEQ ID NO: 157          moltype = AA   length = 119
FEATURE                 Location/Qualifiers
source                  1..119
                        mol_type = protein
                        organism = Homo sapiens
SEQUENCE: 157
QVQLVQSGAE VKKPGSSVNV SCKTSGGTFN TYSINWVRQA PGQGLEWMGE IIPIFDKPNY  60
AQKFQGRVTI TADESTSTAY MELTSLRSDD TAVYYCARGT GYYYGMDVWG QGTTVTVSS   119

SEQ ID NO: 158          moltype = AA   length = 110
FEATURE                 Location/Qualifiers
source                  1..110
                        mol_type = protein
                        organism = Homo sapiens
SEQUENCE: 158
QSVLTQPPSV SGAPRQTVTI SCFGSRSNIG NYPVNWYHQV PGKAPKVVVY YDDLLPSGIS  60
DRFSGYKSGT SASLTISGLR SEDEADYYCA TWDDSLNVWV FGGGTKLTVL            110

SEQ ID NO: 159          moltype = AA   length = 118
FEATURE                 Location/Qualifiers
source                  1..118
                        mol_type = protein
                        organism = Homo sapiens
SEQUENCE: 159
EVQLVQSGAE VKKPGESLKI SCKGSGYSFT SYWIGWVRQM PGKGLEWMGI IYPGDSDTRY  60
SPSFQGQVTI SADKSISTAY LQWSSLKASD TAMYYCARYL SSEGMDVWGK GTTVTVSS    118

SEQ ID NO: 160          moltype = AA   length = 110
FEATURE                 Location/Qualifiers
source                  1..110
                        mol_type = protein
                        organism = Homo sapiens
SEQUENCE: 160
QSVLTQPPSA SGTPGQRVTI SCSGRSSNIG SNPVNWYQQL PGTAPKLLIY NNIQRPSGVP  60
DRFSGSKSGT SASLAISGLQ SEDEAVYYCA SWDDSLNEGV FGGGTQLTVL             110

SEQ ID NO: 161          moltype = AA   length = 119
FEATURE                 Location/Qualifiers
source                  1..119
                        mol_type = protein
                        organism = Homo sapiens
SEQUENCE: 161
QVQLVQSGAE VKKPGSSVKV SCKASGGTFS SYAISWVRQA PGQGLEWMGG IIPIFGTTNY  60
AQKFQGRVTI TADESTSTAY MELSSLRSED TAVYYCARDH GYYYGMDVWG QGTTVTVSS   119

SEQ ID NO: 162          moltype = AA   length = 110
FEATURE                 Location/Qualifiers
source                  1..110
                        mol_type = protein
                        organism = Homo sapiens
SEQUENCE: 162
QSVLTQPSSV SAAPRQRVTL SCSGGDSNIG QNGVNWYLHV PGKAPRLVVY YDYLVSAGMS  60
ARFSGSRSGT SASLAISGLQ SEDEGVYYCA SWDDSLSAWV FGGGTKLTVL             110

SEQ ID NO: 163          moltype = AA   length = 123
FEATURE                 Location/Qualifiers
source                  1..123
                        mol_type = protein
                        organism = Homo sapiens
SEQUENCE: 163
QVQLVQSGAE VKKPGSSVKV SCKASGGTFS SYAISWVRQA PGQGLEWVGG IIPMFNSASY  60
AQKFQGKVTI TADKATNTAY MELSSLRSED TAVYYCARES SGYYYVSNWF DPWGQGTLVT  120
VSS                                                                123

SEQ ID NO: 164          moltype = AA   length = 111
FEATURE                 Location/Qualifiers
source                  1..111
                        mol_type = protein
                        organism = Homo sapiens
SEQUENCE: 164
QSVLTQPSSV SGAPGQRVTI SCTGSSSNIG AGYDVHWYQQ IPGTAPRLLI YANSGRASGV  60
PDRFSGSKSG TSASLAITGL QAEDEADYYC QSYDSSLSGV VFGGGTKLTV L           111

SEQ ID NO: 165          moltype = AA   length = 118
FEATURE                 Location/Qualifiers
source                  1..118
                        mol_type = protein
```

```
                        organism = Homo sapiens
SEQUENCE: 165
EVQLVQSGAE VKKPGESLKI SCKGSGYSFT SYWIGWVRQM PGKGLEWMGI IYPGDSDTRY    60
SPSFQGQVTI SADKSISTAY LQWSSLKASD TAMYYCARGS HYGDYDYWGQ GTLVTVSS    118

SEQ ID NO: 166          moltype = AA  length = 110
FEATURE                 Location/Qualifiers
source                  1..110
                        mol_type = protein
                        organism = Homo sapiens
SEQUENCE: 166
QSVLTQPPSV SAAPGQKVTI SCSGSSSNIG NNYVSWYQQL PGTAPKLLIY DNNKRPSGIP    60
DRFSGSKSGT SATLGITGLQ TGDEADYYCG TWDSSLSAGV FGGGTKLTVL            110

SEQ ID NO: 167          moltype = AA  length = 119
FEATURE                 Location/Qualifiers
source                  1..119
                        mol_type = protein
                        organism = Homo sapiens
SEQUENCE: 167
QVQLQQSGPG LVKPSQTLSL TCAISGDSVS SNSAAWNWIR QSPSRGLEWL GRTYYRSKWY    60
NDYAVSVKNR ITINPDTSKN QFSLQLNSVT PEDTAVYYCA RTIGWYDSWG QGTLVTVSS   119

SEQ ID NO: 168          moltype = AA  length = 108
FEATURE                 Location/Qualifiers
source                  1..108
                        mol_type = protein
                        organism = Homo sapiens
SEQUENCE: 168
SYELMQPPSV SVSPGQTARI TCSGDALPKQ FANWYQQKPG QAPVLLVYRD SERPSGIPER    60
FSGSTSGTTV TLTISGVQAE DEADYYCQSA DSSATYEVFG GGTKVTVL              108

SEQ ID NO: 169          moltype = AA  length = 118
FEATURE                 Location/Qualifiers
source                  1..118
                        mol_type = protein
                        organism = Homo sapiens
SEQUENCE: 169
EVQLVQSGAE VKKPGESLKI SCKGSGYSFT SYWIGWVRQM PGKGLEWMGT IYPGDSDTRY    60
SPSFQGQVTI SADKSISTAY LQWSSLKASD TAIYYCARRQ SGSGYDYWGQ GTLVTVSS   118

SEQ ID NO: 170          moltype = AA  length = 110
FEATURE                 Location/Qualifiers
source                  1..110
                        mol_type = protein
                        organism = Homo sapiens
SEQUENCE: 170
QSVLTQPPSA SGTPGQRVTI SCSGSSSNVG SNSVSWYQQF PGTAPKLLIY TNNQRPSGVP    60
DRFSGSKSGA SASLAISGPQ SEDEADYYCA AWDDSLNGWV FGGGTKLTVL            110

SEQ ID NO: 171          moltype = AA  length = 118
FEATURE                 Location/Qualifiers
source                  1..118
                        mol_type = protein
                        organism = Homo sapiens
SEQUENCE: 171
EVQLVQSGAE VKKPGESLKI SCKGSGYSFT SYWIGWVRQM PGKGLEWMGI IYPGDSDTRY    60
SPSFQGQVTI SADKSISTAY LQWSSLKASD TAMYYCARWS EGNGFDYWGQ GTMVTVSS   118

SEQ ID NO: 172          moltype = AA  length = 110
FEATURE                 Location/Qualifiers
source                  1..110
                        mol_type = protein
                        organism = Homo sapiens
SEQUENCE: 172
QSVLTQPPST SGTPGQWVTI SCSGSSSNIG SNSVSWYQQL PGMAPKLLIY RNDQRPSGVP    60
DRFSASKSGT SASLAISGLQ SEDEADYYCA AWDDSLNGVV FGGGTKLTVL            110

SEQ ID NO: 173          moltype = AA  length = 120
FEATURE                 Location/Qualifiers
source                  1..120
                        mol_type = protein
                        organism = Homo sapiens
SEQUENCE: 173
QVQLVQSGAE VKKPGASVKV SCKASGYTFT GYYLHWVRQA PGQGLEWMGR INPNSGGTNY    60
AQKFQGRVTM TRDTSISTAY MELSRLTSDD TAVYYCLAVA GTGGDAFDIW GQGTTVTVSS 120

SEQ ID NO: 174          moltype = AA  length = 107
FEATURE                 Location/Qualifiers
```

```
source                  1..107
                        mol_type = protein
                        organism = Homo sapiens
SEQUENCE: 174
DIQMTQSPST LSASVGDRVT ITCRASQSIS SWLAWYQQKP GKAPKLLIYA ASSLESGVPS    60
RFSGSGSGTD FTLTISSLQP EDFATYYCQQ GHSFPLTFGG GTKVDIK                 107

SEQ ID NO: 175          moltype = AA   length = 119
FEATURE                 Location/Qualifiers
source                  1..119
                        mol_type = protein
                        organism = Homo sapiens
SEQUENCE: 175
QVQLVESGGG VVQPGRSLRL SCAASGFTFS SYGMHWVRQA PGKGLEWVAV ISYDGSNKYY    60
ADSVKGRFTI SRDNSKNTLY LQMNSLRAED TAVYYCAKEG ELRGAFDIWG QGTMVTVSS    119

SEQ ID NO: 176          moltype = AA   length = 108
FEATURE                 Location/Qualifiers
source                  1..108
                        mol_type = protein
                        organism = Homo sapiens
SEQUENCE: 176
SYVLTQPPSV SVAPGKTARI TCGGDNIESK YVHWYQQKPG QAPVLVIYYD TDRPSGIPER    60
FSGANSGNSA TLTISRVEAG DEADYYCQVW DRTSGHFVFG PGTKVTVL                108

SEQ ID NO: 177          moltype = AA   length = 117
FEATURE                 Location/Qualifiers
source                  1..117
                        mol_type = protein
                        organism = Homo sapiens
SEQUENCE: 177
QVQLVESGGG VVQPGRSLRL SCAASGFSFT NYGMHWVRQA PGKGLEWVAV ISYDGSIKYY    60
EDSLKGRFTV SRDNSKKTLY LQMNSLRAED TAVYYCTRER GTGIDYWGLG TLVTVSS     117

SEQ ID NO: 178          moltype = AA   length = 110
FEATURE                 Location/Qualifiers
source                  1..110
                        mol_type = protein
                        organism = Homo sapiens
SEQUENCE: 178
QSALTQPASV SGYPGQSITL SCTGTKSDIG AYNYVSWYQQ HPGKAPKLMV YDVSNRPSGL    60
SNRFSGSKSD NTASLTISGL QAEDEAHYYC SSYTTSGTVV FGGGTKVTVL              110

SEQ ID NO: 179          moltype = AA   length = 117
FEATURE                 Location/Qualifiers
source                  1..117
                        mol_type = protein
                        organism = Homo sapiens
SEQUENCE: 179
QVQLVESGGG VVQPGRSLRL SCAASGFTFS NYGMHWVRQA PGKGLEWVAV ISYDGSIEYY    60
ADSVKGRFTI SRDNSSNTLY LQMNSLRAED TAVYYCARDE DGAFDIWGQG TTVTVSS     117

SEQ ID NO: 180          moltype = AA   length = 113
FEATURE                 Location/Qualifiers
source                  1..113
                        mol_type = protein
                        organism = Homo sapiens
SEQUENCE: 180
DIVMTQSPES LAVSLGERAT INCKSSESVS YSSSNKNYLS WYQQIPGQPP KLLIYWASTR    60
ESGVPDRFSG SGSGTDFTLT ISSLQAEDVA VYYCQQYYSS PLTFGGGTKV EIK          113

SEQ ID NO: 181          moltype = AA   length = 116
FEATURE                 Location/Qualifiers
source                  1..116
                        mol_type = protein
                        organism = Homo sapiens
SEQUENCE: 181
QVQLVESGGD VVQPGTSLRL SCAASGFTFS DYPLHWVRQA PGKGLEWLAV ISYDGWTKYY    60
ADSVKGRFTI SRDNSKNTLS LQMDSLRPED TAVYYCVRGT DYGDSWGQGT LVTVSS      116

SEQ ID NO: 182          moltype = AA   length = 110
FEATURE                 Location/Qualifiers
source                  1..110
                        mol_type = protein
                        organism = Homo sapiens
SEQUENCE: 182
QSVVTQPPSV SAAPGQKVTI SCSGSSSNIG NNYVSWYQQF PGTAPKFLIY ENNKRPSGIP    60
DRFSGSKSGT SATLGITGLQ TGDEADYYCG TWDNSLSAWV FGGGTKVTVL              110
```

```
SEQ ID NO: 183          moltype = AA   length = 117
FEATURE                 Location/Qualifiers
source                  1..117
                        mol_type = protein
                        organism = Homo sapiens
SEQUENCE: 183
QVQLVESGGG VVQPGTSLRL SCAASGFTFN NYPMFWVRQA PGKGLEWLAL ISYDGNHKVY      60
ADSVKGRFTI SRDNAKNTLY LQMHSLRAED TALYYCASDL SGAEDSWGQG TLVTVSS        117

SEQ ID NO: 184          moltype = AA   length = 110
FEATURE                 Location/Qualifiers
source                  1..110
                        mol_type = protein
                        organism = Homo sapiens
SEQUENCE: 184
QSALTQPASV SGSPGQSITI SCTGTSSDVG GYNYVSWYQQ HPGKAPKLLI YEVSNRPSGV      60
SNRFSGSKSG NTASLTISGL QAEDEADYYC SSYTSSSTWV FGGGTKLTVL                110

SEQ ID NO: 185          moltype = AA   length = 118
FEATURE                 Location/Qualifiers
source                  1..118
                        mol_type = protein
                        organism = Homo sapiens
SEQUENCE: 185
QVQLVESGGG VVQPARSLRL SCAASGFTLS DYPMHWVRQA PGKGLEWVAL MSYDGSLKFY      60
ADSVKGRSTI SRDISENTMY LQMNSLRAED TAVYYCARGN SDGDFDYWGR GTLVTVSS       118

SEQ ID NO: 186          moltype = AA   length = 106
FEATURE                 Location/Qualifiers
source                  1..106
                        mol_type = protein
                        organism = Homo sapiens
SEQUENCE: 186
SYVLTQPPSV SVAPGQTATI TCGGRDIGSR SVHWYQQTPG QAPVLVVYDD TARPSEIRAR      60
FSGFNSGNTA TLTISRVEAG DEATYYCQAW DSSTVVFGGG TKLTVL                    106

SEQ ID NO: 187          moltype = AA   length = 120
FEATURE                 Location/Qualifiers
source                  1..120
                        mol_type = protein
                        organism = Homo sapiens
SEQUENCE: 187
QVQLVESGGG VVQPGTSLRL SCAASGFSFN TFPMHWVRQT PGKGLEWVAS ISYDGSFKFY      60
ADSVKGRFTI SRDNSKNTLI LQLNSLRAED TAVYYCASPG DSDWADFENW GQGTTVTVSS     120

SEQ ID NO: 188          moltype = AA   length = 111
FEATURE                 Location/Qualifiers
source                  1..111
                        mol_type = protein
                        organism = Homo sapiens
SEQUENCE: 188
QSVLTQPPSV SGAPGQRVTI SCTGSSSNIG AGYDVHWYQQ LPGTAPKLLI YGNSNRPSGV      60
PDRFSGSKSG TSASLAITGL QAEDEADYYC QSYDSSLSGY VFGTGTKVTV L              111

SEQ ID NO: 189          moltype = AA   length = 116
FEATURE                 Location/Qualifiers
source                  1..116
                        mol_type = protein
                        organism = Homo sapiens
SEQUENCE: 189
QVQLVESGGG VVQPGRSLRL SCEASGFNFS LYGMHWVRQA PGKGLEWMAV ISYDGSQKYY      60
ADSVKGRFTI SRDNSKNTMY LQMNSLRAED TAVYYCVKGE GSLDYWGQGT LVTVSS         116

SEQ ID NO: 190          moltype = AA   length = 110
FEATURE                 Location/Qualifiers
source                  1..110
                        mol_type = protein
                        organism = Homo sapiens
SEQUENCE: 190
QSALTQPASA SGSPGQSVTI SCTGTTSDVG GYGYVSWYQH HPGKAPQLLI YEVAKRPSGV      60
PDRFSGSKSG NTASLTISGL QAEDEADYYC VSYTLSSLVV FGGGTKLTVL                110

SEQ ID NO: 191          moltype = AA   length = 123
FEATURE                 Location/Qualifiers
source                  1..123
                        mol_type = protein
                        organism = Homo sapiens
SEQUENCE: 191
QVTLRESGPA LVKPTQTLTL TCTFSGFSLN TRGMSVSWIR QPPGKALEWL ALIDWEDDKF      60
```

```
YRTSLMTRLT ISKDIFKNQV VLTMTNVDPV DTGTYYCART YSVGVKYFGM DVWGQGTTVT    120
VSS                                                                 123

SEQ ID NO: 192          moltype = AA  length = 108
FEATURE                 Location/Qualifiers
source                  1..108
                        mol_type = protein
                        organism = Homo sapiens
SEQUENCE: 192
SSELTQDPAV SVALGQTVRI TCQGDSLRNY YASWYRQEPG QAPILLIYGG NYRPSGIPDR    60
FSGSSSGNTA SLTITGAQAE DEADYYCNSR DSSGNHVVFG GGTKLTVL                108

SEQ ID NO: 193          moltype = AA  length = 115
FEATURE                 Location/Qualifiers
source                  1..115
                        mol_type = protein
                        organism = Homo sapiens
SEQUENCE: 193
QVQLQESGGG LVQSGGSRRL SCAVSGNVTS ITLMGWYRHA PGKQREAVGI INDDDRTRYE    60
DSMKGRFTIS RDPAKNMLYL QMTNLKPEDT AVYYCSAKAG GNFYMGQGTQ VTVSS        115

SEQ ID NO: 194          moltype = AA  length = 117
FEATURE                 Location/Qualifiers
source                  1..117
                        mol_type = protein
                        organism = Homo sapiens
SEQUENCE: 194
QVQLQESGGG LVQSGGSLKL SCAASGSIPS VNVMGWYRQA PGKQRELVAA VTSDGRTNYA    60
DSVKGRFTVS RDNAKNTVAL QMDSLKPEDT AVYYCLITNS DHNTLGVGKG TLVTVSS      117

SEQ ID NO: 195          moltype = AA  length = 117
FEATURE                 Location/Qualifiers
source                  1..117
                        mol_type = protein
                        organism = Homo sapiens
SEQUENCE: 195
QVQLQQSGGG LVQSGGSLKL SCAASGSIPS VNVMGWYRQA PGKQRELVAA VTSDGRTSYA    60
DSVKGRFTVS RDNAKNTVAL QMDSLKPEDT AVYYCLITNS DHNTLGVGKG TLVTVSS      117

SEQ ID NO: 196          moltype = AA  length = 117
FEATURE                 Location/Qualifiers
source                  1..117
                        mol_type = protein
                        organism = Homo sapiens
SEQUENCE: 196
QVQLQESGGG LVQSGGSLKL SCAASGSIPS VNVMGWYRQA PGKQRELVAA VTSDGRTNYA    60
DSVKGRFTVS RDNAKNTVAL QMDSLKPEDT AVYYCLITNQ DHNTLGVGKG TLVTVSS      117

SEQ ID NO: 197          moltype = AA  length = 1273
FEATURE                 Location/Qualifiers
source                  1..1273
                        mol_type = protein
                        organism = Betacoronavirus Severe acute respiratory
                        syndrome-related coronavirus 2
SEQUENCE: 197
MFVFLVLLPL VSSQCVNLTT RTQLPPAYTN SFTRGVYYPD KVFRSSVLHS TQDLFLPFFS    60
NVTWFHAIHV SGTNGTKRFD NPVLPFNDGV YFASTEKSNI IRGWIFGTTL DSKTQSLLIV   120
NNATNVVIKV CEFQFCNDPF LGVYYHKNNK SWMESEFRVY SSANNCTFEY VSQPFLMDLE   180
GKQGNFKNLR EFVFKNIDGY FKIYSKHTPI NLVRDLPQGF SALEPLVDLP IGINITRFQT   240
LLALHRSYLT PGDSSSGWTA GAAAYYVGYL QPRTFLLKYN ENGTITDAVD CALDPLSETK   300
CTLKSFTVEK GIYQTSNFRV QPTESIVRFP NITNLCPFGE VFNATRFASV YAWNRKRISN   360
CVADYSVLYN SASFSTFKCY GVSPTKLNDL CFTNVYADSF VIRGDEVRQI APGQTGKIAD   420
YNYKLPDDFT GCVIAWNSNN LDSKVGGNYN YLYRLFRKSN LKPFERDIST EIYQAGSTPC   480
NGVEGFNCYF PLQSYGFQPT NGVGYQPYRV VVLSFELLHA PATVCGPKKS TNLVKNKCVN   540
FNFNGLTGTG VLTESNKKFL PFQQFGRDIA DTTDAVRDPQ TLEILDITPC SFGGVSVITP   600
GTNTSNQVAV LYQDVNCTEV PVAIHADQLT PTWRVYSTGS NVFQTRAGCL IGAEHVNNSY   660
ECDIPIGAGI CASYQTQTNS PRRARSVASQ SIIAYTMSLG AENSVAYSNN SIAIPTNFTI   720
SVTTEILPVS MTKTSVDCTM YICGDSTECS NLLLQYGSFC TQLNRALTGI AVEQDKNTQE   780
VFAQVKQIYK TPPIKDFGGF NFSQILPDPS KPSKRSFIED LLFNKVTLAD AGFIKQYGDC   840
LGDIAARDLI CAQKFNGLTV LPPLLTDEMI AQYTSALLAG TITSGWTFGA GAALQIPFAM   900
QMAYRFNGIG VTQNVLYENQ KLIANQFNSA IGKIQDSLSS TASALGKLQD VVNQNAQALN   960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                    1273

SEQ ID NO: 198          moltype = AA  length = 6
```

```
FEATURE              Location/Qualifiers
source               1..6
                     mol_type = protein
                     organism = Homo sapiens
SEQUENCE: 198
SLRNYY                                                               6

SEQ ID NO: 199       moltype = AA  length = 11
FEATURE              Location/Qualifiers
source               1..11
                     mol_type = protein
                     organism = Homo sapiens
SEQUENCE: 199
NSRDSSGNHV V                                                         11

SEQ ID NO: 200       moltype = DNA  length = 26
FEATURE              Location/Qualifiers
misc_feature         1..26
                     note = Synthetic oligonucleotide
source               1..26
                     mol_type = other DNA
                     organism = synthetic construct
SEQUENCE: 200
acaggtacgt taatagttaa tagcgt                                         26

SEQ ID NO: 201       moltype = DNA  length = 22
FEATURE              Location/Qualifiers
misc_feature         1..22
                     note = Synthetic oligonucleotide
source               1..22
                     mol_type = other DNA
                     organism = synthetic construct
SEQUENCE: 201
atattgcagc agtacgcaca ca                                             22

SEQ ID NO: 202       moltype = DNA  length = 26
FEATURE              Location/Qualifiers
misc_feature         1..26
                     note = Synthetic oligonucleotide
source               1..26
                     mol_type = other DNA
                     organism = synthetic construct
SEQUENCE: 202
acactagcca tccttactgc gcttcg                                         26

SEQ ID NO: 203       moltype = AA  length = 11
FEATURE              Location/Qualifiers
source               1..11
                     mol_type = protein
                     organism = Homo sapiens
SEQUENCE: 203
LITNSDHNTL G                                                         11

SEQ ID NO: 204       moltype = AA  length = 7
FEATURE              Location/Qualifiers
source               1..7
                     mol_type = protein
                     organism = Homo sapiens
SEQUENCE: 204
GYSFTSY                                                              7

SEQ ID NO: 205       moltype = AA  length = 6
FEATURE              Location/Qualifiers
source               1..6
                     mol_type = protein
                     organism = Homo sapiens
SEQUENCE: 205
YPGDSD                                                               6

SEQ ID NO: 206       moltype = AA  length = 9
FEATURE              Location/Qualifiers
source               1..9
                     mol_type = protein
                     organism = Homo sapiens
SEQUENCE: 206
LGDYSGMDV                                                            9

SEQ ID NO: 207       moltype = AA  length = 5
FEATURE              Location/Qualifiers
```

```
SEQ ID NO: 207            moltype = AA   length = 5
FEATURE                   Location/Qualifiers
source                    1..5
                          mol_type = protein
                          organism = Homo sapiens
SEQUENCE: 207
SYWIG                                                                    5

SEQ ID NO: 208            moltype = AA   length = 17
FEATURE                   Location/Qualifiers
source                    1..17
                          mol_type = protein
                          organism = Homo sapiens
SEQUENCE: 208
IIYPGDSDTR YSPSFQG                                                      17

SEQ ID NO: 209            moltype = AA   length = 10
FEATURE                   Location/Qualifiers
source                    1..10
                          mol_type = protein
                          organism = Homo sapiens
SEQUENCE: 209
GYSFTSYWIG                                                              10

SEQ ID NO: 210            moltype = AA   length = 10
FEATURE                   Location/Qualifiers
source                    1..10
                          mol_type = protein
                          organism = Homo sapiens
SEQUENCE: 210
IIYPGDSDTR                                                              10

SEQ ID NO: 211            moltype = AA   length = 6
FEATURE                   Location/Qualifiers
source                    1..6
                          mol_type = protein
                          organism = Homo sapiens
SEQUENCE: 211
TSYWIG                                                                   6

SEQ ID NO: 212            moltype = AA   length = 13
FEATURE                   Location/Qualifiers
source                    1..13
                          mol_type = protein
                          organism = Homo sapiens
SEQUENCE: 212
WMGIIYPGDS DTR                                                          13

SEQ ID NO: 213            moltype = AA   length = 10
FEATURE                   Location/Qualifiers
source                    1..10
                          mol_type = protein
                          organism = Homo sapiens
SEQUENCE: 213
ARLGDYSGMD                                                              10

SEQ ID NO: 214            moltype = AA   length = 114
FEATURE                   Location/Qualifiers
source                    1..114
                          mol_type = protein
                          organism = Homo sapiens
SEQUENCE: 214
QVQLVQSGAE VKKPGASVTV SCKTSGYIFT NYDINWVRQA PGQGLEWVGW VNPNSGKVGY        60
AQKFQGRVIM TRSDSESTAY MELTQLTSDD TAVYYCARGH TDFWGQGTLV TVSS             114

SEQ ID NO: 215            moltype = AA   length = 119
FEATURE                   Location/Qualifiers
source                    1..119
                          mol_type = protein
                          organism = Homo sapiens
SEQUENCE: 215
QVQLVQSGAE VKKPGSSVKV SCKTSGGTFN TYSINWVRQA PGQGLEWMGE IIPIFDKPNY        60
AQKFQGRVTI TADESTSTAY MELTSLRSDD TAVYYCARGT GYYYGMDVWG QGTTVTVSS        119
```